(12) United States Patent
Hoelzemann et al.

(10) Patent No.: US 8,389,554 B2
(45) Date of Patent: Mar. 5, 2013

(54) IMIDAZOTHIADIAZOLE DERIVATIVES

(75) Inventors: Guenter Hoelzemann, Seeheim-Jugenheim (DE); Hartmut Greiner, Weitertadt (DE); Emilie Rossignol, Thoiry (FR); Dominique Swinnen, Beaumont (FR)

(73) Assignee: Merck Patent Gesellschaft mit Beschränkter Haftung, Darmstadt (DE)

( * ) Notice: Subject to any disclaimer, the term of this patent is extended or adjusted under 35 U.S.C. 154(b) by 0 days.

(21) Appl. No.: 13/056,331

(22) PCT Filed: Jul. 1, 2009

(86) PCT No.: PCT/EP2009/004753
§ 371 (c)(1),
(2), (4) Date: Jan. 28, 2011

(87) PCT Pub. No.: WO2010/012345
PCT Pub. Date: Feb. 4, 2010

(65) Prior Publication Data
US 2011/0130396 A1   Jun. 2, 2011

(30) Foreign Application Priority Data
Jul. 29, 2008  (EP) .................................... 08013574

(51) Int. Cl.
*A61K 31/433*   (2006.01)
*A61K 31/4188*   (2006.01)
*C07D 285/135*   (2006.01)
*C07D 235/00*   (2006.01)

(52) U.S. Cl. ..... 514/363; 514/393; 544/124; 546/268.7; 546/256; 548/138; 548/303.1

(58) Field of Classification Search ................... 514/393, 514/363; 548/138, 303.1
See application file for complete search history.

(56) References Cited

U.S. PATENT DOCUMENTS
2008/0306042 A1   12/2008  Cezanne et al.
2009/0170845 A1   7/2009  Durkin et al.

FOREIGN PATENT DOCUMENTS
| WO | WO 03/032916 A2 | 4/2003 |
| WO | WO 2004/078110 A2 | 9/2004 |
| WO | WO 2007/079820 A1 | 7/2007 |
| WO | WO 2007/118318 A1 | 10/2007 |
| WO | WO 2009/040552 A2 | 4/2009 |
| WO | WO 2009040552 A2 * | 4/2009 |

OTHER PUBLICATIONS
International Search Report of PCT/EP2009/004753 (Sep. 2, 2009).

* cited by examiner

*Primary Examiner* — Yong Chu
(74) *Attorney, Agent, or Firm* — Millen, White, Zelano & Branigan, P.C.

(57) ABSTRACT

Novel imidazo[2,1-b][1,3,4]thiadiazole derivatives of formula (I)

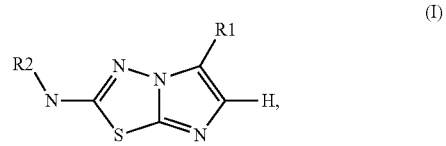

wherein $R^1$ and $R^2$ have the meaning according to claim 1, are inhibitors of TGF-beta receptor I kinase, and can be employed, inter alia, for the treatment of tumors.

14 Claims, No Drawings

IMIDAZOTHIADIAZOLE DERIVATIVES

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by kinases, in particular TGF-beta receptor kinases, plays a role, furthermore to pharmaceutical compositions which comprise these compounds, and to the use of the compounds for the treatment of kinase-induced diseases.

Transforming growth factor beta is the prototype of the TGF-beta superfamily, a family of highly preserved, pleiotrophic growth factors, which carry out important functions both during embryo development and also in the adult organism. In mammals, three isoforms of TGF-beta (TGF-beta 1, 2 and 3) have been identified, TGF-beta 1 being the commonest isoform (Kingsley (1994) Genes Dev 8:133-146). TGF-beta 3 is expressed, for example, only in mesenchymal cells, whereas TGF-beta 1 is found in mesenchymal and epithelial cells. TGF-beta is synthesized as pre-proprotein and is released in inactive form into the extracellular matrix (Derynck (1985) Nature 316: 701-705; Bottinger (1996) PNAS 93: 5877-5882). Besides the proregion cleaved off, which is also known as latency associated peptide (LAP) and remains associated with the mature region, one of the 4 isoforms of the latent TGF-beta binding proteins (LTBP 1-4) may also be bonded to TGF-beta (Gentry (1988) Mol Cell Biol 8: 4162-4168, Munger (1997) Kindey Int 51: 1376-1382). The activation of the inactive complex that is necessary for the development of the biological action of TGF-beta has not yet been clarified in full. However, proteolytic processing, for example by plasmin, plasma transglutaminase or thrombospondin, is certainly necessary (Munger (1997) Kindey Int 51: 1376-1382). The activated ligand TGF-beta mediates its biological action via three TGF-beta receptors on the membrane, the ubiquitously expressed type I and type II receptors and the type III receptors betaglycan and endoglin, the latter only being expressed in endothelial cells (Gougos (1990) J Biol Chem 264: 8361-8364, Loeps-Casillas (1994) J Cell Biol 124:557-568). Both type III TGF-beta receptors lack an intracellular kinase domain which facilitates signal transmission into the cell. Since the type III TGF-beta receptors bind all three TGF-beta isoforms with high affinity and type II TGF-beta receptor also has higher affinity for ligands bonded to type III receptor, the biological function is thought to consist in regulation of the availability of the ligands for type I and type II TGF-beta receptors (Lastres (1996) J Cell Biol 133:1109-1121; Lopes-Casillas (1993) Cell 73: 1435-1344). The structurally closely related type I and type II receptors have a serine/threonine kinase domain, which is responsible for signal transmission, in the cytoplasmatic region. Type II TGF-beta receptor binds TGF-beta, after which the type I TGF-beta receptor is recruited to this signal-transmitting complex. The serine/threonine kinase domain of the type II receptor is constitutively active and is able to phosphorylate seryl radicals in this complex in the so-called GS domain of the type I receptor. This phosphorylation activates the kinase of the type I receptor, which is now itself able to phosphorylate intracellular signal mediators, the SMAD proteins, and thus initiates intracellular signal transmission (summarized in Derynck (1997) Biochim Biophys Acta 1333: F105-F150).

The proteins of the SMAD family serve as substrates for all TGF-beta family receptor kinases. To date, 8 SMAD proteins have been identified, which can be divided into 3 groups: (1) receptor-associated SMADs (R-SMADs) are direct substrates of the TGF-β receptor kinases (SMAD1, 2, 3, 5, 8); (2) co-SMADs, which associate with the R-Smads during the signal cascade (SMAD4); and (3) inhibitory SMADs (SMAD6, 7), which inhibit the activity of the above-mentioned SMAD proteins. Of the various R-SMADs, SMAD2 and SMAD3 are the TGF-beta-specific signal mediators. In the TGF-beta signal cascade, SMAD2/SMAD3 are thus phosphorylated by the type I TGF-beta receptor, enabling them to associate with SMAD4. The resultant complex of SMAD2/SMAD3 and SMAD4 can now be translocated into the cell nucleus, where it can initiate the transcription of the TGF-beta-regulated genes directly or via other proteins (summarized in Itoh (2000) Eur J Biochem 267: 6954-6967; Shi (2003) Cell 113: 685-700).

The spectrum of the functions of TGF-beta is wide-ranging and dependent on cell type and differentiation status (Roberts (1990) Handbook of Experimental Pharmacology: 419-472). The cellular functions which are influenced by TGF-beta include: apoptosis, proliferation, differentiation, mobility and cell adhesion. Accordingly, TGF-beta plays an important role in a very wide variety of biological processes. During embryo development, it is expressed at sites of morphogenesis and in particular in areas with epithelial-mesenchymal interaction, where it induces important differentiation processes (Pelton (1991) J Cell Biol 115:1091-1105). TGF-beta also carries out a key function in the self-renewal and maintenance of an undifferentiated state of stem cells (Mishra (2005) Science 310: 68-71). In addition, TGF-beta also fulfils important functions in the regulation of the immune system. It generally has an immunosuppressive action, since it inhibits, inter alia, the proliferation of lymphocytes and restricts the activity of tissue macrophages. TGF-beta thus allows inflammatory reactions to subside again and thus helps to prevent excessive immune reactions (Bogdan (1993) Ann NY Acad Sci 685: 713-739, summarized in Letterio (1998) Annu Rev Immunol 16: 137-161). Another function of TGF-beta is regulation of cell proliferation. TGF-beta inhibits the growth of cells of endothelial, epithelial and haematopoietic origin, but promotes the growth of cells of mesenchymal origin (Tucker (1984) Science 226:705-707, Shipley (1986) Cancer Res 46:2068-2071, Shipley (1985) PNAS 82: 4147-4151). A further important function of TGF-beta is regulation of cellular adhesion and cell-cell interactions. TGF-beta promotes the build-up of the extracellular matrix by induction of proteins of the extracellular matrix, such as, for example, fibronectin and collagen. In addition, TGF-beta reduces the expression of matrix-degrading metalloproteases and inhibitors of metalloproteases (Roberts (1990) Ann NY Acad Sci 580: 225-232; Ignotz (1986) J Biol Chem 261: 4337-4345; Overall (1989) J Biol Chem 264: 1860-1869); Edwards (1987) EMBO J 6: 1899-1904).

The broad spectrum of action of TGF-beta implies that TGF-beta plays an important role in many physiological situations, such as wound healing, and in pathological processes, such as cancer and fibrosis.

TGF-beta is one of the key growth factors in wound healing (summarized in O'Kane (1997) Int J Biochem Cell Biol 29: 79-89). During the granulation phase, TGF-beta is released from blood platelets at the site of injury. TGF-beta then regulates its own production in macrophages and induces the secretion of other growth factors, for example by monocytes. The most important functions during wound healing include stimulation of chemotaxis of inflammatory cells, the synthesis of extracellular matrix and regulation of the proliferation, differentiation and gene expression of all important cell types involved in the wound-healing process.

Under pathological conditions, these TGF-beta-mediated effects, in particular the regulation of the production of extracellular matrix (ECM), can result in fibrosis or scars in the skin (Border (1994) N Engl J Med 331:1286-1292).

For the fibrotic diseases, diabetic nephropathy and glomeronephritis, it has been shown that TGF-beta promotes renal cell hypertrophy and pathogenic accumulation of the extracellular matrix. Interruption of the TGF-beta signaling pathway by treatment with anti-TGF-beta antibodies prevents expansion of the mesangial matrix, progressive reduction in kidney function and reduces established lesions of diabetic glomerulopathy in diabetic animals (Border (1990) 346: 371-374, Yu (2004) Kindney Int 66: 1774-1784, Fukasawah (2004) Kindney Int 65: 63-74, Sharma (1996) Diabetes 45: 522-530).

TGF-beta also plays an important role in liver fibrosis. The activation, essential for the development of liver fibrosis, of the hepatic stellate cells to give myofibroblasts, the main producer of the extracellular matrix in the course of the development of liver cirrhosis, is stimulated by TGF-beta. It has likewise been shown here that interruption of the TGF-beta signaling pathway reduces fibrosis in experimental models (Yata (2002) Hepatology 35:1022-1030; Arias (2003) BMC Gastroenterol 3:29).

TGF-beta also takes on a key function in the formation of cancer (summarized in Derynck (2001) Nature Genetics: 29: 117-129; Elliott (2005) J Clin One 23: 2078-2093). At early stages of the development of cancer, TGF-beta counters the formation of cancer. This tumor-suppressant action is based principally on the ability of TGF-beta to inhibit the division of epithelial cells. By contrast, TGF-beta promotes cancer growth and the formation of metastases at late tumor stages. This can be attributed to the fact that most epithelial tumors develop a resistance to the growth-inhibiting action of TGF-beta, and TGF-beta simultaneously supports growth of the cancer cells via other mechanisms. These mechanisms include promotion of angiogenesis, the immunosuppressant action, which supports tumor cells in avoiding the control function of the immune system (immunosurveillance), and promotion of invasiveness and the formation of metastases. The formation of an invasive phenotype of the tumor cells is a principal prerequisite for the formation of metastases. TGF-beta promotes this process through its ability to regulate cellular adhesion, motility and the formation of the extracellular matrix. Furthermore, TGF-beta induces the transition from an epithelial phenotype of the cell to the invasive mesenchymal phenotype (epithelial mesenchymal transition=EMT). The important role played by TGF-beta in the promotion of cancer growth is also demonstrated by investigations which show a correlation between strong TGF-beta expression and a poor prognosis. Increased TGF-beta level has been found, inter alia, in patients with prostate, breast, intestinal and lung cancer (Wikström (1998) Prostate 37: 19-29; Hasegawa (2001) Cancer 91: 964-971; Friedman (1995), Cancer Epidemiol Biomarkers Prev. 4:549-54).

Owing to the cancer-promoting actions of TGF-beta described above, inhibition of the TGF-beta signaling pathway, for example via inhibition of the TGF-beta type I receptor, is a possible therapeutic concept. It has been shown in numerous preclinical trials that interruption of the TGF-beta signaling pathway does indeed inhibit cancer growth. Thus, treatment with soluble TGF-beta type II receptor reduces the formation of metastases in transgenic mice, which develop invasive breast cancer in the course of time (Muraoka (2002) J Clin Invest 109: 1551-1559, Yang (2002) J Clin Invest 109: 1607-1615).

Tumor cell lines which express a defective TGF-beta type II receptor exhibit reduced tumor and metastatic growth (Oft (1998) Curr Biol 8: 1243-1252, McEachern (2001) Int J Cancer 91:76-82, Yin (1999) J Clin Invest 103: 197-206).

Conditions "characterized by enhanced TGF-β activity" include those in which TGF-β synthesis is stimulated so that TGF-β is present at increased levels or in which TGF-β latent protein is undesirably activated or converted to active TGF-β protein or in which TGF-β receptors are upregulated or in which the TGF-β protein shows enhanced binding to cells or extracellular matrix in the location of the disease. Thus, in either case "enhanced activity" refers to any condition in which the biological activity of TGF-β is undesirably high, regardless of the cause.

A number of diseases have been associated with TGF-β1 overproduction.

Inhibitors of TGF-β intracellular signaling pathway are useful treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, sclerorma, dermatomyositis, eosinophilic fascitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and sclerorma, chemical contact, or allergies. Another autoimmune disorder associated with fibroproliferative characteristics is rheumatoid arthritis.

Eye diseases associated with a fibroproliferative condition include retinal reattachment surgery accompanying proliferative vitreoretinopathy, cataract extraction with intraocular lens implantation, and post-glaucoma drainage surgery are associated with TGF-β1 overproduction.

Fibrotic diseases associated with TGF-β1 overproduction can be divided into chronic conditions, such as fibrosis of the kidney, lung and liver, and more acute conditions, such as dermal scarring and restenosis (Chamberlain, J. Cardiovascular Drug Reviews, 19 (4): 329-344). Synthesis and secretion of TGF-β1 by tumor cells can also lead to immune suppression, as seen in patients with aggressive brain or breast tumors (Arteaga, et al. (1993) J. Clin. Invest. 92: 2569-2576). The course of Leishmanial infection in mice is drastically altered by TGF-β1 (Barral-Netto, et al. (1992) Science 257: 545-547). TGF-β1 exacerbated the disease, whereas TGF-β1 antibodies halted the progression of the disease in genetically susceptible mice. Genetically resistant mice became susceptible to Leishmanial infection upon administration of TGF-β1.

The profound effects of TGF-β1 on extracellular matrix deposition have been reviewed (Rocco and Ziyadeh (1991) in Contemporary Issues in Nephrology v. 23, Hormones, autocoids and the kidney. ed. Jay Stein, Churchill Livingston, New York pp. 391-410; Roberts, et al. (1988) Rec. Prog. Hormone Res. 44: 157-197) and include the stimulation of the synthesis and the inhibition of degradation of extracellular matrix components. Since the structure and filtration properties of the glomerulus are largely determined by the extracellular matrix composition of the mesangium and glomerular membrane, it is not surprising that TGF-β1 has profound effects on the kidney. The accumulation of mesangial matrix in proliferative glomerulonephritis (Border, et al. (1990) Kidney Int. 37: 689-695) and diabetic nephropathy (Mauer et al. (1984) J. Clin. Invest. 74: 1143-1155) are clear and dominant pathological features of the diseases. TGF-β1 levels are elevated in human diabetic glomerulosclerosis (advanced neuropathy) (Yamamoto, et al. (1993) Proc. Natl. Acad. Sci. 90: 1814-1818). TGF-β1 is an important mediator in the genesis of renal fibrosis in a number of animal models (Phan, et al. (1990) Kidney Int. 37: 426; Okuda, et al. (1990) J. Clin. Invest. 86: 453). Suppression of experimentally induced glomerulonephritis in rats has been demonstrated by antiserum against TGF-β1 (Border, et al. (1990) Nature 346: 371) and by an extracellular matrix protein, decorin, which can bind TGF-61 (Border, et al. (1992) Nature 360: 361-363).

Excessive TGF-β1 leads to dermal scar-tissue formation. Neutralizing TGF-β1 antibodies injected into the margins of healing wounds in rats have been shown to inhibit scarring without interfering with the rate of wound healing or the tensile strength of the wound (Shah, et al. (1992) Lancet 339: 213-214). At the same time there was reduced angiogenesis, a reduced number of macrophages and monocytes in the wound, and a reduced amount of disorganized collagen fiber deposition in the scar tissue.

TGF-β1 may be a factor in the progressive thickening of the arterial wall which results from the proliferation of smooth muscle cells and deposition of extracellular matrix in the artery after balloon angioplasty. The diameter of the restenosed artery may be reduced by 90% by this thickening, and since most of the reduction in diameter is due to extracellular matrix rather than smooth muscle cell bodies, it may be possible to open these vessels to 50% simply by reducing extensive extracellular matrix deposition. In undamaged pig arteries transfected in vivo with a TGF-β1 gene, TGF-β1 gene expression was associated with both extracellular matrix synthesis and hyperplasia (Nabel, et al. (1993) Proc. Natl. Acad. Sci. USA 90: 10759-10763). The TGF-β1 induced hyperplasia was not as extensive as that induced with PDGF-BB, but the extracellular matrix was more extensive with TGF-β1 transfectants. No extracellular matrix deposition was associated with hyperplasia induced by FGF-1 (a secreted form of FGF) in this gene transfer pig model (Nabel (1993) Nature 362: 844-846).

There are several types of cancer where TGF-β1 produced by the tumor may be deleterious. MATLyLu rat prostate cancer cells (Steiner and Barrack (1992) Mol. Endocrinol. 6: 15-25) and MCF-7 human breast cancer cells (Arteaga, et al. (1993) Cell Growth and Differ. 4: 193-201) became more tumorigenic and metastatic after transfection with a vector expressing the mouse TGF-β1. TGF-β1 has been associated with angiogenesis, metastasis and poor prognosis in human prostate and advanced gastric cancer (Wikstrom et al. (1998) Prostate 37: 19-29; Saito et al. (1999) Cancer 86: 1455-1462). In breast cancer, poor prognosis is associated with elevated TGF-β (Dickson, et al. (1987) Proc. Natl. Acad. Sci. USA 84: 837-841; Kasid, et al. (1987) Cancer Res. 47: 5733-5738; Daly, et al. (1990) J. Cell Biochem. 43: 199-211; Barrett-Lee, et al. (1990) Br. J. Cancer 61: 612-617; King, et al. (1989) J. Steroid Biochem. 34: 133-138; Welch, et al. (1990) Proc. Natl. Acad. Sci. USA 87: 7678-7682; Walker, et al. (1992) Eur. J. Cancer 238: 641-644) and induction of TGF-β1 by tamoxifen treatment (Butta, et al. (1992) Cancer Res. 52: 4261-4264) has been associated with failure of tamoxifen treatment for breast cancer (Thompson, et al. (1991) Br. J. Cancer 63: 609-614). Anti-TGF-β1 antibodies inhibit the growth of MDA-231 human breast cancer cells in athymic mice (Arteaga, et al. (1993) J. Clin. Invest. 92: 2569-2576), a treatment that is correlated with an increase in spleen natural killer cell activity. CHO cells transfected with latent TGF-β1 also showed decreased NK activity and increased tumor growth in nude mice (Wallick, et al. (1990) J. Exp. Med. 172: 1777-1784). Thus, TGF-β secreted by breast tumors may cause an endocrine immune suppression. High plasma concentrations of TGF-β1 have been shown to indicate poor prognosis for advanced breast cancer patients (Anscher, et al. (1993) N. Engl. J. Med. 328: 1592-1598). Patients with high circulating TGF-β before high dose chemotherapy and autologous bone marrow transplantation are at high risk of hepatic veno-occlusive disease (15-50% of all patients with a mortality rate up to 50%) and idiopathic interstitial pneumonitis (40-60% of all patients). The implication of these findings is 1) that elevated plasma levels of TGF-β1 can be used to identify at-risk patients and 2) that reduction of TGF-β1 could decrease the morbidity and mortality of these common treatments for breast cancer patients.

Many malignant cells secrete transforming growth factor β (TGF-β), a potent immunosuppressant, suggesting that TGF-β production may represent a significant tumor escape mechanism from host immunosurveillance. Establishment of a leukocyte sub-population with disrupted TGF-β signaling in the tumor-bearing host offers a potential means for immunotherapy of cancer. A transgenic animal model with disrupted TGF-β signaling in T cells is capable of eradicating a normally lethal TGF-β overexpressing lymphoma tumor, EL4 (Gorelik and Flavell, (2001) Nature Medicine 7 (10): 1118-1122).

Downregulation of TGF-β secretion in tumor cells results in restoration of immunogenicity in the host, while T-cell insensitivity to TGF-β results in accelerated differentiation and autoimmunity, elements of which may be required in order to combat self-antigen-expressing tumors in a tolerated host. The immunosuppressive effects of TGF-β have also been implicated in a subpopulation of HIV patients with lower than predicted immune response based on their CD4/CD8 T cell counts (Garba, et al. J. Immunology (2002) 168: 2247-2254). A TGF-β neutralizing antibody was capable of reversing the effect in culture, indicating that TGF-β signaling inhibitors may have utility in reversing the immune suppression present in this subset of HIV patients.

During the earliest stages of carcinogenesis, TGF-β1 can act as a potent tumor suppressor and may mediate the actions of some chemopreventive agents. However, at some point during the development and progression of malignant neoplasms, tumor cells appear to escape from TGF-β-dependent growth inhibition in parallel with the appearance of bioactive TGF-β in the microenvironment. The dual tumor suppression/tumor promotion roles of TGF-β have been most clearly elucidated in a transgenic system overexpressing TGF-β in keratinocytes. While the transgenics were more resistant to formation of benign skin lesions, the rate of metastatic conversion in the transgenics was dramatically increased (Cui, et al (1996) Cell 86 (4): 531-42). The production of TGF-β1 by malignant cells in primary tumors appears to increase with advancing stages of tumor progression. Studies in many of the major epithelial cancers suggest that the increased production of TGF-β by human cancers occurs as a relatively late event during tumor progression. Further, this tumor-associated TGF-β provides the tumor cells with a selective advantage and promotes tumor progression. The effects of TGF-β1 on cell/cell and cell/stroma interactions result in a greater propensity for invasion and metastasis.

Tumor-associated TGF-β may allow tumor cells to escape from immune surveillance since it is a potent inhibitor of the clonal expansion of activated lymphocytes. TGF-β has also been shown to inhibit the production of angiostatin. Cancer therapeutic modalities, such as radiation therapy and chemotherapy, induce the production of activated TGF-β in the tumor, thereby selecting outgrowth of malignant cells that are resistant to TGF-β growth inhibitory effects. Thus, these anticancer treatments increase the risk and hasten the development of tumors with enhanced growth and invasiveness. In this situation, agents targeting TGF-β-mediated signal transduction might be a very effective therapeutic strategy. The resistance of tumor cells to TGF-β has been shown to negate many of the cytotoxic effects of radiation therapy and chemotherapy, and the treatment-dependent activation of TGF-β in the stroma may even be detrimental as it can make the microenvironment more conducive to tumor progression and contributes to tissue damage leading to fibrosis. The development of a TGF-β signal transduction inhibitors is likely to benefit the treatment of progressed cancer alone and in combination with other therapies.

The compounds are suitable for the treatment of cancer and other disease states influenced by TGF-β by inhibiting TGF-β in a patient in need thereof by administration of said compound(s) to said patient. TGF-β would also be useful against atherosclerosis (T. A. McCaffrey: TGF-ps and TGF-β Receptors in Atherosclerosis: Cytokine and Growth Factor Reviews 2000, 11, 103-114) and Alzheimer's (Masliah, E.; Ho, G.; Wyss-Coray, T.: Functional Role of TGF-β in Alzheimer's Disease Microvascular Injury: Lessons from Trangenic Mice Neurochemistry International 2001, 39, 393-400) diseases.

Another key biochemical mechanism of signal transduction involves the reversible phosphorylation of tyrosine residues on proteins. The phosphorylation state of a protein may affect its conformation and/or enzymatic activity as well as its cellular location. The phosphorylation state of a protein is modified through the reciprocal actions of protein tyrosine kinases (PTKs) and protein tyrosine phosphatases (PTPs) at various specific tyrosine residues.

Protein tyrosine kinases comprise a large family of transmembrane receptor and intracellular enzymes with multiple functional domains. The binding of ligand allosterically transduces a signal across the cell membrane where the cytoplasmic portion of the PTKs initiates a cascade of molecular interactions that disseminate the signal throughout the cell and into the nucleus. Many receptor protein tyrosine kinase (RPTKs), such as epidermal growth factor receptor (EGFR) and platelet-derived growth factor receptor (PDGFR) undergo oligomerization upon ligand binding, and the receptors self-phosphorylate (via autophosphorylation or transphosphorylation) on specific tyrosine residues in the cytoplasmic portions of the receptor. Cytoplasmic protein tyrosine kinases (CPTKs), such as Janus kinases (e.g. JAK1, JAK2, TYK2) and Src kinases (e.g. src, lck, fyn), are associated with receptors for cytokines (e.g. IL-2, IL-3, IL-6, erythropoietin) and interferons, and antigen receptors. These receptors also undergo oligomerization and have tyrosine residues that become phosphorylated during activation, but the receptor polypeptides themselves do not possess kinase activity.

Like the PTKs, the protein tyrosine phosphatases (PTPs) comprise a family of transmembrane and cytoplasmic enzymes, possessing at least an approximately 230 amino acid catalytic domain containing a highly conserved active site with a consensus motif. The substrates of PTPs may be PTKs which possess phosphotyrosine residues or the substrates of PTKs.

The levels of tyrosine phosphorylation required for normal cell growth and differentiation at any time are achieved through the coordinated action of PTKs and PTPS. Depending on the cellular context, these two types of enzymes may either antagonize or cooperate with each other during signal transduction. An imbalance between these enzymes may impair normal cell functions leading to metabolic disorders and cellular transformation.

It is also well known, for example, that the overexpression of PTKs, such as HER2, can play a decisive role in the development of cancer and that antibodies capable of blocking the activity of this enzyme can abrogate tumor growth. Blocking the signal transduction capability of tyrosine kinases such as Flk-1 and the PDGF receptor have been shown to block tumor growth in animal models.

It has been found that the compounds according to the invention and salts thereof have very valuable pharmacological properties while being well tolerated. In particular, they exhibit TGF-β receptor I kinase-inhibiting properties.

The compounds according to the invention preferably exhibit an advantageous biological activity, which is easily demonstrated in enzyme-based assays, for example assays as described herein. In such enzyme-based assays, the compounds according to the invention preferably exhibit and cause an inhibiting effect, which is usually documented by IC50 values in a suitable range, preferably in the micromolar range and more preferably in the nanomolar range.

As discussed herein, these signaling pathways are relevant for various diseases. Accordingly, the compounds according to the invention are useful in the prophylaxis and/or treatment of diseases that are dependent on the said signaling pathways by interaction with one or more of the said signaling pathways. The present invention therefore relates to compounds according to the invention as promoters or inhibitors, preferably as inhibitors, of the signaling pathways described herein. The invention therefore preferably relates to compounds according to the invention as promoters or inhibitors, preferably as inhibitors, of the TGF-β signaling pathway.

The present invention furthermore relates to the use of one or more compounds according to the invention in the treatment and/or prophylaxis of diseases, preferably the diseases described herein, that are caused, mediated and/or propagated by an increased TGF-β activity.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases as well as to a method for the treatment of the said diseases comprising the administration of one or more compounds according to the invention to a patient in need of such an administration.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilized in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-Gonzàlez, R. and Glenney, Jr., J. R. 1992, J. Biol. Chem. 267, page 14535).

For the identification of kinase inhibitors, various assay systems are available. In scintillation proximity assay (Sorg et al., J. of. Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214). Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody.

PRIOR ART

Triazole derivatives are known as TGF-beta inhibitors and disclosed in WO 2007/079820.

WO 2003/032916 teaches organosulfur modulators of tyrosine phosphatases and their use in the treatment of diseases which respond to phosphatase inhibition. The compounds can be based on an imidazothiadiazole scaffold that is substituted by several radicals are defined in terms of Markush groups. However, the scaffold lacks an amine function.

SUMMARY OF THE INVENTION

The invention relates to compounds of formula (I)

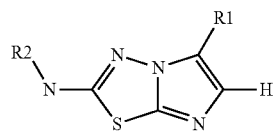

wherein
$R^1$ is unsubstituted, mono-or bicyclic carboaryl or unsubstituted, mono-or bicyclic heteroaryl having 1 to 4 N, O and/or S atoms,
each of which can be substituted by at least one substituent selected from the group of A, Hal, —CN, —$(CH_2)_n OR^3$, —CO—$R^3$, —CO—$NR^3R^3$, —CO—$N(R^3)_2$, —$(CH_2)_n NR^3R^3$, —$(CH_2)_n N(R^3)_2$ and —$SO_2N(R^3)_2$;
$R^2$ is A' or Cyc;
$R^3$ denotes independently from each other in $R^1$, A' and Cyc: H, A, —OH, —OA, acyl or optionally substituted carboaryl;
$Het^1$ denotes independently from each other in $R^1$ and A': saturated, unsaturated or aromatic, mono-or bicyclic heterocycle having 1 to 4 N, O and/or S atoms, optionally substituted by =O;
A denotes independently from each other in $R^1$ and $R^3$: unbranched or branched alkyl having 1-10 C atoms,
in which one or two non-adjacent $CH_2$ groups may be replaced by N and/or NH, and/or in addition 1-7 H atoms may be replaced by Hal, —OH, morpholine and/or amino; and
A' denotes unbranched or branched alkyl having 1-10 C atoms,
in which 1-7 H atoms may be replaced by Cyc, —$OR^3$, —$NR^3R^3$, —$N(R^3)_2$, $Het^1$ and optionally substituted carboaryl;
Cyc denotes independently from each other in $R^2$, $R^3$ and A': cycloalkyl having 3-7 C atoms,
which can be substituted by —$OR^3$, —$NR^3R^3$ or —$N(R^3)_2$;
Hal denotes independently from each other in $R^1$ and A: F, Cl, Br or I; and
n is 0, 1, 2, 3 or 4;
and/or physiologically acceptable salts thereof.

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds.

The term "solvates" of the compounds is taken to mean adductions of inert solvent molecules onto the compounds, which are formed owing to their mutual attractive force. Solvates are, for example, mono-or dihydrates or alkoxides.

The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995). It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in vivo to provide the bioactive agent (i.e. compounds of the invention) is a prodrug within the scope and spirit of the invention. Various forms of prodrugs are well known in the art and are described (e.g. Wermuth C G et al., Chapter 31: 671-696, The Practice of Medicinal Chemistry, Academic Press 1996; Bundgaard H, Design of Prodrugs, Elsevier 1985; Bundgaard H, Chapter 5: 131-191, A Textbook of Drug Design and Development, Harwood Academic Publishers 1991). Said references are incorporated herein by reference. It is further known that chemical substances are converted in the body into metabolites which may where appropriate likewise elicit the desired biological effect—in some circumstances even in more pronounced form. Any biologically active compound that was converted in vivo by metabolism from any of the compounds of the invention is a metabolite within the scope and spirit of the invention.

The compounds of the invention may be present in the form of their double bond isomers as "pure" E or Z isomers, or in the form of mixtures of these double bond isomers. Where possible, the compounds of the invention may be in the form of the tautomers, such as keto-enol tautomers.

All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The nomenclature as used herein for defining compounds, especially the compounds according to the invention, is in general based on the rules of the IUPAC-organization for chemical compounds and especially organic compounds. The terms indicated for explanation of the above compounds of the invention always, unless indicated otherwise in the description or in the claims, have the following meanings:

The term "unsubstituted" means that the corresponding radical, group or moiety has no substituents.

The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent (e.g. $R^3R^3$), the expression of such substituent may differ from each other (e.g. A and H). Hence, if individual radicals occur a number of times within a compound, the radicals adopt the meanings indicated, independently of one another.

The terms "alkyl", "A" or "A'" as well as other groups having the prefix "alk" for the purposes of this invention refer to acyclic saturated or unsaturated hydrocarbon radicals which may be branched or straight-chain and preferably have 1 to 10 carbon atoms, i.e. $C_1$-$C_{10}$-alkanyls, $C_2$-$C_{10}$-alkenyls and $C_2$-$C_{10}$-alkynyls. Alkenyls have at least one C—C double bond and alkynyls at least one C—C triple bond. Alkynyls may additionally also have at least one C—C double bond. Examples of suitable alkyl radicals are methyl, ethyl, n-propyl, isopropyl, n-butyl, isobutyl, sec-butyl, tert-butyl, n-pentyl, iso-pentyl, neo-pentyl, tert-pentyl, 2-or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl, ethylenyl (vinyl), propenyl (—$CH_2CH$=$CH_2$; —CH=CH—$CH_3$, —C(=$CH_2$)—$CH_3$), butenyl, pentenyl, hexenyl, heptenyl, octenyl, octadienyl, octadecenyl, octadec-9-enyl, icosenyl, icos-11-enyl, (Z)-icos-11-enyl, docosnyl, docos-13-enyl, (Z)-docos-13-enyl, ethynyl, propynyl (—$CH_2$—C≡CH, —C≡C—$CH_3$), butynyl, pentynyl, hexynyl, heptynyl and octynyl.

In a preferred embodiment of the invention, "A" denotes unbranched or branched alkyl having 1-10 C atoms, in which one or two non-adjacent $CH_2$ groups may be replaced by N and/or NH, and/or in addition 1-7 H atoms may be replaced by Hal, —OH, morpholine and/or amino. In a more preferred embodiment, the aforementioned preferred "A" is substituted as defined above. Especially preferred is $C_{1-4}$-alkyl. A $C_{1-4}$-alkyl radical is for example a methyl, ethyl, propyl, isopropyl, butyl, isobutyl or tert-butyl.

In another preferred embodiment of the invention, "A'" denotes unbranched or branched alkyl having 1-10 C atoms, in which 1-7 H atoms may be replaced by Cyc, —$OR^3$, —$NR^3R^3$, —$N(R^3)_2$, $Het^1$ and optionally substituted carboaryl. In a more preferred embodiment, the aforementioned preferred "A'" is substituted as defined above.

The terms "cycloalkyl" or "cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi-or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In a preferred embodiment of the invention, "cyc" denotes cycloalkyl having 3-7 C atoms, which can be substituted by —$OR^3$, —$NR^3R^3$ or —$N(R^3)_2$. In a more preferred embodiment, the aforementioned preferred "cyc" is substituted as defined above. Especially preferred are $C_3$-$C_7$-cycloalkyl and $C_4$-$C_7$-cycloalkyl. A $C_4$-$C_7$-cycloalkyl radical is for example a cyclobutyl, cyclopentyl, cyclohexyl and cycloheptyl.

The terms "heterocycle", "heterocyclyl" or "$Het^1$" for the purposes of this invention refers to a mono-or poly-cyclic system of 3 to 20, preferably 5 or 6 to 14 ring atoms comprising carbon atoms and 1, 2, 3, 4 or 5 heteroatoms, which are identical or different, in particular nitrogen, oxygen and/or sulfur. The cyclic system may be saturated, mono-or poly-unsaturated, but may not be aromatic. In the case of a cyclic system consisting of at least two rings the rings may be fused or spiro or otherwise connected. Such "heterocyclyl" radicals can be linked via any ring member. The term "heterocyclyl" also includes systems in which the heterocycle is part of a bi-or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocyclyl radical. The bonding to the compounds of the general formula (I) can be effected via any possible ring member of the heterocyclyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

In a preferred embodiment of the invention, "Het$^1$" denotes saturated, unsaturated or aromatic, mono-or bicyclic heterocycle having 1 to 4 N, O and/or S atoms, optionally substituted by =O, more preferably saturated monocyclic heterocycle having 1 to 4 N, O and/or S atoms, most preferably optionally substituted morpholinyl, tetrahydropyranyl, imidazolidinyl or dioxol. In a highly preferred embodiment, the aforementioned preferred "Het$^1$" is substituted as defined above.

In another preferred embodiment of the invention, "Het$^1$" denotes aromatic monocyclic heterocycle having 1 to 4 N, O and/or S atoms, more preferably aromatic monocyclic heterocycle having 1 to 2 N, O and/or S atoms, most preferably optionally substituted furanyl, thienyl and/or pyridyl.

The term "aryl" or "carboaryl" for the purposes of this invention refers to a mono-or polycyclic aromatic hydrocarbon systems having 3 to 14, preferably 5 to 14, more preferably 6 to 10 carbon atoms. The term "aryl" also includes systems in which the aromatic cycle is part of a bi-or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula (I) can be effected via any possible ring member of the aryl radical. Examples of suitable "aryl" radicals are phenyl, biphenyl, naphthyl, 1-naphthyl, 2-naphthyl and anthracenyl, but likewise in-danyl, indenyl or 1,2,3,4-tetrahydronaphthyl.

Preferred "carboaryls" of the invention are phenyl, naphthyl and biphenyl, more preferably phenyl.

In another preferred embodiment of the invention, the "carboaryl" is defined as "Ar", which denotes phenyl, naphthyl or biphenyl being optionally mono-, di-, tri-, tetra-or pentasubstituted by substituents selected from the group of A, Hal, —CN, —(CH$_2$)$_n$OR$^3$, —COA, —CHO, —CO—NR$^3$(CH$_2$)$_n$OR$^3$, —CO—NR$^3$(CH$_2$)$_p$N(R$^3$)$_2$, —CO—N(R$^3$)$_2$, —(CH$_2$)$_n$NR$^3$—COA, —(CH$_2$)$_n$NR$^3$—SO$_2$A, —(CH$_2$)$_2$N(R$^3$)$_2$ and —SO$_2$N(R$^3$)$_2$.

In another preferred embodiment of the invention, the "carboaryl" is defined as "Ar$^1$", which denotes phenyl being optionally mono-, di-, tri-, tetra-or pentasubstituted by substituents selected from the group of A, Hal, —OR$^3$, —(CH$_2$)$_n$NR$^3$R$^3$, —(CH$_2$)$_n$N(R$^3$)$_2$ and acyl.

In a more preferred embodiment, the aforementioned "Ar" and/or "Ar$^1$" are substituted as defined above.

The term "heteroaryl" or "Het" for the purposes of this invention refers to a 3 to 15, preferably 5 to 14, more preferably 5-, 6-or 7-membered mono-or polycyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, or 3, and that of the oxygen and sulfur atoms is independently 0 or 1. The term "heteroaryl" also includes systems in which the aromatic cycle is part of a bi-or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula (I) can be effected via any possible ring member of the heteroaryl radical. Examples of suitable "heteroaryl" are pyrrolyl, thienyl, furyl, imidazolyl, thiazolyl, isothiazolyl, oxazolyl, oxadiazolyl, isoxazolyl, pyrazolyl, pyridinyl, pyrimidinyl, pyridazinyl, pyrazinyl, indolyl, quinolinyl, isoquinolinyl, imidazolyl, triazolyl, triazinyl, tetrazolyl, phthalazinyl, indazolyl, indolizinyl, quinoxalinyl, quinazolinyl, pteridinyl, carbazolyl, phenazinyl, phenoxazinyl, phenothiazinyl and acridinyl.

It is preferred that "Het" represents thienyl, thiophenyl, pyridyl or pyrazolyl, which can be mono-or disubstituted by substituents selected from the group of A, Hal, —OR$^3$, —O(CH$_2$)$_p$N(R$^3$)$_2$ and —NR$^3$(CH$_2$)$_p$Het$^1$. In a more preferred embodiment, the aforementioned "Het" is substituted as defined above.

For the purposes of the present invention, the terms "alkylcycloalkyl", "cycloalkylalkyl", "alkylheterocyclyl", "heterocyclylalkyl", "alkylaryl", "arylalkyl", "alkylheteroaryl" and "heteroarylalkyl" mean that alkyl, cycloalkyl, heterocycl, aryl and heteroaryl are each as defined above, and the cycloalkyl, heterocyclyl, aryl or heteroaryl radical is bonded to the compounds of the general formula (I) via an alkyl radical, preferably $C_1$-$C_8$-alkyl radical, more preferably $C_1$-$C_4$-alkyl radical.

The term "alkyloxy" or "alkoxy" for the purposes of this invention refers to an alkyl radical according to above definition that is attached to an oxygen atom. The attachment to the compounds of the general formula (I) is via the oxygen atom. Examples are methoxy, ethoxy and n-propyloxy, propoxy and isopropoxy. Preferred is "$C_1$-$C_4$-alkyloxy" having the indicated number of carbon atoms.

The term "cycloalkyloxy" or "cycloalkoxy" for the purposes of this invention refers to a cycloalkyl radical according to above definition that is attached to an oxygen atom. The attachment to the compounds of the general formula (I) is via the oxygen atom. Examples are cyclopropyloxy, cyclobutyloxy, cyclopentyloxy, cyclohexyloxy, cycloheptyloxy and cyclooctyloxy. Preferred is "$C_3$-$C_9$-cycloalkyloxy" having the indicated number of carbon atoms.

The term "heterocyclyloxy" for the purposes of this invention refers to a heterocyclyl radical according to above definition that is attached to an oxygen atom. The attachment to the compounds of the general formula (I) is via the oxygen atom. Examples are pyrrolidinyloxy, thiapyrrolidinyloxy, piperidinyloxy and piperazinyloxy.

The term "aryloxy" for the purposes of this invention refers to an aryl radical according to above definition that is attached to an oxygen atom. The attachment to the compounds of the general formula (I) is via the oxygen atom. Examples are phenyloxy, 2-naphthyloxy, 1-naphthyloxy, biphenyloxy and indanyloxy. Preferred is phenyloxy.

The term "heteroaryloxy" for the purposes of this invention refers to a heteroaryl radical according to above definition that is attached to an oxygen atom. The attachment to the compounds of the general formula (I) is via the oxygen atom. Examples are pyrrolyloxy, thienyloxy, furyloxy, imidazolyloxy and thiazolyloxy.

The term "acyl" for the purposes of this invention refers to radicals that are formed by cleaving a hydroxyl group from acids. The attachment to the compounds of the general formula (I) is via the carbonyl C atom. Preferred examples are —CO—R, —SO$_2$—R and —PO(OR)$_2$, more preferably —SO$_2$—R.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine and chlorine are more preferred, when the halogens are substituted on an alkyl (haloalkyl) or alkoxy group (e.g. CF$_3$ and CF$_3$O).

The term "hydroxyl" means an —OH group.

In a preferred embodiment of the present invention, imidazothiadiazole derivatives of formula (I) are provided, wherein
R$^1$ is unsubstituted phenyl, naphthyl, biphenyl, thienyl, thiophenyl, pyridyl or pyrazol, each of which can be substituted.

In another preferred embodiment of the present invention, imidazothiadiazoles of formula (I) are provided, wherein
R$^3$ is H, A or acyl, more preferably H, unsubstituted A, —(CH$_2$)$_n$C(H)$_m$(Hal)$_o$, —(CH$_2$)$_n$OH, —(CH$_2$)$_p$N(A)$_2$, —CO-A or —SO$_2$-A; and
m, o are independently from each other 0, 1, 2 or 3.

In another preferred embodiment of the present invention, imidazothiadiazole derivatives of formula (I) are provided, wherein
R$^1$ is Ar or Het;
R$^2$ is A, —(CH$_2$)$_n$-Cyc, —(CH$_2$)$_p$OR$^3$, —(CH$_2$)$_p$OAr$^1$, —(CH$_2$)$_p$Ar$^1$ or —(CH$_2$)$_p$Het$^1$;
R$^3$ is H or A;
Ar denotes unsubstituted phenyl, naphthyl or biphenyl,
which can be mono-, di-, tri-, tetra-or pentasubstituted by substituents selected from the group of A, Hal, —CN, —(CH$_2$)$_n$OR$^3$, —COA, —CHO, —CO—NR$^3$(CH$_2$)$_n$OR$^3$, —CO—NR$^3$(CH$_2$)$_p$N(R$^3$)$_2$, —CO—N(R$^3$)$_2$, —(CH$_2$)$_n$NR$^3$—COA, —(CH$_2$)$_n$NR$^3$—SO$_2$A, —(CH$_2$)$_n$N(R$^3$)$_2$ and —SO$_2$N(R$^3$)$_2$;
Het denotes unsubstituted, mono-or bicyclic heteroaryl having 1 to 4 N, O and/or S atoms,
which can be mono-or disubstituted by substituents selected from the group of A, Hal, —OR$^3$, —O(CH$_2$)$_p$N(R$^3$)$_2$ and —NR$^3$(CH$_2$)$_p$Het$^1$;
Ar$^1$ denotes unsubstituted phenyl,
which can be mono-, di-, tri-, tetra-or pentasubstituted by substituents selected from the group of A, Hal, —OR$^3$, —(CH$_2$)$_n$NR$^3$R$^3$, —(CH$_2$)$_n$N(R$^3$)$_2$ and acyl;
Het$^1$ denotes independently from each other in Het and R$^2$: saturated, unsaturated or aromatic, mono-or bicyclic heterocycle having 1 to 4 N, O and/or S atoms, optionally substituted by =O;
A denotes independently from each other in Ar, Het, Ar$^1$, R$^2$ and R$^3$: unbranched or branched alkyl having 1-10 C atoms,
in which one or two non-adjacent CH$_2$ groups may be replaced by N and/or NH, and/or in addition 1-7 H atoms may be replaced by Hal, —OH, morpholine and/or amino;
Cyc denotes cycloalkyl having 3-7 C atoms,
which can be substituted by —OR$^3$, —NR$^3$R$^3$ or —N(R$^3$)$_2$;
Hal denotes independently from each other in Ar, Het, Ar$^1$ and A: F, Cl, Br or I;
n is 0, 1, 2, 3 or 4; and
p is 1, 2, 3 or 4;
and/or physiologically acceptable salts thereof.

In a more preferred embodiment of the present invention, imidazothiadiazole derivatives of formula (I) are provided, wherein
Ar is unsubstituted phenyl, naphthyl or biphenyl,
which can be mono-, di-, tri-, tetra-or pentasubstituted by substituents selected from the group of A, Cl, F, —CN, —OA, —(CH$_2$)$_n$OH, —O—(CH$_2$)$_p$N(CH$_2$)$_p$R$^3$, —COA, —CO—N(R$^3$)$_2$, —(CH$_2$)$_n$NR$^3$—SO$_2$A and —(CH$_2$)$_p$N(R$^3$)$_2$, preferably selected from the group of A, —OA, —(CH$_2$)$_n$OH, —COA and —NR$^3$CH$_3$, more preferably selected from the group of —CH$_3$, —OCH$_3$, —OH, —CH$_2$OH, —COCH$_3$ and —NR$^3$(CH$_3$)$_2$.

In another more preferred embodiment of the present invention, imidazothiadiazole derivatives of formula (I) are provided, wherein
Ar is phenyl,
which is mono-, di-or trisubstituted by substituents selected from the group of A, —OA, —OH and —COA, preferably substituted by trimethoxyphenyl, acetylphenyl or dimethylhydroxyphenyl, more preferably substituted by 3,4,5-trimethoxyphenyl, 3-acetylphenyl or 3,5-dimethyl-4-hydroxyphenyl.

In another more preferred embodiment of the present invention, imidazothiadiazole derivatives of formula (I) are provided, wherein
Ar$^1$ is unsubstituted phenyl,
which can be mono-or disubstituted by substituents selected from the group of methyl, Cl, F, —OA, —N(R$^3$)$_2$ and —SO$_2$—N(R$^3$)$_2$.

In another more preferred embodiment of the present invention, imidazothiadiazole derivatives of formula (I) are provided, wherein
R$^2$ is unbranched alkyl having 1-4 C atoms,
which is optionally substituted by at least one substituent selected from the group of cyclopropyl, methoxy, phenoxy, hydroxyl, morpholine, tetrahydropyran, imidazolidin-2-on, furanyl, thienyl, pyridyl and optionally substituted phenyl, preferably selected from the group of furanyl, pyridyl and optionally substituted phenyl.

In a most preferred embodiment of the present invention, imidazothiadiazole derivatives of formula (I) are provided, wherein
R$^2$ is methyl or ethyl,
each of which is substituted by at least one substituent selected from the group of furanyl, pyridyl and aminesulfonylphenyl, preferably substituted by furanylmethyl, pyridylethyl or aminosulfonylphenyl, more preferably substituted by 3-furanylmethyl, 2-pyridylethyl, 4-pyridylethyl or 1-(4-aminosulfonyl)-phenylethyl.

In a highly preferred embodiment of the present invention, imidazothiadiazoles of formula (I) and the above embodiments are provided, which are selected from the group of:
4-{2-[5-(3,4,5-Trimethoxy-phenyl)-imidazo[2,1-b][1,3,4]thiadiazol-2-ylamino]-ethyl}-benzenesulfonamide;
4-{2-[(Furan-2-ylmethyl)-amino]-imidazo[2,1-b][1,3,4]thiadiazol-5-yl}-2,6-dimethyl-phenol;
(2-Pyridin-2-yl-ethyl)-[5-(3,4,5-trimethoxy-phenyl)-imidazo[2,1-b][1,3,4]thiadiazol-2-yl]-amine;
Thiophen-2-ylmethyl-[5-(3,4,5-trimethoxy-phenyl)-imidazo[2,1-b][1,3,4]thiadiazol-2-yl]-amine;
4-{2-[5-(3-Acetyl-phenyl)-imidazo[2,1-b][1,3,4]thiadiazol-2-ylamino]-ethyl}-benzenesulfonamide;

(2-Pyridin-4-yl-ethyl)-[5-(3,4,5-trimethoxy-phenyl)-imidazo[2,1-b][1,3,4]thiadiazol-2-yl]-amine;
(2-Morpholin-4-yl-ethyl)-[5-(3,4,5-trimethoxy-phenyl)-imidazo[2,1-b][1,3,4]thiadiazol-2-yl]-amine;
4-[5-(3,4,5-Trimethoxy-phenyl)-imidazo[2,1-b][1,3,4]thiadiazol-2-ylamino]-cyclohexanol;
Pyridin-3-ylmethyl-[5-(3,4,5-trimethoxy-phenyl)-imidazo[2,1-b][1,3,4]thiadiazol-2-yl]-amine;
1-{3-[2-(2-Pyridin-4-yl-ethylamino)-imidazo[2,1-b][1,3,4]thiadiazol-5-yl]-phenyl}-ethanone;
2-Methoxy-4-{2-[(thiophen-2-ylmethyl)-amino]-imidazo[2,1-b][1,3,4]thiadiazol-5-yl}-phenol;
3-[5-(3,4,5-Trimethoxy-phenyl)-imidazo[2,1-b][1,3,4]thiadiazol-2-ylamino]-propan-1-ol;
1-{3-[2-(2-Morpholin-4-yl-ethylamino)-imidazo[2,1-b][1,3,4]thiadiazol-5-yl]-phenyl}-ethanone;
(2-Phenoxy-ethyl)-[5-(3,4,5-trimethoxy-phenyl)-imidazo[2,1-b][1,3,4]thiadiazol-2-yl]-amine;
(Tetrahydro-pyran-4-ylmethyl)-[5-(3,4,5-trimethoxy-phenyl)-imidazo[2,1-b][1,3,4]thiadiazol-2-yl]-amine; and
Isobutyl-[5-(3,4,5-trimethoxy-phenyl)-imidazo[2,1-b][1,3,4]thiadiazol-2-yl]-amine.

In another highly preferred embodiment of the present invention, the compound 4-{2-[5-(3,4,5-trimethoxy-phenyl)-imidazo[2,1-b][1,3,4]thiadiazol-2-ylamino]-ethyl}-benzenesulfonamide is provided as imidazothiadiazole according to formula (I) and the above embodiments.

The imidazothiadiazole derivatives according to formula (I) and the starting materials for its preparation, respectively, are produced by methods known per se, as described in the literature (for example in standard works, such as Houben-Weyl, Methoden der organischen Chemie [Methods of Organic Chemistry], Georg-Thieme-Verlag, Stuttgart), i.e. under reaction conditions that are known and suitable for said reactions. Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The reaction is generally carried out in an inert solvent. Depending on the conditions used, the reaction time is between a few minutes and 14 days, the reaction temperature is between about 15° C. and 150° C., normally between 30° C. and 130° C., particularly preferably between 60° C. and 120° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to 1-butanol.

In more detail, the imidazothiadiazole derivatives of formula (I) are accessible via the following route:

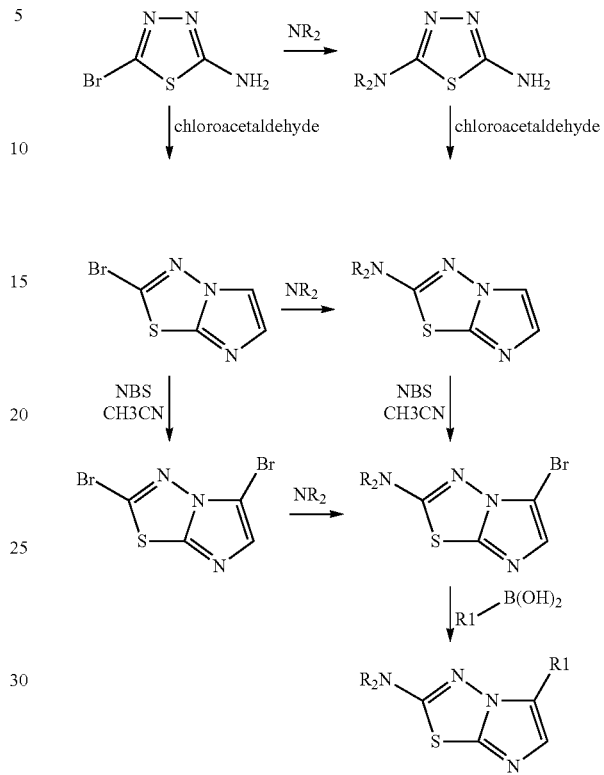

The compounds according to the invention can be preferably obtained by reacting 5-bromo-[1,3,4]thiadiazol-2-ylamine with a compound of the formula $NR^2$ in the initial, second or third reaction step.

Consequently, the present invention also relates to a process for manufacturing compounds of formula (I) comprising the steps of:

(a) reacting 5-bromo-[1,3,4]thiadiazol-2-ylamine with a compound of the formula $NR^2$ to yield a compound of formula (II)

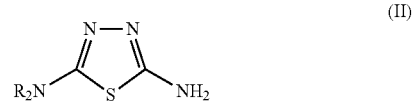

(II)

wherein $R^2$ has the meaning as defined above, (b) reacting the compound of formula (II) with chloroacetaldehyde to yield a compound of formula (III)

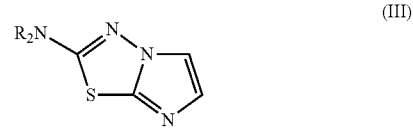

(III)

wherein $R^2$ has the meaning as defined above, (c) reacting the compound of formula (III) with NBS in acetonitrile to yield a compound of formula (IV)

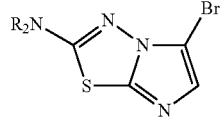

wherein R² has the meaning as defined above, and
(d) reacting the compound of formula (IV) with a compound of formula R¹—B(OH)₂ to yield a compound of formula (I)

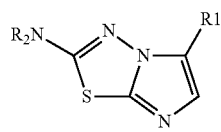

wherein R¹ and R² have the meaning as defined above,
or
(a) reacting 5-bromo-[1,3,4]thiadiazol-2-ylamine with chloroacetaldehyde to yield 2-bromo-imidazo[2,1-b][1,3,4]thiadiazole,
(b) reacting 2-bromo-imidazo[2,1-b][1,3,4]thiadiazole with a compound of the formula NR² to yield a compound of formula (III)

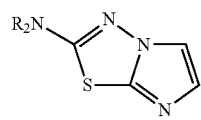

wherein R² has the meaning as defined above,
(c) reacting the compound of formula (III) with NBS in acetonitrile to yield a compound of formula (IV)

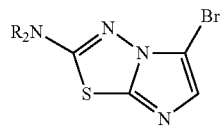

wherein R² has the meaning as defined above, and
(d) reacting the compound of formula (IV) with a compound of formula R¹—B(OH)₂ to yield a compound of formula (I)

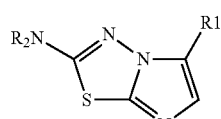

wherein R¹ and R² have the meaning as defined above,
or
(a) reacting 5-bromo-[1,3,4]thiadiazol-2-ylamine with chloroacetaldehyde to yield 2-bromo-imidazo[2,1-b][1,3,4]thiadiazole, (b) reacting 2-bromo-imidazo[2,1-b][1,3,4]thiadiazole with NBS in acetonitrile to yield 2,5-dibromo-imidazo[2,1-b][1,3,4]thiadiazole,
(c) reacting 2,5-dibromo-imidazo[2,1-b][1,3,4]thiadiazole with a compound of the formula NR² to yield a compound of formula (IV)

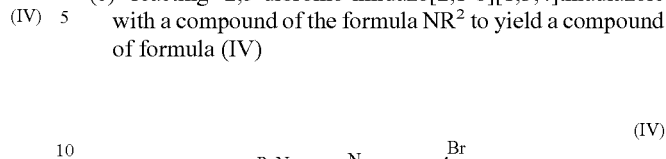

wherein R² has the meaning as defined above, and
(d) reacting the compound of formula (IV) with a compound of formula R¹—B(OH)₂ to yield a compound of formula (I)

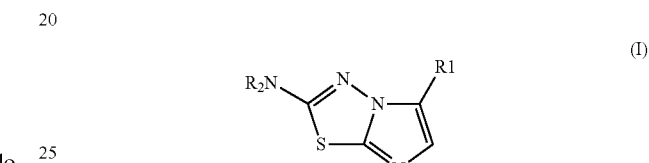

wherein R¹ and R² have the meaning as defined above, and/or
(e) converting a base or a acid of the compound of formula (I) into a salt thereof.

In detail, the brome radical of 5-bromo-[1,3,4]thiadiazol-2-ylamine, 2-bromo-imidazo[2,1-b][1,3,4]thiadiazole or 2,5-dibromo-imidazo[2,1-b][1,3,4]thiadiazole is substituted by the compound of formula NR², thereby introducing the R² radical of choice. The substitution can be performed in step (a) (cf. first alternative of the manufacturing process according to the invention), in step (b) (cf. second alternative of the manufacturing process according to the invention) or in step (c) (cf. third of the manufacturing process according to the invention). The ring closure reaction with chloroacetaldehyde can be performed prior the substitution reaction, which corresponds to step (a) in the second and third alternative of the manufacturing process according to the invention, or after the substitution reaction, which corresponds to step (b) in the first alternative of the manufacturing process according to the invention. Similarly, the bromination reaction with NBS in acetonitrile can be performed prior the substitution reaction, which corresponds to step (b) in the third alternative of the manufacturing process according to the invention, or after the substitution reaction, which corresponds to step (c) in the first and second alternative of the manufacturing process according to the invention. The step (d) is identically performed in all alternatives of the manufacturing process according to the invention and involves the introduction of the R¹ radical of interest by Suzuki cross coupling with a compound the formula R¹—B(OH)₂.

In the final step (e), a salt of the compound according to formula (I) is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminum salts of the compounds according to the invention are likewise included. In the case of certain compounds according to the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl-and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds according to the invention which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternized using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water-and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds according to the invention are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds according to the invention are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Object of the present invention is also the use of compounds according to formula (I) and/or physiologically acceptable salts thereof for inhibiting kinases. The term "inhibition" denotes any reduction in kinase activity, which is based on the action of the specific inventive compounds capable to interact with the target kinase in such a manner that makes recognition, binding and blocking possible. The compounds are characterized by such a high affinity to at least one kinase, which ensures a reliable binding and preferably a complete blocking of kinase activity. More preferably, the substances are mono-specific in order to guarantee an exclusive and directed recognition with the chosen single kinase target. In the context of the present invention, the term "recognition"—without being limited thereto—relates to any type of interaction between the specific substances and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

In an embodiment of the invention the kinases either belongs to the group of tyrosine kinases and serine/threonine kinases. In a preferred embodiment of the invention, the serine/threonine kinases are selected form the group of TGF-beta receptor kinase, protein kinase A, protein kinase B, protein kinase C, Raf and PDK1. It is more preferred to inhibit the TGF-beta receptor kinase. In another preferred embodiment of the invention, the tyrosine kinases are selected form the group of KDR, Tie2 and Met. Further kinases are known to the skilled artisan and their knockout can be tested by a matter of routine.

The kinase are especially half inhibited if the concentration of the compounds amounts to less than 1.000 nM, preferably less than 500 nM, more preferably less than 300 nM, most preferably less than 200 nM. Such concentration is also referred to as 1050.

The use according to the previous paragraphs of the specification may be either performed in-vitro or in-vivo models. The inhibition can be monitored by the techniques described in the course of the present specification. The in-vitro use is preferably applied to samples of humans suffering from cancer, tumor growth, metastatic growth, fibrosis, restenosis, HIV infection, Alzheimer's, atherosclerosis and/or wound healing disorders. Testing of several specific compounds and/or derivatives thereof makes the selection of that active ingredient possible that is best suited for the treatment of the human subject. The in-vivo dose rate of the chosen derivative is advantageously pre-adjusted to the kinase susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of kinase activity if expedient.

The invention furthermore relates comprising at least one compound according to the invention and/or pharmaceutically usable derivatives, salts, solvates and stereoisomers thereof, including mixtures thereof in all ratios, and optionally excipients and/or adjuvants.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Consequently, the invention also relates to a pharmaceutical composition comprising as active ingredient an effective amount of at least one compound according to formula (I) and/or physiologically acceptable salts thereof together with pharmaceutically tolerable adjuvants.

A "medicament", "pharmaceutical composition" or "pharmaceutical formulation" in the meaning of the invention is any agent in the field of medicine, which comprises one or more compounds of formula (I) or preparations thereof and can be used in prophylaxis, therapy, follow-up or aftercare of patients who suffer from diseases, which are associated with kinase activity, in such a way that a pathogenic modification of their overall condition or of the condition of particular regions of the organism could establish at least temporarily.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

The present compounds are suitable for combination with known anticancer agents. These known anticancer agents include the following: (1) oestrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors. The present compounds are particularly suitable for administration at the same time as radiotherapy. The synergistic effects of inhibiting VEGF in combination with radiotherapy have been described in the art (see WO 00/61186).

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cisretinoic acid, 9-cisretinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumor necrosis factors, intercalators, microtubulin inhibitors and topoisomerase inhibitors. Examples of cytotoxic agents include, but are not limited to, tirapazimine, sertenef, cachectin, ifosfamide, tasonermin, lonidamine, carboplatin, altretamine, prednimustine, dibromoodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cisaminedichloro(2-methylpyridine)platinum, benzylguanine, glufosfamide, GPX100, (trans,trans,trans)bismu-(hexane-1,6-diamine)-mu-[diamineplatinum(II)]bis-[diamine(chloro)platinum(II)] tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Further examples of cytotoxic agents being microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoroo-4-methoxyphenyl)benzenesulfonamide, anhydrovinblastine, N,N-dimethyl-L-valyl-L-valyl-N-methyl-L-valyl-L-prolyl-L-prolinet-butylamide, TDX258 and BMS188797.

Further examples of cytotoxic agents being topoisomerase inhibitors are, for example, topotecan, hycaptamine, irinotecan, rubitecan, 6-ethoxypropionyl-3'',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoroo-2,3-dihydro-9-hydroxy-4-methyl-1H,12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydro-furo(3',':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoroomethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetra-decadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluoroouracil, alanosine, 11-acetyl-8-(carbamoyloxymethyl)-4-formyl-6-methoxy-14-oxa-1,11-diazatetracyclo-(7.4.1.0.0)tetradeca-2,4,6-trien-9-ylacetic acid ester, swainsonine, lometrexol, dexrazoxane, methioninase, 2'-cyanoo-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumor suppressor genes, such as p53, which can be delivered via recombinant virus-mediated gene transfer (see U.S. Pat. No. 6,069,134, for example).

The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, such as lactose or starch, magnesium stearate, talc, and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavor, preservative, dispersant and dye may likewise be present.

Capsules are produced by preparing a powder mixture as described above and filling shaped gelatin shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatin, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatin or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavor, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavor additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The active ingredient according to the invention can also be fused or complexed with another molecule that promotes the directed transport to the destination, the incorporation and/or distribution within the target cells.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamido-phenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurized dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is orally or parenterally administered, more preferably orally. In particular, the active ingredient is provided in a water-soluble form, such as a pharmaceutically acceptable salt, which is meant to include both acid and base addition salts. Furthermore, the compounds of formula (I) and salts thereof, may be lyophilized and the resulting lyophilizates used, for example, to produce preparations for injection. The preparations indicated may be sterilized and/or may comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases, cancer and/or fibrotic diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by kinase activity. It is particularly preferred that the diseases are selected from the group of cancer, tumor growth, metastatic growth, fibrosis, restenosis, HIV infection, Alzheimer's, atherosclerosis and wound healing disorders. The compounds of formula (I) are also useful for promoting wound healing. It shall be understood that the host of the compound is included in the present scope of protection according to the present invention.

Particular preference is given to the treatment and/or monitoring of a tumor and/or cancer disease. The tumor is preferably selected from the group of tumors of the squamous epithelium, the bladder, the stomach, the kidneys, the head, the neck, the oesophagus, the cervix, the thyroid, the intestine, the liver, the brain, the prostate, the urogenital tract, the lymphatic system, the stomach, the larynx and/or the lung.

The tumor is furthermore preferably selected from the group of lung adenocarcinoma, small-cell lung carcinomas, pancreatic cancer, glioblastomas, colon carcinoma and breast carcinoma. In addition, preference is given to the treatment and/or monitoring of a tumor of the blood and immune system, more preferably for the treatment and/or monitoring of a tumor selected from the group of acute myeloid leukaemia, chronic myeloid leukaemia, acute lymphatic leukaemia and/or chronic lymphatic leukaemia. Such tumors can also be designated as cancers in the meaning of the invention.

In a more preferred embodiment of the invention, the aforementioned tumors are solid tumors.

In another preferred embodiment of the invention, the compounds of formula (I) are applied for the prophylactic or therapeutic treatment and/or monitoring of retroviral diseases or for the manufacture of a medicament for the prophylactic or therapeutic treatment and/or monitoring of retroviral diseases, respectively, preferably of retroviral immune diseases, more preferably an HIV infection. The agent can be either administered to reducing the likelihood of infection or to prevent the infection of a mammal with a retrovirus and the onset of the disease in advance, or to treat the disease caused by the infectious agent. Particularly, later stages of virus internalization can be reduced and/or prevented. It is the intention of a prophylactic inoculation to reduce the likelihood of infection or to prevent the infection with a retrovirus after the infiltration of single viral representatives, e.g. into a wound, such that the subsequent propagation of the virus is strictly diminished, or it is even completely inactivated. If an infection of the patient is already given, a therapeutic administration is performed in order to inactivate the retrovirus being present in the body or to stop its propagation. Numerous retroviral diseases can be successfully combated by applying the inventive compounds, particularly AIDS caused by HIV.

The invention also relates to the use of compounds according to formula (I) and/or physiologically acceptable salts thereof for the prophylactic or therapeutic treatment and/or monitoring of diseases that are caused, mediated and/or propagated by kinase activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by kinase activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

In another embodiment of the present invention, the compounds according to formula (I) and/or physiologically acceptable salts thereof are used for the production of a combination preparation for the prophylactic or therapeutic treatment and/or monitoring of solid tumors, wherein the combination preparation comprises an effective amount of an active ingredient selected from the group of (1) oestrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors.

The compounds of formula (I) according to the invention can be administered before or following an onset of disease once or several times acting as therapy. The aforementioned medical products of the inventive use are particularly used for the therapeutic treatment. A therapeutically relevant effect relieves to some extent one or more symptoms of an autoimmune disease, or returns to normality, either partially or completely, one or more physiological or biochemical parameters associated with or causative of the disease or pathological conditions. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disease or even prevent the initiation of diseases associated with increased kinase activity in advance or to treat the arising and continuing symptoms. The diseases as concerned by the invention are preferably cancer and/or fibrotic diseases. In the meaning of the invention, prophylactic treatment is advisable if the subject possesses any preconditions for the aforementioned physiological or pathological conditions, such as a familial disposition, a genetic defect, or a previously passed disease.

The prior teaching of the present specification concerning the pharmaceutical composition is valid and applicable without restrictions to the use of compounds according to formula (I) and their salts for the production of a medicament and/or combination preparation for prophylaxis and therapy of said diseases.

It is another object of the invention to provide a method for treating diseases that are caused, mediated and/or propagated by kinase activity, wherein an effective amount of at least one compound according to formula (I) and/or physiologically acceptable salts thereof is administered to a mammal in need of such treatment. The preferred treatment is an oral or parenteral administration. The treatment of the patients with cancer, tumor growth, metastatic growth, fibrosis, restenosis, HIV infection, Alzheimer's, atherosclerosis and/or wound healing disorders or people bearing a risk of developing such diseases on the basis of existing preconditions by means of the compounds of formula (I) improves the whole-body state of health and ameliorates symptoms in these individuals. The inventive method is particularly suitable for treating solid tumors.

The method is particularly performed in such a manner that an effective amount of another active ingredient selected from the group of (1) oestrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors is administered in combination with the effective amount of the compound of formula (I) and/or physiologically acceptable salts thereof.

In a preferred embodiment of the method, the treatment with the present compounds is combined with radiotherapy. It is even more preferred to administer a therapeutically effective amount of a compound according formula (I) in combination with radiotherapy and another compound from the groups (1) to (10) as defined above. The synergistic effects of inhibiting VEGF in combination with radiotherapy have already been described.

The prior teaching of the invention and its embodiments is valid and applicable without restrictions to the method of treatment if expedient.

In the scope of the present invention, imidazothiadiazole derivatives of formula (I) are provided for the first time. The inventive compounds strongly and/or selectively target kinases, particularly to TGF-β receptor kinases, and such structures are not disclosed in prior art. The compounds of formula (I) and derivatives thereof are characterized by a high specificity and stability; low manufacturing costs and convenient handling. These features form the basis for a reproducible action, wherein the lack of cross-reactivity is included, and for a reliable and safe interaction with their matching target structures. The current invention also comprises the use of present imidazothiadiazole derivatives in the inhibition, the regulation and/or modulation of the signal cascade of kinases, especially the TGF-β receptor kinases, which can be advantageously applied as research and/or diagnostic tool. Furthermore, pharmaceutical compositions containing said compounds and the use of said compounds to treat kinase related illnesses is a promising, novel approach for a broad spectrum of therapies causing a direct and immediate reduction of symptoms. The impact is of special benefit to efficiently combat severe diseases, such as cancer and fibrotic diseases and other illnesses arising from TGF-β kinase activity. Due to their surprisingly strong and/or selective enzyme inhibition, the compounds of the invention can be advantageously administered at lower doses compared to other less potent or selective inhibitors of the prior art while still achieving equivalent or even superior desired biological effects. In addition, such a dose reduction may advantageously lead to less or even no medicinal adverse effects. Further, the high inhibition selectivity of the compounds of the invention may translate into a decrease of undesired side effects on its own regardless of the dose applied.

It is to be understood that this invention is not limited to the particular compounds, pharmaceutical compositions, uses and methods described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a compound" includes a single or several different compounds, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The example are particularly to be interpreted such that they are not limited to the explicitly demonstrated combinations of features, but the exemplified features may be unrestrictedly combined again if the technical problem of the invention is solved.

EXAMPLE 1

Cellular Assay for Testing TGF-Beta Receptor I Kinase Inhibitors

As an example, the ability of the inhibitors to eliminate TGF-beta-mediated growth inhibition was tested. Cells of the lung epithelial cell line Mv1 Lu were sown in a defined cell density in a 96-well microtiter plate and cultivated overnight under standard conditions. Next day, the medium was replaced by medium which comprises 0.5% of FCS and 1 ng/ml of TGF-beta, and the test substances were added in defined concentrations, generally in the form of dilution series with 5 fold steps. The concentration of the solvent DMSO was constant at 0.5%. After a further two days, Crystal Violet staining of the cells was carried out. After extraction of the Crystal Violet from the fixed cells, the absorption was measured spectrophotometrically at 550 nm. It could be used as a quantitative measure of the adherent cells present and thus of the cell proliferation during the culture.

EXAMPLE 2

In-Vitro (Enzyme) Assay for Determination of the Efficacy of Inhibitors of the Inhibition of TGF-Beta-Mediated Effects The kinase assay was carried out as 384-well flashplate assay. 31.2 nM of GST-ALK5, 439 nM of GST-SMAD2 and 3 mM of ATP (with 0.3 μCi of $^{33}$P-ATP/well) were incubated in a total volume of 35 μl (20 mM of HEPES, 10 mM of $MgCl_2$, 5 mM of $MnCl_2$, 1 mM of DTT, 0.1% of BSA, pH 7.4) without or with test substance (5-10 concentrations) at 30° C. for 45 min. The reaction was stopped using 25 μl of 200 mM EDTA solution, filtered with suction at room temperature after 30 min, and the wells were washed with 3 times 100 μl of 0.9% NaCl solution. Radioactivity was measured in the TopCount. The $IC_{50}$ values were calculated using RS1 (Table 1). Above and below, all temperatures were indicated in ° C.

TABLE 1

Inhibition of TGF-beta

| No | Name | Activity IC50 nM |
|---|---|---|
| 464 | 4-{2-[5-(3,4,5-Trimethoxy-phenyl)-imidazo[2,1-b][1,3,4]thiadiazol-2-ylamino]-ethyl}-benzene-sulfonamide | 160 |
| 38 | 4-{2-[(Furan-2-ylmethyl)-amino]-imidazo[2,1-b][1,3,4]thiadiazol-5-yl}-2,6-dimethyl-phenol | 240 |

TABLE 1-continued

Inhibition of TGF-beta

| No | Name | Activity IC50 nM |
|---|---|---|
| 20 | (2-Pyridin-2-yl-ethyl)-[5-(3,4,5-trimethoxy-phenyl)-imidazo[2,1-b][1,3,4]thiadiazol-2-yl]-amine | 270 |
| 165 | Thiophen-2-ylmethyl-[5-(3,4,5-trimethoxy-phenyl)-imidazo[2,1-b][1,3,4]thiadiazol-2-yl]-amine | 330 |
| 490 | 4-{2-[5-(3-Acetyl-phenyl)-imidazo[2,1-b][1,3,4]thiadiazol-2-ylamino]-ethyl}-benzenesulfonamide | 360 |
| 442 | (2-Pyridin-4-yl-ethyl)-[5-(3,4,5-trimethoxy-phenyl)-imidazo[2,1-b][1,3,4]thiadiazol-2-yl]-amine | 480 |
| 495 | (2-Morpholin-4-yl-ethyl)-[5-(3,4,5-trimethoxy-phenyl)-imidazo[2,1-b][1,3,4]thiadiazol-2-yl]-amine | 490 |
| 363 | 4-[5-(3,4,5-Trimethoxy-phenyl)-imidazo[2,1-b][1,3,4]thiadiazol-2-ylamino]-cyclohexanol | 570 |
| 416 | Pyridin-3-ylmethyl-[5-(3,4,5-trimethoxy-phenyl)-imidazo[2,1-b][1,3,4]thiadiazol-2-yl]-amine | 670 |
| 360 | 1-{3-[2-(2-Pyridin-4-yl-ethylamino)-imidazo[2,1-b][1,3,4]thiadiazol-5-yl]-phenyl}-ethanone | 700 |
| 307 | 2-Methoxy-4-{2-[(thiophen-2-ylmethyl)-amino]-imidazo[2,1-b][1,3,4]thiadiazol-5-yl}-phenol | 740 |
| 456 | 3-[5-(3,4,5-Trimethoxy-phenyl)-imidazo[2,1-b][1,3,4]thiadiazol-2-ylamino]-propan-1-ol | 740 |
| 158 | 1-{3-[2-(2-Morpholin-4-yl-ethylamino)-imidazo[2,1-b][1,3,4]thiadiazol-5-yl]-phenyl}-ethanone | 780 |
| 277 | (2-Phenoxy-ethyl)-[5-(3,4,5-trimethoxy-phenyl)-imidazo[2,1-b][1,3,4]thiadiazol-2-yl]-amine | 780 |
| 274 | (Tetrahydro-pyran-4-ylmethyl)-[5-(3,4,5-trimethoxy-phenyl)-imidazo[2,1-b][1,3,4]thiadiazol-2-yl]-amine | 810 |
| 266 | Isobutyl-[5-(3,4,5-trimethoxy-phenyl)-imidazo[2,1-b][1,3,4]thiadiazol-2-yl]-amine | 820 |

In the following examples, "conventional workup" means: water was added if necessary, the pH was adjusted, if necessary, to a value of between 2 and 10, depending on the constitution of the end product, the mixture was extracted with ethyl acetate or dichloro-methane, the phases were separated, the organic phase was dried over sodium sulfate and evaporated, and the product was purified by chromatography on silica gel and/or by crystallization. $R_f$ values were determined on silica gel. The eluent was ethyl acetate/methanol 9:1.

The following mass spectrometry (MS) was applied: EI (electron impact ionization) $M^+$, FAB (fast atom bombardment) $(M+H)^+$, ESI (electrospray ionization) $(M+H)^+$, APCI-MS (atmospheric pressure chemical ionization-mass spectrometry) $(M+H)^+$.

Retention time $R_f$ [min] determination was carried out by HPLC:
Column: Chromolith SpeedROD, 50×4.6 mm² (Order No. 1.51450.0001) (Merck)
Gradient: 5.0 min, t=0 min, A:B=95:5, t=4.4 min: A:B=25:75, t=4.5 min to t=5.0 min: A:B=0:100
Flow rate: 3.00 ml/min
Eluent A: water+0.1% of TFA (trifluorooacetic acid),
Eluent B: acetonitrile+0.08% of TFA
Wavelength: 220 nm

EXAMPLE 3

Synthesis of 4-{2-[5-(3,4,5-trimethoxy-phenyl)-imidazo[2,1-b][1,3,4]thiadiazol-2-ylamino]-ethyl}-benzenesulfonamide The preparation of 4-{2-[5-(3,4,5-trimethoxy-phenyl)-imidazo[2,1-b][1,3,4]thiadiazol-2-ylamino]-ethyl}-benzenesulfonamide was carried out in accordance to the following scheme:

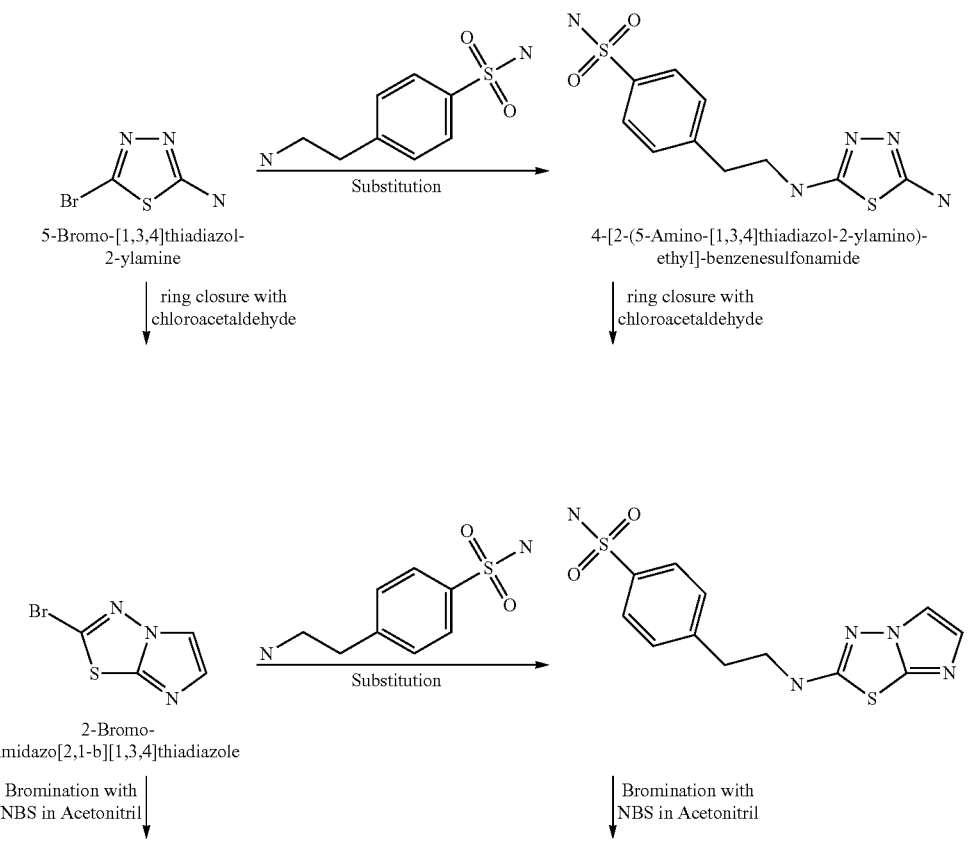

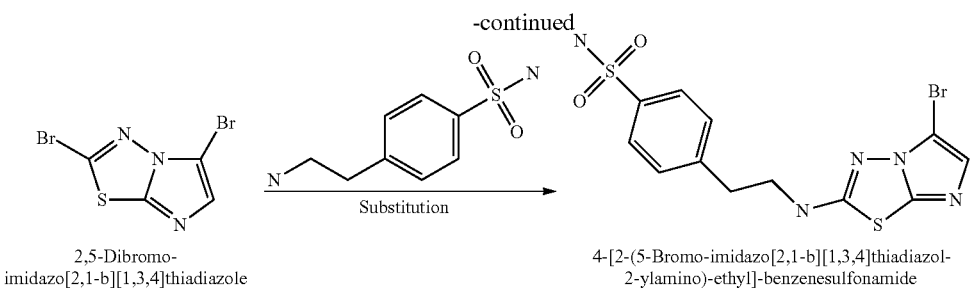
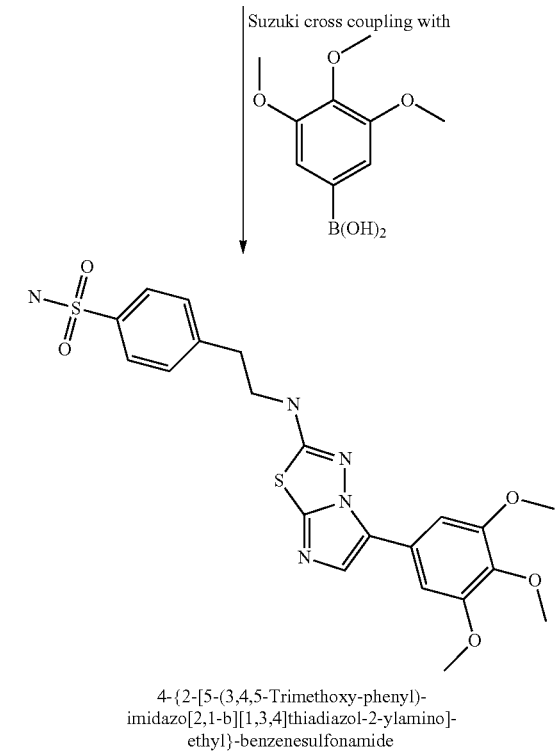
4-{2-[5-(3,4,5-Trimethoxy-phenyl)-
imidazo[2,1-b][1,3,4]thiadiazol-2-ylamino]-
ethyl}-benzenesulfonamide
EXAMPLE 4
Synthesis of propyl-[5-(3,4,5-trimethoxy-phenyl)-imidazo[2,1-b]thiadiazol-2-yl]amine
The preparation of propyl-[5-(3,4,5-trimethoxy-phenyl)-imidazo[2,1-b]thiadiazol-2-yl]amine was carried out in accordance with the following scheme:
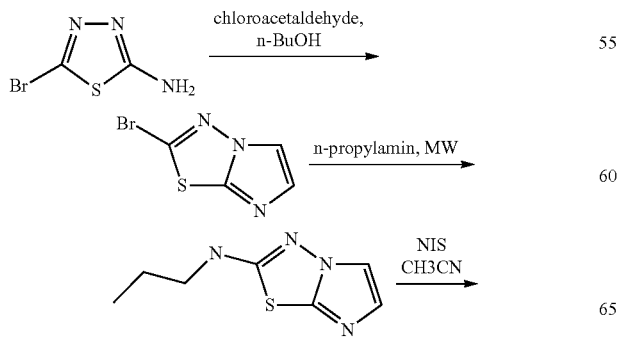
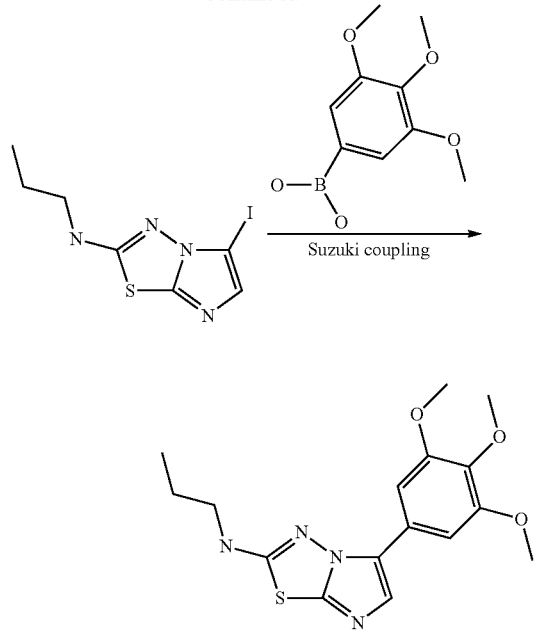

5-Bromo-[1,3,4]thiadiazol-2-ylamine 5 g of [1,3,4]thiadiazol-2-ylamine were dissolved in 50 ml of acetic acid. After stirring for 10 min at room temperature, 2.5 ml of bromine were slowly added to the solution. The reaction mixture was stirred over night at 60° C. The resulting suspension was evaporated and the residue treated with a NaHCO$_3$ solution. The resulting solid was separated by filtration. 7.2 g of the desired product were obtained.
HPLC-MS: [M+H]$^+$ 180

2-Bromo-imidazo[2,1-b][1,3,4]thiadiazole 20 g of 5-bromo-[1,3,4]thiadiazol-2-ylamine were dissolved in 60 ml of n-butanol. 15 ml of chloroacetaldehyde (55% in water) were added to the solution. The mixture was heated for 3 h at 120° C. After cooling the reaction mixture was poured into a NaHCO$_3$ solution. The mixture was extracted three times with ethylacetate and the organic phase dried with sodium sulphate and evaporated. The resulting material was purified via silica-gel column chromatography using a petroleum ether-ethylacetate gradient. 2.9 g yellow crystals of the desired product were obtained.
HPLC-MS: [M+H]$^+$ 204

Imidazo[2,1-b][1,3,4]thiadiazol-2-yl-propyl-amine 1.5 g of 2-bromo-imidazo[2,1-b][1,3,4]thiadiazole were dissolved in 10 ml methanol and 10 ml of propylamine were added to the solution. The resulting mixture was heated in a microwave oven at 175° C. for 15 min. The resulting suspension was evaporated and dissolved in ethylacetate. It was washed with water, dried with sodium sulphate and evaporated. Silica-gel chromatography with petroleum ether-ethylacetate gave 519 mg of the desired product as solid material.
HPLC-MS: [M+H]$^+$ 183

(5-Iodo-imidazo[2,1-b][1,3,4]thiadiazol-2-yl)-propyl-amine 663 mg of imidazo[2,1-b][1,3,4]thiadiazol-2-yl-propyl-amine were dissolved in 20 ml of acetonitrile. 822 mg of N-iodosuccinimide were added to the solution. The reaction mixture was stirred for 4 h at room temperature. For work-up, the mixture was cooled on ice and filtrated. 410 mg of the desired product were obtained.
HPLC-MS: [M+H]$^+$ 309

Propyl-[5-(3,4,5-trimethoxy-phenyl)-imidazo[2,1-b]thiadiazol-2-yl]amine 200 mg of (5-iodo-imidazo[2,1-b][1,3,4]thiadiazol-2-yl)-propyl-amine, 230 mg of 3,4,5-trimethoxyphenylboronic acid, 150 mg of bis(dibenzylideneacetone)palladium(0), and 80 mg of tri-o-tolylphosphin were dissolved in 10 ml of dimethoxyethane. Subsequently, 0.9 ml of a saturated NaHCO$_3$ solution were added. The reaction was performed in a microwave oven for 30 min at 80° C. The resulting mixture was purified by preparative HPLC using a RP 18 column and a acetonitrile/water/01. % TFA gradient. 33 mg of a white powder were obtained.
HPLC-MS: [M+H]$^+$ 349
NMR: $^1$H NMR (500 MHz, DMSO) δ 8.19 (s, 1H, NH), 7.68 (s, 1H, imidazole), 7.36 (s, 2H, benzene), 3.85 (s, 6H, methyl), 3.70 (s, 3H, methyl), 3.34 (dd, J=6.9, 12.5, 2H, propyl), 1.69 (dd, J=7.2, 14.3, 2H, propyl), 0.95 (t, J=7.4, 3H, propyl)

EXAMPLE 5

Synthesis of benzyl-[5-(3,4-dimethoxy-phenyl)-imidazo[2,1-b][1,3,4]thiadiazol-2-yl]-amine The preparation of benzyl-[5-(3,4-dimethoxy-phenyl)-imidazo[2,1-b][1,3,4]thiadiazol-2-yl]-amine was carried out in accordance with the following scheme:

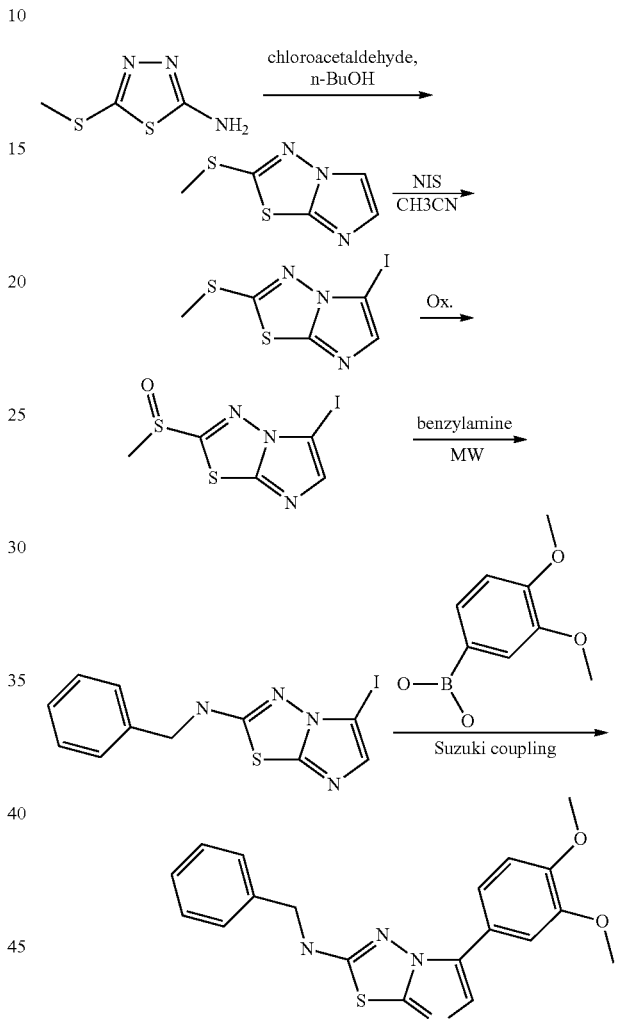

2-Methylsulfanyl-imidazo[2,1-b][1,3,4]thiadiazole

2-Amino-5-methylthio-1,3,4-thiadiazole (10.00 g; 67.92 mmol; 1.00 eq.) was refluxed in 1-butanol (100.00 ml) until complete dissolution of starting material. Then, chloroacetaldehyde (21.91 ml; 169.81 mmol; 2.50 eq.) was slowly added and the reaction was refluxed for 2 h. Diisopropyethylamine (11.63 ml) was slowly added over 2 h using a syringe pump. After 18 h, the reaction was allowed to cool to room temperature. Then, water was added and the aqueous phase was extracted 4 times with EtOAc. The combined organics were washed with brine, dried over MgSO$_4$ to give 17 g of a viscous brown oil. The crude was purified by flash chromatography (preabsorption using MeOH an silica) using 95/5 dichloromethane/methanol. The combined fractions gave 3.05 g of the desired product as a pale orange solid.

5-Iodo-2-methylsulfanyl-imidazo[2,1-b][1,3,4]thiadiazole

2-Methylsulfanyl-imidazo[2,1-b][1,3,4]thiadiazole (100.00 mg; 0.43 mmol; 1.00 eq.) was dissolved in $CH_3CN$ (4.00 ml) protected from light. Then, n-iodosuccinimide (97.22 mg; 0.43 mmol; 1.00 eq.) was added and the reaction was stirred overnight. The reaction was not completed. N-iodosuccinimide (388.88 mg; 1.73 mmol; 4.00 eq.) was added and the reaction was stirred at room temperature. After 1 day, the reaction was finished. A saturated solution of sodium thiosulfate was added and the aqueous phase was extracted 2 times with DCM. The combined organics were washed with saturated aqueous $NaHCO_3$, $NH_4Cl$, brine, dried over $MgSO_4$ to give 127.6 mg of the desired product as a pale yellow solid.

5-Iodo-2-methanesulfinyl-imidazo[2,1-b][1,3,4]thiadiazole

Oxone(r), monopersulfate compound (263.99 mg; 0.43 mmol; 1.00 eq.) was added to a solution of 5-iodo-2-methylsulfanyl-imidazo[2,1-b][1,3,4]thiadiazole (127.60 mg; 0.43 mmol; 1.00 eq.) in MeOH (1.50 ml) and water (1.50 ml) at room temperature. After 1 h, the reaction was finished. Water was added and the reaction was extracted 2 times with dichloromethane. The combined organic extracts were dried over magnesium sulphate, filtered and concentrated to give 106.9 mg of the desired product as a beige solid.

Benzyl-(5-iodo-imidazo[2,1-b][1,3,4]thiadiazol-2-yl)-amine

5-Iodo-2-methanesulfinyl-imidazo[2,1-b][1,3,4]thiadiazole (500.00 mg; 1.60 mmol; 1.00 eq.) was dissolved in dichloromethane (1.60 ml) and benzylamine (622.18 µl; 4.79 mmol; 3.00 eq.) was added. Then, the reaction was refluxed overnight. The reaction was concentrated in vacuo. Then, 5 ml of isopropanol were added and the suspended solution was heated under reflux for 15 min. The mixture was allowed to cool to room temperature and then cooled to 0° C. After 15 min at 0° C., the solid was filtered and washed with isopropanol to give a white solid. The solid was dried at 60° C. for 1 h to give 460.2 mg of the desired product.

NMR: $^1H$ NMR (DMSO-d6) δ 8.51 (t, J=5.6 Hz, 1H, NH), 7.35 (m, 5H, Ph), 7.04 (s, 1H, H-imidazole), 4.50 (d, J=5.6 Hz, 2H, PhCH2).

Benzyl-[5-(3,4-dimethoxy-phenyl)-imidazo[2,1-b][1,3,4]thiadiazol-2-yl]-amine An aqueous solution of NaOH (1.00 ml) was added to a mixture of benzyl-(5-iodo-imidazo[2,1-b][1,3,4]thiadiazol-2-yl)-amine (250.00 mg; 0.70 mmol; 1.00 eq.), 3,4-dimethoxyphenylboronic acid (191.59 mg; 1.05 mmol; 1.50 eq.), Pd(PPh3)4 and dimethoxyethane (5.00 ml) under $N_2$. The resulting suspension was heated in the microwave at 90° C. for 30 minutes under $N_2$. The reaction was filtered, washed with dimethoxyethane, water and dried at 40° C. for 18 h. 135.5 mg of the desired product were obtained as a white solid.

NMR: $^1H$ NMR (DMSO-d6) δ 8.57 (t, J=5.7 Hz, 1H, NH), 7.50-7.25 (m, 8H, Ph), 7.00 (d, J=8.7 Hz, 1H, Ph), 4.56 (d, J=5.7 Hz, 2H, PhCH2), 3.77 (s, 3H, OMe), 3.72 (s, 3H, OMe).

EXAMPLE 6

Synthesis of Compounds of Formula (I)

Referring to Examples 3 to 5, the following compounds are obtained analogously.

| No | Structure | Name | HPLC/MS [M + H]+ | NMR DMSO |
|---|---|---|---|---|
| 1 | 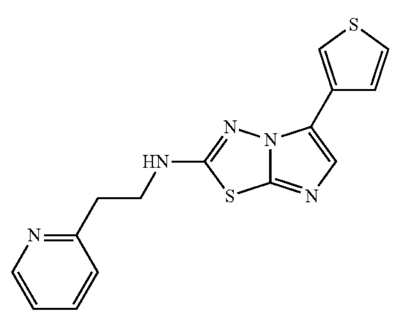 [SMILES: c1ccc(CCNc2nn3c(-c4ccsc4)cnc3s2)nc1] | (2-Pyridin-2-yl-ethyl)-(5-thiophen-3-yl-imidazo[2,1-b][1,3,4]thiadiazol-2-yl)-amine | 328 | |
| 2 | 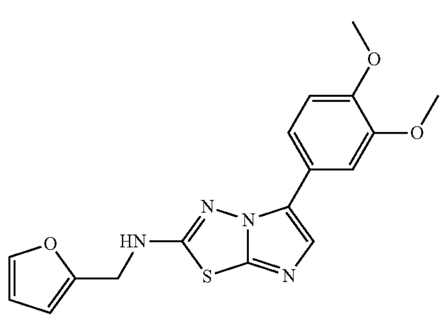 [SMILES: COc1ccc(-c2cnc3sc(NCc4ccco4)nn23)cc1OC] | [5-(3,4-Dimethoxy-phenyl)-imidazo[2,1-b][1,3,4]thiadiazol-2-yl]-furan-2-ylmethyl-amine | 357 | |

| No | Structure | Name | HPLC/MS [M + H]+ | NMR DMSO |
|---|---|---|---|---|
| 3 | 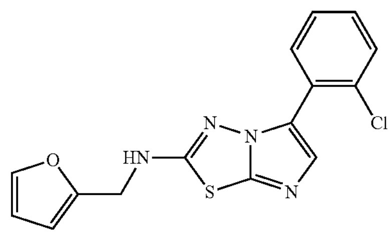 [SMILES: Clc1ccccc1-c1cnc2sc(NCc3ccco3)nn12] | [5-(2-Chloro-phenyl)-imidazo[2,1-b][1,3,4]thiadiazol-2-yl]-furan-2-ylmethyl-amine | 332 | |
| 4 | 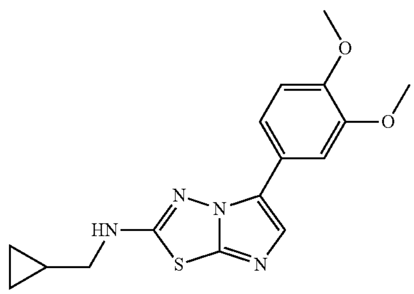 [SMILES: COc1ccc(-c2cnc3sc(NCC4CC4)nn23)cc1OC] | Cyclopropylmethyl-[5-(3,4-dimethoxy-phenyl)-imidazo[2,1-b][1,3,4]thiadiazol-2-yl]-amine | 331 | |
| 5 | 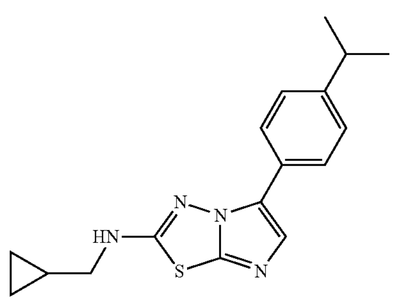 [SMILES: CC(C)c1ccc(-c2cnc3sc(NCC4CC4)nn23)cc1] | Cyclopropylmethyl-[5-(4-isopropyl-phenyl)-imidazo[2,1-b][1,3,4]thiadiazol-2-yl]-amine | 312 | |
| 6 | 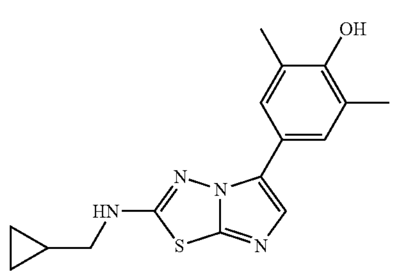 [SMILES: Cc1cc(-c2cnc3sc(NCC4CC4)nn23)cc(C)c1O] | 4-[2-(Cyclopropylmethyl-amino)-imidazo[2,1-b][1,3,4]thiadiazol-5-yl]-2,6-dimethyl-phenol | 315 | |
| 7 | 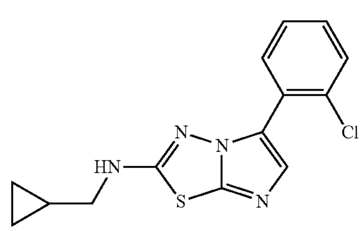 [SMILES: Clc1ccccc1-c1cnc2sc(NCC3CC3)nn12] | [5-(2-Chloro-phenyl)-imidazo[2,1-b][1,3,4]thiadiazol-2-yl]-cyclopropylmethyl-amine | 306 | |

| No | Structure | Name | HPLC/MS [M + H]+ | NMR DMSO |
|---|---|---|---|---|
| 8 | 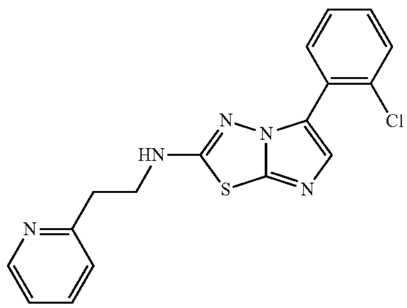 [SMILES: Clc1ccccc1-c1cnc2sc(NCCc3ccccn3)nn12] | [5-(2-Chloro-phenyl)-imidazo[2,1-b][1,3,4]thiadiazol-2-yl]-(2-pyridin-2-yl-ethyl)-amine | 357 | |
| 9 | 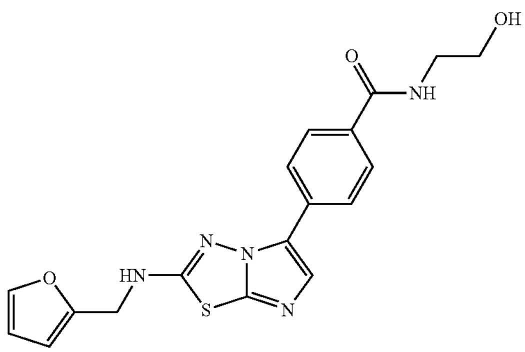 [SMILES: O=C(NCCO)c1ccc(-c2cnc3sc(NCc4ccco4)nn23)cc1] | 4-{2-[(Furan-2-ylmethyl)-amino]-imidazo[2,1-b][1,3,4]thiadiazol-5-yl}-N-(2-hydroxy-ethyl)-benzamide | 384 | |
| 10 | 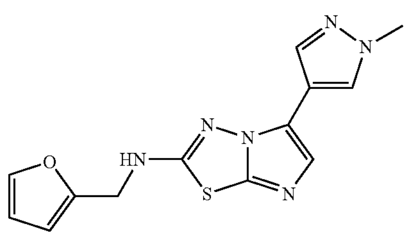 [SMILES: Cn1cc(-c2cnc3sc(NCc4ccco4)nn23)cn1] | Furan-2-ylmethyl-[5-(1-methyl-1H-pyrazol-4-yl)-imidazo[2,1-b][1,3,4]thiadiazol-2-yl]-amine | 301 | δ 8.4 (t, 1H), 8.11 (s, 1H), 7.84 (s, 1H), 7.6 (s, 1H), 7.2 (s, 1H), 6.5 (m, 2H), 4.6 (m, 2H) 4.3 (s, 3H) |
| 11 | 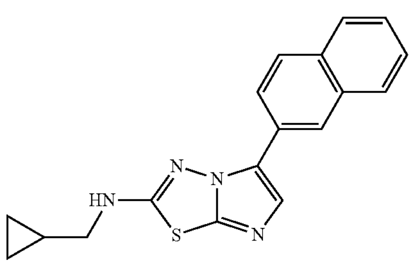 [SMILES: c1ccc2cc(-c3cnc4sc(NCC5CC5)nn34)ccc2c1] | Cyclopropylmethyl-(5-naphthalen-2-yl-imidazo[2,1-b][1,3,4]thiadiazol-2-yl)-amine | 321 | |
| 12 | 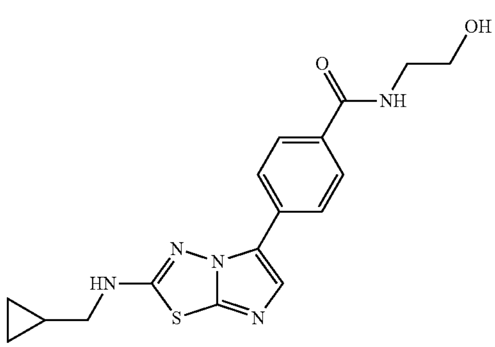 [SMILES: O=C(NCCO)c1ccc(-c2cnc3sc(NCC4CC4)nn23)cc1] | 4-[2-(Cyclopropylmethyl-amino)-imidazo[2,1-b][1,3,4]thiadiazol-5-yl]-N-(2-hydroxy-ethyl)-benzamide | 358 | δ 8.4 (t, 1H), 8.2 (m, 1H), 8.0 (d, 2H), 7.9 (d, 2H), 7.6 (s, 1H), 3.5 (m, 2H), 3.3-3.2 (m, 4H) 1.1 (m, 1H), 0.5 (m, 2H), 0.3 (m, 2H) |

-continued

| No | Structure | Name | HPLC/MS [M + H]+ | NMR DMSO |
|---|---|---|---|---|
| 13 | 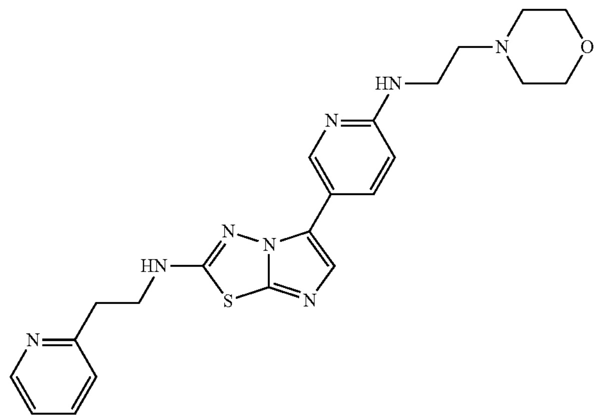 [SMILES: c1ccc(CCNc2nn3c(-c4ccc(NCCN5CCOCC5)nc4)cnc3s2)nc1] | {5-[6-(2-Morpholin-4-yl-ethylamino)-pyridin-3-yl]-imidazo[2,1-b][1,3,4]thiadiazol-2-yl}-(2-pyridin-2-yl-ethyl)-amine | 451 | |
| 14 | 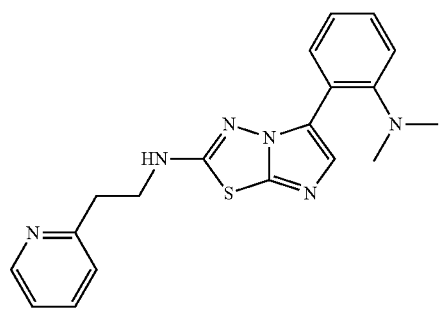 [SMILES: CN(C)c1ccccc1-c1cnc2sc(NCCc3ccccn3)nn12] | [5-(2-Dimethylamino-phenyl)-imidazo[2,1-b][1,3,4]thiadiazol-2-yl]-(2-pyridin-2-yl-ethyl)-amine | 365 | |
| 15 | 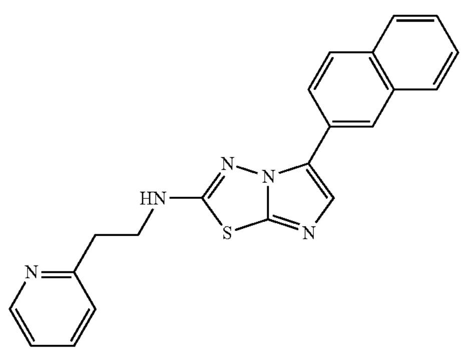 [SMILES: c1ccc(CCNc2nn3c(-c4ccc5ccccc5c4)cnc3s2)nc1] | (5-Naphthalen-2-yl-imidazo[2,1-b][1,3,4]thiadiazol-2-yl)-(2-pyridin-2-yl-ethyl)-amine | 372 | |
| 16 | 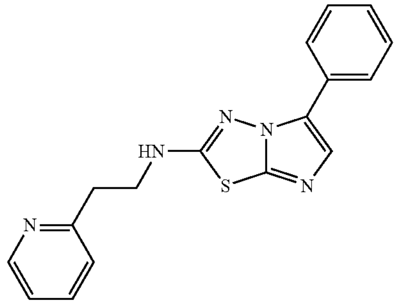 [SMILES: c1ccc(-c2cnc3sc(NCCc4ccccn4)nn23)cc1] | (5-Phenyl-imidazo[2,1-b][1,3,4]thiadiazol-2-yl)-(2-pyridin-2-yl-ethyl)-amine | 322 | |

| No | Structure | Name | HPLC/MS [M + H]+ | NMR DMSO |
|---|---|---|---|---|
| 17 | 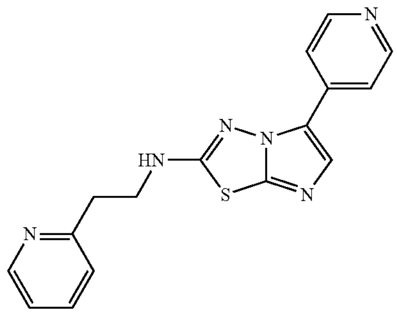 [SMILES: c1ccc(CCNc2nn3c(-c4ccncc4)cnc3s2)nc1] | (2-Pyridin-2-yl-ethyl)-(5-pyridin-4-yl-imidazo[2,1-b][1,3,4]thiadiazol-2-yl)-amine | 323 | |
| 18 | 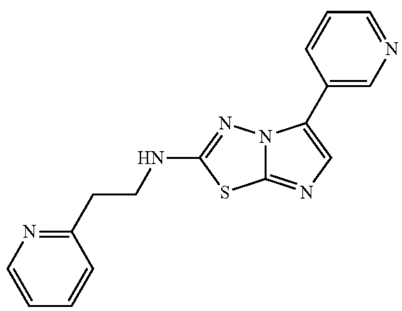 [SMILES: c1ccc(CCNc2nn3c(-c4cccnc4)cnc3s2)nc1] | (2-Pyridin-2-yl-ethyl)-(5-pyridin-3-yl-imidazo[2,1-b][1,3,4]thiadiazol-2-yl)-amine | 323 | |
| 19 | 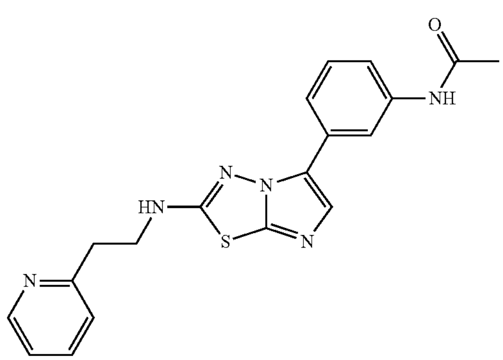 [SMILES: CC(=O)Nc1cccc(-c2cnc3sc(NCCc4ccccn4)nn23)c1] | N-{3-[2-(2-Pyridin-2-yl-ethylamino)-imidazo[2,1-b][1,3,4]thiadiazol-5-yl]-phenyl}-acetamide | 379 | |
| 20 | 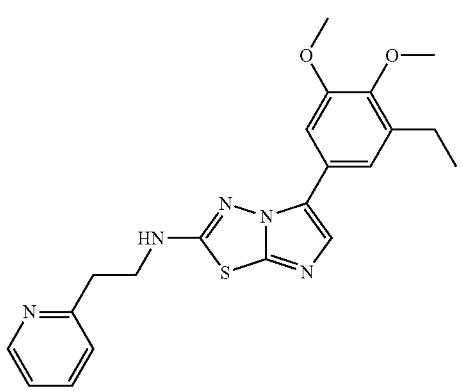 [SMILES: CCc1cc(-c2cnc3sc(NCCc4ccccn4)nn23)cc(OC)c1OC] | (2-Pyridin-2-yl-ethyl)-[5-(3,4,5-trimethoxy-phenyl)-imidazo[2,1-b][1,3,4]thiadiazol-2-yl]-amine | 412 | |

-continued

| No | Structure | Name | HPLC/MS [M + H]+ | NMR DMSO |
|----|-----------|------|------------------|----------|
| 21 | 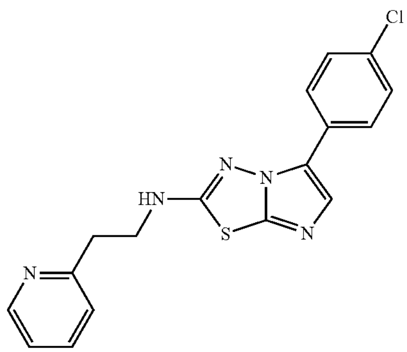 [SMILES: Clc1ccc(-c2cnc3sc(NCCc4ccccn4)nn23)cc1] | [5-(4-Chloro-phenyl)-imidazo[2,1-b][1,3,4]thiadiazol-2-yl]-(2-pyridin-2-yl-ethyl)-amine | 357 | |
| 22 | 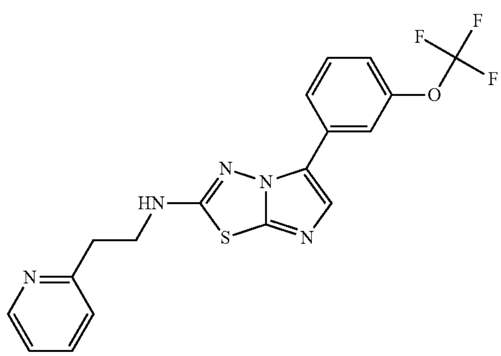 [SMILES: FC(F)(F)Oc1cccc(-c2cnc3sc(NCCc4ccccn4)nn23)c1] | (2-Pyridin-2-yl-ethyl)-[5-(3-trifluoromethoxy-phenyl)-imidazo[2,1-b][1,3,4]thiadiazol-2-yl]-amine | 406 | |
| 23 | 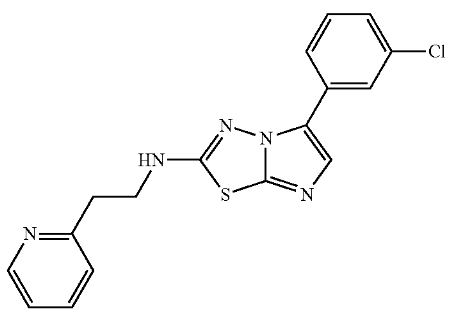 [SMILES: Clc1cccc(-c2cnc3sc(NCCc4ccccn4)nn23)c1] | [5-(3-Chloro-phenyl)-imidazo[2,1-b][1,3,4]thiadiazol-2-yl]-(2-pyridin-2-yl-ethyl)-amine | 356 | |
| 24 | 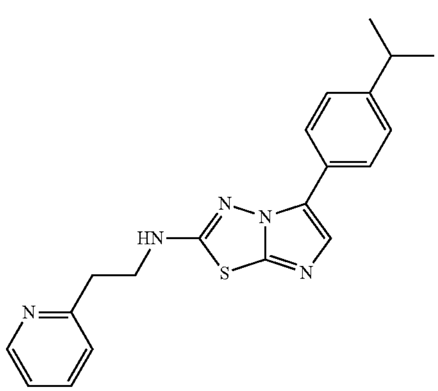 [SMILES: CC(C)c1ccc(-c2cnc3sc(NCCc4ccccn4)nn23)cc1] | [5-(4-Isopropyl-phenyl)-imidazo[2,1-b][1,3,4]thiadiazol-2-yl]-(2-pyridin-2-yl-ethyl)-amine | 364 | |

-continued

| No | Structure | Name | HPLC/MS [M + H]+ | NMR DMSO |
|---|---|---|---|---|
| 25 | 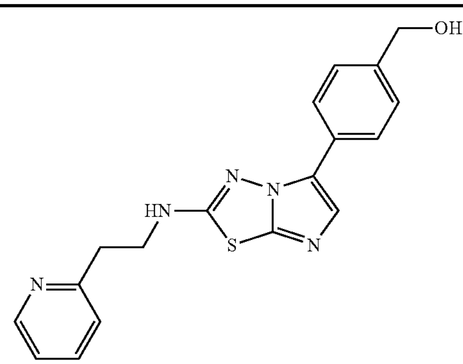 | {4-[2-(2-Pyridin-2-yl-ethylamino)-imidazo[2,1-b][1,3,4]thiadiazol-5-yl]-phenyl}-methanol | 352 | |
| 26 | 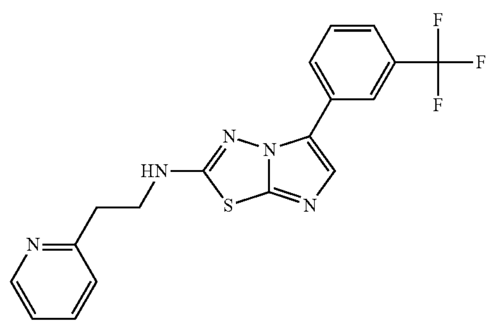 [SMILES: FC(F)(F)c1cccc(-c2cnc3sc(NCCc4ccccn4)nn23)c1] | (2-Pyridin-2-yl-ethyl)-[5-(3-trifluoromethyl-phenyl)-imidazo[2,1-b][1,3,4]thiadiazol-2-yl]-amine | 390 | |
| 27 | 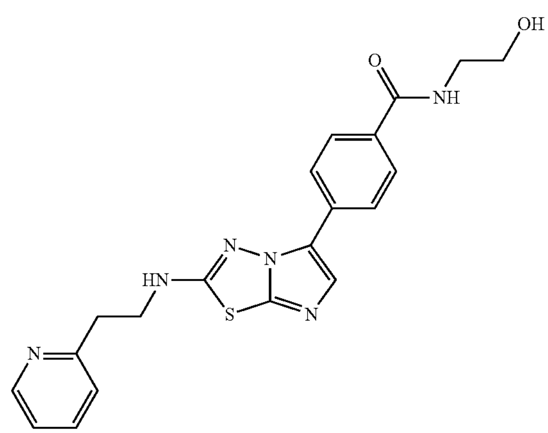 [SMILES: O=C(NCCO)c1ccc(-c2cnc3sc(NCCc4ccccn4)nn23)cc1] | N-(2-Hydroxy-ethyl)-4-[2-(2-pyridin-2-yl-ethylamino)-imidazo[2,1-b][1,3,4]thiadiazol-5-yl]-benzamide | 409 | |
| 28 | 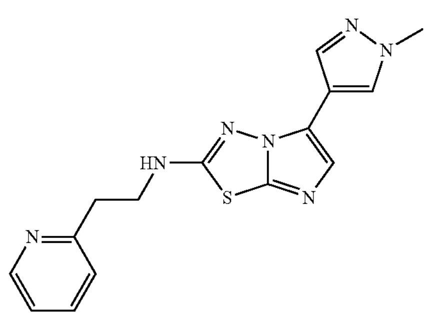 [SMILES: Cn1cc(-c2cnc3sc(NCCc4ccccn4)nn23)cn1] | [5-(1-Methyl-1H-pyrazol-4-yl)-imidazo[2,1-b][1,3,4]thiadiazol-2-yl]-(2-pyridin-2-yl-ethyl)-amine | 326 | |

-continued

| No | Structure | Name | HPLC/MS [M + H]+ | NMR DMSO |
|---|---|---|---|---|
| 29 | 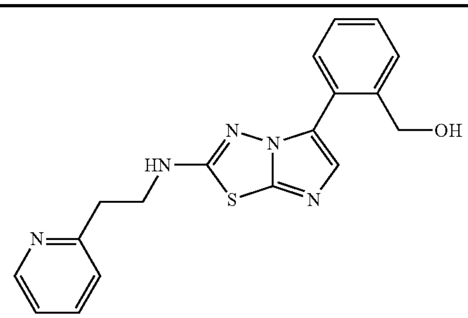 | {2-[2-(2-Pyridin-2-yl-ethylamino)-imidazo[2,1-b][1,3,4]thiadiazol-5-yl]-phenyl}-methanol | 352 | |
| 30 | 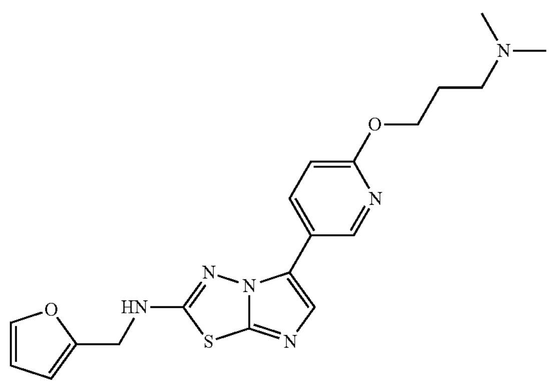 [SMILES: CN(C)CCCOc1ccc(-c2cnc3sc(NCc4ccco4)nn23)cn1] | {5-[6-(3-Dimethylamino-propoxy)-pyridin-3-yl]-imidazo[2,1-b][1,3,4]thiadiazol-2-yl}-furan-2-ylmethyl-amine | 399 | |
| 31 | 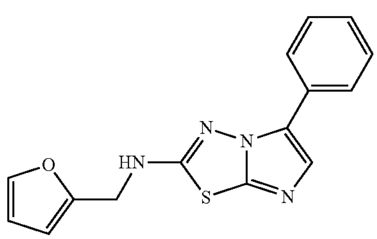 [SMILES: c1ccc(-c2cnc3sc(NCc4ccco4)nn23)cc1] | Furan-2-ylmethyl-(5-phenyl-imidazo[2,1-b][1,3,4]thiadiazol-2-yl)-amine | 297 | |
| 32 | 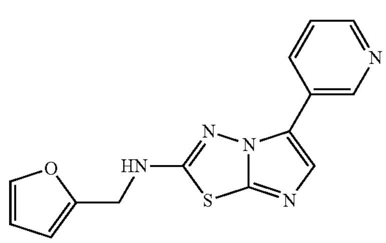 [SMILES: c1cncc(-c2cnc3sc(NCc4ccco4)nn23)c1] | Furan-2-ylmethyl-(5-pyridin-3-yl-imidazo[2,1-b][1,3,4]thiadiazol-2-yl)-amine | 298 | |
| 33 | 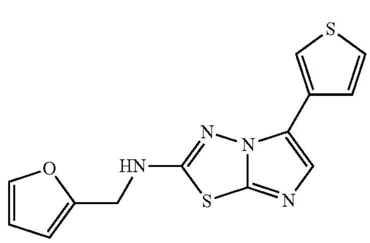 [SMILES: c1coc(CNc2nn3c(-c4ccsc4)cnc3s2)c1] | Furan-2-ylmethyl-(5-thiophen-3-yl-imidazo[2,1-b][1,3,4]thiadiazol-2-yl)-amine | 303 | |

-continued
| No | Structure | Name | HPLC/MS [M + H]+ | NMR DMSO |
|---|---|---|---|---|
| 34 | 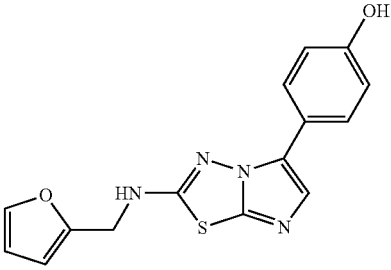 [SMILES: Oc1ccc(-c2cnc3sc(NCc4ccco4)nn23)cc1] | 4-{2-[(Furan-2-ylmethyl)-amino]-imidazo[2,1-b][1,3,4]thiadiazol-5-yl}-phenol | 313 | |
| 35 | 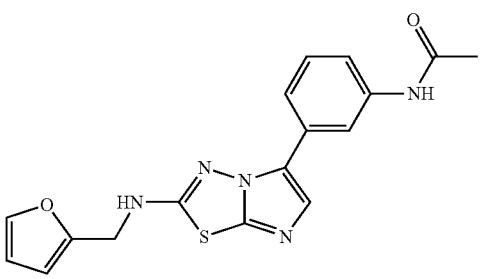 [SMILES: CC(=O)Nc1cccc(-c2cnc3sc(NCc4ccco4)nn23)c1] | N-(3-{2-[(Furan-2-ylmethyl)-amino]-imidazo[2,1-b][1,3,4]thiadiazol-5-yl}-phenyl)-acetamide | 354 | |
| 36 | 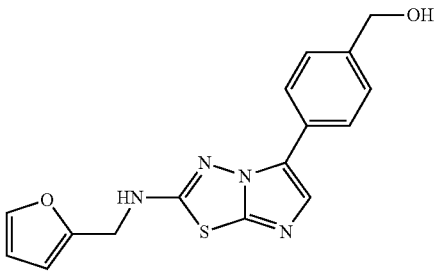 [SMILES: OCc1ccc(-c2cnc3sc(NCc4ccco4)nn23)cc1] | (4-{2-[(Furan-2-ylmethyl)-amino]-imidazo[2,1-b][1,3,4]thiadiazol-5-yl}-phenyl)-methanol | 327 | |
| 37 | 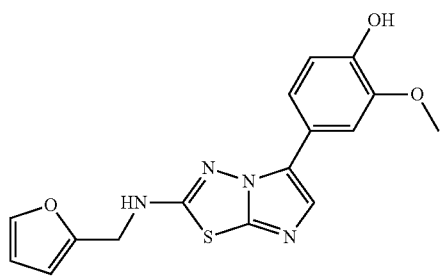 [SMILES: COc1cc(-c2cnc3sc(NCc4ccco4)nn23)ccc1O] | 4-{2-[(Furan-2-ylmethyl)-amino]-imidazo[2,1-b][1,3,4]thiadiazol-5-yl}-2-methoxy-phenol | 343 | |
| 38 | 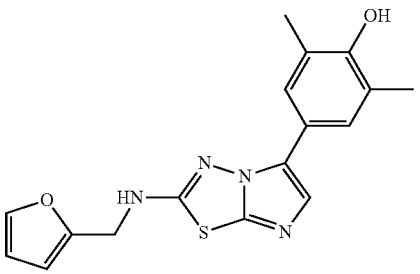 [SMILES: Cc1cc(-c2cnc3sc(NCc4ccco4)nn23)cc(C)c1O] | 4-{2-[(Furan-2-ylmethyl)-amino]-imidazo[2,1-b][1,3,4]thiadiazol-5-yl}-2,6-dimethyl-phenol | 341 | |

| No | Structure | Name | HPLC/MS [M + H]+ | NMR DMSO |
|---|---|---|---|---|
| 39 | 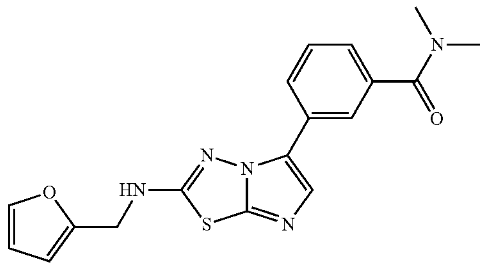 [SMILES: CN(C)C(=O)c1cccc(-c2cnc3sc(NCc4ccco4)nn23)c1] | 3-{2-[(Furan-2-ylmethyl)-amino]-imidazo[2,1-b][1,3,4]thiadiazol-5-yl}-N,N-dimethyl-benzamide | 368 | |
| 40 | 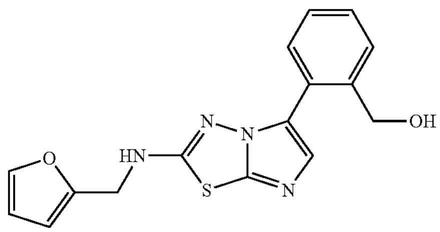 [SMILES: OCc1ccccc1-c1cnc2sc(NCc3ccco3)nn12] | (2-{2-[(Furan-2-ylmethyl)-amino]-imidazo[2,1-b][1,3,4]thiadiazol-5-yl}-phenyl)-methanol | 326 | |
| 41 | 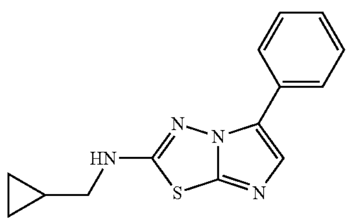 [SMILES: c1ccc(-c2cnc3sc(NCC4CC4)nn23)cc1] | Cyclopropylmethyl-(5-phenyl-imidazo[2,1-b][1,3,4]thiadiazol-2-yl)-amine | 271 | |
| 42 | 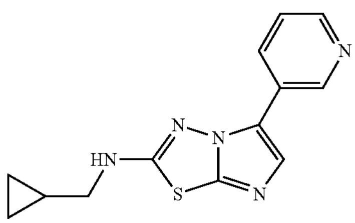 [SMILES: c1cncc(-c2cnc3sc(NCC4CC4)nn23)c1] | Cyclopropylmethyl-(5-pyridin-3-yl-imidazo[2,1-b][1,3,4]thiadiazol-2-yl)-amine | 272 | |
| 43 | 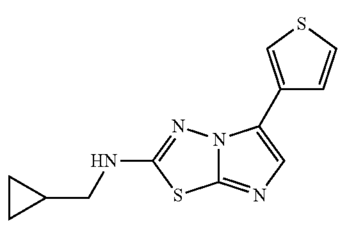 [SMILES: c1cc(-c2cnc3sc(NCC4CC4)nn23)cs1] | Cyclopropylmethyl-(5-thiophen-3-yl-imidazo[2,1-b][1,3,4]thiadiazol-2-yl)-amine | 277 | |
| 44 | 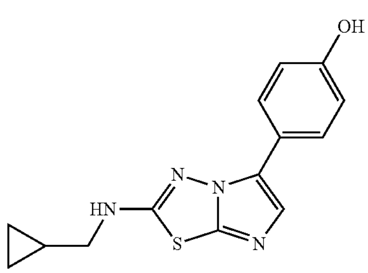 [SMILES: Oc1ccc(-c2cnc3sc(NCC4CC4)nn23)cc1] | 4-[2-(Cyclopropylmethyl-amino)-imidazo[2,1-b][1,3,4]thiadiazol-5-yl]-phenol | 287 | |

-continued

| No | Structure | Name | HPLC/MS [M + H]+ | NMR DMSO |
|---|---|---|---|---|
| 45 | 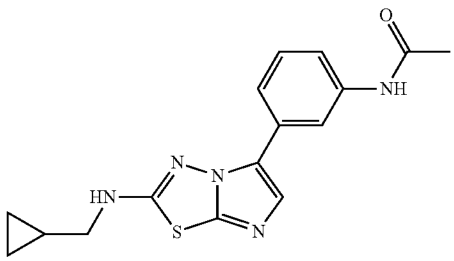 [SMILES: CC(=O)Nc1cccc(-c2cnc3sc(NCC4CC4)nn23)c1] | N-{3-[2-(Cyclopropylmethyl-amino)-imidazo[2,1-b][1,3,4]thiadiazol-5-yl]-phenyl}-acetamide | 328 | |
| 46 | 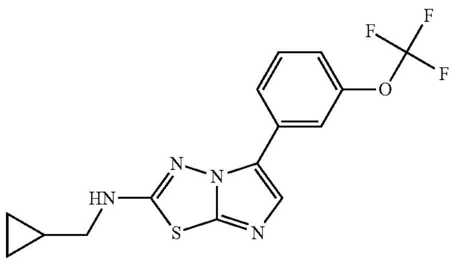 [SMILES: FC(F)(F)Oc1cccc(-c2cnc3sc(NCC4CC4)nn23)c1] | Cyclopropylmethyl-[5-(3-trifluoromethoxy-phenyl)-imidazo[2,1-b][1,3,4]thiadiazol-2-yl]-amine | 355 | |
| 47 | 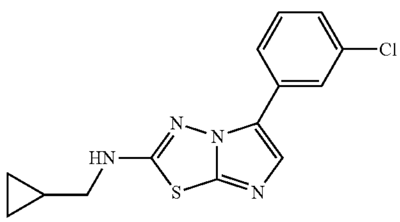 [SMILES: Clc1cccc(-c2cnc3sc(NCC4CC4)nn23)c1] | [5-(3-Chloro-phenyl)-imidazo[2,1-b][1,3,4]thiadiazol-2-yl]-cyclopropylmethyl-amine | 305 | |
| 48 | 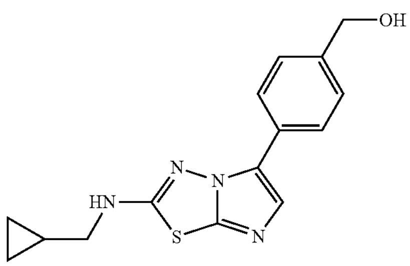 [SMILES: OCc1ccc(-c2cnc3sc(NCC4CC4)nn23)cc1] | {4-[2-(Cyclopropylmethyl-amino)-imidazo[2,1-b][1,3,4]thiadiazol-5-yl]-phenyl}-methanol | 301 | |
| 49 | 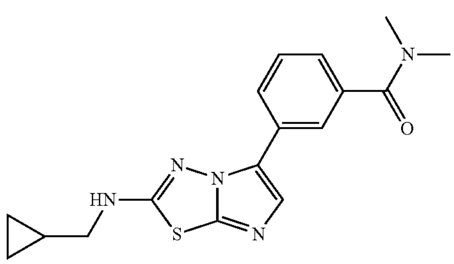 [SMILES: CN(C)C(=O)c1cccc(-c2cnc3sc(NCC4CC4)nn23)c1] | 3-[2-(Cyclopropylmethyl-amino)-imidazo[2,1-b][1,3,4]thiadiazol-5-yl]-N,N-dimethyl-benzamide | 342 | δ 8.2 (t, 1H), 8.0 (d, 1H), 7.9 (s, 1H), 7.6 (s, 1H), 7.5 (t, 1H), 7.3 (d, 1H), 3.2 (t, 2H) 3.0 (d, 6H), 1.1 (m, 1H), 0.5 (m, 2H), 0.3 (m, 2H) |
| 50 | 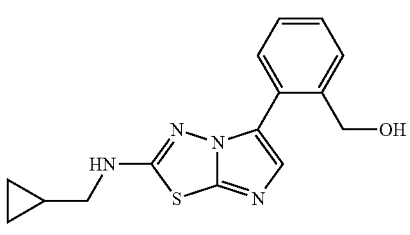 [SMILES: OCc1ccccc1-c1cnc2sc(NCC3CC3)nn12] | {2-[2-(Cyclopropylmethyl-amino)-imidazo[2,1-b][1,3,4]thiadiazol-5-yl]-phenyl}-methanol | 301 | |

-continued

| No | Structure | Name | HPLC/MS [M + H]+ | NMR DMSO |
|---|---|---|---|---|
| 51 | 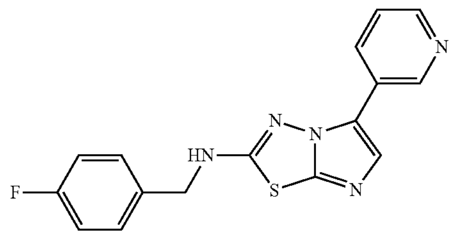 [SMILES: Fc1ccc(CNc2nn3c(-c4cccnc4)cnc3s2)cc1] | (4-Fluoro-benzyl)-(5-pyridin-3-yl-imidazo[2,1-b][1,3,4]thiadiazol-2-yl)-amine | 326 | |
| 52 | 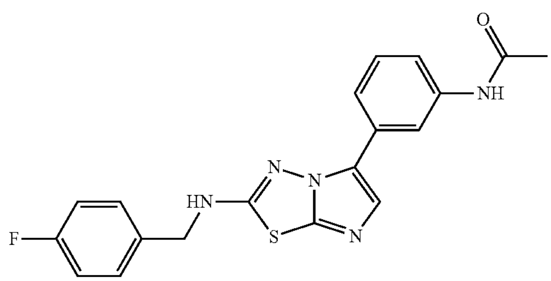 [SMILES: CC(=O)Nc1cccc(-c2cnc3sc(NCc4ccc(F)cc4)nn23)c1] | N-{3-[2-(4-Fluoro-benzylamino)-imidazo[2,1-b][1,3,4]thiadiazol-5-yl]-phenyl}-acetamide | 382 | |
| 53 | 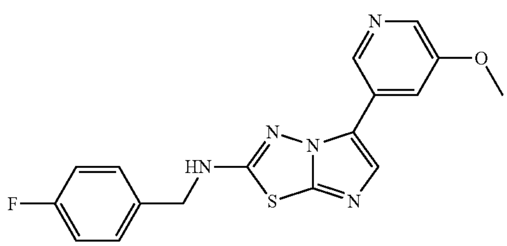 [SMILES: COc1cncc(-c2cnc3sc(NCc4ccc(F)cc4)nn23)c1] | (4-Fluoro-benzyl)-[5-(5-methoxy-pyridin-3-yl)-imidazo[2,1-b][1,3,4]thiadizol-2-yl]-amine | 356 | |
| 54 | 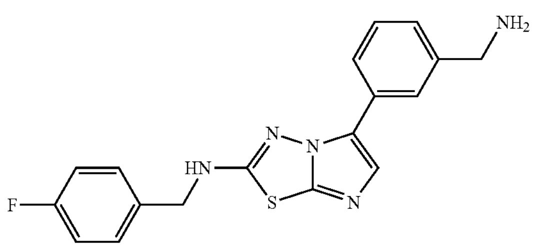 [SMILES: NCc1cccc(-c2cnc3sc(NCc4ccc(F)cc4)nn23)c1] | [5-(3-Aminomethyl-phenyl)-imidazo[2,1-b][1,3,4]thiadiazol-2-yl]-(4-fluoro-benzyl)-amine | 354 | |
| 55 | 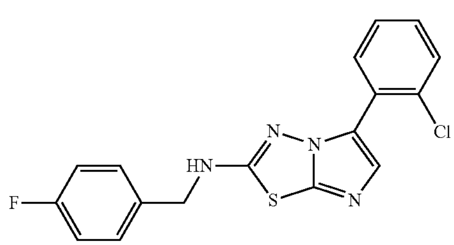 [SMILES: Fc1ccc(CNc2nn3c(-c4ccccc4Cl)cnc3s2)cc1] | [5-(2-Chloro-phenyl)-imidazo[2,1-b][1,3,4]thiadiazol-2-yl]-(4-fluoro-benzyl)-amine | 359 | |
| 56 | 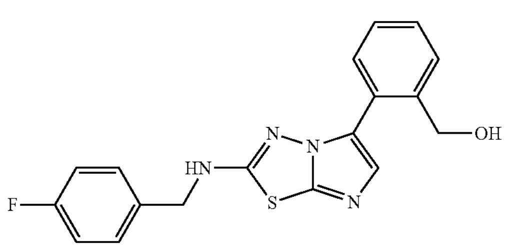 [SMILES: OCc1ccccc1-c1cnc2sc(NCc3ccc(F)cc3)nn12] | {2-[2-(4-Fluoro-benzylamino)-imidazo[2,1-b][1,3,4]thiadiazol-5-yl]-phenyl}-methanol | 355 | |

-continued

| No | Structure | Name | HPLC/MS [M + H]+ | NMR DMSO |
|---|---|---|---|---|
| 57 | 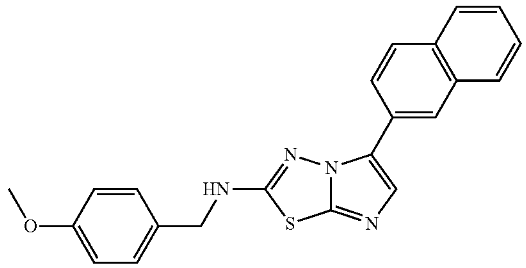 [SMILES: COc1ccc(CNc2nn3c(-c4ccc5ccccc5c4)cnc3s2)cc1] | (4-Methoxy-benzyl)-(5-naphthalen-2-yl-imidazo[2,1-b][1,3,4]thiadiazol-2-yl)-amine | 387 | |
| 58 | 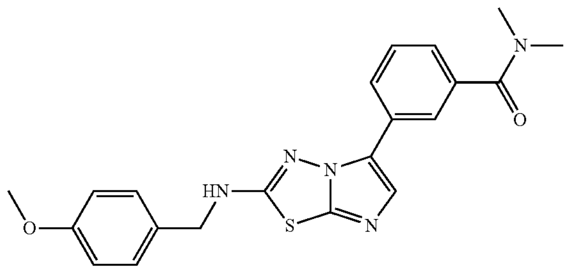 | 3-[2-(4-Methoxy-benzylamino)-imidazo[2,1-b][1,3,4]thiadiazol-5-yl]-N,N-dimethyl-benzamide | 408 | |
| 59 | 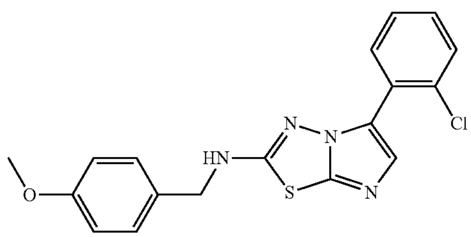 [SMILES: COc1ccc(CNc2nn3c(-c4ccccc4Cl)cnc3s2)cc1] | [5-(2-Chloro-phenyl)-imidazo[2,1-b][1,3,4]thiadiazol-2-yl]-(4-methoxy-benzyl)-amine | 371 | |
| 60 | 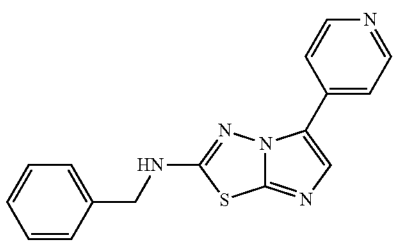 [SMILES: c1ccc(CNc2nn3c(-c4ccncc4)cnc3s2)cc1] | Benzyl-(5-pyridin-4-yl-imidazo[2,1-b][1,3,4]thiadiazol-2-yl)-amine | 308 | |
| 61 | 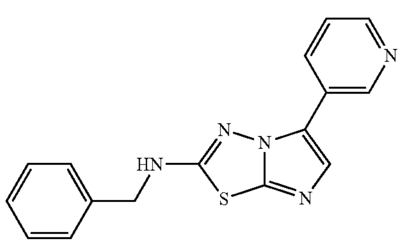 [SMILES: c1ccc(CNc2nn3c(-c4cccnc4)cnc3s2)cc1] | Benzyl-(5-pyridin-3-yl-imidazo[2,1-b][1,3,4]thiadiazol-2-yl)-amine | 308 | |
| 62 | 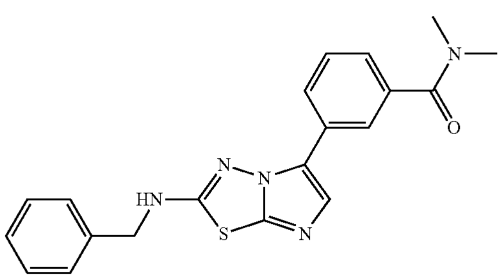 [SMILES: CN(C)C(=O)c1cccc(-c2cnc3sc(NCc4ccccc4)nn23)c1] | 3-(2-Benzylamino-imidazo[2,1-b][1,3,4]thiadiazol-5-yl)-N,N-dimethyl-benzamide | 378 | |

-continued
| No | Structure | Name | HPLC/MS [M + H]+ | NMR DMSO |
|---|---|---|---|---|
| 63 | 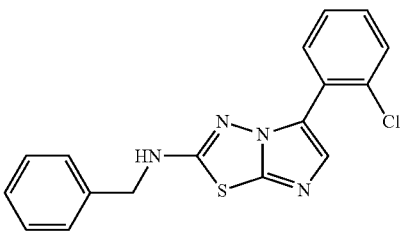 [SMILES: Clc1ccccc1-c1cnc2sc(NCc3ccccc3)nn12] | Benzyl-[5-(2-chloro-phenyl)-imidazo[2,1-b][1,3,4]thiadiazol-2-yl]-amine | 341 | |
| 64 | 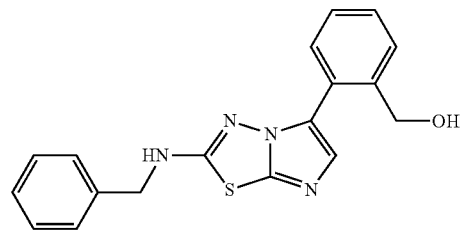 [SMILES: OCc1ccccc1-c1cnc2sc(NCc3ccccc3)nn12] | [2-(2-Benzylamino-imidazo[2,1-b][1,3,4]thiadiazol-5-yl)-phenyl]-methanol | 337 | |
| 65 | 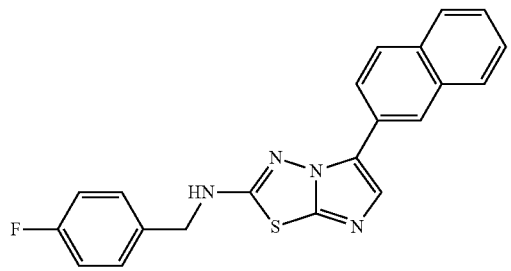 [SMILES: Fc1ccc(CNc2nn3c(-c4ccc5ccccc5c4)cnc3s2)cc1] | (4-Fluoro-benzyl)-(5-naphthalen-2-yl-imidazo[2,1-b][1,3,4]thiadiazol-2-yl)-amine | 375 | |
| 66 | 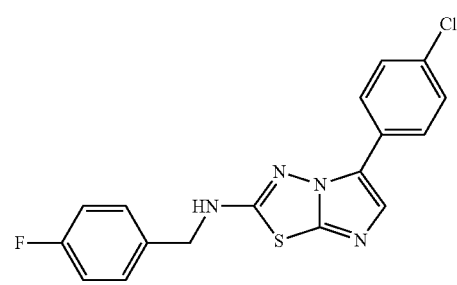 [SMILES: Fc1ccc(CNc2nn3c(-c4ccc(Cl)cc4)cnc3s2)cc1] | [5-(4-Chloro-phenyl)-imidazo[2,1-b][1,3,4]thiadiazol-2-yl]-(4-fluoro-benzyl)-amine | 358 | |
| 67 | 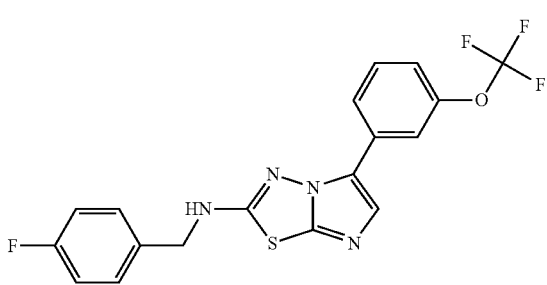 [SMILES: Fc1ccc(CNc2nn3c(-c4cccc(OC(F)(F)F)c4)cnc3s2)cc1] | (4-Fluoro-benzyl)-[5-(3-trifluoromethoxy-phenyl)-imidazo[2,1-b][1,3,4]thiadiazol-2-yl]-amine | 409 | |

-continued

| No | Structure | Name | HPLC/MS [M + H]+ | NMR DMSO |
|----|-----------|------|------------------|----------|
| 68 | 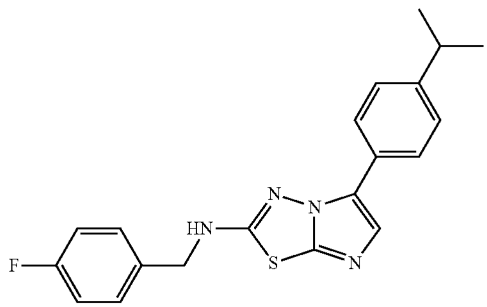 [SMILES: CC(C)c1ccc(-c2cnc3sc(NCc4ccc(F)cc4)nn23)cc1] | (4-Fluoro-benzyl)-[5-(4-isopropyl-phenyl)-imidazo[2,1-b][1,3,4]thiadiazol-2-yl]-amine | 367 | |
| 69 | 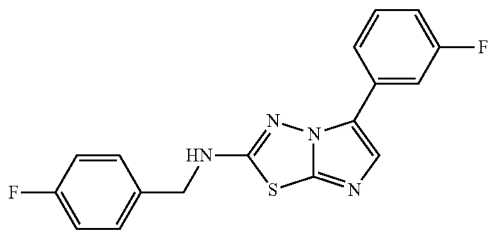 [SMILES: Fc1ccc(CNc2nn3c(-c4cccc(F)c4)cnc3s2)cc1] | (4-Fluoro-benzyl)-[5-(3-fluoro-phenyl)-imidazo[2,1-b][1,3,4]thiadiazol-2-yl]-amine | 343 | |
| 70 | 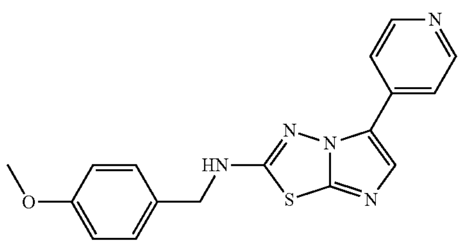 [SMILES: COc1ccc(CNc2nn3c(-c4ccncc4)cnc3s2)cc1] | (4-Methoxy-benzyl)-(5-pyridin-4-yl-imidazo[2,1-b][1,3,4]thiadiazol-2-yl)-amine | 338 | |
| 71 | 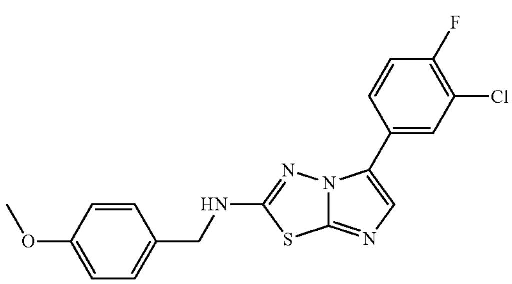 [SMILES: COc1ccc(CNc2nn3c(-c4ccc(F)c(Cl)c4)cnc3s2)cc1] | [5-(3-Chloro-4-fluoro-phenyl)-imidazo[2,1-b][1,3,4]thiadiazol-2-yl]-(4-methoxy-benzyl)-amine | 389 | |
| 72 | 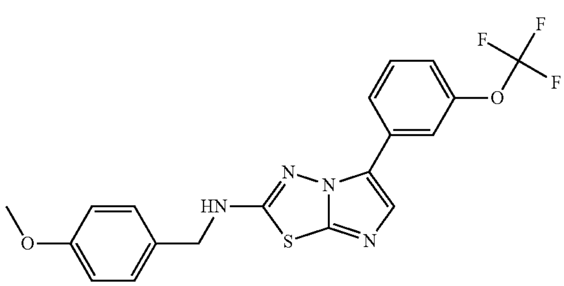 [SMILES: COc1ccc(CNc2nn3c(-c4cccc(OC(F)(F)F)c4)cnc3s2)cc1] | (4-Methoxy-benzyl)-[5-(3-trifluoromethoxy-phenyl)-imidazo[2,1-b][1,3,4]thiadiazol-2-yl]-amine | 421 | |

-continued

| No | Structure | Name | HPLC/MS [M + H]+ | NMR DMSO |
|---|---|---|---|---|
| 73 | 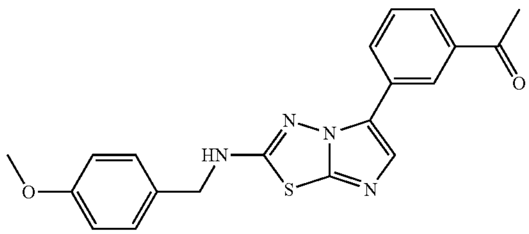 [SMILES: COc1ccc(CNc2nn3c(-c4cccc(C(C)=O)c4)cnc3s2)cc1] | 1-{3-[2-(4-Methoxy-benzylamino)-imidazo[2,1-b][1,3,4]thiadiazol-5-yl]-phenyl}-ethanone | 379 | |
| 74 | 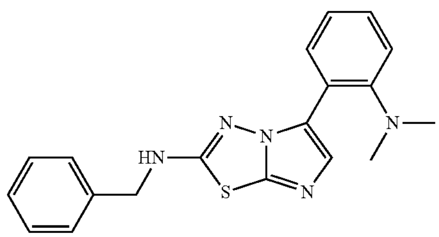 [SMILES: CN(C)c1ccccc1-c1cnc2sc(NCc3ccccc3)nn12] | Benzyl-[5-(2-dimethylamino-phenyl)-imidazo[2,1-b][1,3,4]thiadiazol-2-yl]-amine | 350 | |
| 75 | 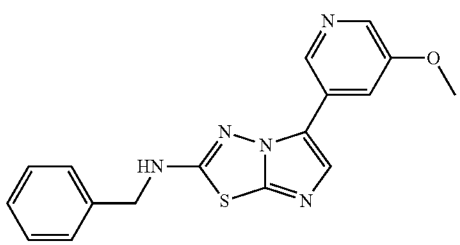 [SMILES: COc1cncc(-c2cnc3sc(NCc4ccccc4)nn23)c1] | Benzyl-[5-(5-methoxy-pyridin-3-yl)-imidazo[2,1-b][1,3,4]thiadiazol-2-yl]-amine | 338 | |
| 76 | 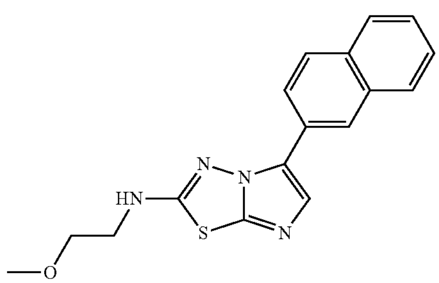 [SMILES: COCCNc1nn2c(-c3ccc4ccccc4c3)cnc2s1] | (2-Methoxy-ethyl)-(5-naphthalen-2-yl-imidazo[2,1-b][1,3,4]thiadiazol-2-yl)-amine | 325 | |
| 77 | 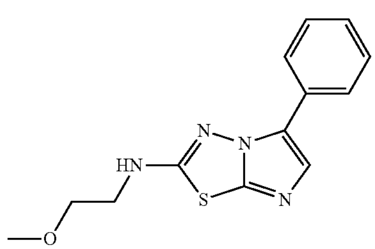 [SMILES: COCCNc1nn2c(-c3ccccc3)cnc2s1] | (2-Methoxy-ethyl)-(5-phenyl-imidazo[2,1-b][1,3,4]thiadiazol-2-yl)-amine | 275 | |
| 78 | 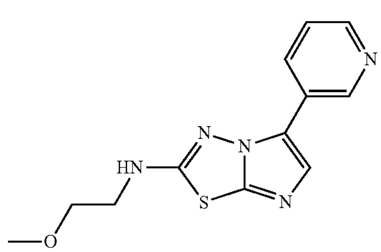 [SMILES: COCCNc1nn2c(-c3cccnc3)cnc2s1] | (2-Methoxy-ethyl)-(5-pyridin-3-yl-imidazo[2,1-b][1,3,4]thiadiazol-2-yl)-amine | 276 | |

-continued

| No | Structure | Name | HPLC/MS [M + H]+ | NMR DMSO |
|---|---|---|---|---|
| 79 | 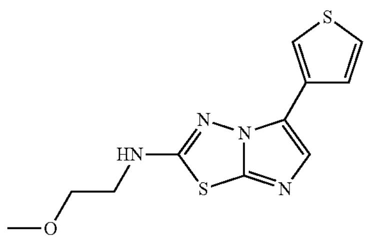 [SMILES: COCCNc1nn2c(-c3ccsc3)cnc2s1] | (2-Methoxy-ethyl)-(5-thiophen-3-yl-imidazo[2,1-b][1,3,4]thiadiazol-2-yl)-amine | 281 | |
| 80 | 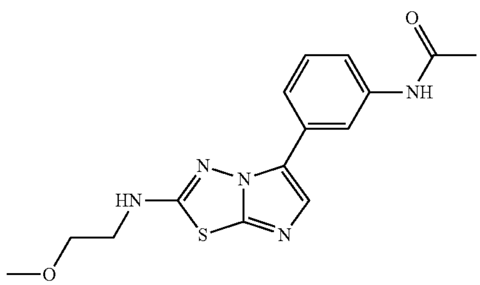 [SMILES: COCCNc1nn2c(-c3cccc(NC(C)=O)c3)cnc2s1] | N-{3-[2-(2-Methoxy-ethylamino)-imidazo[2,1-b][1,3,4]thiadiazol-5-yl]-phenyl}-acetamide | 332 | δ 10.0 (s, 1H), 8.2 (s, 1H), 8.1 (t, 1H), 7.6 (d, 1H), 7.4 (d, 1H), 7.3 (m, 2H), 3.6 (m, 4H), 3.3 (s, 3H), 2.1 (s, 3H) |
| 81 | 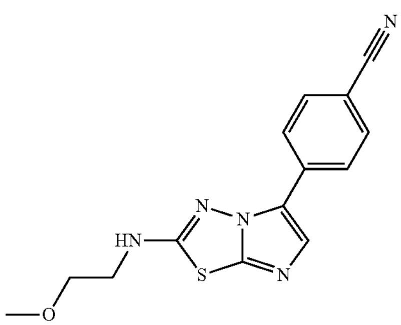 [SMILES: COCCNc1nn2c(-c3ccc(C#N)cc3)cnc2s1] | 4-[2-(2-Methoxy-ethylamino)-imidazo[2,1-b][1,3,4]thiadiazol-5-yl]-benzonitrile | 300 | |
| 82 | 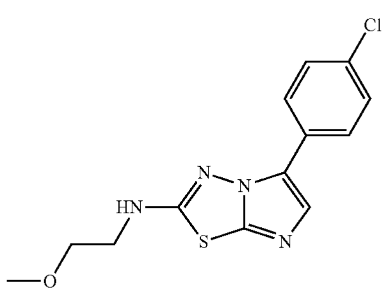 [SMILES: COCCNc1nn2c(-c3ccc(Cl)cc3)cnc2s1] | [5-(4-Chloro-phenyl)-imidazo[2,1-b][1,3,4]thiadiazol-2-yl]-(2-methoxy-ethyl)-amine | 309 | |
| 83 | 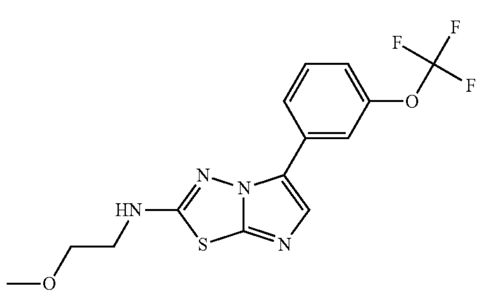 [SMILES: COCCNc1nn2c(-c3cccc(OC(F)(F)F)c3)cnc2s1] | (2-Methoxy-ethyl)-[5-(3-trifluoromethoxy-phenyl)-imidazo[2,1-b][1,3,4]thiadiazol-2-yl]-amine | 359 | |

-continued

| No | Structure | Name | HPLC/MS [M + H]+ | NMR DMSO |
|---|---|---|---|---|
| 84 | 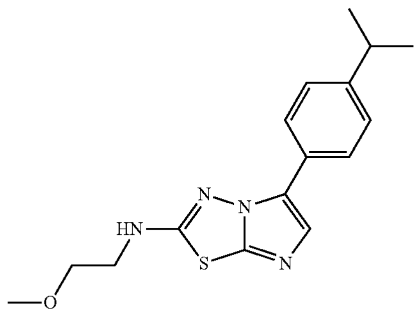 [SMILES: COCCNc1nn2c(-c3ccc(C(C)C)cc3)cnc2s1] | [5-(4-Isopropyl-phenyl)-imidazo[2,1-b][1,3,4]thiadiazol-2-yl]-(2-methoxy-ethyl)-amine | 317 | |
| 85 | 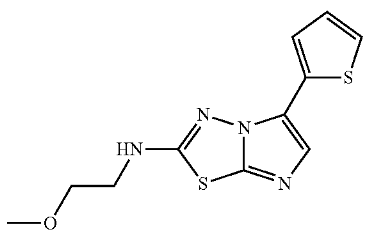 [SMILES: COCCNc1nn2c(-c3cccs3)cnc2s1] | (2-Methoxy-ethyl)-(5-thiophen-2-yl-imidazo[2,1-b][1,3,4]thiadiazol-2-yl)-amine | 281 | |
| 86 | 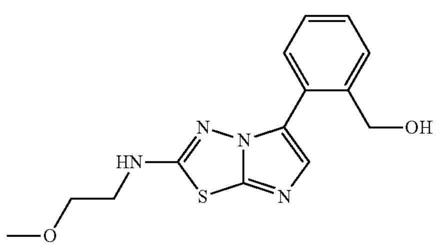 [SMILES: COCCNc1nn2c(-c3ccccc3CO)cnc2s1] | {2-[2-(2-Methoxy-ethylamino)-imidazo[2,1-b][1,3,4]thiadiazol-5-yl]-phenyl}-methanol | 305 | |
| 87 | 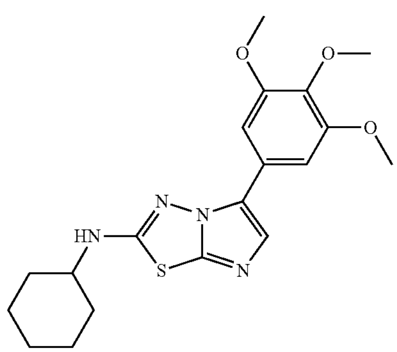 [SMILES: COc1cc(-c2cnc3sc(NC4CCCCC4)nn23)cc(OC)c1OC] | Cyclohexyl-[5-(3,4,5-trimethoxy-phenyl)-imidazo[2,1-b][1,3,4]thiadiazol-2-yl]-amine | 389 | |
| 88 | 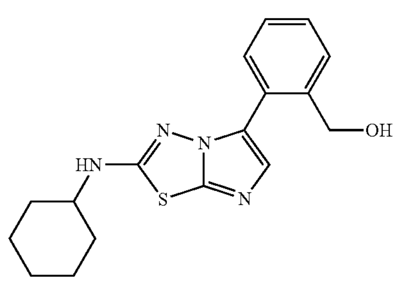 [SMILES: OCc1ccccc1-c1cnc2sc(NC3CCCCC3)nn12] | [2-(2-Cyclohexylamino-imidazo[2,1-b][1,3,4]thiadiazol-5-yl)-phenyl]-methanol | 329 | |

| No | Structure | Name | HPLC/MS [M + H]+ | NMR DMSO |
|---|---|---|---|---|
| 89 | 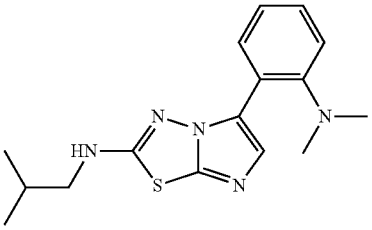 [SMILES: CC(C)CNc1nn2c(-c3ccccc3N(C)C)cnc2s1] | [5-(2-Dimethylamino-phenyl)-imidazo[2,1-b][1,3,4]thiadiazol-2-yl]-isobutyl-amine | 316 | |
| 90 | 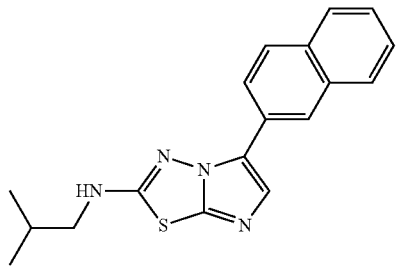 [SMILES: CC(C)CNc1nn2c(-c3ccc4ccccc4c3)cnc2s1] | Isobutyl-(5-naphthalen-2-yl-imidazo[2,1-b][1,3,4]thiadiazol-2-yl)-amine | 323 | |
| 91 | 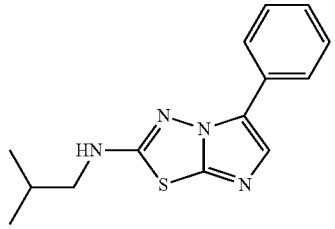 [SMILES: CC(C)CNc1nn2c(-c3ccccc3)cnc2s1] | Isobutyl-(5-phenyl-imidazo[2,1-b][1,3,4]thiadiazol-2-yl)-amine | 273 | |
| 92 | 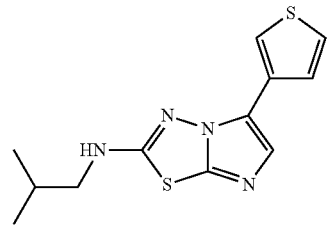 [SMILES: CC(C)CNc1nn2c(-c3ccsc3)cnc2s1] | Isobutyl-(5-thiophen-3-yl-imidazo[2,1-b][1,3,4]thiadiazol-2-yl)-amine | 279 | |
| 93 | 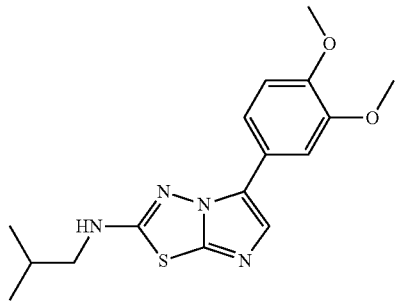 [SMILES: COc1ccc(-c2cnc3sc(NCC(C)C)nn23)cc1OC] | [5-(3,4-Dimethoxy-phenyl)-imidazo[2,1-b][1,3,4]thiadiazol-2-yl]-isobutyl-amine | 333 | |
| 94 | 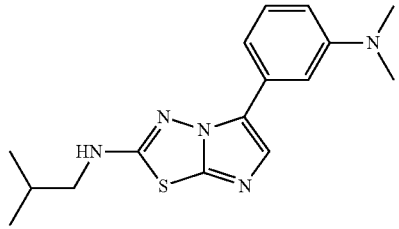 [SMILES: CC(C)CNc1nn2c(-c3cccc(N(C)C)c3)cnc2s1] | [5-(3-Dimethylamino-phenyl)-imidazo[2,1-b][1,3,4]thiadiazol-2-yl]-isobutyl-amine | 316 | |

| No | Structure | Name | HPLC/MS [M + H]+ | NMR DMSO |
|---|---|---|---|---|
| 95 | 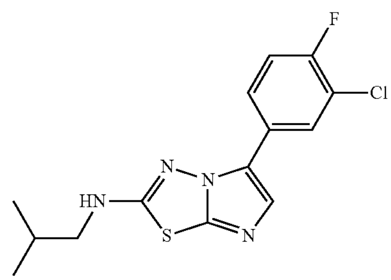 [SMILES: CC(C)CNc1nn2c(-c3ccc(F)c(Cl)c3)cnc2s1] | [5-(3-Chloro-4-fluoro-phenyl)-imidazo[2,1-b][1,3,4]thiadiazol-2-yl]-isobutyl-amine | 325 | |
| 96 | 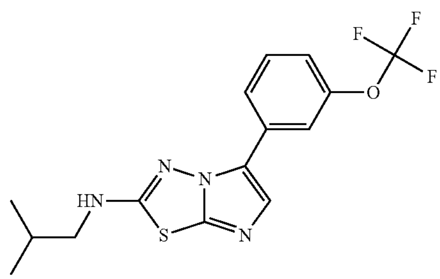 [SMILES: CC(C)CNc1nn2c(-c3cccc(OC(F)(F)F)c3)cnc2s1] | Isobutyl-[5-(3-trifluoromethoxy-phenyl)-imidazo[2,1-b][1,3,4]thiadiazol-2-yl]-amine | 357 | |
| 97 | 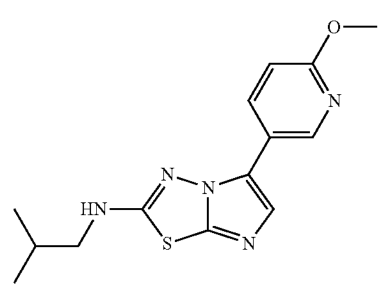 [SMILES: COc1ccc(-c2cnc3sc(NCC(C)C)nn23)cn1] | Isobutyl-[5-(6-methoxy-pyridin-3-yl)-imidazo[2,1-b][1,3,4]thiadiazol-2-yl]-amine | 304 | |
| 98 | 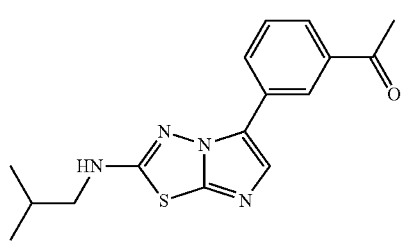 [SMILES: CC(=O)c1cccc(-c2cnc3sc(NCC(C)C)nn23)c1] | 1-[3-(2-Isobutylamino-imidazo[2,1-b][1,3,4]thiadiazol-5-yl)-phenyl]-ethanone | 315 | |
| 99 | 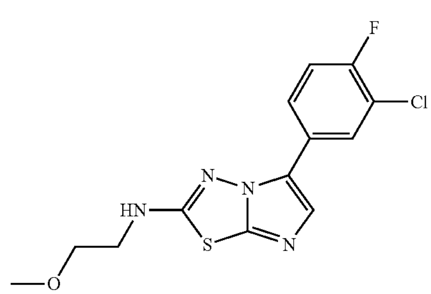 [SMILES: COCCNc1nn2c(-c3ccc(F)c(Cl)c3)cnc2s1] | [5-(3-Chloro-4-fluoro-phenyl)-imidazo[2,1-b][1,3,4]thiadiazol-2-yl]-(2-methoxy-ethyl)-amine | 327 | |

-continued

| No | Structure | Name | HPLC/MS [M + H]+ | NMR DMSO |
|---|---|---|---|---|
| 100 | 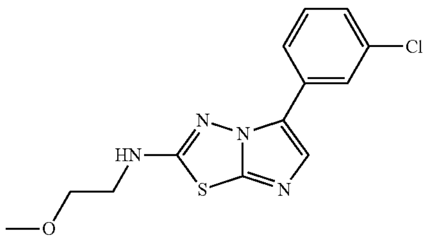 [SMILES: COCCNc1nn2c(-c3cccc(Cl)c3)cnc2s1] | [5-(3-Chloro-phenyl)-imidazo[2,1-b][1,3,4]thiadiazol-2-yl]-(2-methoxy-ethyl)-amine | 309 | |
| 101 | 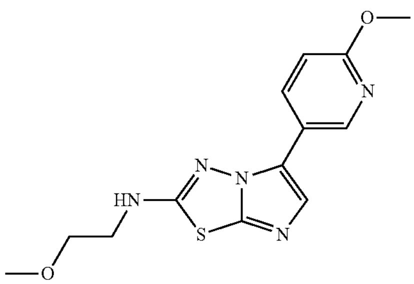 | (2-Methoxy-ethyl)-[5-(6-methoxy-pyridin-3-yl)-imidazo[2,1-b][1,3,4]thiadiazol-2-yl]-amine | 306 | |
| 102 | 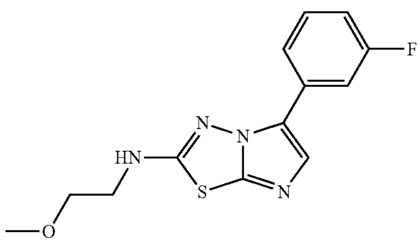 [SMILES: COCCNc1nn2c(-c3cccc(F)c3)cnc2s1] | [5-(3-Fluoro-phenyl)-imidazo[2,1-b][1,3,4]thiadiazol-2-yl]-(2-methoxy-ethyl)-amine | 293 | |
| 103 | 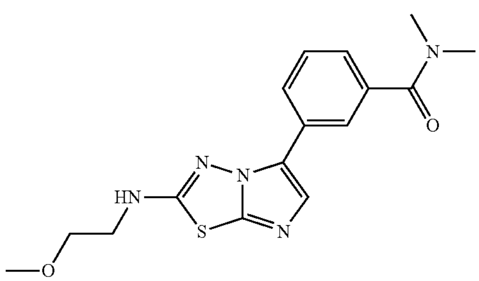 | 3-[2-(2-Methoxy-ethylamino)-imidazo[2,1-b][1,3,4]thiadiazol-5-yl]-N,N-dimethyl-benzamide | 346 | δ 8.2 (t, 1H), 8.0 (d, 1H), 7.9 (s, 1H), 7.6 (s, 1H), 7.5 (t, 1H), 7.3 (d, 1H), 3.6 (m, 2H) 3.5 (m, 2H), 3.3 (s, 3H), 3.0 (d, 6H) |
| 104 | 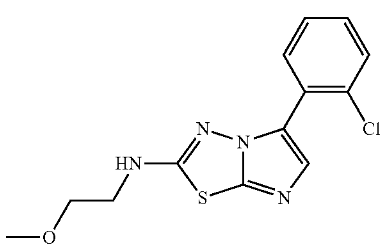 [SMILES: COCCNc1nn2c(-c3ccccc3Cl)cnc2s1] | [5-(2-Chloro-phenyl)-imidazo[2,1-b][1,3,4]thiadiazol-2-yl]-(2-methoxy-ethyl)-amine | 309 | |
| 105 | 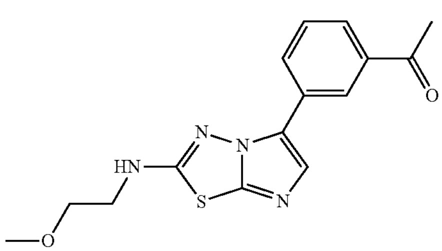 [SMILES: COCCNc1nn2c(-c3cccc(C(C)=O)c3)cnc2s1] | 1-{3-[2-(2-Methoxy-ethylamino)-imidazo[2,1-b][1,3,4]thiadiazol-5-yl]-phenyl}-ethanone | 316 | |

-continued

| No | Structure | Name | HPLC/MS [M + H]+ | NMR DMSO |
|---|---|---|---|---|
| 106 | 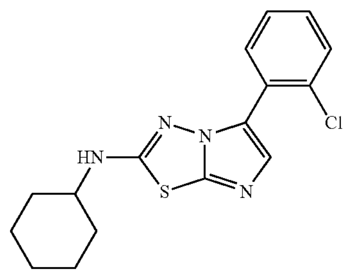 [SMILES: Clc1ccccc1-c1cnc2sc(NC3CCCCC3)nn12] | [5-(2-Chloro-phenyl)-imidazo[2,1-b][1,3,4]thiadiazol-2-yl]-cyclohexyl-amine | 333 | |
| 107 | 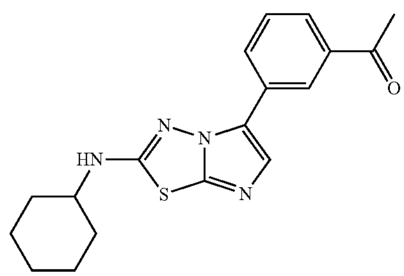 [SMILES: CC(=O)c1cccc(-c2cnc3sc(NC4CCCCC4)nn23)c1] | 1-[3-(2-Cyclohexylamino-imidazo[2,1-b][1,3,4]thiadiazol-5-yl)-phenyl]-ethanone | 341 | |
| 108 | 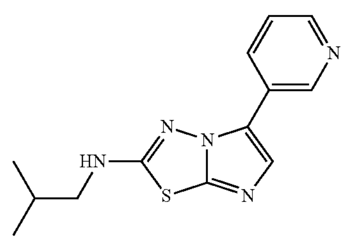 [SMILES: CC(C)CNc1nn2c(-c3cccnc3)cnc2s1] | Isobutyl-(5-pyridin-3-yl-imidazo[2,1-b][1,3,4]thiadiazol-2-yl)-amine | 274 | |
| 109 | 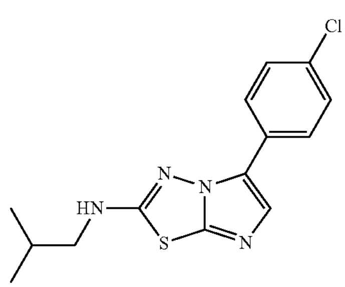 [SMILES: CC(C)CNc1nn2c(-c3ccc(Cl)cc3)cnc2s1] | [5-(4-Chloro-phenyl)-imidazo[2,1-b][1,3,4]thiadiazol-2-yl]-isobutyl-amine | 307 | |
| 110 | 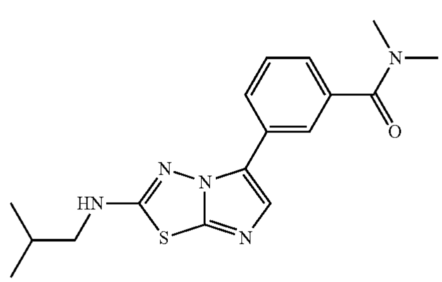 [SMILES: CC(C)CNc1nn2c(-c3cccc(C(=O)N(C)C)c3)cnc2s1] | 3-(2-Isobutylamino-imidazo[2,1-b][1,3,4]thiadiazol-5-yl)-N,N-dimethyl-benzamide | 344 | |

-continued

| No | Structure | Name | HPLC/MS [M + H]+ | NMR DMSO |
|---|---|---|---|---|
| 111 | 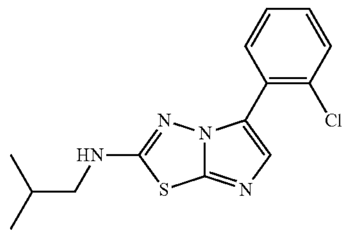 [SMILES: CC(C)CNc1nn2c(-c3ccccc3Cl)cnc2s1] | [5-(2-Chloro-phenyl)-imidazo[2,1-b][1,3,4]thiadiazol-2-yl]-isobutyl-amine | 307 | |
| 112 | 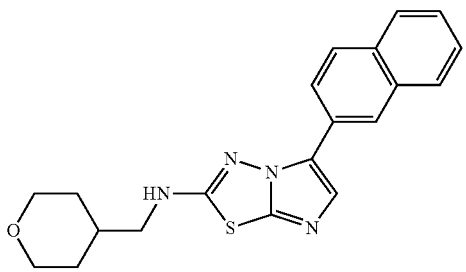 [SMILES: c1ccc2cc(-c3cnc4sc(NCC5CCOCC5)nn34)ccc2c1] | (5-Naphthalen-2-yl-imidazo[2,1-b][1,3,4]thiadiazol-2-yl)-(tetrahydro-pyran-4-ylmethyl)-amine | 365 | |
| 113 | 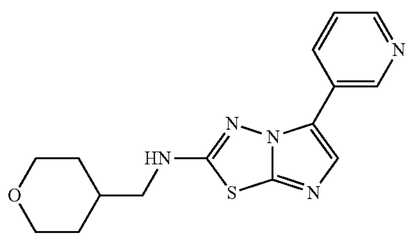 [SMILES: c1cncc(-c2cnc3sc(NCC4CCOCC4)nn23)c1] | (5-Pyridin-3-yl-imidazo[2,1-b][1,3,4]thiadiazol-2-yl)-(tetrahydro-pyran-4-ylmethyl)-amine | 316 | |
| 114 | 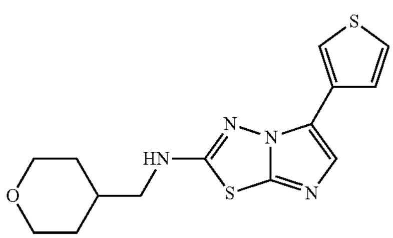 [SMILES: c1cc(-c2cnc3sc(NCC4CCOCC4)nn23)cs1] | (Tetrahydro-pyran-4-ylmethyl)-(5-thiophen-3-yl-imidazo[2,1-b][1,3,4]thiadiazol-2-yl)-amine | 321 | |
| 115 | 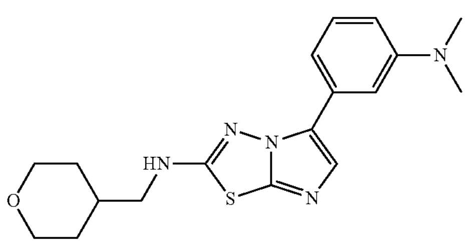 [SMILES: CN(C)c1cccc(-c2cnc3sc(NCC4CCOCC4)nn23)c1] | [5-(3-Dimethylamino-phenyl)-imidazo[2,1-b][1,3,4]thiadiazol-2-yl]-(tetrahydro-pyran-4-ylmethyl)-amine | 358 | |
| 116 | 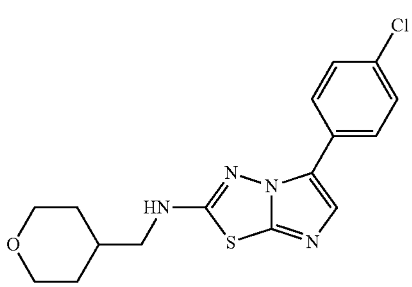 [SMILES: Clc1ccc(-c2cnc3sc(NCC4CCOCC4)nn23)cc1] | [5-(4-Chloro-phenyl)-imidazo[2,1-b][1,3,4]thiadiazol-2-yl]-(tetrahydro-pyran-4-ylmethyl)-amine | 349 | |

| No | Name | HPLC/MS [M + H]+ |
|---|---|---|
| 117 | [5-(3-Chloro-phenyl)-imidazo[2,1-b][1,3,4]thiadiazol-2-yl]-(tetrahydro-pyran-4-ylmethyl)-amine | 349 |
| 118 | [5-(4-Isopropyl-phenyl)-imidazo[2,1-b][1,3,4]thiadiazol-2-yl]-(tetrahydro-pyran-4-ylmethyl)-amine | 357 |
| 119 | [5-(6-Methoxy-pyridin-3-yl)-imidazo[2,1-b][1,3,4]thiadiazol-2-yl]-(tetrahydro-pyran-4-ylmethyl)-amine | 346 |
| 120 | [5-(3-Fluoro-phenyl)-imidazo[2,1-b][1,3,4]thiadiazol-2-yl]-(tetrahydro-pyran-4-ylmethyl)-amine | 333 |
| 121 | [5-(2-Chloro-phenyl)-imidazo[2,1-b][1,3,4]thiadiazol-2-yl]-(tetrahydro-pyran-4-ylmethyl)-amine | 349 |
| 122 | 1-(3-{2-[(Tetrahydro-pyran-4-ylmethyl)-amino]-imidazo[2,1-b][1,3,4]thiadiazol-5-yl}-phenyl)-ethanone | 357 |

-continued

| No | Structure | Name | HPLC/MS [M + H]+ | NMR DMSO |
|---|---|---|---|---|
| 123 | 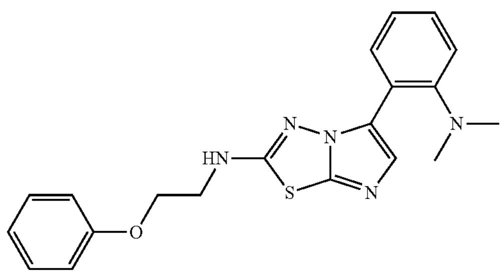 [SMILES: CN(C)c1ccccc1-c1cnc2sc(NCCOc3ccccc3)nn12] | [5-(2-Dimethylamino-phenyl)-imidazo[2,1-b][1,3,4]thiadiazol-2-yl]-(2-phenoxy-ethyl)-amine | 380 | |
| 124 | 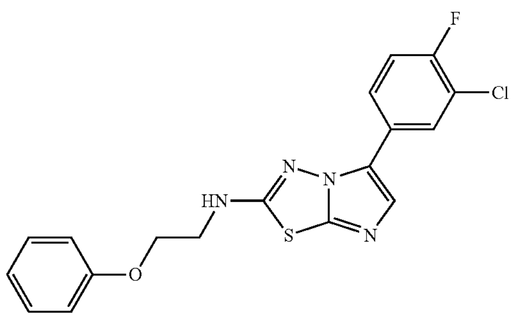 [SMILES: Fc1ccc(-c2cnc3sc(NCCOc4ccccc4)nn23)cc1Cl] | [5-(3-Chloro-4-fluoro-phenyl)-imidazo[2,1-b][1,3,4]thiadiazol-2-yl]-(2-phenoxy-ethyl)-amine | 389 | |
| 125 | 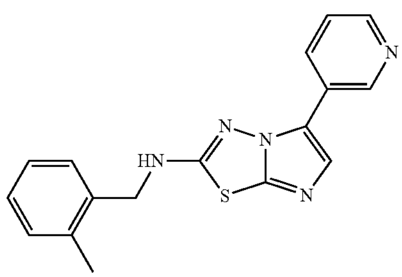 [SMILES: Cc1ccccc1CNc1nn2c(-c3cccnc3)cnc2s1] | (2-Methyl-benzyl)-(5-pyridin-3-yl-imidazo[2,1-b][1,3,4]thiadiazol-2-yl)-amine | 322 | |
| 126 | 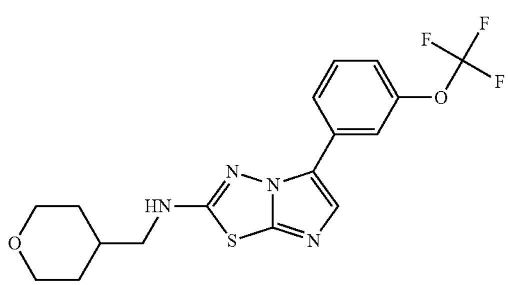 [SMILES: FC(F)(F)Oc1cccc(-c2cnc3sc(NCC4CCOCC4)nn23)c1] | (Tetrahydro-pyran-4-ylmethyl)-[5-(3-trifluoromethoxy-phenyl)-imidazo[2,1-b][1,3,4]thiadiazol-2-yl]-amine | 399 | |
| 127 | 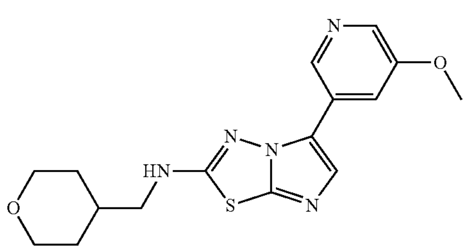 [SMILES: COc1cncc(-c2cnc3sc(NCC4CCOCC4)nn23)c1] | [5-(5-Methoxy-pyridin-3-yl)-imidazo[2,1-b][1,3,4]thiadiazol-2-yl]-(tetrahydro-pyran-4-ylmethyl)-amine | 346 | |

| No | Structure | Name | HPLC/MS [M + H]+ | NMR DMSO |
|---|---|---|---|---|
| 128 | 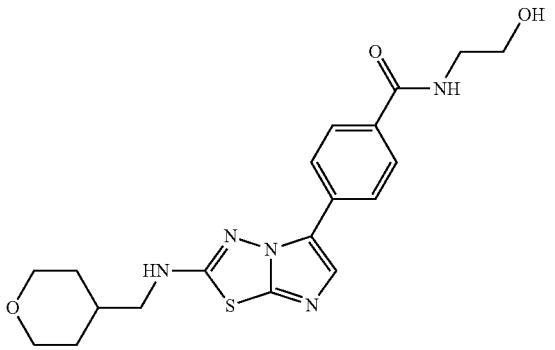 [SMILES: O=C(NCCO)c1ccc(-c2cnc3sc(NCC4CCOCC4)nn23)cc1] | N-(2-Hydroxy-ethyl)-4-{2-[(tetrahydro-pyran-4-ylmethyl)-amino]-imidazo[2,1-b][1,3,4]thiadiazol-5-yl}-benzamide | 402 | |
| 129 | 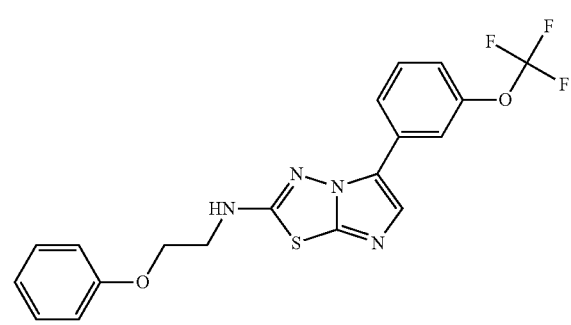 [SMILES: FC(F)(F)Oc1cccc(-c2cnc3sc(NCCOc4ccccc4)nn23)c1] | (2-Phenoxy-ethyl)-[5-(3-trifluoromethoxy-phenyl)-imidazo[2,1-b][1,3,4]thiadiazol-2-yl]-amine | 421 | |
| 130 | 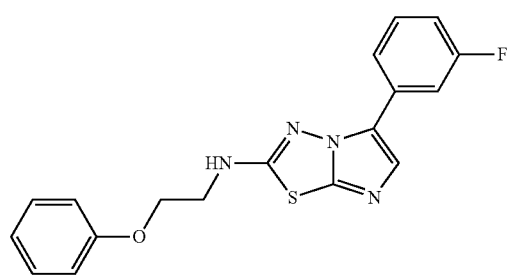 [SMILES: Fc1cccc(-c2cnc3sc(NCCOc4ccccc4)nn23)c1] | [5-(3-Fluoro-phenyl)-imidazo[2,1-b][1,3,4]thiadiazol-2-yl]-(2-phenoxy-ethyl)-amine | 355 | |
| 131 | 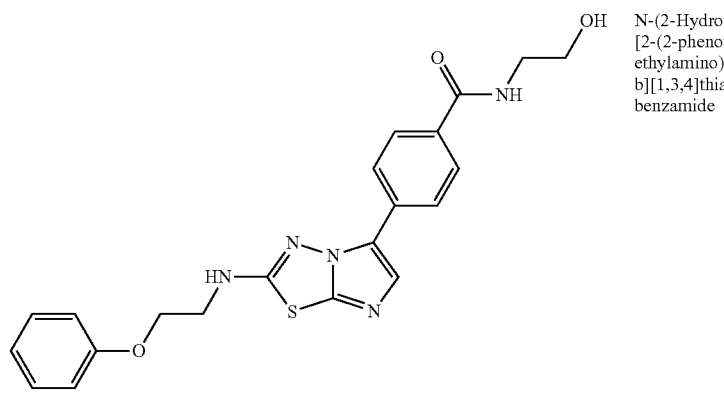 | N-(2-Hydroxy-ethyl)-4-[2-(2-phenoxy-ethylamino)-imidazo[2,1-b][1,3,4]thiadiazol-5-yl]-benzamide | 423 | |
| 132 | 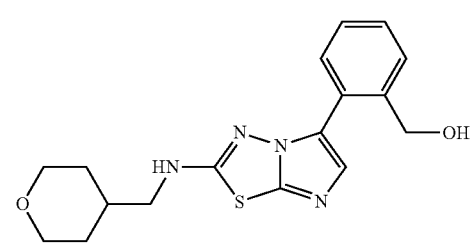 [SMILES: OCc1ccccc1-c1cnc2sc(NCC3CCOCC3)nn12] | (2-{2-[(Tetrahydro-pyran-4-ylmethyl)-amino]-imidazo[2,1-b][1,3,4]thiadiazol-5-yl}-phenyl)-methanol | 345 | |

| No | Structure | Name | HPLC/MS [M + H]+ | NMR DMSO |
|---|---|---|---|---|
| 133 | 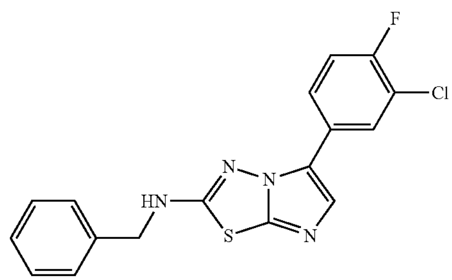 [SMILES: Fc1ccc(-c2cnc3sc(NCc4ccccc4)nn23)cc1Cl] | Benzyl-[5-(3-chloro-4-fluoro-phenyl)-imidazo[2,1-b][1,3,4]thiadiazol-2-yl]-amine | 359 | |
| 134 | 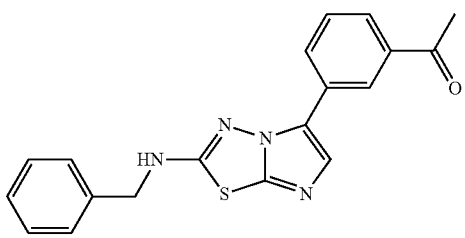 [SMILES: CC(=O)c1cccc(-c2cnc3sc(NCc4ccccc4)nn23)c1] | 1-[3-(2-Benzylamino-imidazo[2,1-b][1,3,4]thiadiazol-5-yl)-phenyl]-ethanone | 349 | |
| 135 | 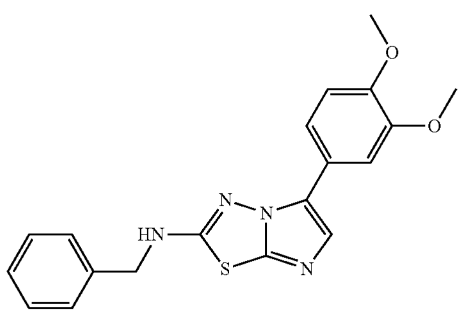 [SMILES: COc1ccc(-c2cnc3sc(NCc4ccccc4)nn23)cc1OC] | Benzyl-[5-(3,4-dimethoxy-phenyl)-imidazo[2,1-b][1,3,4]thiadiazol-2-yl]-amine | 367 | δ 8.5 (t, 1H), 7.5 (s, 1H), 7.4 (m, 6H), 7.3 (t, 1H), 7.0 (d, 1H), 4.6 (d, 2H), 3.8 (s, 3H), 3.7 (s, 3H) |
| 136 | 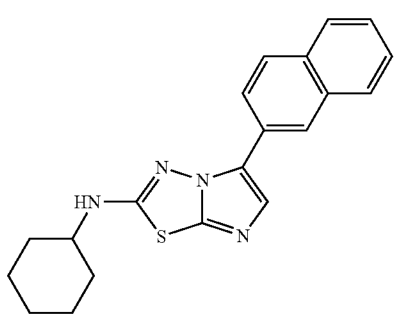 [SMILES: c1ccc2cc(-c3cnc4sc(NC5CCCCC5)nn34)ccc2c1] | Cyclohexyl-(5-naphthalen-2-yl-imidazo[2,1-b][1,3,4]thiadiazol-2-yl)-amine | 349 | |
| 137 | 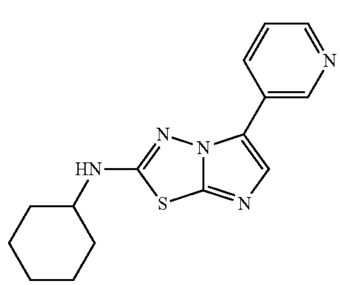 [SMILES: c1cncc(-c2cnc3sc(NC4CCCCC4)nn23)c1] | Cyclohexyl-(5-pyridin-3-yl-imidazo[2,1-b][1,3,4]thiadiazol-2-yl)-amine | 300 | |

-continued
| No | Structure | Name | HPLC/MS [M + H]+ | NMR DMSO |
|---|---|---|---|---|
| 138 | 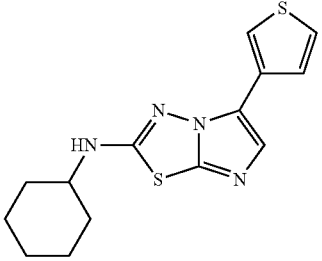 [SMILES: c1cc(-c2cnc3sc(NC4CCCCC4)nn23)cs1] | Cyclohexyl-(5-thiophen-3-yl-imidazo[2,1-b][1,3,4]thiadiazol-2-yl)-amine | 305 | |
| 139 | 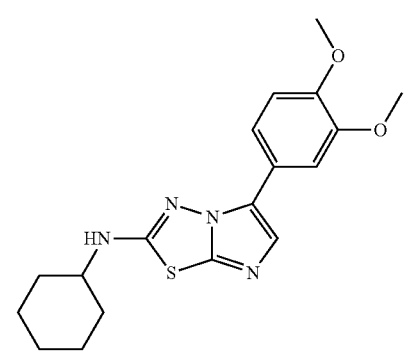 [SMILES: COc1ccc(-c2cnc3sc(NC4CCCCC4)nn23)cc1OC] | Cyclohexyl-[5-(3,4-dimethoxy-phenyl)-imidazo[2,1-b][1,3,4]thiadiazol-2-yl]-amine | 359 | |
| 140 | 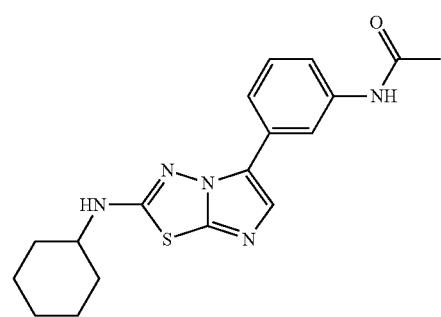 [SMILES: CC(=O)Nc1cccc(-c2cnc3sc(NC4CCCCC4)nn23)c1] | N-[3-(2-Cyclohexylamino-imidazo[2,1-b][1,3,4]thiadiazol-5-yl)-phenyl]-acetamide | 356 | |
| 141 | 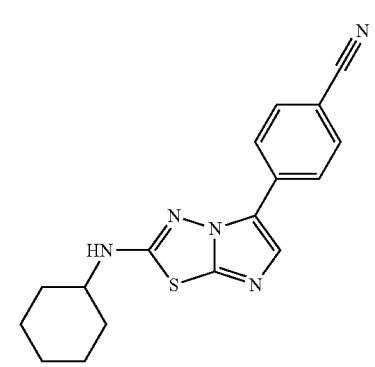 [SMILES: N#Cc1ccc(-c2cnc3sc(NC4CCCCC4)nn23)cc1] | 4-(2-Cyclohexylamino-imidazo[2,1-b][1,3,4]thiadiazol-5-yl)-benzonitrile | 324 | |

| No | Structure | Name | HPLC/MS [M + H]+ | NMR DMSO |
|---|---|---|---|---|
| 142 | 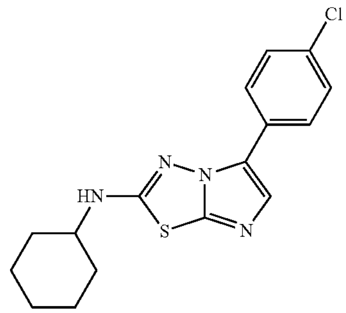 [SMILES: Clc1ccc(-c2cnc3sc(NC4CCCCC4)nn23)cc1] | [5-(4-Chloro-phenyl)-imidazo[2,1-b][1,3,4]thiadiazol-2-yl]-cyclohexyl-amine | 333 | |
| 143 | 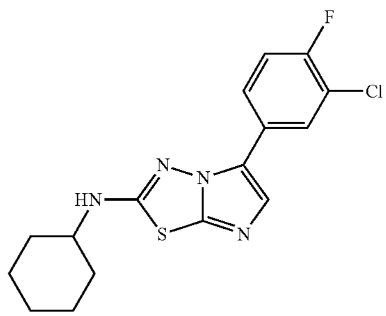 [SMILES: Fc1ccc(-c2cnc3sc(NC4CCCCC4)nn23)cc1Cl] | [5-(3-Chloro-4-fluoro-phenyl)-imidazo[2,1-b][1,3,4]thiadiazol-2-yl]-cyclohexyl-amine | 351 | |
| 144 | 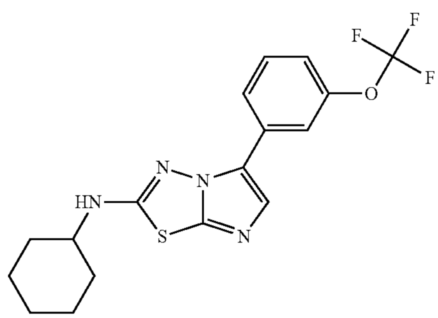 [SMILES: FC(F)(F)Oc1cccc(-c2cnc3sc(NC4CCCCC4)nn23)c1] | Cyclohexyl-[5-(3-trifluoromethoxy-phenyl)-imidazo[2,1-b][1,3,4]thiadiazol-2-yl]-amine | 383 | |
| 145 | 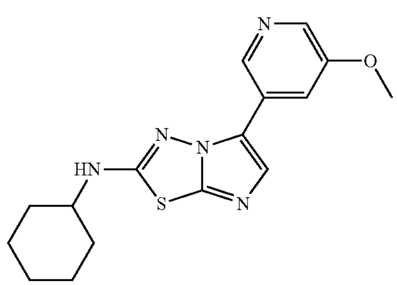 [SMILES: COc1cncc(-c2cnc3sc(NC4CCCCC4)nn23)c1] | Cyclohexyl-[5-(5-methoxy-pyridin-3-yl)-imidazo[2,1-b][1,3,4]thiadiazol-2-yl]-amine | 330 | |
| 146 | 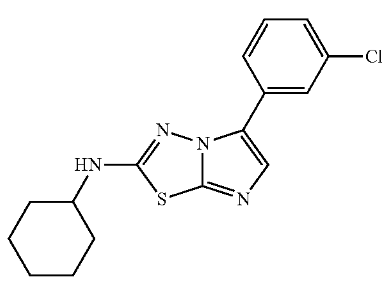 [SMILES: Clc1cccc(-c2cnc3sc(NC4CCCCC4)nn23)c1] | [5-(3-Chloro-phenyl)-imidazo[2,1-b][1,3,4]thiadiazol-2-yl]-cyclohexyl-amine | 333 | |

| No | Structure | Name | HPLC/MS [M + H]+ | NMR DMSO |
|----|-----------|------|------------------|----------|
| 147 | 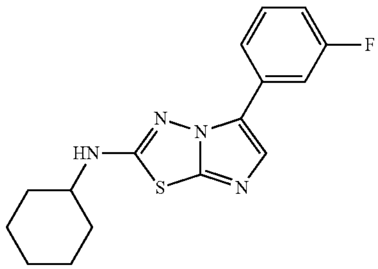 [SMILES: Fc1cccc(-c2cnc3sc(NC4CCCCC4)nn23)c1] | Cyclohexyl-[5-(3-fluoro-phenyl)-imidazo[2,1-b][1,3,4]thiadiazol-2-yl]-amine | 317 | |
| 148 | 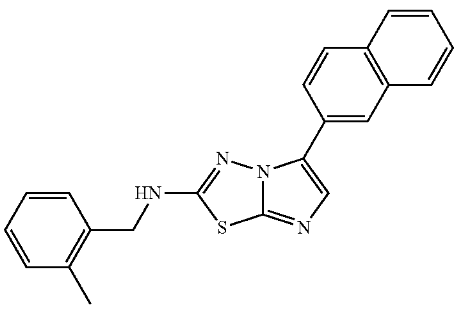 [SMILES: Cc1ccccc1CNc1nn2c(-c3ccc4ccccc4c3)cnc2s1] | (2-Methyl-benzyl)-(5-naphthalen-2-yl-imidazo[2,1-b][1,3,4]thiadiazol-2-yl)-amine | 371 | |
| 149 | 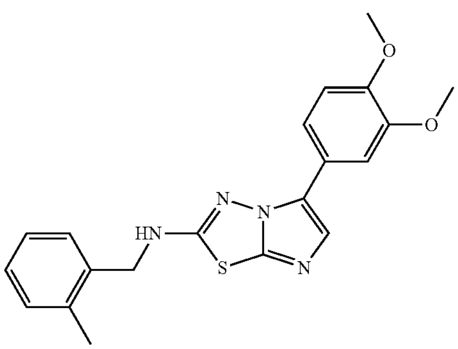 [SMILES: COc1ccc(-c2cnc3sc(NCc4ccccc4C)nn23)cc1OC] | [5-(3,4-Dimethoxy-phenyl)-imidazo[2,1-b][1,3,4]thiadiazol-2-yl]-(2-methyl-benzyl)-amine | 381 | |
| 150 | 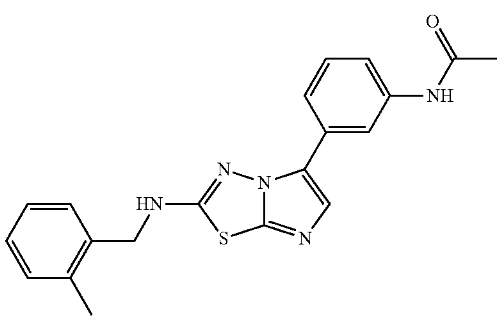 [SMILES: CC(=O)Nc1cccc(-c2cnc3sc(NCc4ccccc4C)nn23)c1] | N-{3-[2-(2-Methyl-benzylamino)-imidazo[2,1-b][1,3,4]thiadiazol-5-yl]-phenyl}-acetamide | 378 | |
| 151 | 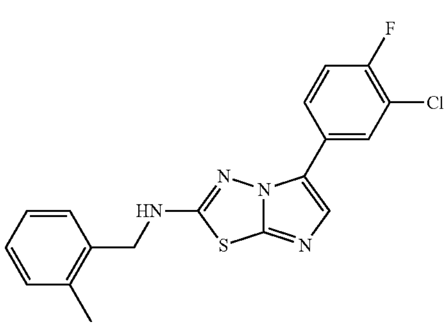 [SMILES: Cc1ccccc1CNc1nn2c(-c3ccc(F)c(Cl)c3)cnc2s1] | [5-(3-Chloro-4-fluoro-phenyl)-imidazo[2,1-b][1,3,4]thiadiazol-2-yl]-(2-methyl-benzyl)-amine | 373 | |

-continued

| No | Structure | Name | HPLC/MS [M + H]+ | NMR DMSO |
|---|---|---|---|---|
| 152 | 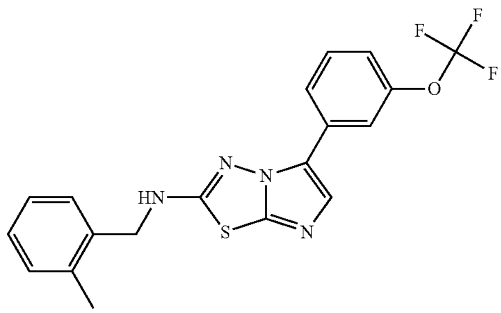 [SMILES: Cc1ccccc1CNc1nn2c(-c3cccc(OC(F)(F)F)c3)cnc2s1] | (2-Methyl-benzyl)-[5-(3-trifluoromethoxy-phenyl)-imidazo[2,1-b][1,3,4]thiadiazol-2-yl]-amine | 405 | |
| 153 | 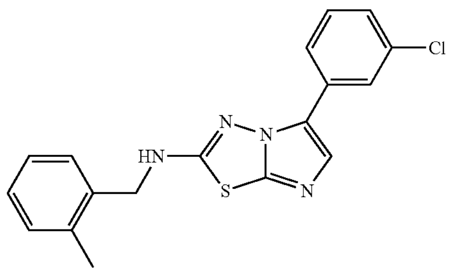 [SMILES: Cc1ccccc1CNc1nn2c(-c3cccc(Cl)c3)cnc2s1] | [5-(3-Chloro-phenyl)-imidazo[2,1-b][1,3,4]thiadiazol-2-yl]-(2-methyl-benzyl)-amine | 355 | |
| 154 | 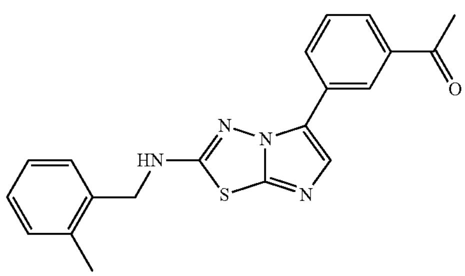 [SMILES: CC(=O)c1cccc(-c2cnc3sc(NCc4ccccc4C)nn23)c1] | 1-{3-[2-(2-Methyl-benzylamino)-imidazo[2,1-b][1,3,4]thiadiazol-5-yl]-phenyl}-ethanone | 363 | |
| 155 | 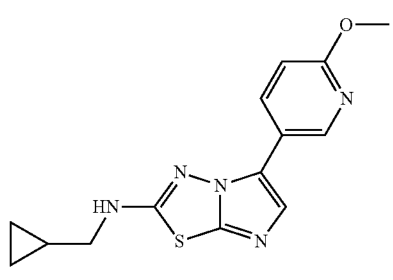 [SMILES: COc1ccc(-c2cnc3sc(NCC4CC4)nn23)cn1] | Cyclopropylmethyl-[5-(6-methoxy-pyridin-3-yl)-imidazo[2,1-b][1,3,4]thiadiazol-2-yl]-amine | 302 | |
| 156 | 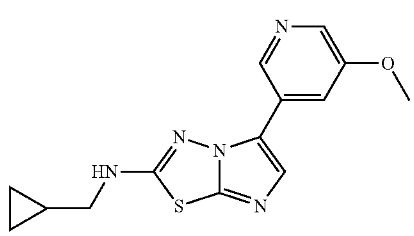 [SMILES: COc1cncc(-c2cnc3sc(NCC4CC4)nn23)c1] | Cyclopropylmethyl-[5-(5-methoxy-pyridin-3-yl)-imidazo[2,1-b][1,3,4]thiadiazol-2-yl]-amine | 302 | |

-continued

| No | Structure | Name | HPLC/MS [M + H]+ | NMR DMSO |
|---|---|---|---|---|
| 157 | 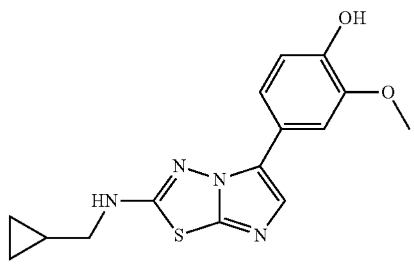 [SMILES: COc1cc(-c2cnc3sc(NCC4CC4)nn23)ccc1O] | 4-[2-(Cyclopropylmethyl-amino)-imidazo[2,1-b][1,3,4]thiadiazol-5-yl]-2-methoxy-phenol | 317 | |
| 158 | 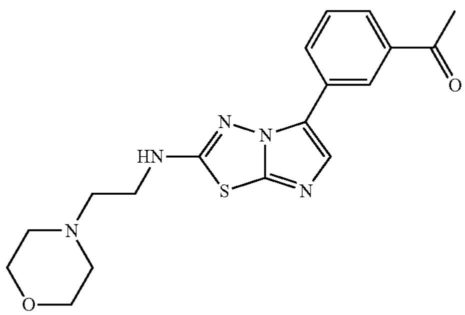 [SMILES: CC(=O)c1cccc(-c2cnc3sc(NCCN4CCOCC4)nn23)c1] | 1-{3-[2-(2-Morpholin-4-yl-ethylamino)-imidazo[2,1-b][1,3,4]thiadiazol-5-yl]-phenyl}-ethanone | 372 | |
| 159 | 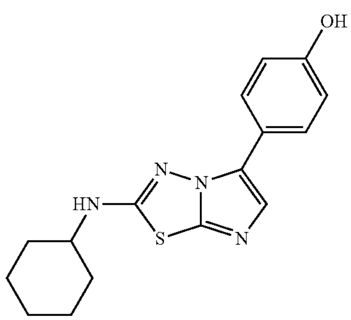 [SMILES: Oc1ccc(-c2cnc3sc(NC4CCCCC4)nn23)cc1] | 4-(2-Cyclohexylamino-imidazo[2,1-b][1,3,4]thiadiazol-5-yl)phenol | 315 | |
| 160 | 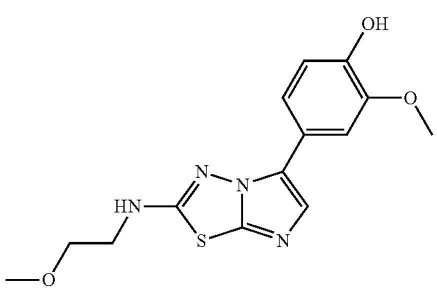 | 2-Methoxy-4-[2-(2-methoxy-ethylamino)-imidazo[2,1-b][1,3,4]thiadiazol-5-yl]-phenol | 321 | δ 9.1 (s, 1H), 8.1 (t, 1H), 7.6 (s, 1H), 7.3 (m, 2H), 6.8 (d, 1H), 3.8 (s, 3H), 3.6 (m, 2H), 3.5 (m, 2H), 3.3 (s, 3H) |
| 161 | 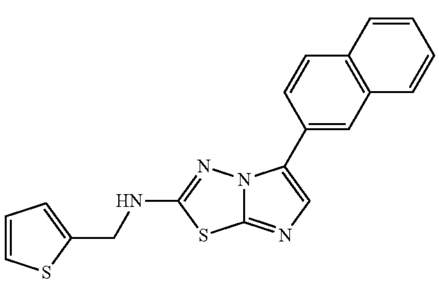 [SMILES: c1csc(CNc2nn3c(-c4ccc5ccccc5c4)cnc3s2)c1] | (5-Naphthalen-2-yl-imidazo[2,1-b][1,3,4]thiadiazol-2-yl)-thiophen-2-ylmethyl-amine | 363 | |

-continued

| No | Structure | Name | HPLC/MS [M + H]+ | NMR DMSO |
|---|---|---|---|---|
| 162 | 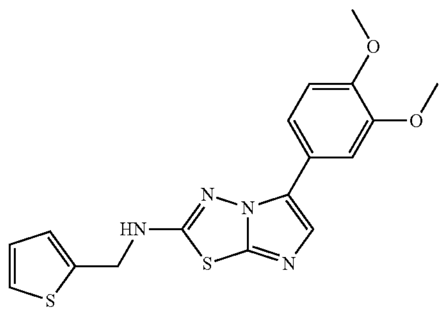 [SMILES: COc1ccc(-c2cnc3sc(NCc4cccs4)nn23)cc1OC] | [5-(3,4-Dimethoxy-phenyl)-imidazo[2,1-b][1,3,4]thiadiazol-2-yl]-thiophen-2-ylmethyl-amine | 373 | |
| 163 | 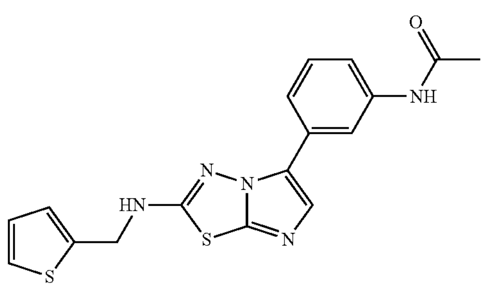 [SMILES: CC(=O)Nc1cccc(-c2cnc3sc(NCc4cccs4)nn23)c1] | N-(3-{2-[(Thiophen-2-ylmethyl)-amino]-imidazo[2,1-b][1,3,4]thiadiazol-5-yl}-phenyl)-acetamide | 370 | |
| 164 | 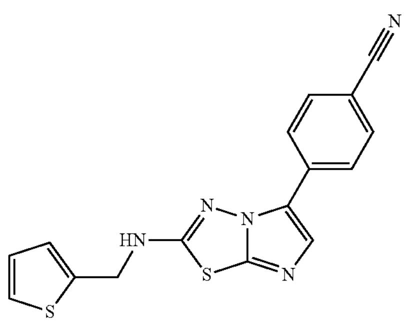 [SMILES: N#Cc1ccc(-c2cnc3sc(NCc4cccs4)nn23)cc1] | 4-{2-[(Thiophen-2-ylmethyl)-amino]-imidazo[2,1-b][1,3,4]thiadiazol-5-yl}-benzonitrile | 338 | |
| 165 | 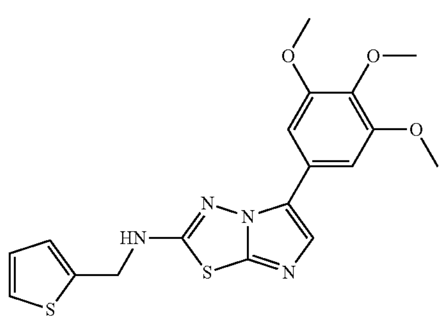 [SMILES: COc1cc(-c2cnc3sc(NCc4cccs4)nn23)cc(OC)c1OC] | Thiophen-2-ylmethyl-[5-(3,4,5-trimethoxy-phenyl)-imidazo[2,1-b][1,3,4]thiadiazol-2-yl]-amine | 403 | |
| 166 | 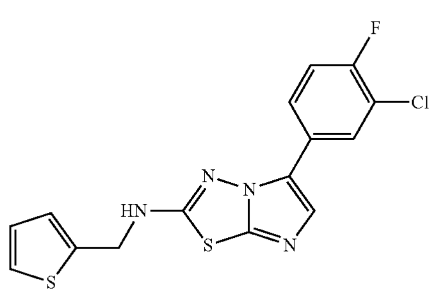 [SMILES: Fc1ccc(-c2cnc3sc(NCc4cccs4)nn23)cc1Cl] | [5-(3-Chloro-4-fluoro-phenyl)-imidazo[2,1-b][1,3,4]thiadiazol-2-yl]-thiophen-2-ylmethyl-amine | 365 | |

| No | Structure | Name | HPLC/MS [M + H]+ | NMR DMSO |
|---|---|---|---|---|
| 167 | 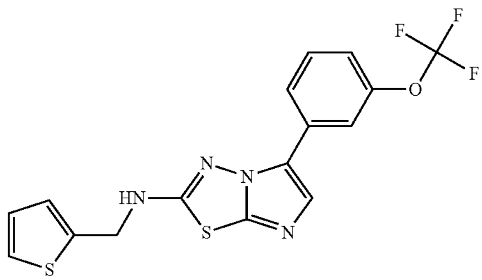 [SMILES: FC(F)(F)Oc1cccc(-c2cnc3sc(NCc4cccs4)nn23)c1] | Thiophen-2-ylmethyl-[5-(3-trifluoromethoxy-phenyl)-imidazo[2,1-b][1,3,4]thiadiazol-2-yl]-amine | 397 | |
| 168 | 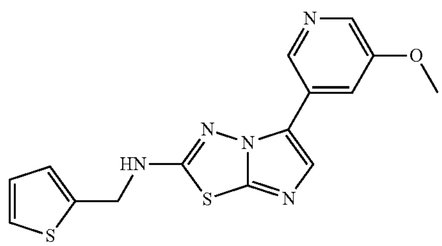 [SMILES: COc1cncc(-c2cnc3sc(NCc4cccs4)nn23)c1] | [5-(5-Methoxy-pyridin-3-yl)-imidazo[2,1-b][1,3,4]thiadiazol-2-yl]-thiophen-2-ylmethyl-amine | 344 | |
| 169 | 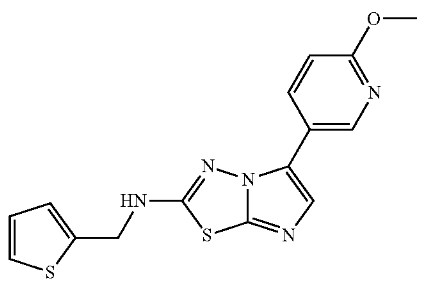 [SMILES: COc1ccc(-c2cnc3sc(NCc4cccs4)nn23)cn1] | [5-(6-Methoxy-pyridin-3-yl)-imidazo[2,1-b][1,3,4]thiadiazol-2-yl]-thiophen-2-ylmethyl-amine | 344 | |
| 170 | 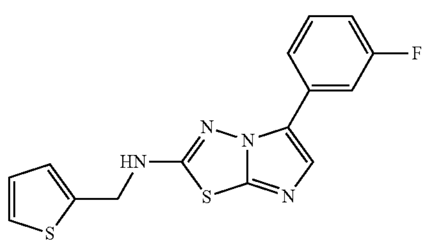 [SMILES: Fc1cccc(-c2cnc3sc(NCc4cccs4)nn23)c1] | [5-(3-Fluoro-phenyl)-imidazo[2,1-b][1,3,4]thiadiazol-2-yl]-thiophen-2-ylmethyl-amine | 331 | |
| 171 | 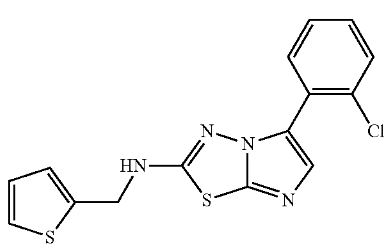 [SMILES: Clc1ccccc1-c1cnc2sc(NCc3cccs3)nn12] | [5-(2-Chloro-phenyl)-imidazo[2,1-b][1,3,4]thiadiazol-2-yl]-thiophen-2-ylmethyl-amine | 347 | |
| 172 | 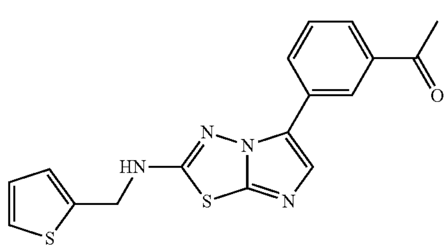 [SMILES: CC(=O)c1cccc(-c2cnc3sc(NCc4cccs4)nn23)c1] | 1-(3-{2-[(Thiophen-2-ylmethyl)-amino]-imidazo[2,1-b][1,3,4]thiadiazol-5-yl}-phenyl)-ethanone | 355 | |

-continued

| No | Structure | Name | HPLC/MS [M + H]+ | NMR DMSO |
|---|---|---|---|---|
| 173 | 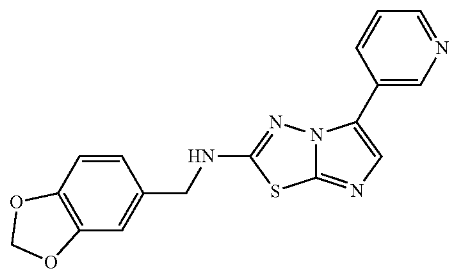 [SMILES: c1cncc(-c2cnc3sc(NCc4ccc5c(c4)OCO5)nn23)c1] | Benzo[1,3]dioxol-5-ylmethyl-(5-pyridin-3-yl-imidazo[2,1-b][1,3,4]thiadiazol-2-yl)-amine | 352 | |
| 174 | 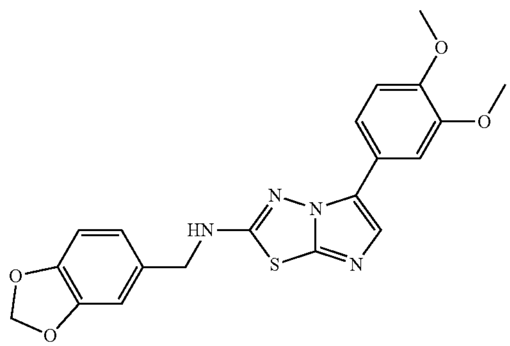 [SMILES: COc1ccc(-c2cnc3sc(NCc4ccc5c(c4)OCO5)nn23)cc1OC] | Benzo[1,3]dioxol-5-ylmethyl-[5-(3,4-dimethoxy-phenyl)-imidazo[2,1-b][1,3,4]thiadiazol-2-yl]-amine | 411 | |
| 175 | 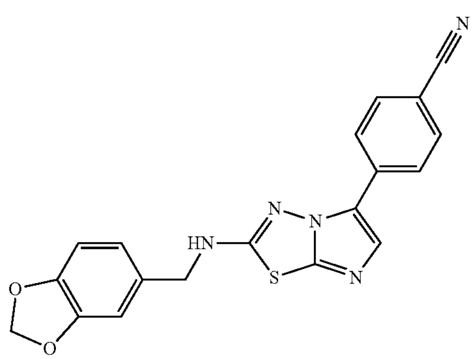 [SMILES: N#Cc1ccc(-c2cnc3sc(NCc4ccc5c(c4)OCO5)nn23)cc1] | 4-{2-[(Benzo[1,3]dioxol-5-ylmethyl)-amino]-imidazo[2,1-b][1,3,4]thiadiazol-5-yl}-benzonitrile | 276 | |
| 176 | 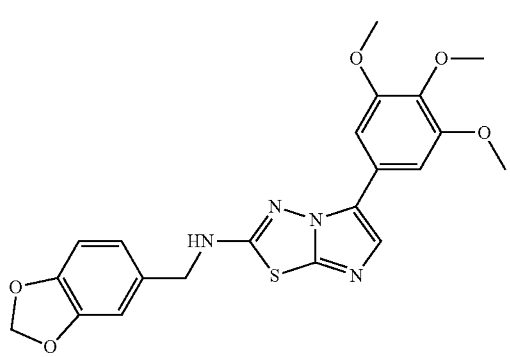 [SMILES: COc1cc(-c2cnc3sc(NCc4ccc5c(c4)OCO5)nn23)cc(OC)c1OC] | Benzo[1,3]dioxol-5-ylmethyl-[5-(3,4,5-trimethoxy-phenyl)-imidazo[2,1-b][1,3,4]thiadiazol-2-yl]-amine | 441 | |

-continued

| No | Structure | Name | HPLC/MS [M + H]+ | NMR DMSO |
|---|---|---|---|---|
| 177 | 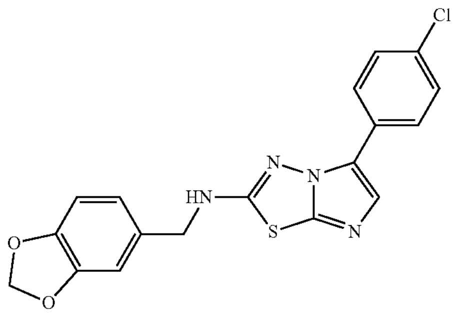 [SMILES: Clc1ccc(-c2cnc3sc(NCc4ccc5c(c4)OCO5)nn23)cc1] | Benzo[1,3]dioxol-5-ylmethyl-[5-(4-chloro-phenyl)-imidazo[2,1-b][1,3,4]thiadiazol-2-yl]-amine | 385 | |
| 178 | 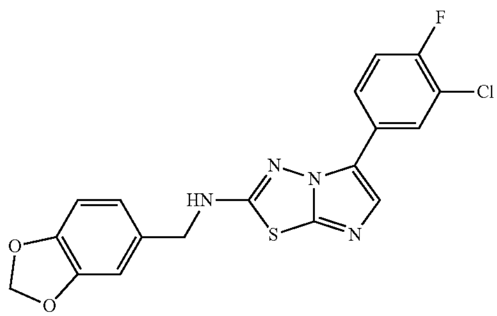 [SMILES: Fc1ccc(-c2cnc3sc(NCc4ccc5c(c4)OCO5)nn23)cc1Cl] | Benzo[1,3]dioxol-5-ylmethyl-[5-(3-chloro-4-fluoro-phenyl)-imidazo[2,1-b][1,3,4]thiadiazol-2-yl]-amine | 403 | |
| 179 | 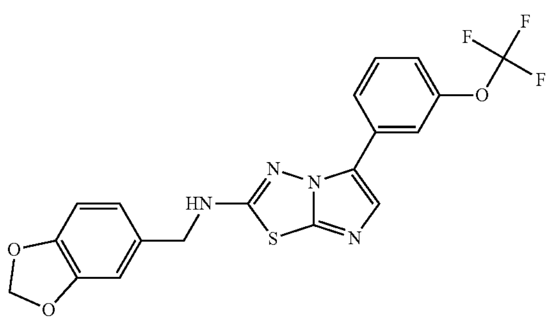 [SMILES: FC(F)(F)Oc1cccc(-c2cnc3sc(NCc4ccc5c(c4)OCO5)nn23)c1] | Benzo[1,3]dioxol-5-ylmethyl-[5-(3-trifluoromethoxy-phenyl)-imidazo[2,1-b][1,3,4]thiadiazol-2-yl]-amine | 435 | |
| 180 | 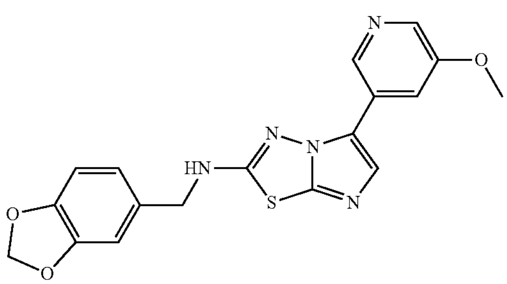 [SMILES: COc1cncc(-c2cnc3sc(NCc4ccc5c(c4)OCO5)nn23)c1] | Benzo[1,3]dioxol-5-ylmethyl-[5-(5-methoxy-pyridin-3-yl)-imidazo[2,1-b][1,3,4]thiadiazol-2-yl]-amine | 382 | |
| 181 | 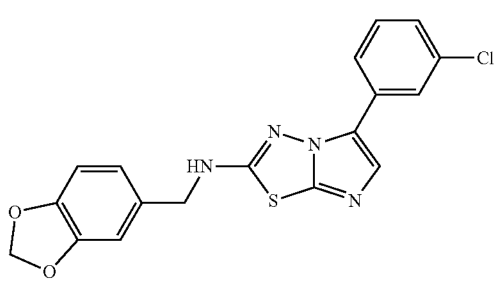 [SMILES: Clc1cccc(-c2cnc3sc(NCc4ccc5c(c4)OCO5)nn23)c1] | Benzo[1,3]dioxol-5-ylmethyl-[5-(3-chloro-phenyl)-imidazo[2,1-b][1,3,4]thiadiazol-2-yl]-amine | 385 | |

-continued

| No | Structure | Name | HPLC/MS [M + H]+ | NMR DMSO |
|---|---|---|---|---|
| 182 | 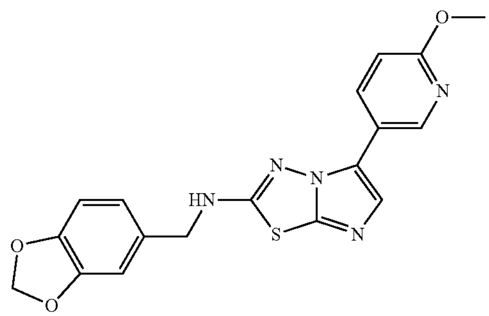 [SMILES: COc1ccc(-c2cnc3sc(NCc4ccc5c(c4)OCO5)nn23)cn1] | Benzo[1,3]dioxol-5-ylmethyl-[5-(6-methoxy-pyridin-3-yl)-imidazo[2,1-b][1,3,4]thiadiazol-2-yl]-amine | 382 | |
| 183 | 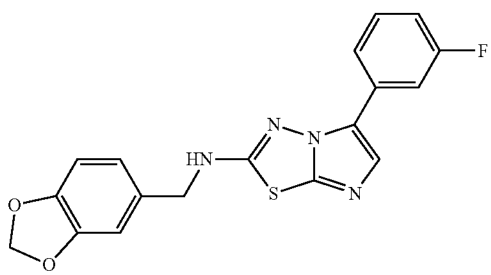 [SMILES: Fc1cccc(-c2cnc3sc(NCc4ccc5c(c4)OCO5)nn23)c1] | Benzo[1,3]dioxol-5-ylmethyl-[5-(3-fluoro-phenyl)-imidazo[2,1-b][1,3,4]thiadiazol-2-yl]-amine | 369 | |
| 184 | 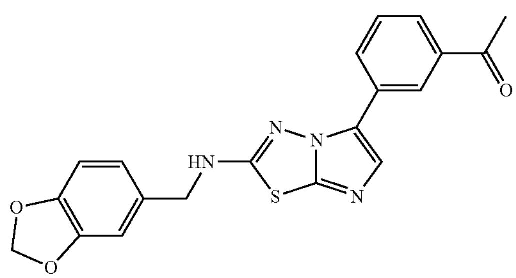 [SMILES: CC(=O)c1cccc(-c2cnc3sc(NCc4ccc5c(c4)OCO5)nn23)c1] | 1-(3-{2-[(Benzo[1,3]dioxol-5-ylmethyl)-amino]-imidazo[2,1-b][1,3,4]thiadiazol-5-yl}-phenyl)-ethanone | 393 | |
| 185 | 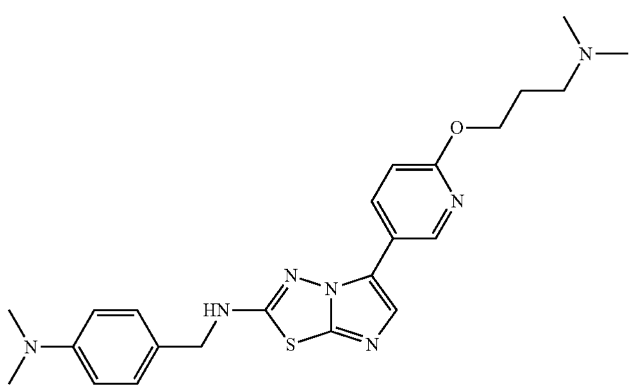 | (4-Dimethylamino-benzyl)-{5-[6-(3-dimethylamino-propoxy)-pyridin-3-yl]-imidazo[2,1-b][1,3,4]thiadiazol-2-yl}-amine | 453 | |
| 186 | 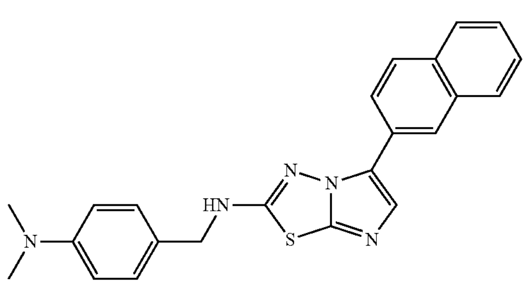 [SMILES: CN(C)c1ccc(CNc2nn3c(-c4ccc5ccccc5c4)cnc3s2)cc1] | (4-Dimethylamino-benzyl)-(5-naphthalen-2-yl-imidazo[2,1-b][1,3,4]thiadiazol-2-yl)-amine | 401 | |

-continued

| No | Structure | Name | HPLC/MS [M + H]+ | NMR DMSO |
|---|---|---|---|---|
| 187 | 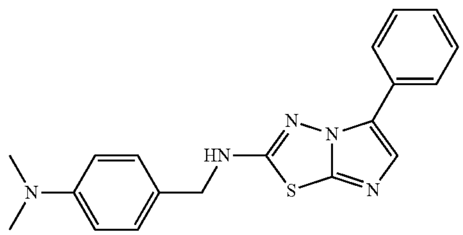 [SMILES: CN(C)c1ccc(CNc2nn3c(-c4ccccc4)cnc3s2)cc1] | (4-Dimethylamino-benzyl)-(5-phenyl-yl-imidazo[2,1-b][1,3,4]thiadiazol-2-yl)-amine | 350 | |
| 188 | 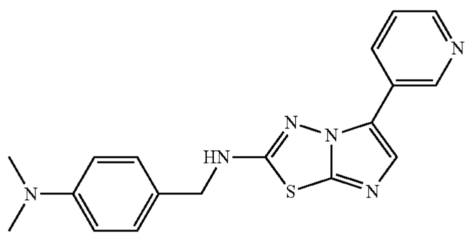 [SMILES: CN(C)c1ccc(CNc2nn3c(-c4cccnc4)cnc3s2)cc1] | (4-Dimethylamino-benzyl)-(5-pyridin-3-yl-yl-imidazo[2,1-b][1,3,4]thiadiazol-2-yl)-amine | 351 | |
| 189 | 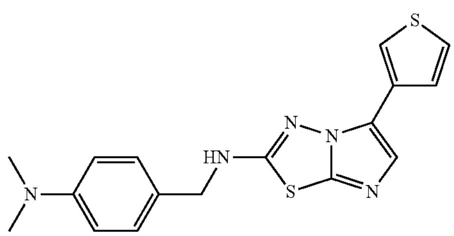 [SMILES: CN(C)c1ccc(CNc2nn3c(-c4ccsc4)cnc3s2)cc1] | (4-Dimethylamino-benzyl)-(5-thiophen-3-yl-imidazo[2,1-b][1,3,4]thiadiazol-2-yl)-amine | 356 | |
| 190 | 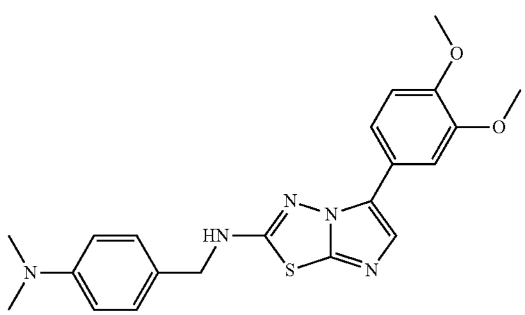 | [5-(3,4-Dimethoxy-phenyl)-imidazo[2,1-b][1,3,4]thiadiazol-2-yl]-(4-dimethylamino-benzyl)-amine | 411 | δ 8.3 (t, 1H), 7.54 (s, 1H), 7.5 (d, 1H), 7.4 (s, 1H), 7.3 (d, 2H), 7.0 (d, 1H), 6.7 (m, 2H), 4.4 (d, 2H), 3.8 (s, 3H), 3.3 (s, 6H), 2.9 (s, 3H) |
| 191 | 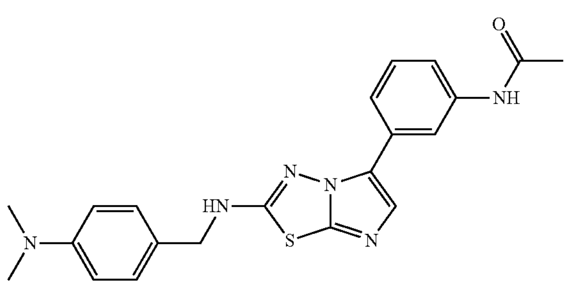 [SMILES: CC(=O)Nc1cccc(-c2cnc3sc(NCc4ccc(N(C)C)cc4)nn23)c1] | N-{3-[2-(4-Dimethylamino-benzylamino)-imidazo[2,1-b][1,3,4]thiadiazol-5-yl]-phenyl}-acetamide | 408 | |

| No | Structure | Name | HPLC/MS [M + H]+ | NMR DMSO |
|---|---|---|---|---|
| 192 | 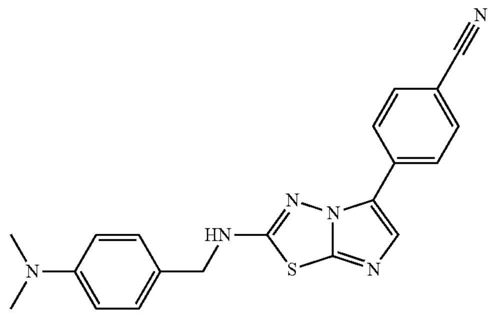 [SMILES: CN(C)c1ccc(CNc2nn3c(-c4ccc(C#N)cc4)cnc3s2)cc1] | 4-[2-(4-Dimethylamino-benzylamino)-imidazo[2,1-b][1,3,4]thiadiazol-5-yl]-benzonitrile | 375 | |
| 193 | 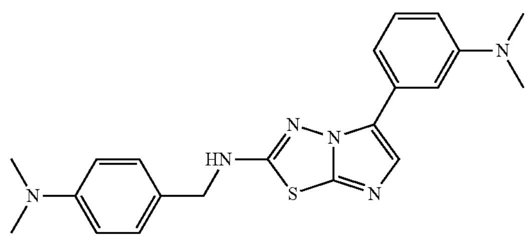 | (4-Dimethylamino-benzyl)-[5-(3-dimethylamino-phenyl)-imidazo[2,1-b][1,3,4]thiadiazol-2-yl]-amine | 394 | |
| 194 | 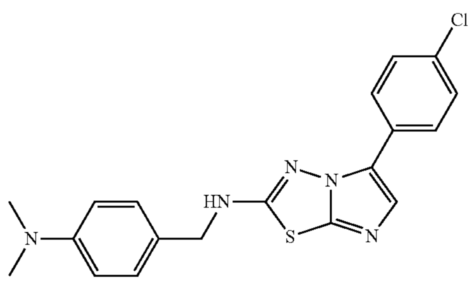 [SMILES: CN(C)c1ccc(CNc2nn3c(-c4ccc(Cl)cc4)cnc3s2)cc1] | [5-(4-Chloro-phenyl)-imidazo[2,1-b][1,3,4]thiadiazol-2-yl]-(4-dimethylamino-benzyl)-amine | 385 | |
| 195 | 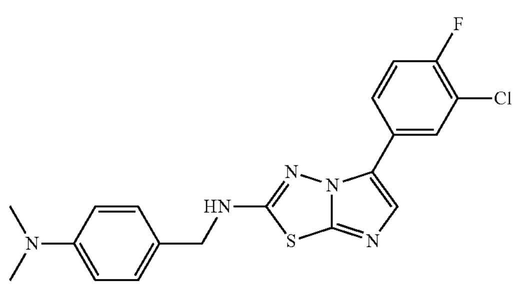 [SMILES: CN(C)c1ccc(CNc2nn3c(-c4ccc(F)c(Cl)c4)cnc3s2)cc1] | [5-(3-Chloro-4-fluoro-phenyl)-imidazo[2,1-b][1,3,4]thiadiazol-2-yl]-(4-dimethylamino-benzyl)-amine | 402 | |
| 196 | 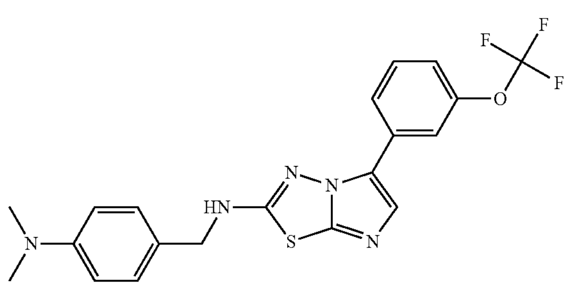 [SMILES: CN(C)c1ccc(CNc2nn3c(-c4cccc(OC(F)(F)F)c4)cnc3s2)cc1] | (4-Dimethylamino-benzyl)-[5-(3-trifluoromethyoxy-phenyl)-imidazo[2,1-b][1,3,4]thiadiazol-2-yl]-amine | 434 | |

| No | Structure | Name | HPLC/MS [M + H]+ | NMR DMSO |
|----|-----------|------|------------------|----------|
| 197 | 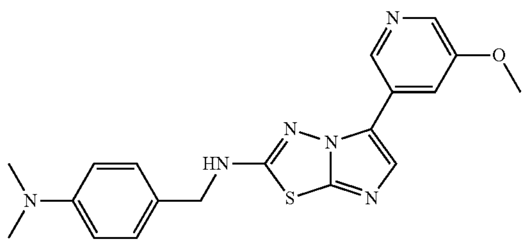 | (4-Dimethylamino-benzyl)-[5-(5-methoxy-pyridin-3-yl)-imidazo[2,1-b][1,3,4]thiadiazol-2-yl]-amine | 381 | |
| 198 | 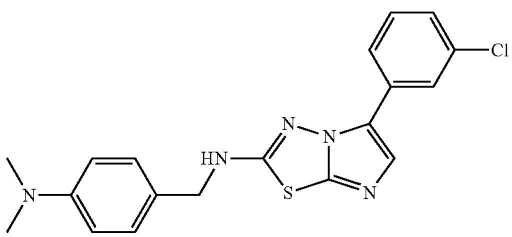 [SMILES: CN(C)c1ccc(CNc2nn3c(-c4cccc(Cl)c4)cnc3s2)cc1] | [5-(3-Chloro-phenyl)-imidazo[2,1-b][1,3,4]thiadiazol-2-yl]-(4-dimethylamino-benzyl)-amine | 384 | |
| 199 | 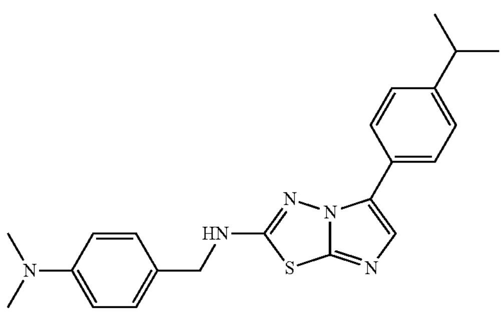 [SMILES: CC(C)c1ccc(-c2cnc3sc(NCc4ccc(N(C)C)cc4)nn23)cc1] | (4-Dimethylamino-benzyl)-[5-(4-isopropyl-phenyl)-imidazo[2,1-b][1,3,4]thiadiazol-2-yl]-amine | 393 | |
| 200 | 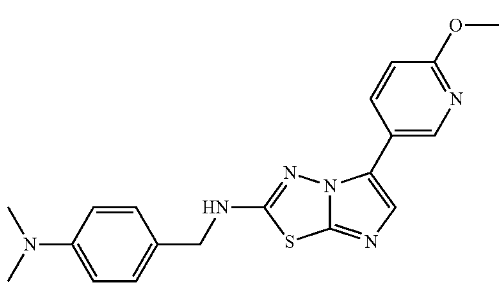 | (4-Dimethylamino-benzyl)-[5-(6-methoxy-pyridin-3-yl)-imidazo[2,1-b][1,3,4]thiadiazol-2-yl]-amine | 381 | |
| 201 | 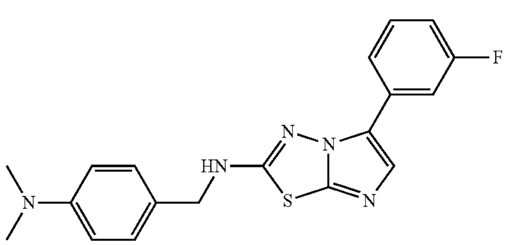 [SMILES: CN(C)c1ccc(CNc2nn3c(-c4cccc(F)c4)cnc3s2)cc1] | (4-Dimethylamino-benzyl)-[5-(3-fluoro-phenyl)-imidazo[2,1-b][1,3,4]thiadiazol-2-yl]-amine | 368 | |

-continued

| No | Structure | Name | HPLC/MS [M + H]+ | NMR DMSO |
|---|---|---|---|---|
| 202 | 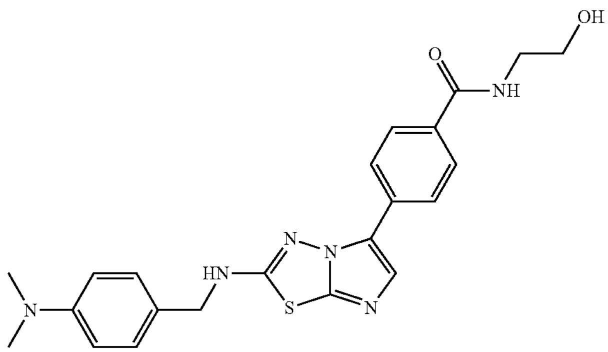 | 4-[2-(4-Dimethylamino-benzylamino)-imidazo[2,1-b][1,3,4]thiadiazol-5-yl]-N-(2-hydroxy-ethyl)-benzamide | 438 | |
| 203 | 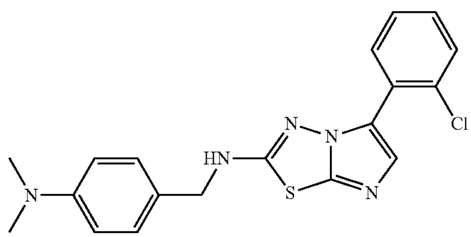 [SMILES: CN(C)c1ccc(CNc2nn3c(-c4ccccc4Cl)cnc3s2)cc1] | [5-(2-Chloro-phenyl)-imidazo[2,1-b][1,3,4]thiadiazol-2-yl]-(4-dimethylamino-benzyl)-amine | 384 | |
| 204 | 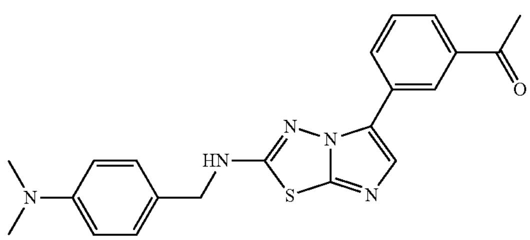 [SMILES: CC(=O)c1cccc(-c2cnc3sc(NCc4ccc(N(C)C)cc4)nn23)c1] | 1-{3-[2-(4-Dimethylamino-benzylamino)-imidazo[2,1-b][1,3,4]thiadiazol-5-yl]-phenyl}-ethanone | 392 | |
| 205 | 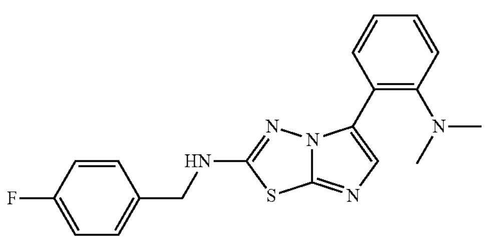 [SMILES: CN(C)c1ccccc1-c1cnc2sc(NCc3ccc(F)cc3)nn12] | [5-(2-Dimethylamino-phenyl)-imidazo[2,1-b][1,3,4]thiadiazol-2-yl]-(4-fluoro-benzyl)-amine | 368 | |
| 206 | 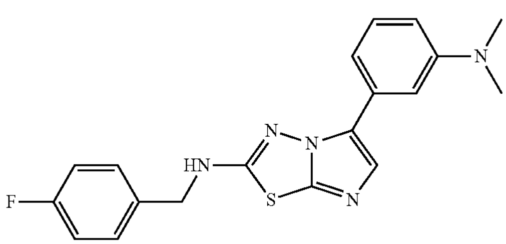 [SMILES: CN(C)c1cccc(-c2cnc3sc(NCc4ccc(F)cc4)nn23)c1] | [5-(3-Dimethylamino-phenyl)-imidazo[2,1-b][1,3,4]thiadiazol-2-yl]-(4-fluoro-benzyl)-amine | 368 | |
| 207 | 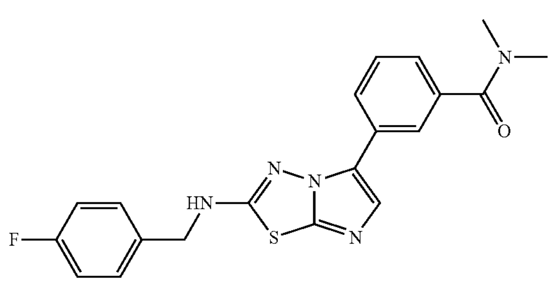 [SMILES: CN(C)C(=O)c1cccc(-c2cnc3sc(NCc4ccc(F)cc4)nn23)c1] | 3-[2-(4-Fluoro-benzylamino)-imidazo[2,1-b][1,3,4]thiadiazol-5-yl]-N,N-dimethyl-benzamide | 396 | |

-continued

| No | Structure | Name | HPLC/MS [M + H]+ | NMR DMSO |
|---|---|---|---|---|
| 208 | 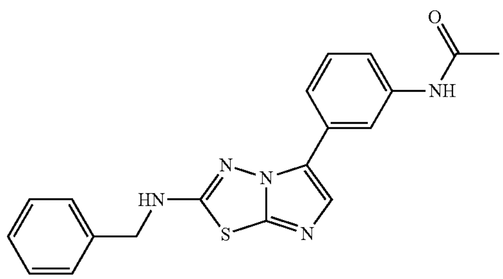 [SMILES: CC(=O)Nc1cccc(-c2cnc3sc(NCc4ccccc4)nn23)c1] | N-[3-(2-Benzylamino)-imidazo[2,1-b][1,3,4]thiadiazol-5-yl)phenyl]-acetamide | 364 | |
| 209 | 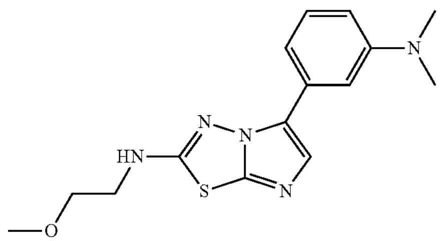 | [5-(3-Dimethylamino-phenyl)-imidazo[2,1-b][1,3,4]thiadiazol-2-yl]-(2-methoxy-ethyl)-amine | 318 | |
| 210 | 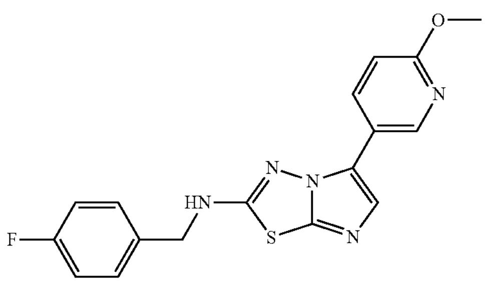 [SMILES: COc1ccc(-c2cnc3sc(NCc4ccc(F)cc4)nn23)cn1] | (4-Fluoro-benzyl)-[5-(6-methoxy-pyridin-3-yl)-imidazo[2,1-b][1,3,4]thiadiazol-2-yl]-amine | 356 | |
| 211 | 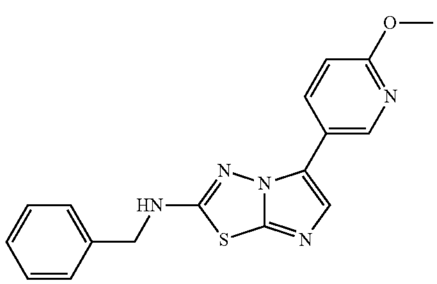 [SMILES: COc1ccc(-c2cnc3sc(NCc4ccccc4)nn23)cn1] | Benzyl)-[5-(6-methoxy-pyridin-3-yl)-imidazo[2,1-b][1,3,4]thiadiazol-2-yl]-amine | 338 | |
| 212 | 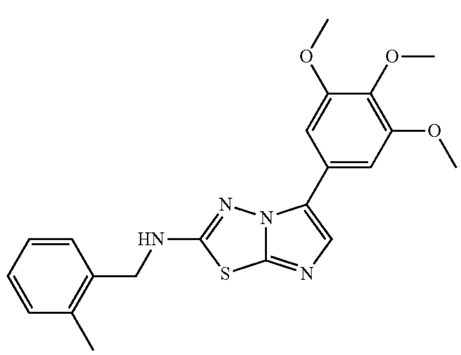 [SMILES: COc1cc(-c2cnc3sc(NCc4ccccc4C)nn23)cc(OC)c1OC] | (2-Methyl-benzyl)-[5-(3,4,5-trimethoxy-phenyl)-imidazo[2,1-b][1,3,4]thiadiazol-2-yl]-amine | 411 | |

-continued

| No | Structure | Name | HPLC/MS [M + H]+ | NMR DMSO |
|---|---|---|---|---|
| 213 | 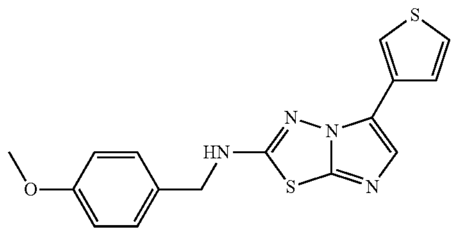 [SMILES: COc1ccc(CNc2nn3c(-c4ccsc4)cnc3s2)cc1] | (4-Methoxy-benzyl)-(5-thiophen-3-yl-imidazo[2,1-b][1,3,4]thiadiazol-2-yl)-amine | 342 | |
| 214 | 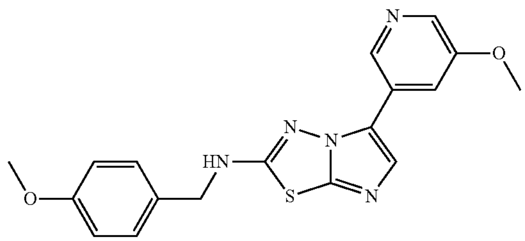 | (4-Methoxy-benzyl)-[5-(5-methoxy-pyridin-3-yl)-imidazo[2,1-b][1,3,4]thiadiazol-2-yl]-amine | 368 | |
| 215 | 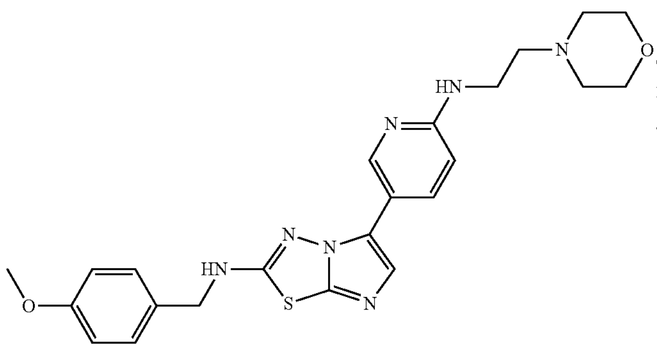 [SMILES: COc1ccc(CNc2nn3c(-c4ccc(NCCN5CCOCC5)nc4)cnc3s2)cc1] | (4-Methoxy-benzyl)-{5-[6-(2-morpholin-4-yl-ethylamino)-pyridin-3-yl]-imidazo[2,1-b][1,3,4]thiadiazol-2-yl}-amine | 467 | |
| 216 | 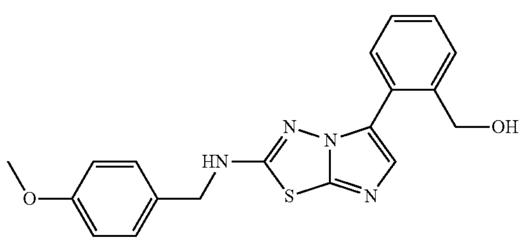 [SMILES: COc1ccc(CNc2nn3c(-c4ccccc4CO)cnc3s2)cc1] | {2-[2-(4-Methoxy-benzylamino)-imidazo[2,1-b][1,3,4]thiadiazol-5-yl]-phenyl}-methanol | 367 | |
| 217 | 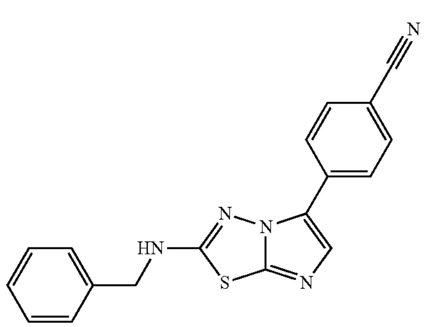 [SMILES: N#Cc1ccc(-c2cnc3sc(NCc4ccccc4)nn23)cc1] | 4-(2-Benzylamino)-imidazo[2,1-b][1,3,4]thiadiazol-5-yl)benzonitrile | 332 | |

| No | Structure | Name | HPLC/MS [M + H]+ | NMR DMSO |
|---|---|---|---|---|
| 218 | 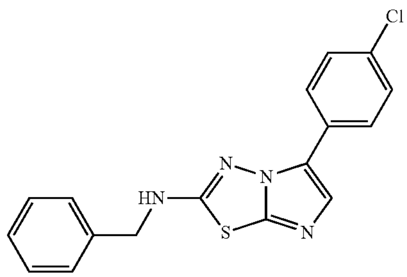 [SMILES: Clc1ccc(-c2cnc3sc(NCc4ccccc4)nn23)cc1] | Benzyl-[5-(4-chloro-phenyl)-imidazo[2,1-b][1,3,4]thiadiazol-2-yl]-amine | 341 | |
| 219 | 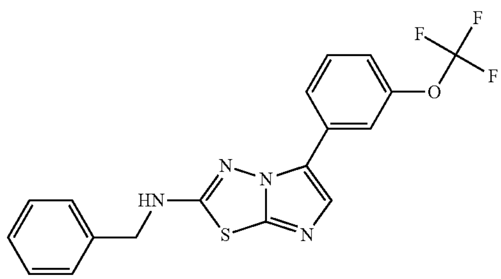 [SMILES: FC(F)(F)Oc1cccc(-c2cnc3sc(NCc4ccccc4)nn23)c1] | Benzyl-[5-(3-trifluoromethoxy-phenyl)-imidazo[2,1-b][1,3,4]thiadiazol-2-yl]-amine | 391 | |
| 220 | 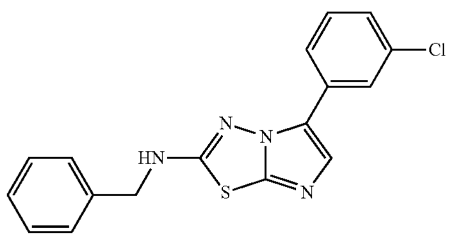 [SMILES: Clc1cccc(-c2cnc3sc(NCc4ccccc4)nn23)c1] | Benzyl-[5-(3-chloro-phenyl)-imidazo[2,1-b][1,3,4]thiadiazol-2-yl]-amine | 341 | |
| 221 | 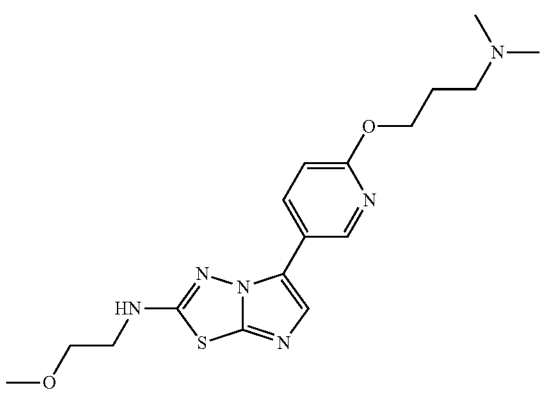 | {5-[6-(3-Dimethylamino-propoxy)-pyridin-3-yl]-imidazo[2,1-b][1,3,4]thiadiazol-2-yl}-(2-methoxy-ethyl)-amine | 377 | |
| 222 | 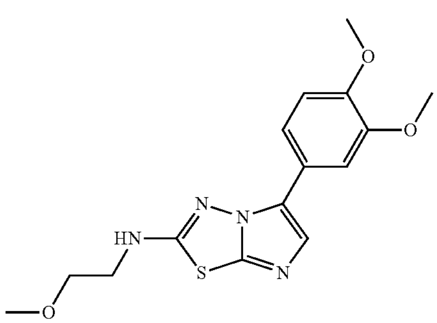 | [5-(3,4-Dimethoxy-phenyl)-imidazo[2,1-b][1,3,4]thiadiazol-2-yl]-(2-methoxy-ethyl)-amine | 335 | δ 8.1 (t, 1H), 7.6 (s, 1H), 7.5 (d, 1H), 7.4 (s, 1H), 7.0 (d, 1H), 3.8 (s, 3H), 3.78 (s, 3H), 3.6 (m, 2H), 3.5 (m, 2H), 3.3 (s, 3H) |

-continued

| No | Structure | Name | HPLC/MS [M + H]+ | NMR DMSO |
|---|---|---|---|---|
| 223 | 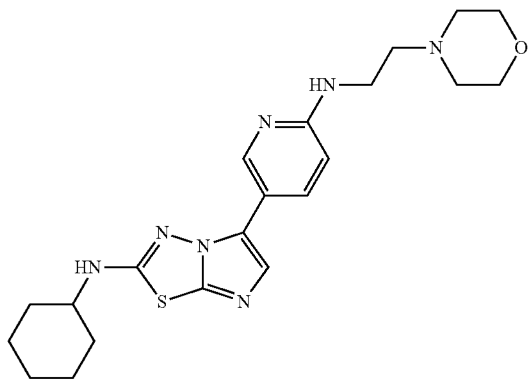 [SMILES: c1cc(NCCN2CCOCC2)ncc1-c1cnc2sc(NC3CCCCC3)nn12] | Cyclohexyl-{5-[6-(2-morpholin-4-yl-ethylamino)-pyridin-3-yl]-imidazo[2,1-b][1,3,4]thiadiazol-2-yl}-amine | 429 | |
| 224 | 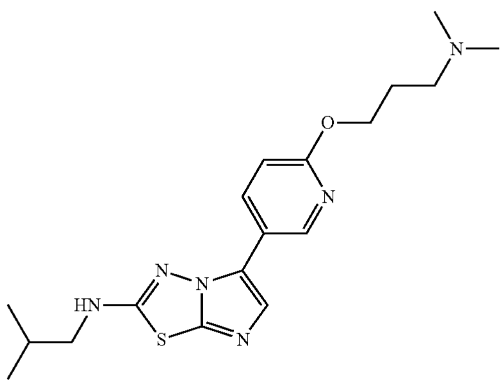 [SMILES: CC(C)CNc1nn2c(-c3ccc(OCCCN(C)C)nc3)cnc2s1] | {5-[6-(3-Dimethylamino-propoxy)-pyridin-3-yl]-imidazo[2,1-b][1,3,4]thiadiazol-2-yl}-isobutyl-amine | 376 | |
| 225 | 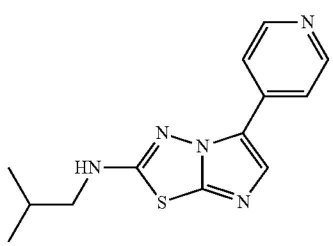 [SMILES: CC(C)CNc1nn2c(-c3ccncc3)cnc2s1] | Isobutyl-(5-pyridin-4-yl-imidazo[2,1-b][1,3,4]thiadiazol-2-yl)-amine | 274 | |
| 226 | 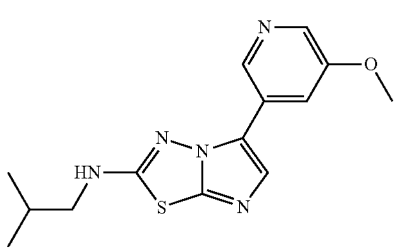 [SMILES: COc1cncc(-c2cnc3sc(NCC(C)C)nn23)c1] | Isobutyl-[5-(5-methoxy-pyridin-3-yl)-imidazo[2,1-b][1,3,4]thiadiazol-2-yl]-amine | 304 | |

-continued

| No | Structure | Name | HPLC/MS [M + H]+ | NMR DMSO |
|---|---|---|---|---|
| 227 | 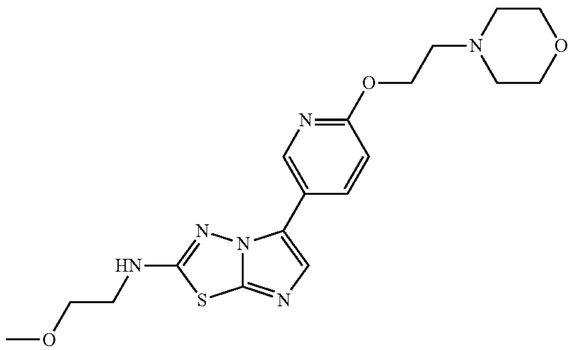 [SMILES: COCCNc1nn2c(-c3ccc(OCCN4CCOCC4)nc3)cnc2s1] | (2-Methoxy-ethyl)-{5-[6-(2-morpholin-4-yl-ethylamino)-pyridin-3-yl]-imidazo[2,1-b][1,3,4]thiadiazol-2-yl}-amine | 405 | |
| 228 | 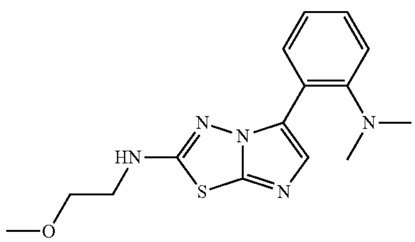 | [5-(2-Dimethylamino-phenyl)-imidazo[2,1-b][1,3,4]thiadiazol-2-yl]-(2-methoxy-ethyl)-amine | 318 | |
| 229 | 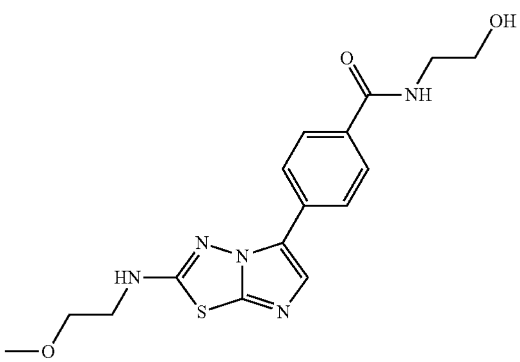 [SMILES: COCCNc1nn2c(-c3ccc(C(=O)NCCO)cc3)cnc2s1] | N-(2-Hydroxy-ethyl)-4-[2-(2-methoxy-ethylamino)-imidazo[2,1-b][1,3,4]thiadiazol-5-yl]-benzamide | 362 | |
| 230 | 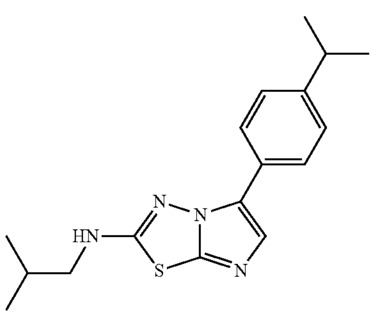 [SMILES: CC(C)CNc1nn2c(-c3ccc(C(C)C)cc3)cnc2s1] | Isobutyl-[5-(4-isopropyl-phenyl)-imidazo[2,1-b][1,3,4]thiadiazol-2-yl]-amine | 315 | |
| 231 | 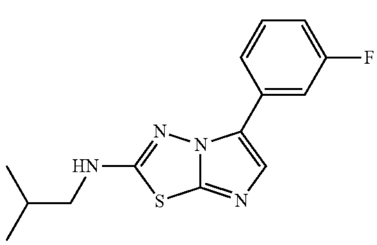 [SMILES: CC(C)CNc1nn2c(-c3cccc(F)c3)cnc2s1] | [5-(3-Fluoro-phenyl)-imidazo[2,1-b][1,3,4]thiadiazol-2-yl]-isobutyl-amine | 291 | |

-continued

| No | Structure | Name | HPLC/MS [M + H]+ | NMR DMSO |
|----|-----------|------|------------------|----------|
| 232 | 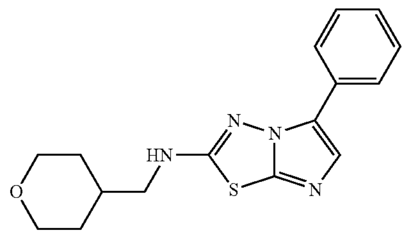 [SMILES: c1ccc(-c2cnc3sc(NCC4CCOCC4)nn23)cc1] | (5-Phenyl-imidazo[2,1-b][1,3,4]thiadiazol-2-yl)-(tetrahydro-pyran-4-ylmethyl)-amine | 315 | |
| 233 | 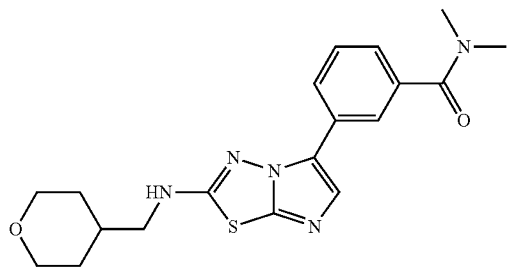 [SMILES: CN(C)C(=O)c1cccc(-c2cnc3sc(NCC4CCOCC4)nn23)c1] | N,N-Dimethyl-3-{2-[(tetrahydro-pyran-4-ylmethyl)-amino]-imidazo[2,1-b][1,3,4]thiadiazol-5-yl}-benzamide | 386 | |
| 234 | 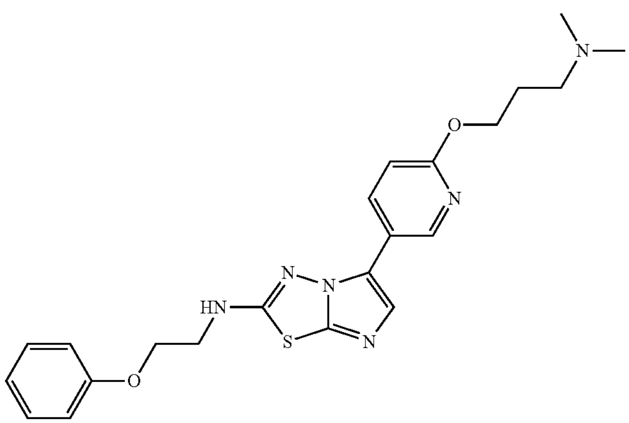 [SMILES: CN(C)CCCOc1ccc(-c2cnc3sc(NCCOc4ccccc4)nn23)cn1] | {5-[6-(3-Dimethylamino-propoxy)-pyridin-3-yl]-imidazo[2,1-b][1,3,4]thiadiazol-2-yl}-(2-phenoxy-ethyl)-amine | 440 | |
| 235 | 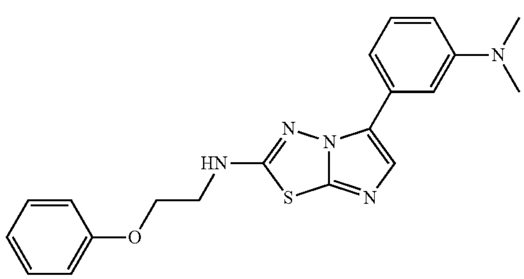 [SMILES: CN(C)c1cccc(-c2cnc3sc(NCCOc4ccccc4)nn23)c1] | [5-(3-Dimethylamino-phenyl)-imidazo[2,1-b][1,3,4]thiadiazol-2-yl]-(2-phenoxy-ethyl)-amine | 380 | |
| 236 | 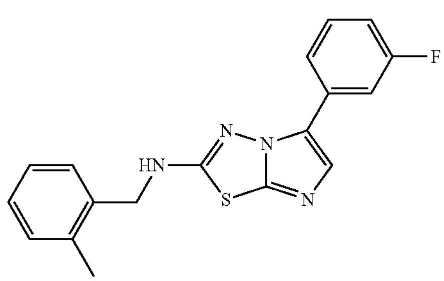 [SMILES: Cc1ccccc1CNc1nn2c(-c3cccc(F)c3)cnc2s1] | [5-(3-Fluoro-phenyl)-imidazo[2,1-b][1,3,4]thiadiazol-2-yl]-(2-methyl-benzyl)-amine | 339 | |

-continued

| No | Structure | Name | HPLC/MS [M + H]+ | NMR DMSO |
|---|---|---|---|---|
| 237 | 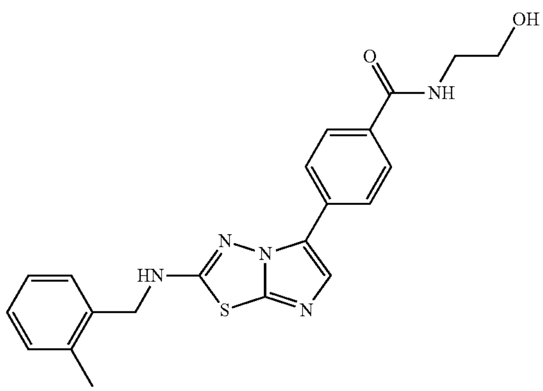 [SMILES: Cc1ccccc1CNc1nn2c(-c3ccc(C(=O)NCCO)cc3)cnc2s1] | N-(2-Hydroxy-ethyl)-4-[2-(2-methyl-benzylamino)-imidazo[2,1-b][1,3,4]thiadiazol-5-yl]-benzamide | 408 | |
| 238 | 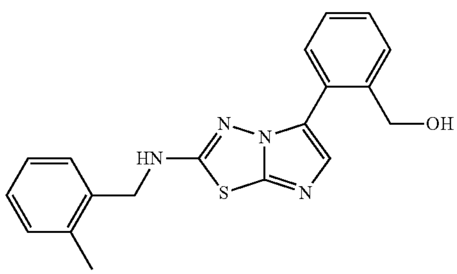 [SMILES: Cc1ccccc1CNc1nn2c(-c3ccccc3CO)cnc2s1] | {2-[2-(2-Methyl-benzylamino)-imidazo[2,1-b][1,3,4]thiadiazol-5-yl]-phenyl}-methanol | 351 | |
| 239 | 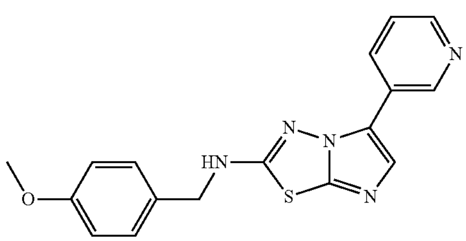 [SMILES: COc1ccc(CNc2nn3c(-c4cccnc4)cnc3s2)cc1] | (4-Methoxy-benzyl)-(5-pyridin-3-yl-imidazo[2,1-b][1,3,4]thiadiazol-2-yl)-amine | 338 | |
| 240 | 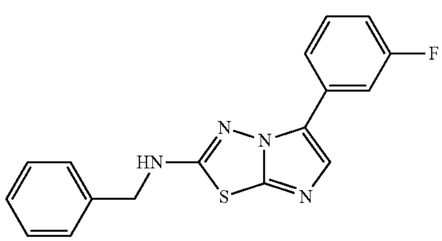 [SMILES: Fc1cccc(-c2cnc3sc(NCc4ccccc4)nn23)c1] | Benzyl-[5-(3-fluoro-phenyl)-imidazo[2,1-b][1,3,4]thiadiazol-2-yl]-amine | 325 | |
| 241 | 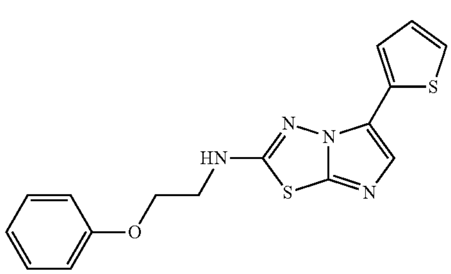 [SMILES: c1ccc(OCCNc2nn3c(-c4cccs4)cnc3s2)cc1] | (2-Phenoxy-ethyl)-(5-thiophen-2-yl-imidazo[2,1-b][1,3,4]thiadiazol-2-yl)-amine | 343 | |

-continued

| No | Structure | Name | HPLC/MS [M + H]+ | NMR DMSO |
|---|---|---|---|---|
| 242 | 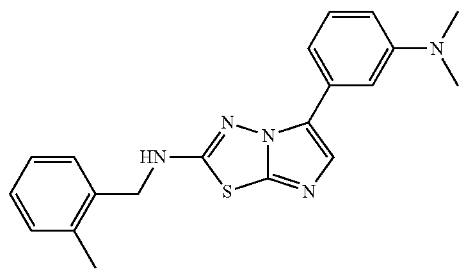 [SMILES: Cc1ccccc1CNc1nn2c(-c3cccc(N(C)C)c3)cnc2s1] | [5-(3-Dimethylamino-phenyl)-imidazo[2,1-b][1,3,4]thiadiazol-2-yl]-(2-methyl-benzyl)-amine | 364 | |
| 243 | 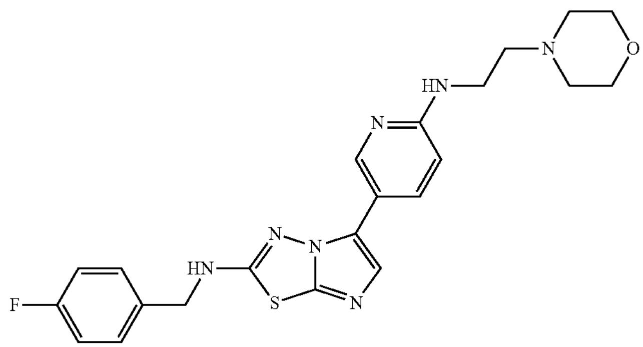 [SMILES: Fc1ccc(CNc2nn3c(-c4ccc(NCCN5CCOCC5)nc4)cnc3s2)cc1] | (4-Fluoro-benzyl)-{5-[6-(2-morpholin-4-yl-ethylamino)-pyridin-3-yl]-imidazo[2,1-b][1,3,4]thiadiazol-2-yl}-amine | 455 | |
| 244 | 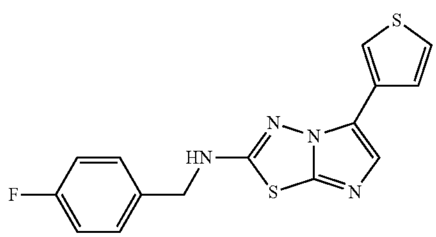 [SMILES: Fc1ccc(CNc2nn3c(-c4ccsc4)cnc3s2)cc1] | (4-Fluoro-benzyl)-(5-thiophen-3-yl-imidazo[2,1-b][1,3,4]thiadiazol-2-yl)-amine | 331 | |
| 245 | 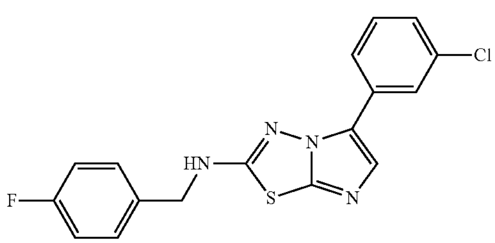 [SMILES: Fc1ccc(CNc2nn3c(-c4cccc(Cl)c4)cnc3s2)cc1] | [5-(3-Chloro-phenyl)-imidazo[2,1-b][1,3,4]thiadiazol-2-yl]-(4-fluoro-benzyl)-amine | 359 | |
| 246 | 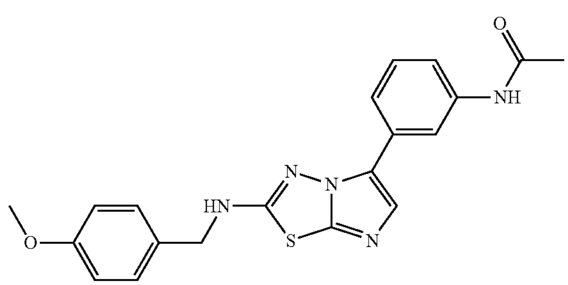 [SMILES: COc1ccc(CNc2nn3c(-c4cccc(NC(C)=O)c4)cnc3s2)cc1] | N-{3-[2-(4-Methoxy-benzylamino)-imidazo[2,1-b][1,3,4]thiadiazol-5-yl]-phenyl}-acetamide | 394 | |

-continued

| No | Structure | Name | HPLC/MS [M + H]+ | NMR DMSO |
|---|---|---|---|---|
| 247 | 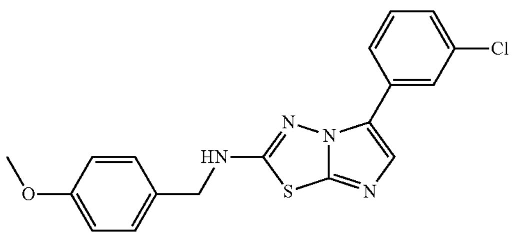 [SMILES: COc1ccc(CNc2nn3c(-c4cccc(Cl)c4)cnc3s2)cc1] | [5-(3-Chloro-phenyl)-imidazo[2,1-b][1,3,4]thiadiazol-2-yl]-(4-methoxy-benzyl)-amine | 371 | |
| 248 | 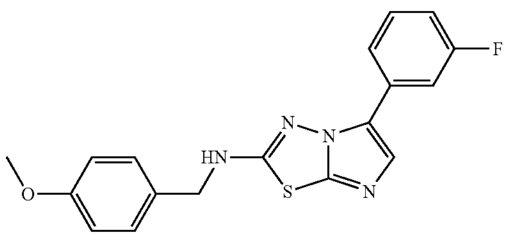 [SMILES: COc1ccc(CNc2nn3c(-c4cccc(F)c4)cnc3s2)cc1] | [5-(3-Fluoro-phenyl)-imidazo[2,1-b][1,3,4]thiadiazol-2-yl]-(4-methoxy-benzyl)-amine | 355 | |
| 249 | 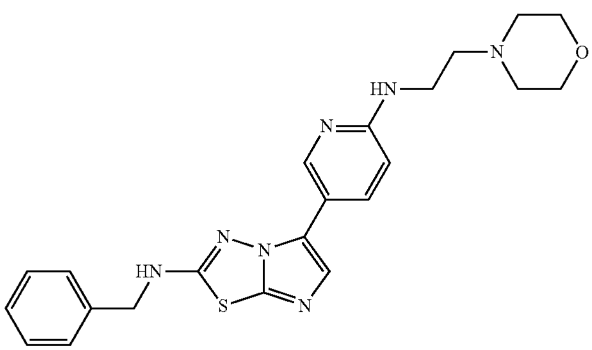 [SMILES: c1ccc(CNc2nn3c(-c4ccc(NCCN5CCOCC5)nc4)cnc3s2)cc1] | Benzyl-{5-[6-(2-morpholin-4-yl-ethylamino)-pyridin-3-yl]-imidazo[2,1-b][1,3,4]thiadiazol-2-yl}-amine | 437 | |
| 250 | 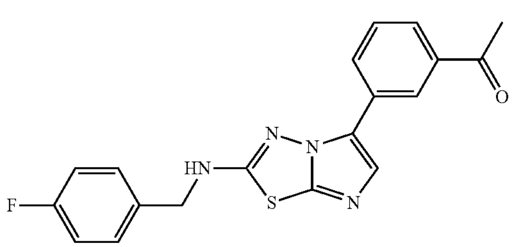 [SMILES: CC(=O)c1cccc(-c2cnc3sc(NCc4ccc(F)cc4)nn23)c1] | 1-{3-[2-(4-Fluoro-benzylamino)-imidazo[2,1-b][1,3,4]thiadiazol-5-yl]-phenyl}-ethanone | 367 | |
| 251 | 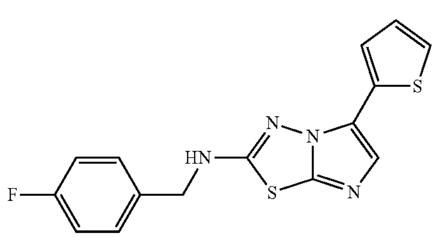 [SMILES: Fc1ccc(CNc2nn3c(-c4cccs4)cnc3s2)cc1] | (4-Fluoro-benzyl)-(5-thiophen-2-yl-imidazo[2,1-b][1,3,4]thiadiazol-2-yl)-amine | 331 | |

-continued

| No | Structure | Name | HPLC/MS [M + H]+ | NMR DMSO |
|---|---|---|---|---|
| 252 | 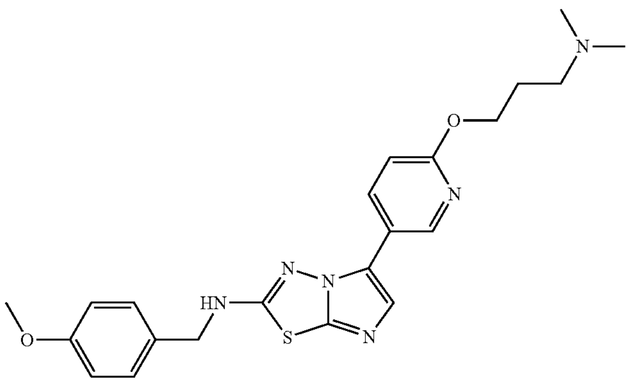 | {5-[6-(3-Dimethylamino-propoxy)-pyridin-3-yl]-imidazo[2,1-b][1,3,4]thiadiazol-2-yl}-(4-methoxy-benzyl)-amine | 440 | |
| 253 | 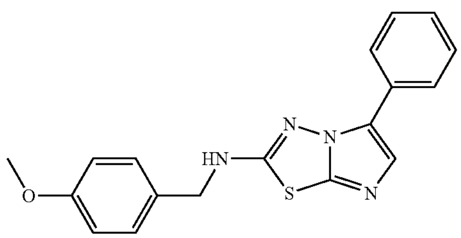 [SMILES: COc1ccc(CNc2nn3c(-c4ccccc4)cnc3s2)cc1] | (4-Methoxy-benzyl)-(5-phenyl)-imidazo[2,1-b][1,3,4]thiadiazol-2-yl)-amine | 337 | |
| 254 | 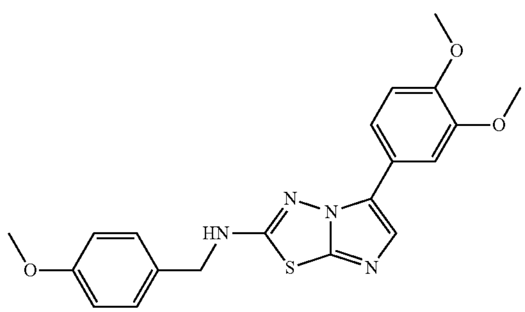 | [5-(3,4-Dimethoxy-phenyl)-imidazo[2,1-b][1,3,4]thiadiazol-2-yl]-(4-methoxy-benzyl)-amine | 397 | δ 8.4 (t, 1H), 7.5 (s, 1H), 7.46 (d, 1H), 7.4 (s, 1H), 7.3 (d, 2H), 7.0 (d, 1H), 6.9 (d, 2H), 4.5 (d, 2H), 3.8 (d, 6H), 3.7 (s, 3H) |
| 255 | 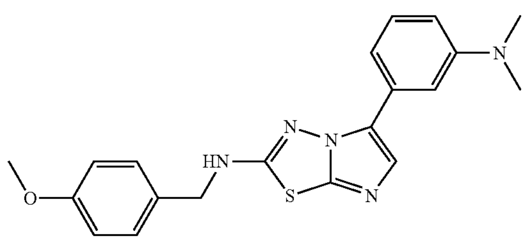 | [5-(3-Dimethylamino-phenyl)-imidazo[2,1-b][1,3,4]thiadiazol-2-yl]-(4-methoxy-benzyl)-amine | 380 | |
| 256 | 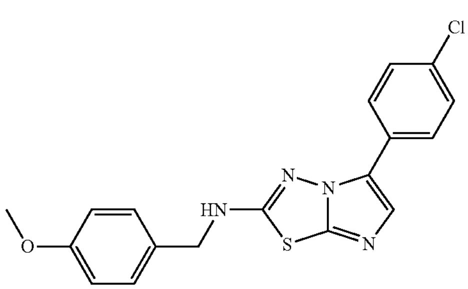 [SMILES: COc1ccc(CNc2nn3c(-c4ccc(Cl)cc4)cnc3s2)cc1] | [5-(4-Chloro-phenyl)-imidazo[2,1-b][1,3,4]thiadiazol-2-yl]-(4-methoxy-benzyl)-amine | 371 | |

| No | Structure | Name | HPLC/MS [M + H]+ | NMR DMSO |
|---|---|---|---|---|
| 257 | 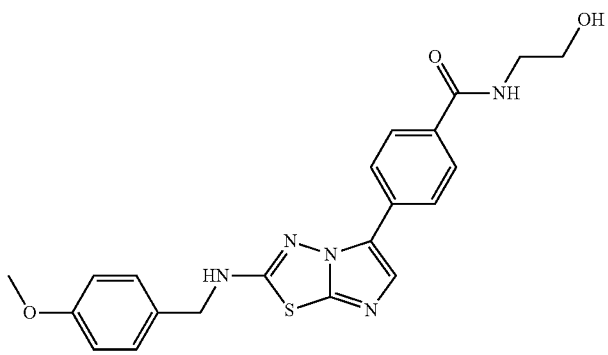 [SMILES: COc1ccc(CNc2nn3c(-c4ccc(C(=O)NCCO)cc4)cnc3s2)cc1] | N-(2-Hydroxy-ethyl)-4-[2-(4-methoxy-benzylamino)-imidazo[2,1-b][1,3,4]thiadiazol-5-yl]-benzamide | 424 | |
| 258 | 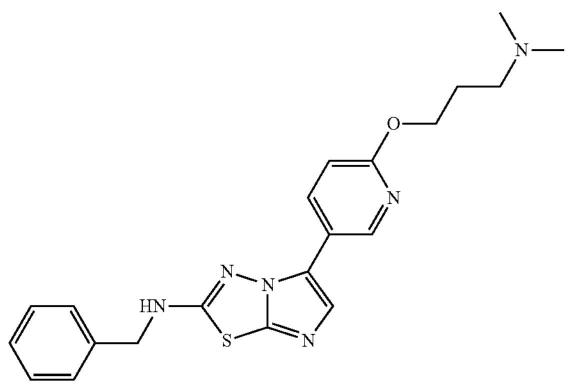 [SMILES: CN(C)CCCOc1ccc(-c2cnc3sc(NCc4ccccc4)nn23)cn1] | Benzyl-{5-[6-(3-dimethylamino-propoxy)-pyridin-3-yl]-imidazo[2,1-b][1,3,4]thiadiazol-2-yl}-amine | 410 | |
| 259 | 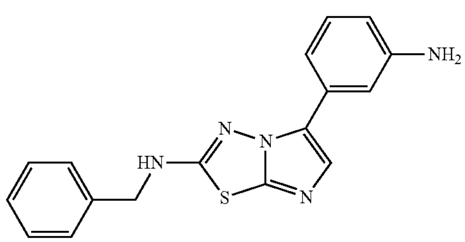 [SMILES: Nc1cccc(-c2cnc3sc(NCc4ccccc4)nn23)c1] | [5-(3-Amino-phenyl)-imidazo[2,1-b][1,3,4]thiadiazol-2-yl]-benzyl-amine | 322 | |
| 260 | 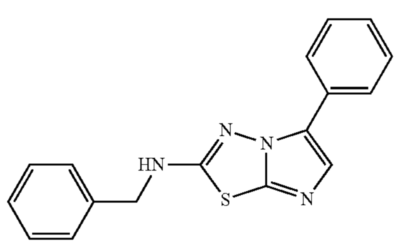 [SMILES: c1ccc(CNc2nn3c(-c4ccccc4)cnc3s2)cc1] | Benzyl-(5-phenyl-imidazo[2,1-b][1,3,4]thiadiazol-2-yl)-amine | 307 | |
| 261 | 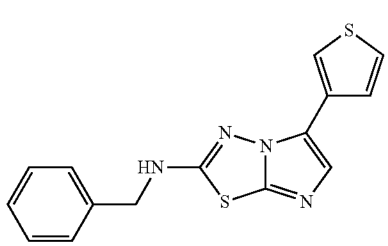 [SMILES: c1ccc(CNc2nn3c(-c4ccsc4)cnc3s2)cc1] | Benzyl-(5-thiophen-3-yl-imidazo[2,1-b][1,3,4]thiadiazol-2-yl)-amine | 313 | |

| No | Structure | Name | HPLC/MS [M + H]+ | NMR DMSO |
|---|---|---|---|---|
| 262 | 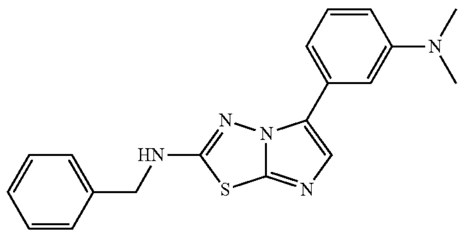 [SMILES: CN(C)c1cccc(-c2cnc3sc(NCc4ccccc4)nn23)c1] | Benzyl-[5-(3-dimethylamino-phenyl)-imidazo[2,1-b][1,3,4]thiadiazol-2-yl]-amine | 350 | |
| 263 | 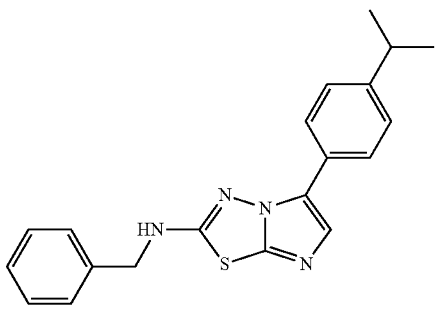 [SMILES: CC(C)c1ccc(-c2cnc3sc(NCc4ccccc4)nn23)cc1] | Benzyl-[5-(4-isopropyl-phenyl)-imidazo[2,1-b][1,3,4]thiadiazol-2-yl]-amine | 349 | |
| 264 | 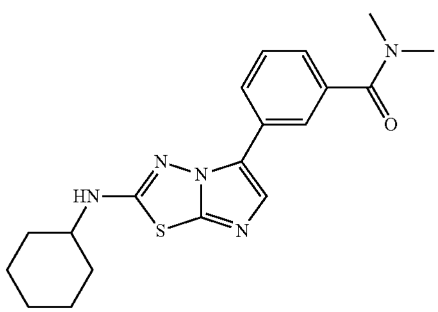 [SMILES: CN(C)C(=O)c1cccc(-c2cnc3sc(NC4CCCCC4)nn23)c1] | 3-(2-Cyclohexylamino-imidazo[2,1-b][1,3,4]thiadiazol-5-yl)-N,N-dimethyl-benzamide | 370 | |
| 265 | 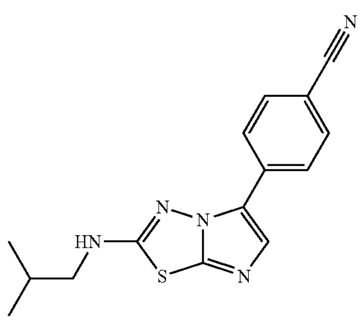 [SMILES: CC(C)CNc1nn2c(-c3ccc(C#N)cc3)cnc2s1] | 4-(2-Isobutylamino-imidazo[2,1-b][1,3,4]thiadiazol-5-yl)-benzonitrile | 298 | |
| 266 | 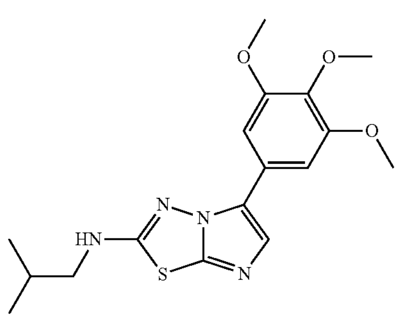 [SMILES: COc1cc(-c2cnc3sc(NCC(C)C)nn23)cc(OC)c1OC] | Isobutyl-[5-(3,4,5-trimethoxy-phenyl)-imidazo[2,1-b][1,3,4]thiadiazol-2-yl]-amine | 363 | |

| No | Structure | Name | HPLC/MS [M + H]+ | NMR DMSO |
|----|-----------|------|------------------|----------|
| 267 | 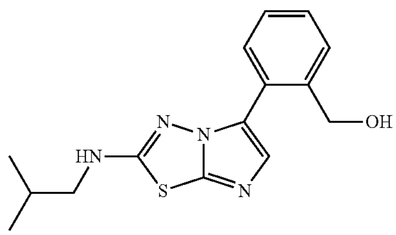 [SMILES: CC(C)CNc1nn2c(-c3ccccc3CO)cnc2s1] | [2-(2-Isobutylamino-imidazo[2,1-b][1,3,4]thiadiazol-5-yl)-phenyl]-methanol | 303 | |
| 268 | 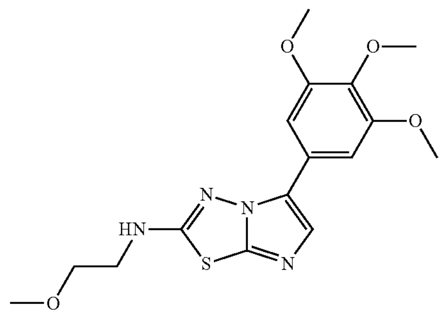 | (2-Methoxy-ethyl)-[5-(3,4,5-trimethoxy-phenyl)-imidazo[2,1-b][1,3,4]thiadiazol-2-yl]-amine | 365 | |
| 269 | 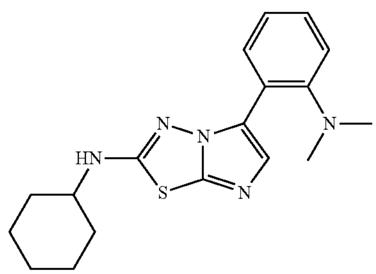 [SMILES: CN(C)c1ccccc1-c1cnc2sc(NC3CCCCC3)nn12] | Cyclohexyl-[5-(2-dimethylamino-phenyl)-imidazo[2,1-b][1,3,4]thiadiazol-2-yl]-amine | 342 | |
| 270 | 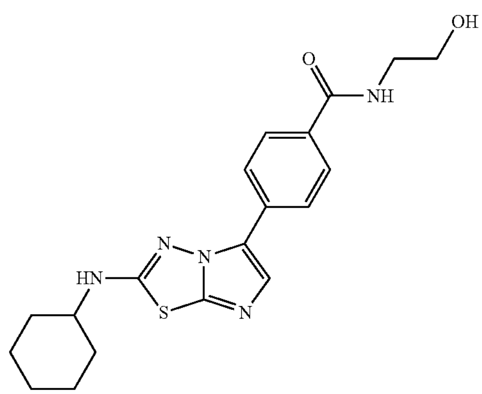 [SMILES: O=C(NCCO)c1ccc(-c2cnc3sc(NC4CCCCC4)nn23)cc1] | 4-(2-Cyclohexylamino-imidazo[2,1-b][1,3,4]thiadiazol-5-yl)-N-(2-hydroxy-ethyl)-benzamide | 386 | |
| 271 | 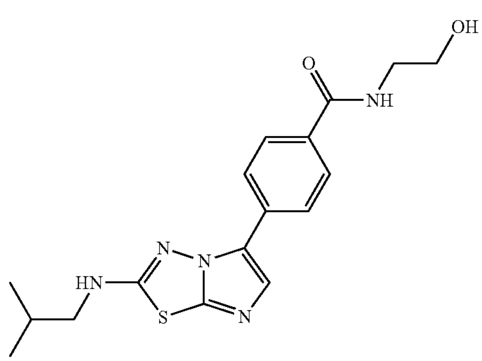 [SMILES: CC(C)CNc1nn2c(-c3ccc(C(=O)NCCO)cc3)cnc2s1] | N-(2-Hydroxy-ethyl)-4-(2-isobutylamino-imidazo[2,1-b][1,3,4]thiadiazol-5-yl)-benzamide | 360 | |

| No | Structure | Name | HPLC/MS [M + H]+ | NMR DMSO |
|---|---|---|---|---|
| 272 | 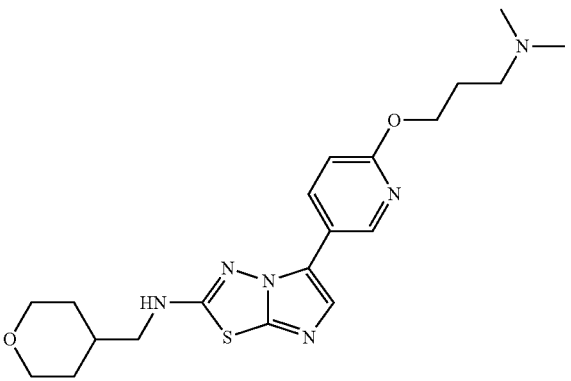 [SMILES: CN(C)CCCOc1ccc(-c2cnc3sc(NCC4CCOCC4)nn23)cn1] | {5-[6-(3-Dimethylamino-propoxy)-pyridin-3-yl]-imidazo[2,1-b][1,3,4]thiadiazol-2-yl}-(tetrahydro-pyran-4-ylmethyl)-amine | 418 | |
| 273 | 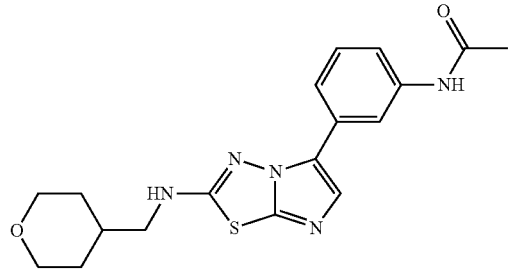 [SMILES: CC(=O)Nc1cccc(-c2cnc3sc(NCC4CCOCC4)nn23)c1] | N-(3-{2-[(Tetrahydro-pyran-4-ylmethyl)-amino]-imidazo[2,1-b][1,3,4]thiadiazol-5-yl}-phenyl)-acetamide | 372 | |
| 274 | 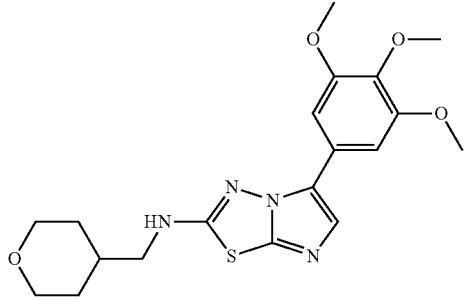 [SMILES: COc1cc(-c2cnc3sc(NCC4CCOCC4)nn23)cc(OC)c1OC] | (Tetrahydro-pyran-4-ylmethyl)-[5-(3,4,5-trimethoxy-phenyl)-imidazo[2,1-b][1,3,4]thiadiazol-2-yl]-amine | 405 | |
| 275 | 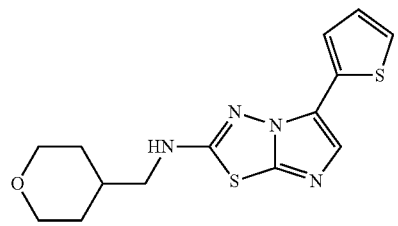 [SMILES: c1csc(-c2cnc3sc(NCC4CCOCC4)nn23)c1] | (Tetrahydro-pyran-4-ylmethyl)-(5-thiophen-2-yl-imidazo[2,1-b][1,3,4]thiadiazol-2-yl)-amine | 321 | |

-continued
| No | Structure | Name | HPLC/MS [M + H]+ | NMR DMSO |
|---|---|---|---|---|
| 276 | 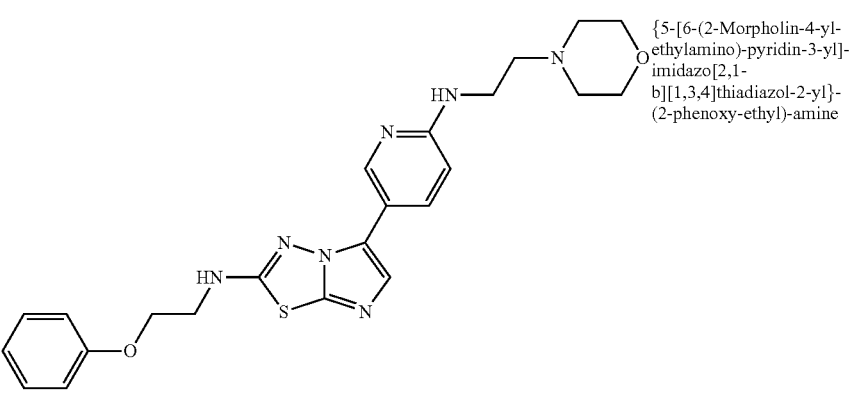 | {5-[6-(2-Morpholin-4-yl-ethylamino)-pyridin-3-yl]-imidazo[2,1-b][1,3,4]thiadiazol-2-yl}-(2-phenoxy-ethyl)-amine | 467 | |
| 277 | 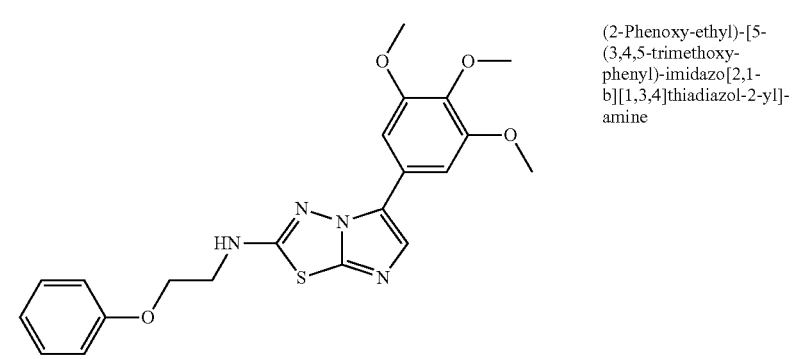 | (2-Phenoxy-ethyl)-[5-(3,4,5-trimethoxy-phenyl)-imidazo[2,1-b][1,3,4]thiadiazol-2-yl]-amine | 427 | |
| 278 | 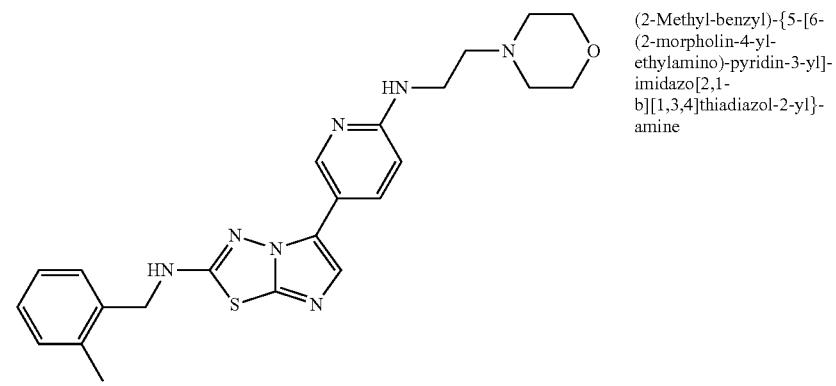 | (2-Methyl-benzyl)-{5-[6-(2-morpholin-4-yl-ethylamino)-pyridin-3-yl]-imidazo[2,1-b][1,3,4]thiadiazol-2-yl}-amine | 451 | |
| 279 | 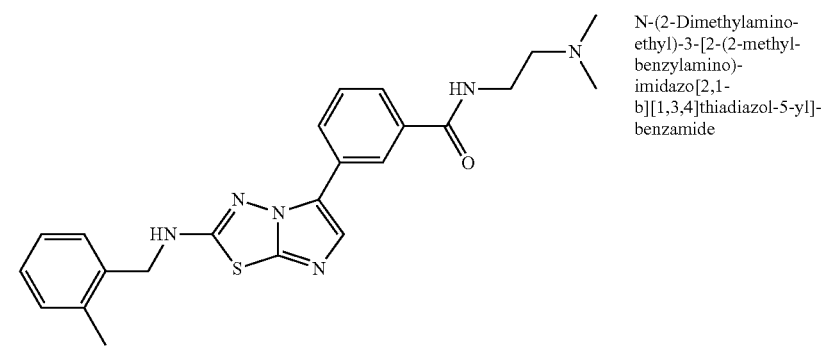 | N-(2-Dimethylamino-ethyl)-3-[2-(2-methyl-benzylamino)-imidazo[2,1-b][1,3,4]thiadiazol-5-yl]-benzamide | 436 | |

-continued

| No | Structure | Name | HPLC/MS [M + H]+ | NMR DMSO |
|---|---|---|---|---|
| 280 | 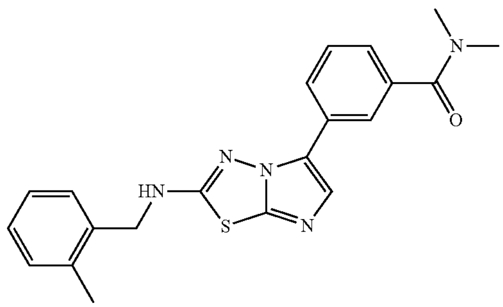 [SMILES: Cc1ccccc1CNc1nn2c(-c3cccc(C(=O)N(C)C)c3)cnc2s1] | N,N-Dimethyl-3-[2-(2-methyl-benzylamino)-imidazo[2,1-b][1,3,4]thiadiazol-5-yl]-benzamide | 392 | |
| 281 | 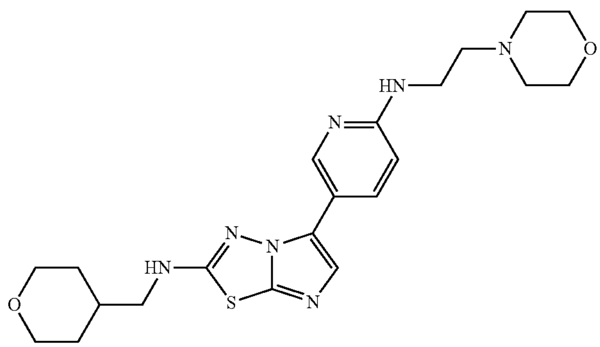 [SMILES: c1cc(NCCN2CCOCC2)ncc1-c1cnc2sc(NCC3CCOCC3)nn12] | {5-[6-(2-Morpholin-4-yl-ethylamino)-pyridin-3-yl]-imidazo[2,1-b][1,3,4]thiadiazol-2-yl}-(tetrahydro-pyran-4-ylmethyl)-amine | 445 | |
| 282 | 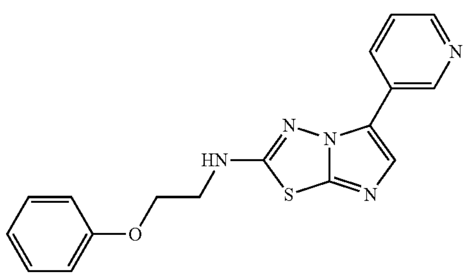 [SMILES: c1ccc(OCCNc2nn3c(-c4cccnc4)cnc3s2)cc1] | (2-Phenoxy-ethyl)-(5-pyridin-3-yl-imidazo[2,1-b][1,3,4]thiadiazol-2-yl)-amine | 338 | |
| 283 | 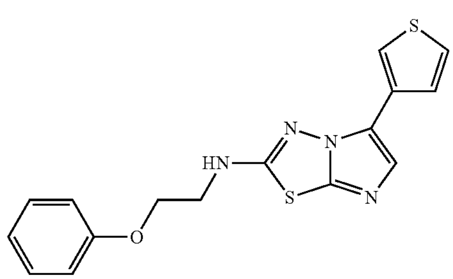 [SMILES: c1ccc(OCCNc2nn3c(-c4ccsc4)cnc3s2)cc1] | (2-Phenoxy-ethyl)-(5-thiophen-3-yl-imidazo[2,1-b][1,3,4]thiadiazol-2-yl)-amine | 343 | |
| 284 | 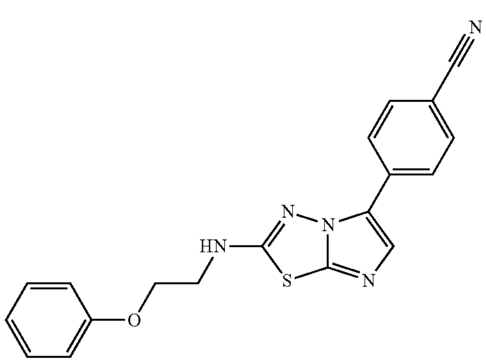 [SMILES: N#Cc1ccc(-c2cnc3sc(NCCOc4ccccc4)nn23)cc1] | 4-[2-(2-Phenoxy-ethylamino)-imidazo[2,1-b][1,3,4]thiadiazol-5-yl]-benzonitrile | 362 | |

-continued

| No | Structure | Name | HPLC/MS [M + H]+ | NMR DMSO |
|---|---|---|---|---|
| 285 | 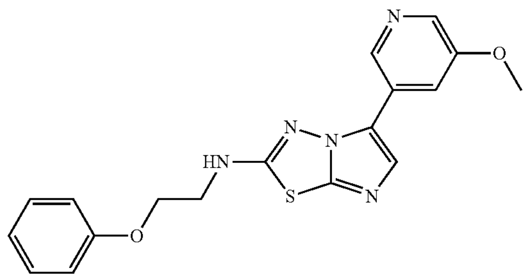 [SMILES: COc1cncc(-c2cnc3sc(NCCOc4ccccc4)nn23)c1] | [5-(5-Methoxy-pyridin-3-yl)-imidazo[2,1-b][1,3,4]thiadiazol-2-yl]-(2-phenoxy-ethyl)-amine | 368 | |
| 286 | 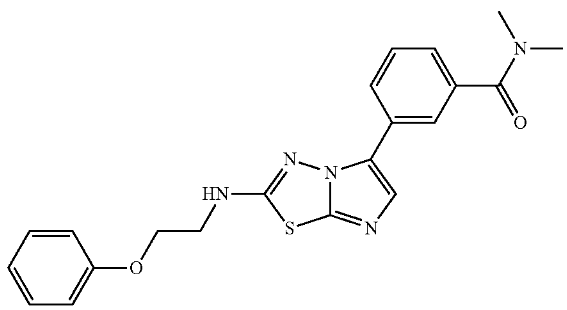 [SMILES: CN(C)C(=O)c1cccc(-c2cnc3sc(NCCOc4ccccc4)nn23)c1] | N,N-Dimethyl-3-[2-(2-phenoxy-ethylamino)-imidazo[2,1-b][1,3,4]thiadiazol-5-yl]-benzamide | 408 | |
| 287 | 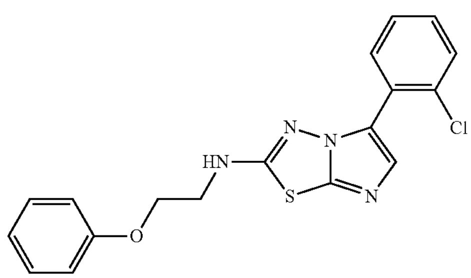 [SMILES: Clc1ccccc1-c1cnc2sc(NCCOc3ccccc3)nn12] | [5-(2-Chloro-phenyl)-imidazo[2,1-b][1,3,4]thiadiazol-2-yl]-(2-phenoxy-ethyl)-amine | 371 | |
| 288 | 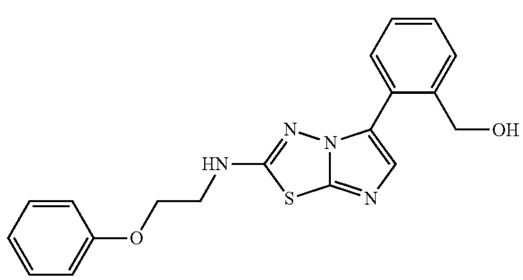 [SMILES: OCc1ccccc1-c1cnc2sc(NCCOc3ccccc3)nn12] | {2-[2-(2-Phenoxy-ethylamino)-imidazo[2,1-b][1,3,4]thiadiazol-5-yl]-phenyl}-methanol | 367 | |
| 289 | 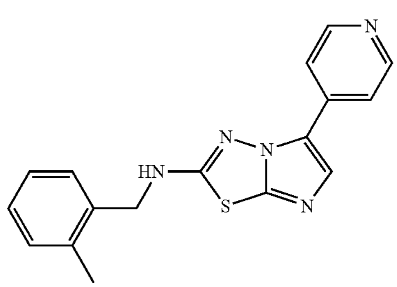 [SMILES: Cc1ccccc1CNc1nn2c(-c3ccncc3)cnc2s1] | (2-Methyl-benzyl)-(5-pyridin-4-yl-imidazo[2,1-b][1,3,4]thiadiazol-2-yl)-amine | 322 | |

-continued

| No | Structure | Name | HPLC/MS [M + H]+ | NMR DMSO |
|---|---|---|---|---|
| 290 | 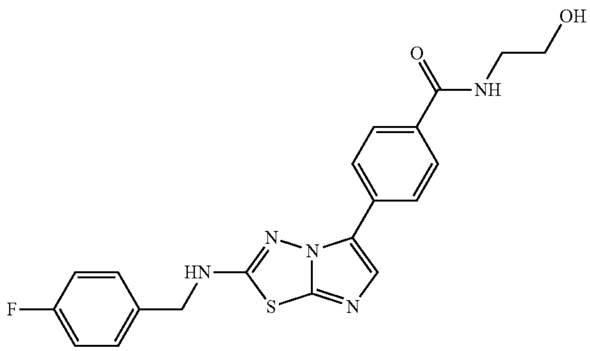 [SMILES: O=C(NCCO)c1ccc(-c2cnc3sc(NCc4ccc(F)cc4)nn23)cc1] | 4-[2-(4-Fluoro-benzylamino)-imidazo[2,1-b][1,3,4]thiadiazol-5-yl]-N-(2-hydroxy-ethyl)-benzamide | 412 | |
| 291 | 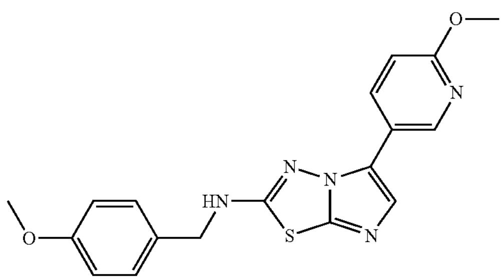 | (4-Methoxy-benzyl)-[5-(6-methoxy-pyridin-3-yl)-imidazo[2,1-b][1,3,4]thiadiazol-2-yl]-amine | 368 | |
| 292 | 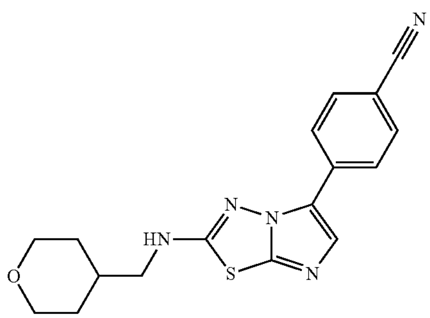 [SMILES: N#Cc1ccc(-c2cnc3sc(NCC4CCOCC4)nn23)cc1] | 4-{2-[(Tetrahydro-pyran-4-ylmethyl)-amino]-imidazo[2,1-b][1,3,4]thiadiazol-5-yl}-benzonitrile | 340 | |
| 293 | 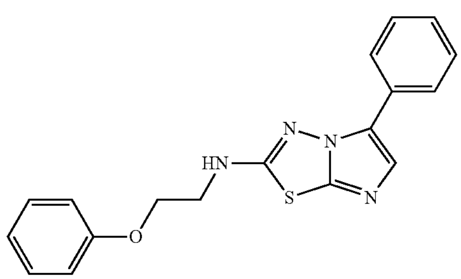 [SMILES: c1ccc(OCCNc2nn3c(-c4ccccc4)cnc3s2)cc1] | (2-Phenoxy-ethyl)-(5-phenyl-imidazo[2,1-b][1,3,4]thiadiazol-2-yl)-amine | 337 | |
| 294 | 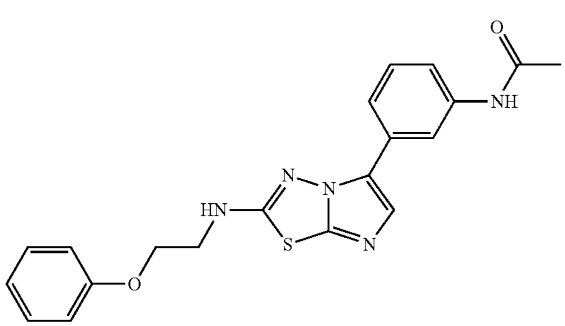 [SMILES: CC(=O)Nc1cccc(-c2cnc3sc(NCCOc4ccccc4)nn23)c1] | N-{3-[2-(2-Phenoxy-ethylamino)-imidazo[2,1-b][1,3,4]thiadiazol-5-yl]-phenyl}-acetamide | 394 | methanol |

-continued

| No | Structure | Name | HPLC/MS [M + H]+ | NMR DMSO |
|---|---|---|---|---|
| 295 | 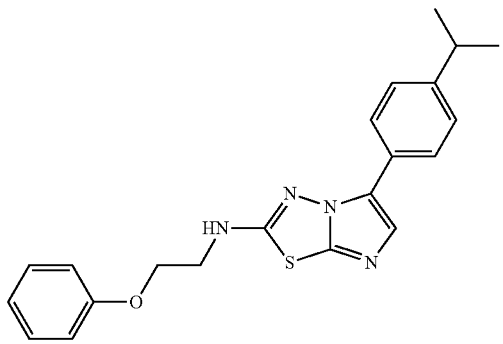 [SMILES: CC(C)c1ccc(-c2cnc3sc(NCCOc4ccccc4)nn23)cc1] | [5-(4-Isopropyl-phenyl)-imidazo[2,1-b][1,3,4]thiadiazol-2-yl]-(2-phenoxy-ethyl)-amine | 379 | |
| 296 | 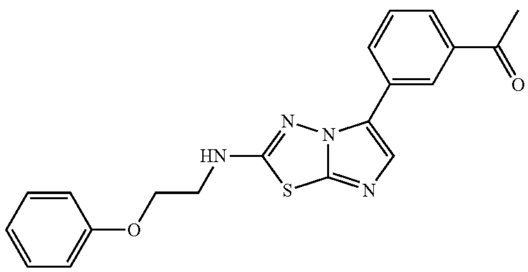 [SMILES: CC(=O)c1cccc(-c2cnc3sc(NCCOc4ccccc4)nn23)c1] | 1-{3-[2-(2-Phenoxy-ethylamino)-imidazo[2,1-b][1,3,4]thiadiazol-5-yl]-phenyl}-ethanone | 379 | |
| 297 | 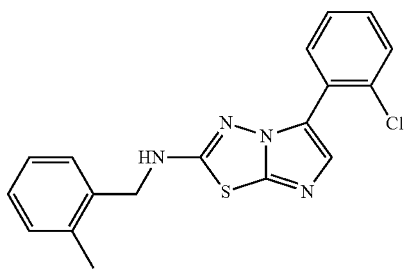 [SMILES: Cc1ccccc1CNc1nn2c(-c3ccccc3Cl)cnc2s1] | [5-(2-Chloro-phenyl)-imidazo[2,1-b][1,3,4]thiadiazol-2-yl]-(2-methyl-benzyl)-amine | 355 | |
| 298 | 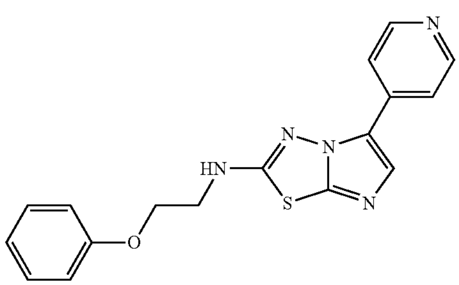 [SMILES: c1ccc(OCCNc2nn3c(-c4ccncc4)cnc3s2)cc1] | (2-Phenoxy-ethyl)-(5-pyridin-4-yl-imidazo[2,1-b][1,3,4]thiadiazol-2-yl)-amine | 338 | |
| 299 | 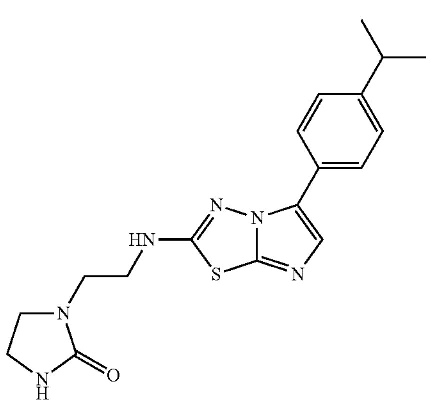 [SMILES: CC(C)c1ccc(-c2cnc3sc(NCCN4CCNC4=O)nn23)cc1] | 1-{2-[5-(4-Isopropyl-phenyl-imidazo[2,1-b][1,3,4]thiadiazol-2-ylamino]-ethyl}-imidazolidin-2-one | 371 | |

-continued

| No | Structure | Name | HPLC/MS [M + H]+ | NMR DMSO |
|----|-----------|------|------------------|----------|
| 300 | 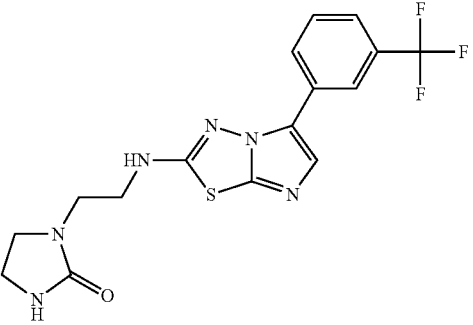 [SMILES: O=C1NCCN1CCNc1nn2c(-c3cccc(C(F)(F)F)c3)cnc2s1] | 1-{2-[5-(3-Trifluoromethyl-phenyl)-imidazo[2,1-b][1,3,4]thiadiazol-2-ylamino]-ethyl}-imidazolidin-2-one | 397 | |
| 301 | 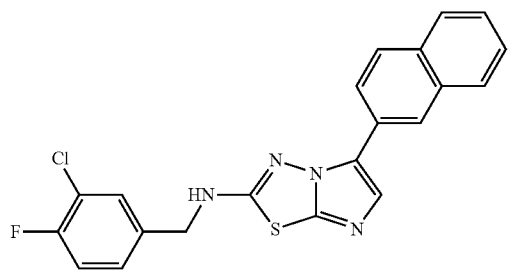 [SMILES: Fc1ccc(CNc2nn3c(-c4ccc5ccccc5c4)cnc3s2)cc1Cl] | (3-Chloro-4-fluoro-benzyl)-(5-naphthalen-2-yl-imidazo[2,1-b][1,3,4]thiadiazol-2-yl)-amine | 409 | |
| 302 | 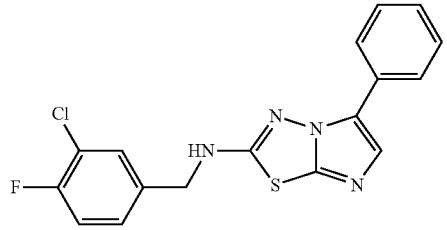 [SMILES: Fc1ccc(CNc2nn3c(-c4ccccc4)cnc3s2)cc1Cl] | (3-Chloro-4-fluoro-benzyl)-(5-phenyl-imidazo[2,1-b][1,3,4]thiadiazol-2-yl)-amine | 359 | |
| 303 | 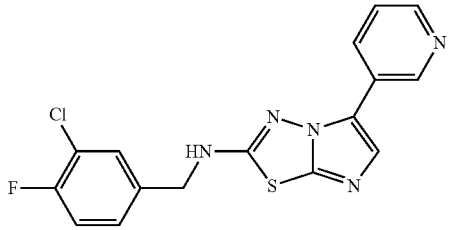 [SMILES: Fc1ccc(CNc2nn3c(-c4cccnc4)cnc3s2)cc1Cl] | (3-Chloro-4-fluoro-benzyl)-(5-pyridin-3-yl-imidazo[2,1-b][1,3,4]thiadiazol-2-yl)-amine | 360 | |
| 304 | 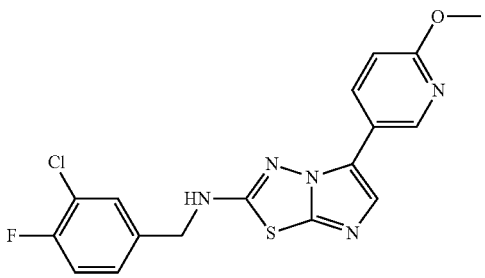 [SMILES: COc1ccc(-c2cnc3sc(NCc4ccc(F)c(Cl)c4)nn23)cn1] | (3-Chloro-4-fluoro-benzyl)-[5-(6-methoxy-pyridin-3-yl)-imidazo[2,1-b][1,3,4]thiadiazol-2-yl]-amine | 390 | |

| No | Structure | Name | HPLC/MS [M + H]+ | NMR DMSO |
|---|---|---|---|---|
| 305 | 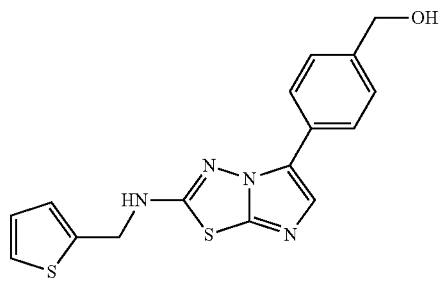 [SMILES: OCc1ccc(-c2cnc3sc(NCc4cccs4)nn23)cc1] | (4-{2-[(Thiophen-2-ylmethyl)-amino]-imidazo[2,1-b][1,3,4]thiadiazol-5-yl}-phenyl)-methanol | 343 | |
| 306 | 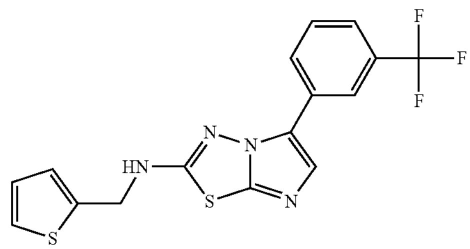 [SMILES: FC(F)(F)c1cccc(-c2cnc3sc(NCc4cccs4)nn23)c1] | Thiophen-2-ylmethyl-[5-(3-trifluoromethyl-phenyl-imidazo[2,1-b][1,3,4]thiadiazol-2-yl] amine | 381 | |
| 307 | 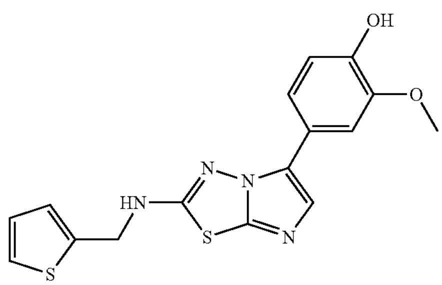 [SMILES: COc1cc(-c2cnc3sc(NCc4cccs4)nn23)ccc1O] | 2-Methoxy-4-{2-[(thiophen-2-ylmethyl)-amino]-imidazo[2,1-b][1,3,4]thiadiazol-5-yl}-phenol | 359 | |
| 308 | 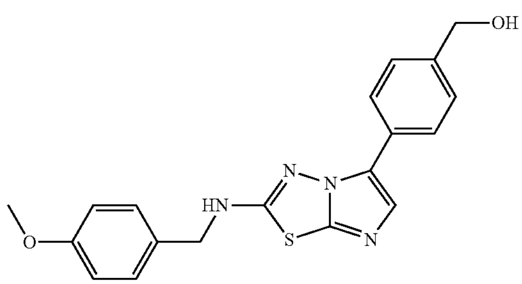 [SMILES: COc1ccc(CNc2nn3c(-c4ccc(CO)cc4)cnc3s2)cc1] | {4-[2-(4-Methoxy-benzylamino)-imidazo[2,1-b][1,3,4]thiadiazol-5-yl]-phenyl}-methanol | 367 | |
| 309 | 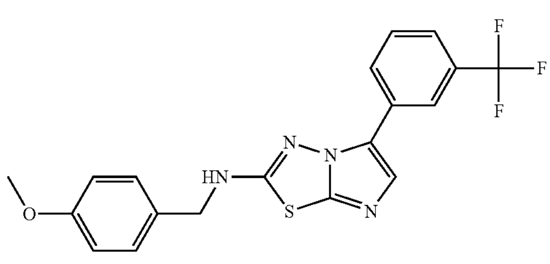 [SMILES: COc1ccc(CNc2nn3c(-c4cccc(C(F)(F)F)c4)cnc3s2)cc1] | (4-Methoxy-benzyl)-[5-(3-trifluoromethyl-phenyl-imidazo[2,1-b][1,3,4]thiadiazol-2-yl]-amine | 405 | |

-continued

| No | Structure | Name | HPLC/MS [M + H]+ | NMR DMSO |
|---|---|---|---|---|
| 310 | 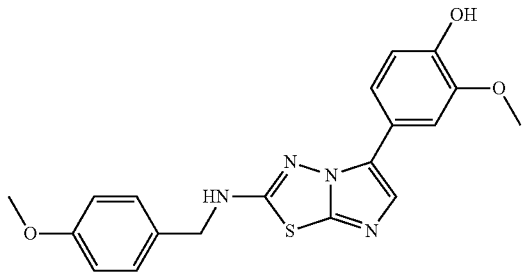 | 2-Methoxy-4-[2-(4-methoxy-benzylamino)-imidazo[2,1-b][1,3,4]thiadiazol-5-yl]-phenol | 383 | |
| 311 | 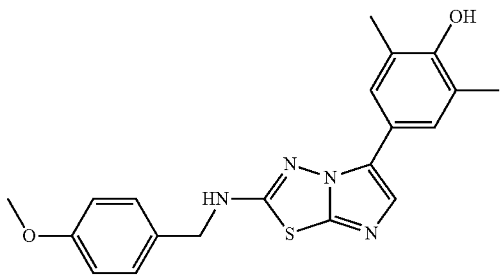 | 4-[2-(4-Methoxy-benzylamino)-imidazo[2,1-b][1,3,4]thiadiazol-5-yl]-2,6-dimethyl-phenol | 381 | |
| 312 | 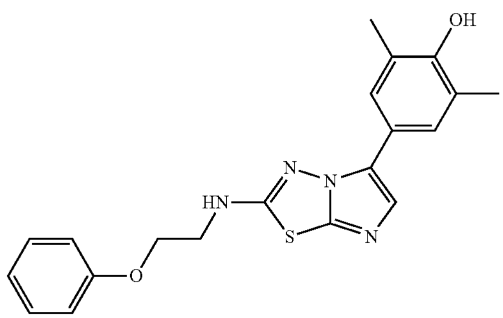 [SMILES: Cc1cc(-c2cnc3sc(NCCOc4ccccc4)nn23)cc(C)c1O] | 2,6-Dimethyl-4-[2-(2-phenoxy-ethylamino)-imidazo[2,1-b][1,3,4]thiadiazol-5-yl]-phenol | 381 | |
| 313 | 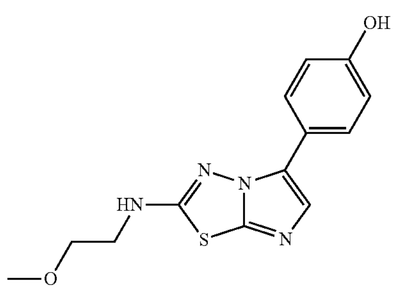 [SMILES: COCCNc1nn2c(-c3ccc(O)cc3)cnc2s1] | 4-[2-(2-Methoxy-ethylamino)imidazo[2,1-b][1,3,4]thiadiazol-5-yl]-phenol | 291 | |
| 314 | 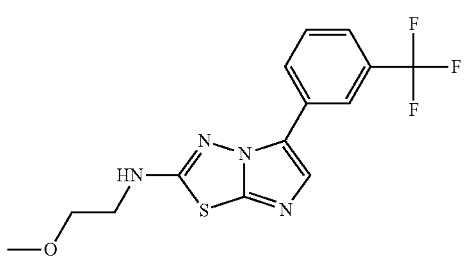 [SMILES: COCCNc1nn2c(-c3cccc(C(F)(F)F)c3)cnc2s1] | (2-Methoxy-ethyl)-[5-(3-trifluoromethyl-phenyl)-imidazo[2,1-b][1,3,4]thiadiazol-2-yl]-amine | 343 | |

-continued

| No | Structure | Name | HPLC/MS [M + H]+ | NMR DMSO |
|---|---|---|---|---|
| 315 | 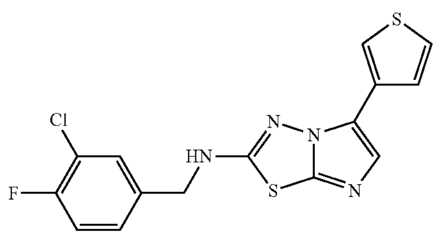 [SMILES: Fc1ccc(CNc2nn3c(-c4ccsc4)cnc3s2)cc1Cl] | (3-Chloro-4-fluoro-benzyl)-(5-thiophen-3-yl-imidazo[2,1-b][1,3,4]thiadiazol-2-yl)-amine | 365 | |
| 316 | 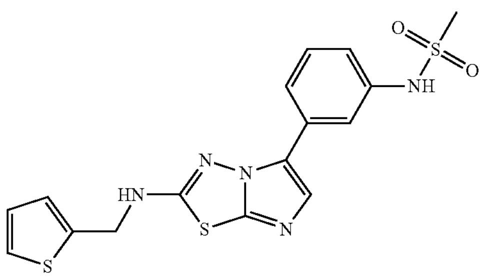 [SMILES: CS(=O)(=O)Nc1cccc(-c2cnc3sc(NCc4cccs4)nn23)c1] | N-(3-{2-[(Thiophen-2-ylmethyl)-amino]-imidazo[2,1-b][1,3,4]thiadiazol-5-yl}-phenyl)-methanesulfonamide | 407 | |
| 317 | 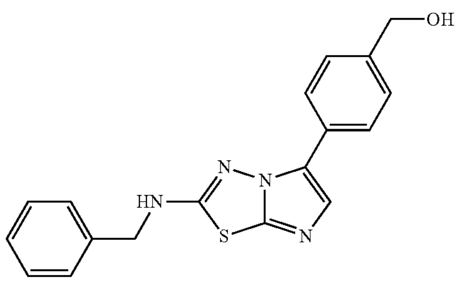 [SMILES: OCc1ccc(-c2cnc3sc(NCc4ccccc4)nn23)cc1] | [4-(2-Benzylamino-imidazo[2,1-b][1,3,4]thiadiazol-5-yl)-phenyl]-methanol | 337 | |
| 318 | 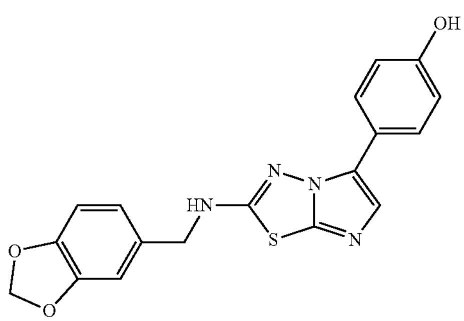 [SMILES: Oc1ccc(-c2cnc3sc(NCc4ccc5c(c4)OCO5)nn23)cc1] | 4-{2-[(Benzo[1,3]dioxol-5-ylmethyl)-amino]-imidazo[2,1-b][1,3,4]thiadiazol-5-yl}-phenol | 367 | |
| 319 | 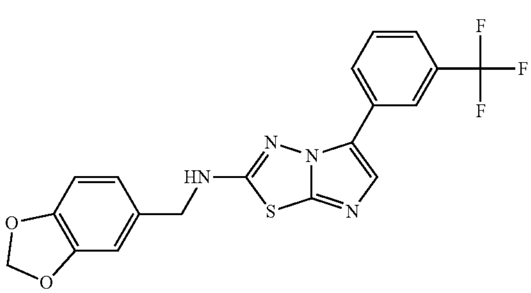 [SMILES: FC(F)(F)c1cccc(-c2cnc3sc(NCc4ccc5c(c4)OCO5)nn23)c1] | Benzo[1,3]dioxol-5-ylmethyl-[5-(3-trifluoromethyl-phenyl)-imidazo[2,1-b][1,3,4]thiadiazol-2-yl]-amine | 419 | |

-continued

| No | Structure | Name | HPLC/MS [M + H]+ | NMR DMSO |
|---|---|---|---|---|
| 320 | 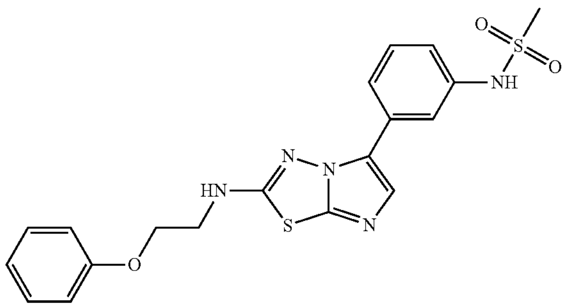 [SMILES: CS(=O)(=O)Nc1cccc(-c2cnc3sc(NCCOc4ccccc4)nn23)c1] | N-{3-[2-(2-Phenoxy-ethylamino)-imidazo[2,1-b][1,3,4]thiadiazol-5-yl]-phenyl}-methanesulfonamide | 431 | |
| 321 | 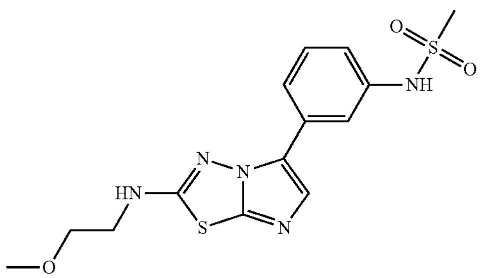 [SMILES: COCCNc1nn2c(-c3cccc(NS(C)(=O)=O)c3)cnc2s1] | N-{3-[2-(2-Methoxy-ethylamino)-imidazo[2,1-b][1,3,4]thiadiazol-5-yl]-phenyl}-methanesulfonamide | 368 | |
| 322 | 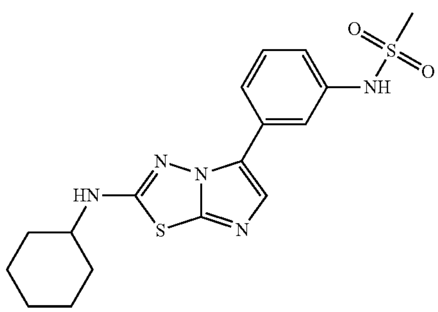 [SMILES: CS(=O)(=O)Nc1cccc(-c2cnc3sc(NC4CCCCC4)nn23)c1] | N-[3-(2-Cyclohexylamino-imidazo[2,1-b][1,3,4]thiadiazol-5-yl)-phenyl]-methanesulfonamide | 393 | |
| 323 | 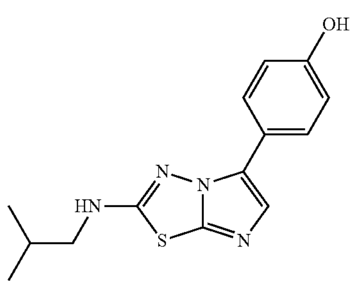 [SMILES: CC(C)CNc1nn2c(-c3ccc(O)cc3)cnc2s1] | 4-(2-Isobutylamino-imidazo[2,1-b][1,3,4]thiadiazol-5-yl)-phenol | 289 | |
| 324 | 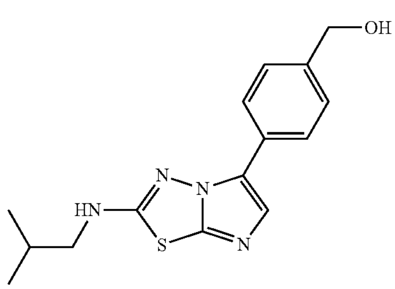 [SMILES: CC(C)CNc1nn2c(-c3ccc(CO)cc3)cnc2s1] | [4-(2-Isobutylamino-imidazo[2,1-b][1,3,4]thiadiazol-5-yl)-phenyl]-methanol | 303 | |

-continued

| No | Structure | Name | HPLC/MS [M + H]+ | NMR DMSO |
|---|---|---|---|---|
| 325 | 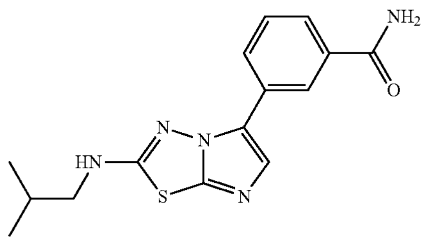 [SMILES: CC(C)CNc1nn2c(-c3cccc(C(N)=O)c3)cnc2s1] | 3-(2-Isobutylamino-imidazo[2,1-b][1,3,4]thiadiazol-5-yl)-benzamide | 316 | |
| 326 | 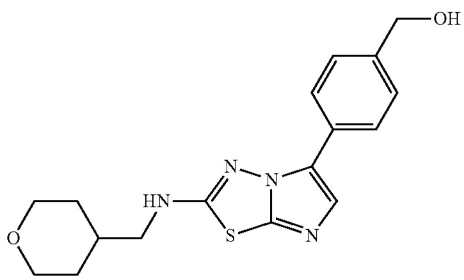 [SMILES: OCc1ccc(-c2cnc3sc(NCC4CCOCC4)nn23)cc1] | (4-{2-[(Tetrahydro-pyran-4-ylmethyl)-amino]-imidazo[2,1-b][1,3,4]thiadiazol-5-yl}-phenyl)-methanol | 345 | |
| 327 | 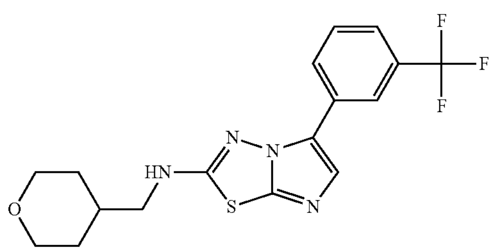 [SMILES: FC(F)(F)c1cccc(-c2cnc3sc(NCC4CCOCC4)nn23)c1] | (Tetrahydro-pyran-4-ylmethyl)-[5-(3-trifluoromethyl-phenyl)-imidazo[2,1-b][1,3,4]thiadiazol-2-yl]-amine | 383 | |
| 328 | 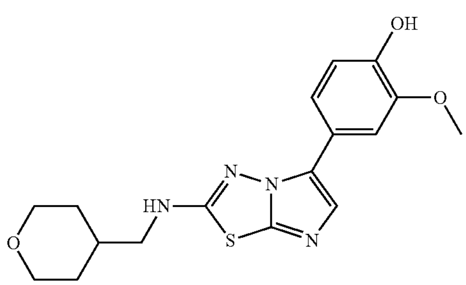 [SMILES: COc1cc(-c2cnc3sc(NCC4CCOCC4)nn23)ccc1O] | 2-Methoxy-4-{2-[(tetrahydro-pyran-4-ylmethyl)-amino]-imidazo[2,1-b][1,3,4]thiadiazol-5-yl}-phenol | 361 | |
| 329 | 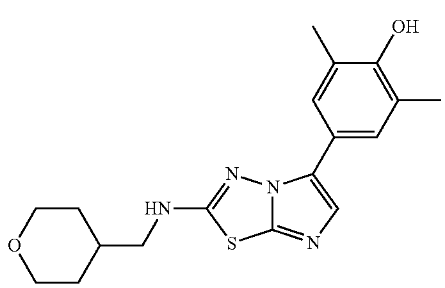 [SMILES: Cc1cc(-c2cnc3sc(NCC4CCOCC4)nn23)cc(C)c1O] | 2,6-Dimethyl-4-{2-[(tetrahydro-pyran-4-ylmethyl)-amino]-imidazo[2,1-b][1,3,4]thiadiazol-5-yl}-phenol | 359 | |

-continued

| No | Structure | Name | HPLC/MS [M + H]+ | NMR DMSO |
|---|---|---|---|---|
| 330 | 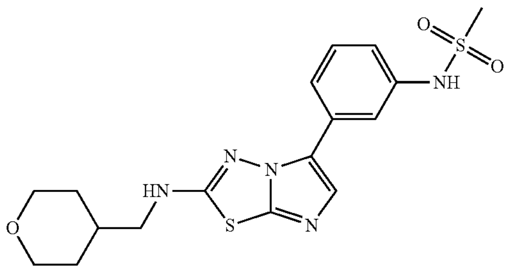 [SMILES: CS(=O)(=O)Nc1cccc(-c2cnc3sc(NCC4CCOCC4)nn23)c1] | N-(3-{2-[(Tetrahydro-pyran-4-ylmethyl)-amino]-imidazo[2,1-b][1,3,4]thiadiazol-5-yl}-phenyl)-methanesulfonamide | 409 | |
| 331 | 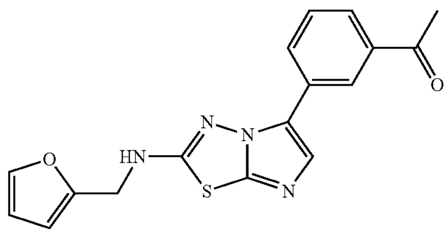 [SMILES: CC(=O)c1cccc(-c2cnc3sc(NCc4ccco4)nn23)c1] | 1-(3-{2-[(Furan-2-ylmethyl)-amino]-imidazo[2,1-b][1,3,4]thiadiazol-5-yl}-phenyl)-ethanone | 339 | |
| 332 | 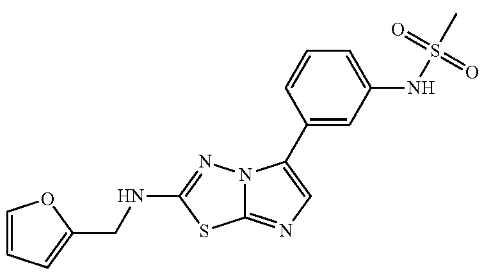 [SMILES: CS(=O)(=O)Nc1cccc(-c2cnc3sc(NCc4ccco4)nn23)c1] | N-(3-{2-[(Furan-2-ylmethyl)-amino]-imidazo[2,1-b][1,3,4]thiadiazol-5-yl}-phenyl)-methanesulfonamide | 390 | |
| 333 | 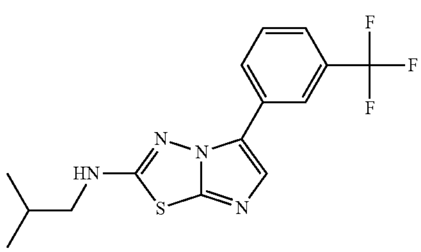 [SMILES: CC(C)CNc1nn2c(-c3cccc(C(F)(F)F)c3)cnc2s1] | Isobutyl-[5-(3-trifluoromethyl-phenyl)-imidazo[2,1-b][1,3,4]thiadiazol-2-yl]-amine | 341 | |
| 334 | 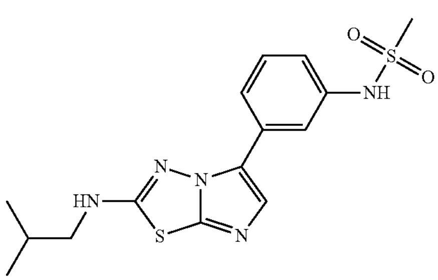 [SMILES: CC(C)CNc1nn2c(-c3cccc(NS(C)(=O)=O)c3)cnc2s1] | N-[3-(2-Isobutylamino-imidazo[2,1-b][1,3,4]thiadiazol-5-yl)-phenyl]-methanesulfonamide | 366 | |

| No | Structure | Name | HPLC/MS [M + H]+ | NMR DMSO |
|---|---|---|---|---|
| 335 | 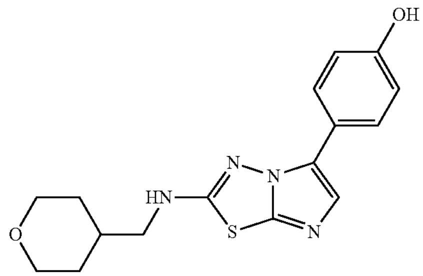 [SMILES: Oc1ccc(-c2cnc3sc(NCC4CCOCC4)nn23)cc1] | 4-{2-[(Tetrahydro-pyran-4-ylmethyl)-amino]-imidazo[2,1-b][1,3,4]thiadiazol-5-yl}-phenol | 331 | |
| 336 | 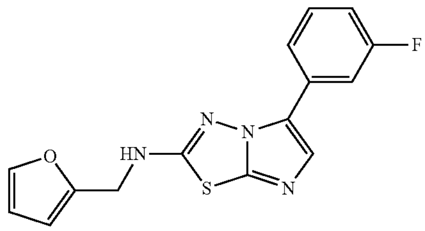 [SMILES: Fc1cccc(-c2cnc3sc(NCc4ccco4)nn23)c1] | [5-(3-Fluoro-phenyl)-imidazo[2,1-b][1,3,4]thiadiazol-2-yl]-furan-2-ylmethyl-amine | 315 | |
| 337 | 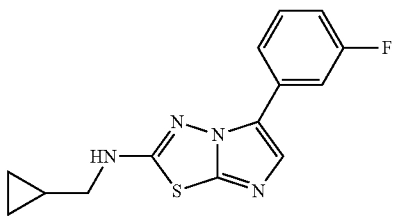 [SMILES: Fc1cccc(-c2cnc3sc(NCC4CC4)nn23)c1] | Cyclopropylmethyl-[5-(3-fluoro-phenyl)-imidazo[2,1-b][1,3,4]thiadiazol-2-yl]-amine | 289 | |
| 338 | 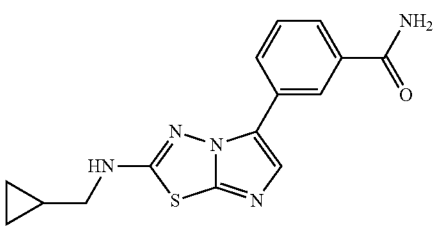 [SMILES: NC(=O)c1cccc(-c2cnc3sc(NCC4CC4)nn23)c1] | 3-[2-(Cyclopropylmethyl-amino)-imidazo[2,1-b][1,3,4]thiadiazol-5-yl]-benzamide | 314 | |
| 339 | 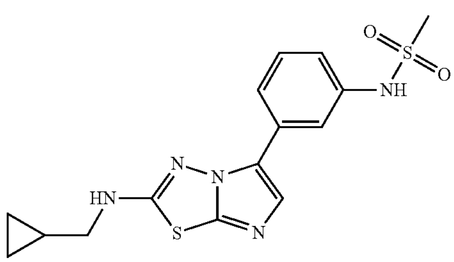 [SMILES: CS(=O)(=O)Nc1cccc(-c2cnc3sc(NCC4CC4)nn23)c1] | N-{3-[2-(Cyclopropylmethyl-amino)-imidazo[2,1-b][1,3,4]thiadiazol-5-yl]-phenyl}-methanesulfonamide | 364 | |
| 340 | 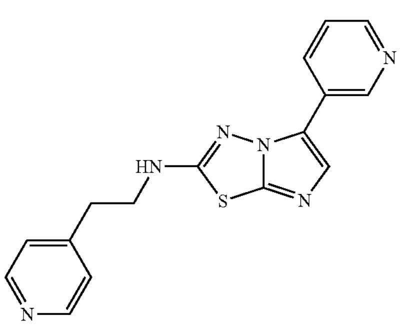 [SMILES: c1cncc(-c2cnc3sc(NCCc4ccncc4)nn23)c1] | (2-Pyridin-4-yl-ethyl)-(5-pyridin-3-yl-imidazo[2,1-b][1,3,4]thiadiazol-2-yl)-amine | 323 | |

-continued

| No | Structure | Name | HPLC/MS [M + H]+ | NMR DMSO |
|---|---|---|---|---|
| 341 | 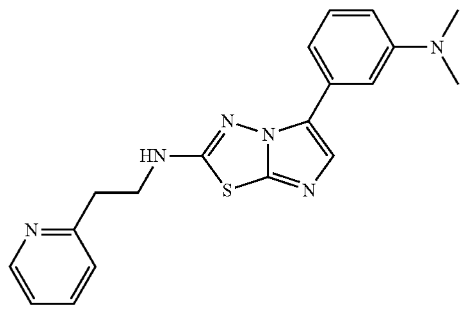 [SMILES: CN(C)c1cccc(-c2cnc3sc(NCCc4ccccn4)nn23)c1] | [5-(3-Dimethylamino-phenyl)-imidazo[2,1-b][1,3,4]thiadiazol-2-yl]-(2-pyridin-2-yl-ethyl)-amine | 365 | |
| 342 | 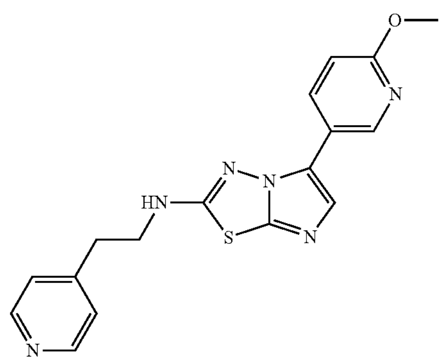 [SMILES: COc1ccc(-c2cnc3sc(NCCc4ccncc4)nn23)cn1] | [5-(6-Methoxy-pyridin-3-yl)-imidazo[2,1-b][1,3,4]thiadiazol-2-yl]-(2-pyridin-2-yl-ethyl)-amine | 353 | |
| 343 | 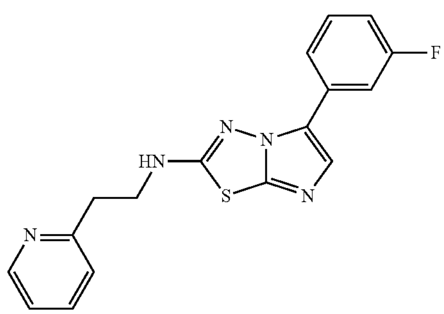 [SMILES: Fc1cccc(-c2cnc3sc(NCCc4ccccn4)nn23)c1] | [5-(3-Fluoro-phenyl)-imidazo[2,1-b][1,3,4]thiadiazol-2-yl]-(2-pyridin-2-yl-ethyl)-amine | 340 | |
| 344 | 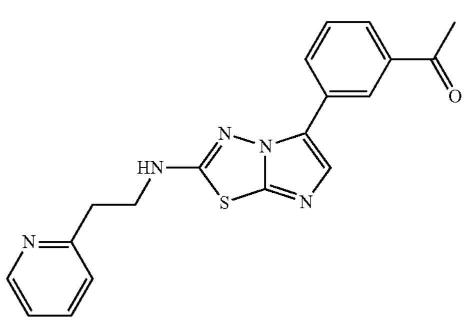 [SMILES: CC(=O)c1cccc(-c2cnc3sc(NCCc4ccccn4)nn23)c1] | 1-{3-[2-(2-Pyridin-2-yl-ethylamino)-imidazo[2,1-b][1,3,4]thiadiazol-5-yl]-phenyl}-ethanone | 364 | |

-continued

| No | Structure | Name | HPLC/MS [M + H]+ | NMR DMSO |
|---|---|---|---|---|
| 345 | 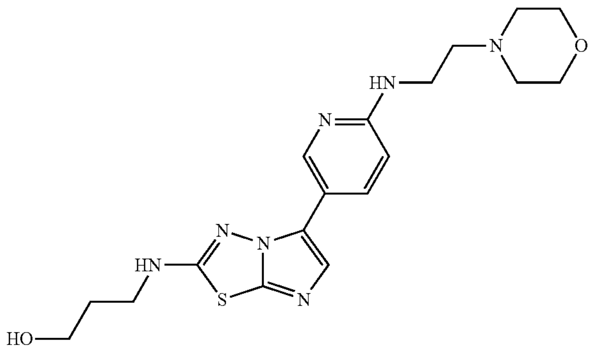 [SMILES: OCCCNc1nn2c(-c3ccc(NCCN4CCOCC4)nc3)cnc2s1] | 3-{5-[6-(2-Morpholin-4-yl-ethylamino)-pyridin-3-yl]-imidazo[2,1-b][1,3,4]thiadiazol-2-ylamino}-propan-1-ol | 405 | |
| 346 | 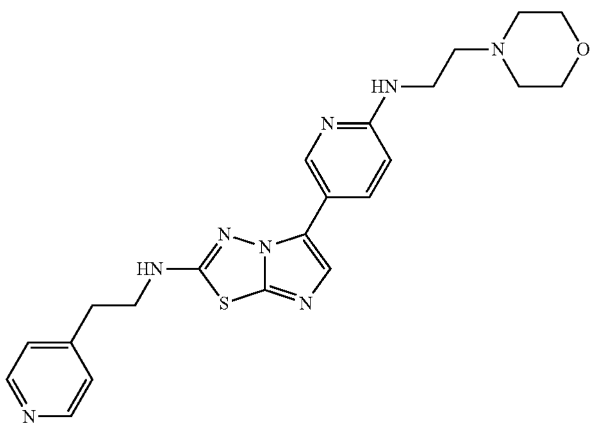 [SMILES: c1cc(CCNc2nn3c(-c4ccc(NCCN5CCOCC5)nc4)cnc3s2)ccn1] | {5-[6-(2-Morpholin-4-yl-ethylamino)-pyridin-3-yl]-imidazo[2,1-b][1,3,4]thiadiazol-2-yl}-(2-pyridin-4-yl-ethyl)-amine | 452 | |
| 347 | 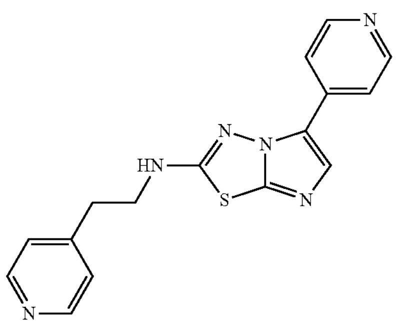 [SMILES: c1cc(CCNc2nn3c(-c4ccncc4)cnc3s2)ccn1] | (2-Pyridin-4-yl-ethyl)-(5-pyridin-4-yl-imidazo[2,1-b][1,3,4]thiadiazol-2-yl)-amine | 323 | |
| 348 | 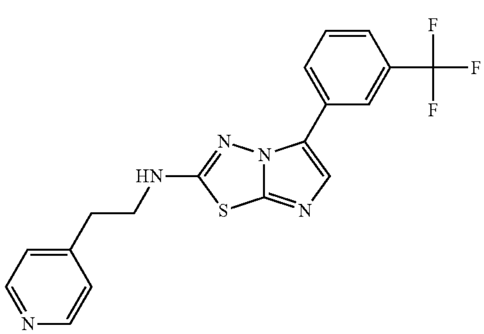 [SMILES: FC(F)(F)c1cccc(-c2cnc3sc(NCCc4ccncc4)nn23)c1] | (2-Pyridin-4-yl-ethyl)-[5-(3-trifluoromethyl-phenyl)-imidazo[2,1-b][1,3,4]thiadiazol-2-yl]-amine | 390 | |

| No | Structure | Name | HPLC/MS [M + H]+ | NMR DMSO |
|---|---|---|---|---|
| 349 | 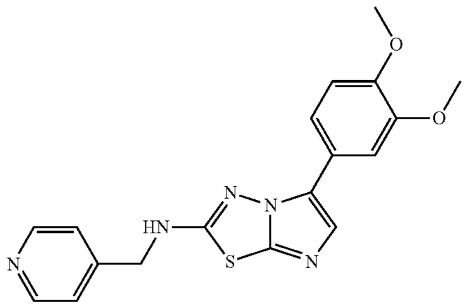 [SMILES: COc1ccc(-c2cnc3sc(NCc4ccncc4)nn23)cc1OC] | [5-(3,4-Dimethoxy-phenyl)-imidazo[2,1-b][1,3,4]thiadiazol-2-yl]-pyridin-4-ylmethyl-amine | 368 | δ 8.6 (t, 1H), 8.5 (d, 2H), 7.4 (m, 4H), 7.0 (d, 2H), 4.6 (d, 2H), 3.7 (s, 3H), 3.6 (s, 3H) |
| 350 | 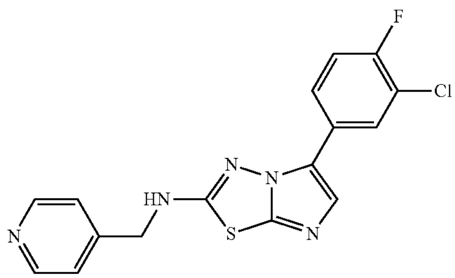 [SMILES: Fc1ccc(-c2cnc3sc(NCc4ccncc4)nn23)cc1Cl] | [5-(3-Chloro-4-fluoro-phenyl)-imidazo[2,1-b][1,3,4]thiadiazol-2-yl]-pyridin-4-ylmethyl)-amine | 361 | |
| 351 | 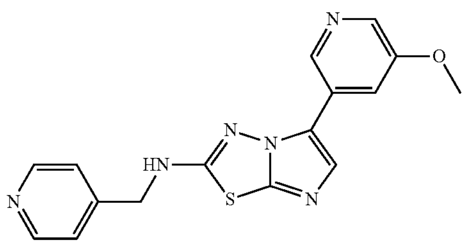 [SMILES: COc1cncc(-c2cnc3sc(NCc4ccncc4)nn23)c1] | [5-(5-Methoxy-pyridin-3-yl)-imidazo[2,1-b][1,3,4]thiadiazol-2-yl]-pyridin-4-ylmethyl-amine | 339 | |
| 352 | 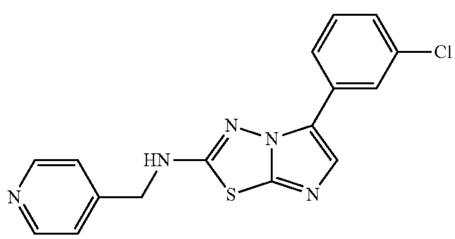 [SMILES: Clc1cccc(-c2cnc3sc(NCc4ccncc4)nn23)c1] | [5-(3-Chloro-phenyl)-imidazo[2,1-b][1,3,4]thiadiazol-2-yl]-pyridin-4-ylmethyl-amine | 342 | |
| 353 | 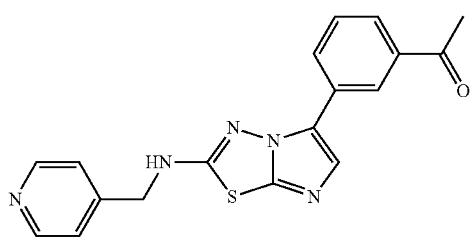 [SMILES: CC(=O)c1cccc(-c2cnc3sc(NCc4ccncc4)nn23)c1] | 1-(3-{2-[(Pyridin-4-ylmethyl)-amino]-imidazo[2,1-b][1,3,4]thiadiazol-5-yl}-phenyl)-ethanone | 350 | |
| 354 | 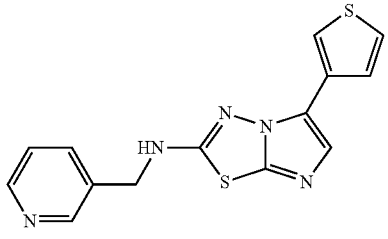 [SMILES: c1cncc(CNc2nn3c(-c4ccsc4)cnc3s2)c1] | Pyridin-3-ylmethyl-(5-thiophen-3-yl-imidazo[2,1-b][1,3,4]thiadiazol-2-yl)-amine | 315 | |

| No | Structure | Name | HPLC/MS [M + H]+ | NMR DMSO |
|---|---|---|---|---|
| 355 | 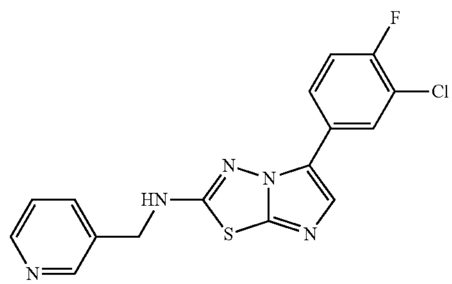 [SMILES: Fc1ccc(-c2cnc3sc(NCc4cccnc4)nn23)cc1Cl] | [5-(3-Chloro-4-fluoro-phenyl)-imidazo[2,1-b][1,3,4]thiadiazol-2-yl]-pyridin-3-ylmethyl-amine | 360 | |
| 356 | 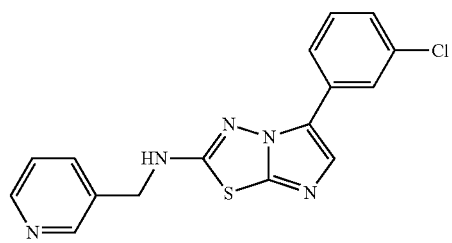 [SMILES: Clc1cccc(-c2cnc3sc(NCc4cccnc4)nn23)c1] | [5-(3-Chloro-phenyl)-imidazo[2,1-b][1,3,4]thiadiazol-2-yl]-pyridin-3-ylmethyl-amine | 342 | |
| 357 | 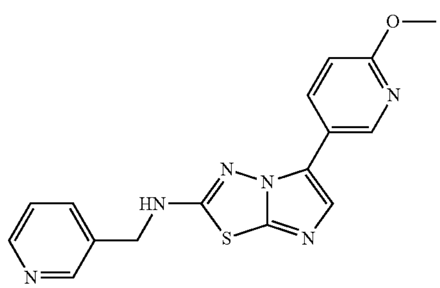 [SMILES: COc1ccc(-c2cnc3sc(NCc4cccnc4)nn23)cn1] | [5-(6-Methoxy-pyridin-3-yl)-imidazo[2,1-b][1,3,4]thiadiazol-2-yl]-pyridin-3-ylmethyl-amine | 339 | |
| 358 | 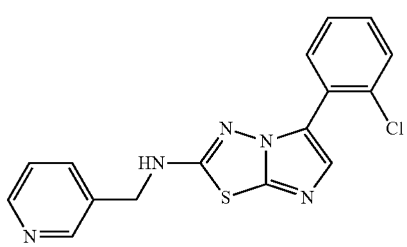 [SMILES: Clc1ccccc1-c1cnc2sc(NCc3cccnc3)nn12] | [5-(2-Chloro-phenyl)-imidazo[2,1-b][1,3,4]thiadiazol-2-yl]-pyridin-3-ylmethyl-amine | 342 | |
| 359 | 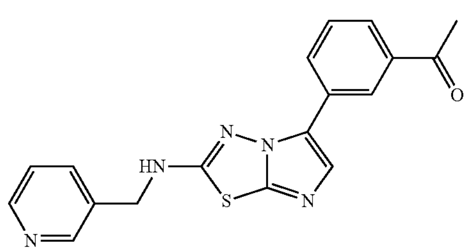 [SMILES: CC(=O)c1cccc(-c2cnc3sc(NCc4cccnc4)nn23)c1] | 1-(3-{2-[(Pyridin-3-ylmethyl)-amino]-imidazo[2,1-b][1,3,4thiadiazol-5-yl}-phenyl)-ethanone | 350 | |

| No | Structure | Name | HPLC/MS [M + H]+ | NMR DMSO |
|---|---|---|---|---|
| 360 | 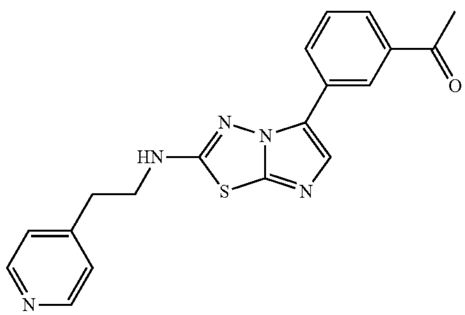 [SMILES: CC(=O)c1cccc(-c2cnc3sc(NCCc4ccncc4)nn23)c1] | 1-{3-[2-(2-Pyridin-4-yl-ethylamino)-imidazo[2,1-b][1,3,4thiadiazol-5-yl]-phenyl}-ethanone | 364 | |
| 361 | 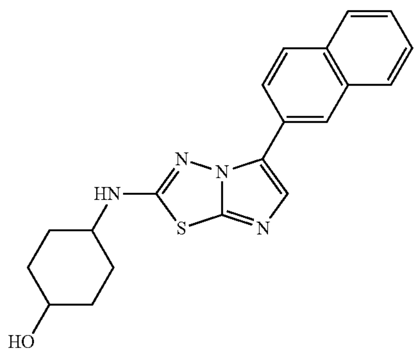 [SMILES: OC1CCC(Nc2nn3c(-c4ccc5ccccc5c4)cnc3s2)CC1] | 4-(5-Naphthalen-2-yl-imidazo[2,1-b][1,3,4]thiadiazol-2-ylamino)-cyclohexanol | 365 | |
| 362 | 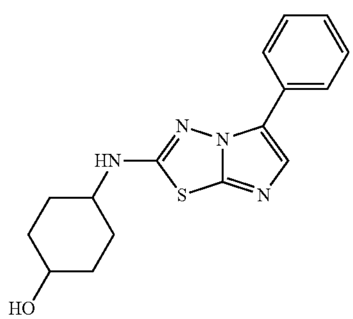 [SMILES: OC1CCC(Nc2nn3c(-c4ccccc4)cnc3s2)CC1] | 4-(5-Phenyl-imidazo[2,1-b][1,3,4]thiadiazol-2-ylamino)-cyclohexanol | 315 | |
| 363 | 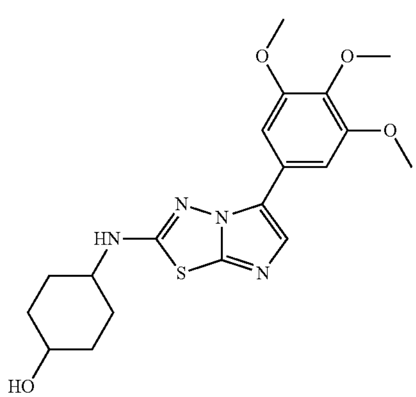 [SMILES: COc1cc(-c2cnc3sc(NC4CCC(O)CC4)nn23)cc(OC)c1OC] | 4-[5-(3,4,5-Trimethoxy-phenyl)-imidazo[2,1-b][1,3,4]thiadiazol-2-ylamino]-cyclohexanol | 405 | |

-continued

| No | Structure | Name | HPLC/MS [M + H]+ | NMR DMSO |
|---|---|---|---|---|
| 364 | 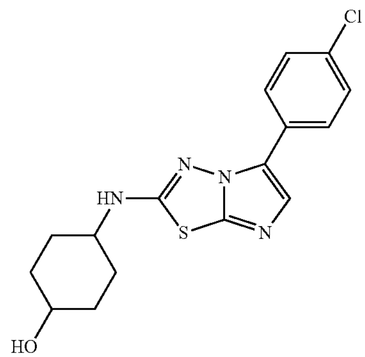 [SMILES: OC1CCC(Nc2nn3c(-c4ccc(Cl)cc4)cnc3s2)CC1] | 4-[5-(4-Chloro-phenyl)-imidazo[2,1-b][1,3,4]thiadiazol-2-ylamino]-cyclohexanol | 349 | |
| 365 | 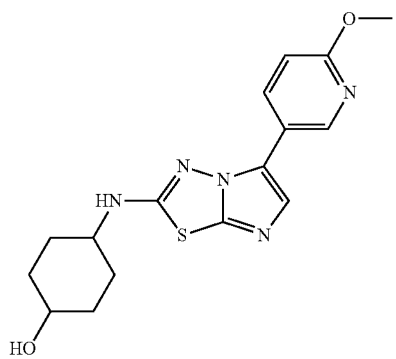 [SMILES: COc1ccc(-c2cnc3sc(NC4CCC(O)CC4)nn23)cn1] | 4-[5-(6-Methoxy-pyridin-3-yl)-imidazo[2,1-b][1,3,4]thiadiazol-2-ylamino]-cyclohexanol | 346 | |
| 366 | 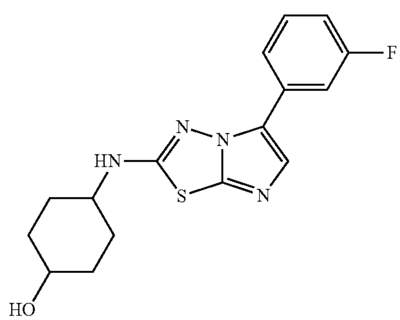 [SMILES: OC1CCC(Nc2nn3c(-c4cccc(F)c4)cnc3s2)CC1] | 4-[5-(3-Fluoro-phenyl)-imidazo[2,1-b][1,3,4]thiadiazol-2-ylamino]-cyclohexanol | 333 | |
| 367 | 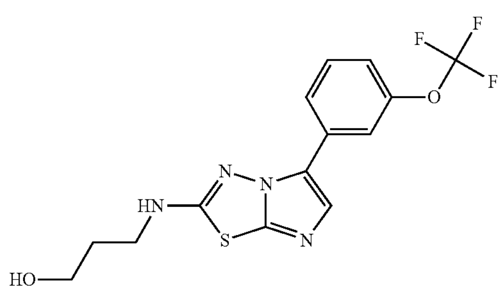 [SMILES: OCCCNc1nn2c(-c3cccc(OC(F)(F)F)c3)cnc2s1] | 3-[5-(3-Trifluoromethoxy-phenyl)-imidazo[2,1-b][1,3,4]thiadiazol-2-ylamino]-propan-1-ol | 359 | |
| 368 | 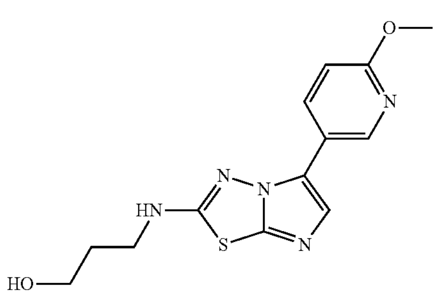 [SMILES: COc1ccc(-c2cnc3sc(NCCCO)nn23)cn1] | 3-[5-(6-Methoxy-pyridin-3-yl)-imidazo[2,1-b][1,3,4]thiadiazol-2-ylamino]-propan-1-ol | 306 | |

-continued

| No | Structure | Name | HPLC/MS [M + H]+ | NMR DMSO |
|---|---|---|---|---|
| 369 | 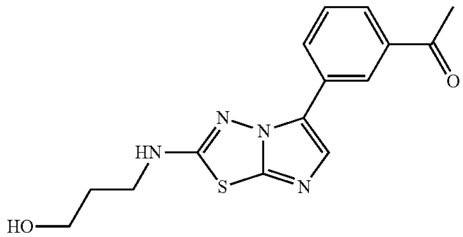 [SMILES: CC(=O)c1cccc(-c2cnc3sc(NCCCO)nn23)c1] | 1-{3-[2-(3-Hydroxy-propylamino)-imidazo[2,1-b][1,3,4]thiadiazol-5-yl]-phenyl}-ethanone | 317 | |
| 370 | 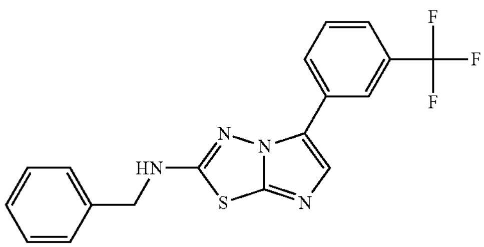 [SMILES: FC(F)(F)c1cccc(-c2cnc3sc(NCc4ccccc4)nn23)c1] | Benzyl-[5-(3-trifluoromethyl-phenyl)-imidazo[2,1-b][1,3,4]thiadiazol-2-yl]-amine | 375 | |
| 371 | 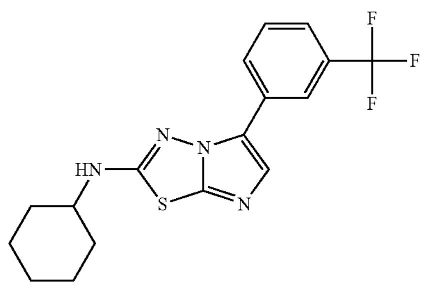 [SMILES: FC(F)(F)c1cccc(-c2cnc3sc(NC4CCCCC4)nn23)c1] | Cyclohexyl-[5-(3-trifluoromethyl-phenyl)-imidazo[2,1-b][1,3,4]thiadiazol-2-yl]-amine | 367 | |
| 372 | 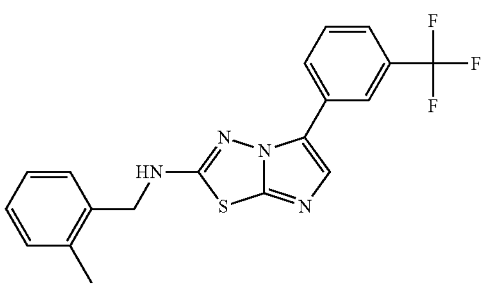 [SMILES: Cc1ccccc1CNc1nn2c(-c3cccc(C(F)(F)F)c3)cnc2s1] | (2-Methyl-benzyl)-[5-(3-trifluoromethyl-phenyl)-imidazo[2,1-b][1,3,4]thiadiazol-2-yl]-amine | 389 | |
| 373 | 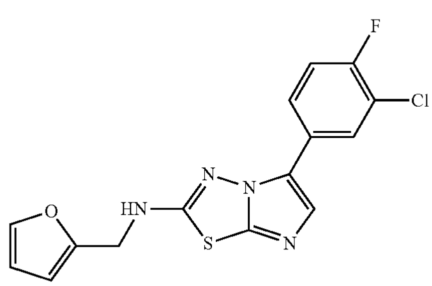 [SMILES: Fc1ccc(-c2cnc3sc(NCc4ccco4)nn23)cc1Cl] | [5-(3-Chloro-4-fluoro-phenyl)-imidazo[2,1-b][1,3,4]thiadiazol-2-yl]-furan-2-ylmethyl-amine | 349 | |

| No | Structure | Name | HPLC/MS [M + H]+ | NMR DMSO |
|---|---|---|---|---|
| 374 | 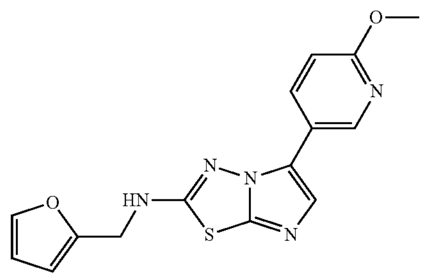 [SMILES: COc1ccc(-c2cnc3sc(NCc4ccco4)nn23)cn1] | Furan-2-ylmethyl-[5-(6-methoxy-pyridin-3-yl)-imidazo[2,1-b][1,3,4]thiadiazol-2-yl]-amine | 328 | |
| 375 | 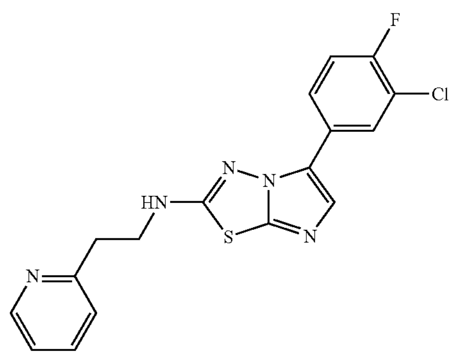 [SMILES: Fc1ccc(-c2cnc3sc(NCCc4ccccn4)nn23)cc1Cl] | [5-(3-Chloro-4-fluoro-phenyl)-imidazo[2,1-b][1,3,4]thiadiazol-2-yl]-(2-pyridin-2-yl-ethyl)-amine | 374 | |
| 376 | 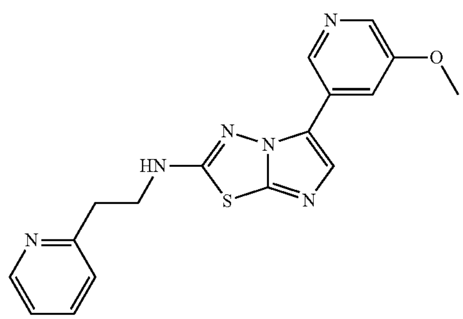 [SMILES: COc1cncc(-c2cnc3sc(NCCc4ccccn4)nn23)c1] | [5-(5-Methoxy-pyridin-3-yl)-imidazo[2,1-b][1,3,4]thiadiazol-2-yl]-(2-pyridin-2-yl-ethyl)-amine | 353 | |
| 377 | 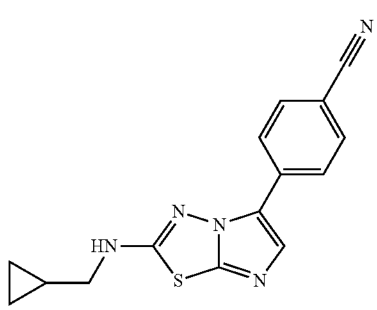 [SMILES: N#Cc1ccc(-c2cnc3sc(NCC4CC4)nn23)cc1] | 4-[2-(Cyclopropylmethyl-amino)-imidazo[2,1-b][1,3,4]thiadiazol-5-yl]-benzonitrile | 295 | |
| 378 | 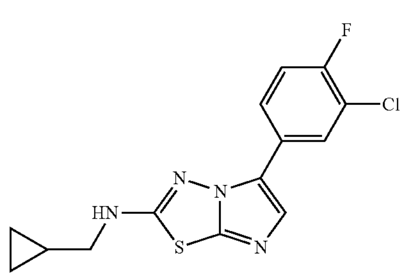 [SMILES: Fc1ccc(-c2cnc3sc(NCC4CC4)nn23)cc1Cl] | [5-(3-Chloro-4-fluoro-phenyl)-imidazo[2,1-b][1,3,4]thiadiazol-2-yl]-cyclopropylmethyl-amine | 323 | |

-continued

| No | Structure | Name | HPLC/MS [M + H]+ | NMR DMSO |
|---|---|---|---|---|
| 379 | 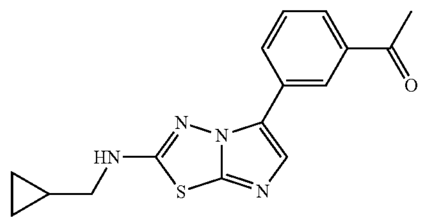 [SMILES: CC(=O)c1cccc(-c2cnc3sc(NCC4CC4)nn23)c1] | 1-{3-[2-(Cyclopropylmethyl-amino)-imidazo[2,1-b][1,3,4]thiadiazol-5-yl]-phenyl}-ethanone | 313 | |
| 380 | 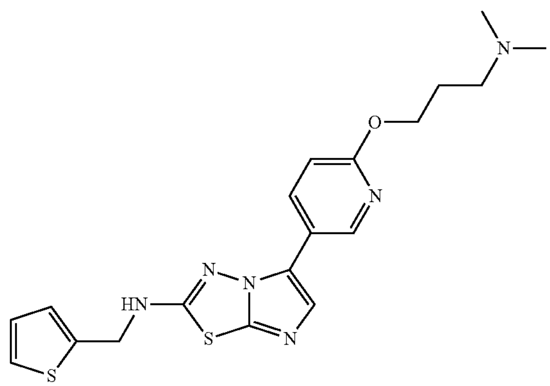 [SMILES: CN(C)CCCOc1ccc(-c2cnc3sc(NCc4cccs4)nn23)cn1] | {5-[6-(3-Dimethylamino-propoxy)-pyridin-3-yl]-imidazo[2,1-b][1,3,4]thiadiazol-2-yl}-thiophen-2-ylmethyl-amine | 416 | |
| 381 | 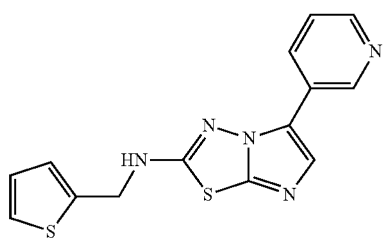 [SMILES: c1cncc(-c2cnc3sc(NCc4cccs4)nn23)c1] | (5-Pyridin-3-yl-imidazo[2,1-b][1,3,4]thiadiazol-2-yl)-thiophen-2-ylmethyl-amine | 314 | |
| 382 | 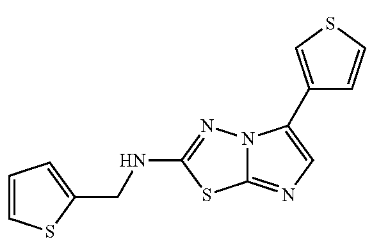 [SMILES: c1csc(CNc2nn3c(-c4ccsc4)cnc3s2)c1] | (5-Thiophen-3-yl-imidazo[2,1-b][1,3,4]thiadiazol-2-yl)-thiophen-2-ylmethyl-amine | 319 | |
| 383 | 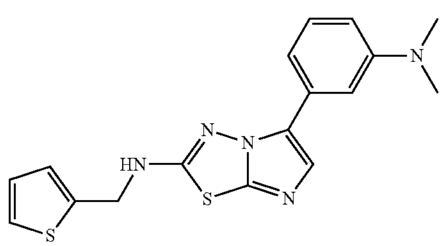 [SMILES: CN(C)c1cccc(-c2cnc3sc(NCc4cccs4)nn23)c1] | [5-(3-Dimethylamino-phenyl)-imidazo[2,1-b][1,3,4]thiadiazol-2-yl]-thiophen-2-ylmethyl-amine | 356 | |
| 384 | 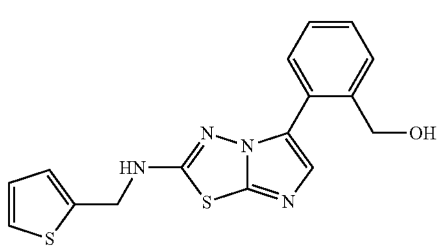 [SMILES: OCc1ccccc1-c1cnc2sc(NCc3cccs3)nn12] | (2-{2-[(Thiophen-2-ylmethyl)-amino]-imidazo[2,1-b][1,3,4]thiadiazol-5-yl}-phenyl)-methanol | 343 | |

-continued

| No | Structure | Name | HPLC/MS [M + H]+ | NMR DMSO |
|---|---|---|---|---|
| 385 | 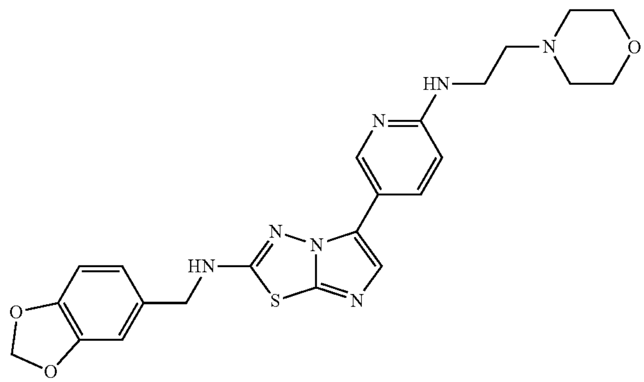 [SMILES: c1cc2c(cc1CNc1nn3c(-c4ccc(NCCN5CCOCC5)nc4)cnc3s1)OCO2] | Benzo[1,3]dioxol-5-ylmethyl-{5-[6-(2-morpholin-4-yl-ethylamino)-pyridin-3-yl]-imidazo[2,1-b][1,3,4]thiadiazol-2-yl}-amine | 481 | |
| 386 | 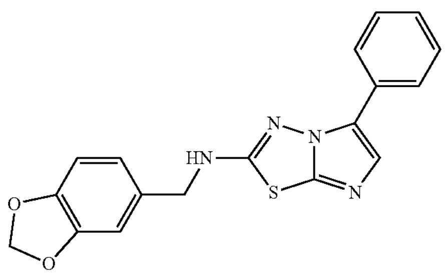 [SMILES: c1ccc(-c2cnc3sc(NCc4ccc5c(c4)OCO5)nn23)cc1] | Benzo[1,3]dioxol-5-ylmethyl-(5-phenyl-imidazo[2,1-b][1,3,4]thiadiazol-2-yl)-amine | 351 | |
| 387 | 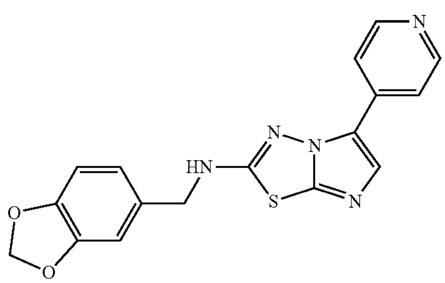 [SMILES: c1cc(-c2cnc3sc(NCc4ccc5c(c4)OCO5)nn23)ccn1] | Benzo[1,3]dioxol-5-ylmethyl-(5-pyridin-4-yl-imidazo[2,1-b][1,3,4]thiadiazol-2-yl)-amine | 352 | |
| 388 | 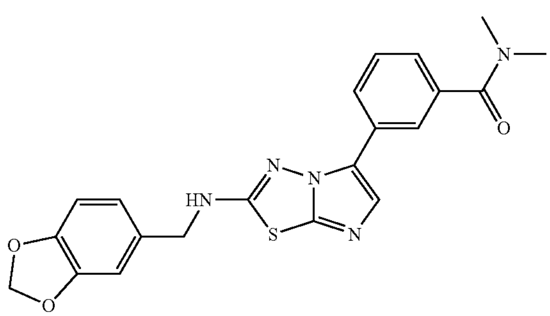 [SMILES: CN(C)C(=O)c1cccc(-c2cnc3sc(NCc4ccc5c(c4)OCO5)nn23)c1] | 3-{2-[(Benzo[1,3]dioxol-5-ylmethyl)-amino]-imidazo[2,1-b][1,3,4]thiadiazol-5-yl}-N,N-dimethyl-benzamide | 422 | |
| 389 | 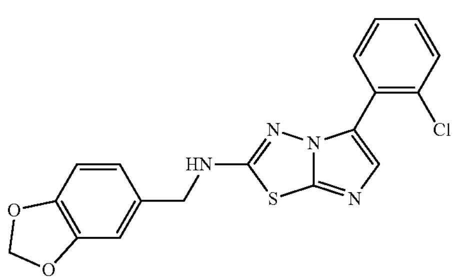 [SMILES: Clc1ccccc1-c1cnc2sc(NCc3ccc4c(c3)OCO4)nn12] | Benzo[1,3]dioxol-5-ylmethyl-[5-(2-chloro-phenyl)-imidazo[2,1-b][1,3,4]thiadiazol-2-yl]-amine | 385 | |

| No | Structure | Name | HPLC/MS [M + H]+ | NMR DMSO |
|---|---|---|---|---|
| 390 | 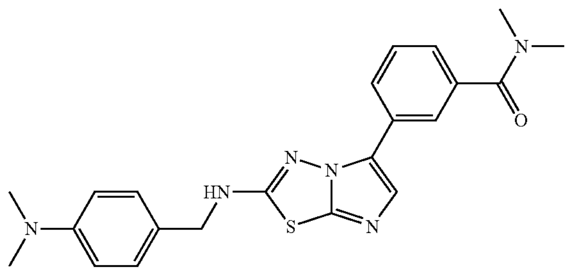 | 3-[2-(4-Dimethylamino-benzylamino)-imidazo[2,1-b][1,3,4]thiadiazol-5-yl]-N,N-dimethyl-benzamide | 422 | |
| 391 | 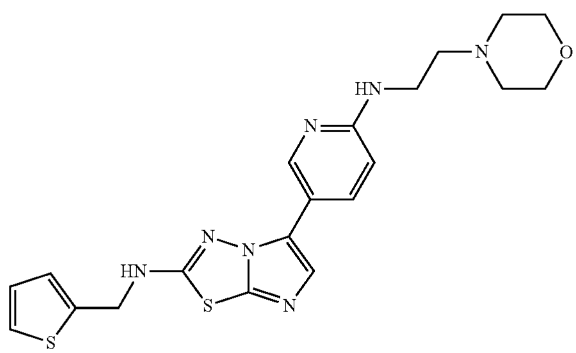 [SMILES: c1csc(CNc2nn3c(-c4ccc(NCCN5CCOCC5)nc4)cnc3s2)c1] | {5-[6-(2-Morpholin-4-yl-ethylamino)-pyridin-3-yl]-imidazo[2,1-b][1,3,4]thiadiazol-2-yl]-thiophen-2-ylmethyl-amine | 443 | |
| 392 | 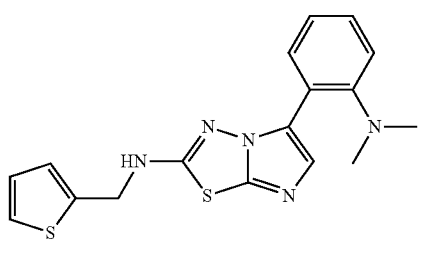 [SMILES: CN(C)c1ccccc1-c1cnc2sc(NCc3cccs3)nn12] | [5-(2-Dimethylamino-phenyl)-imidazo[2,1-b][1,3,4]thiadiazol-2-yl]-thiophen-2-ylmethyl-amine | 356 | |
| 393 | 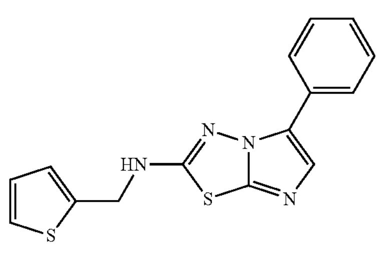 [SMILES: c1ccc(-c2cnc3sc(NCc4cccs4)nn23)cc1] | (5-Phenyl-imidazo[2,1-b][1,3,4]thiadiazol-2-yl)-thiophen-2-ylmethyl-amine | 313 | |
| 394 | 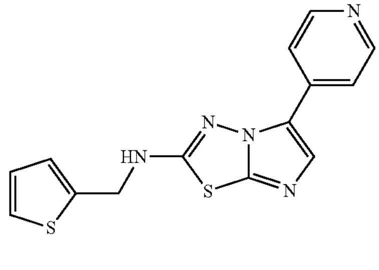 [SMILES: c1csc(CNc2nn3c(-c4ccncc4)cnc3s2)c1] | (5-Pyridin-4-yl-imidazo[2,1-b][1,3,4]thiadiazol-2-yl)-thiophen-2-ylmethyl-amine | 314 | |

| No | Structure | Name | HPLC/MS [M + H]+ | NMR DMSO |
|---|---|---|---|---|
| 395 | 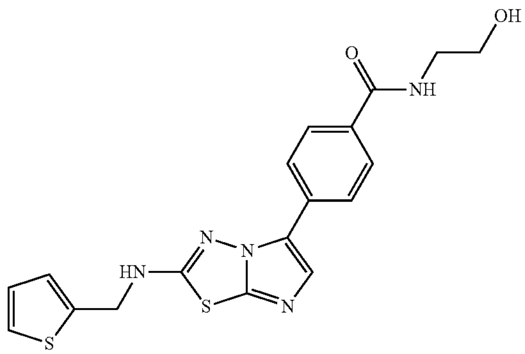 [SMILES: O=C(NCCO)c1ccc(-c2cnc3sc(NCc4cccs4)nn23)cc1] | N-(2-Hydroxy-ethyl)-4-{2-[(thiophen-2-ylmethyl)-amino]-imidazo[2,1-b][1,3,4]thiadiazol-5-yl}-benzamide | 400 | |
| 396 | 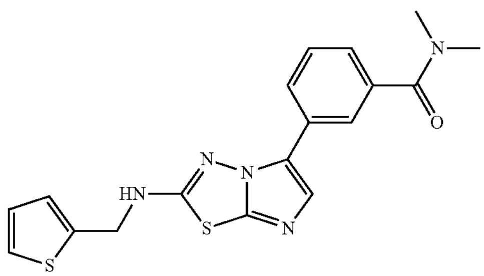 [SMILES: CN(C)C(=O)c1cccc(-c2cnc3sc(NCc4cccs4)nn23)c1] | N,N-Dimethyl-3-{2-[(thiophen-2-ylmethyl)-amino]-imidazo[2,1-b][1,3,4]thiadiazol-5-yl}-benzamide | 384 | |
| 397 | 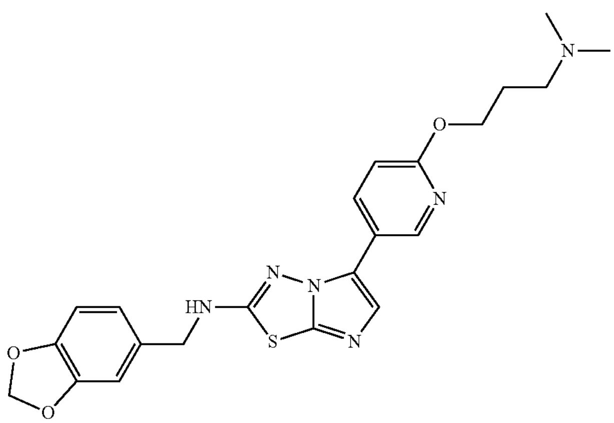 [SMILES: CN(C)CCCOc1ccc(-c2cnc3sc(NCc4ccc5c(c4)OCO5)nn23)cn1] | Benzo[1,3]dioxol-5-ylmethyl-{5-[6-(3-dimethylamino-propoxy)-pyridin-3-yl]-imidazo[2,1-b][1,3,4]thiadiazol-2-yl}-amine | 454 | |
| 398 | 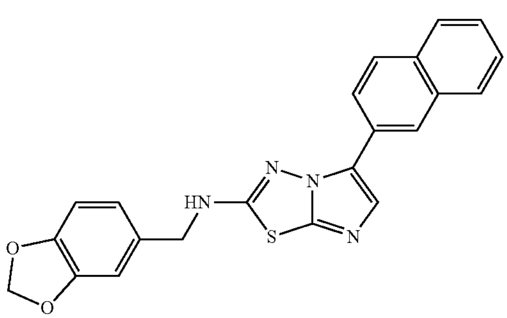 [SMILES: c1ccc2cc(-c3cnc4sc(NCc5ccc6c(c5)OCO6)nn34)ccc2c1] | Benzo[1,3]dioxol-5-ylmethyl-(5-naphthalen-2-yl-imidazo[2,1-b][1,3,4]thiadiazol-2-yl)-amine | 401 | |

-continued

| No | Structure | Name | HPLC/MS [M + H]+ | NMR DMSO |
|---|---|---|---|---|
| 399 | 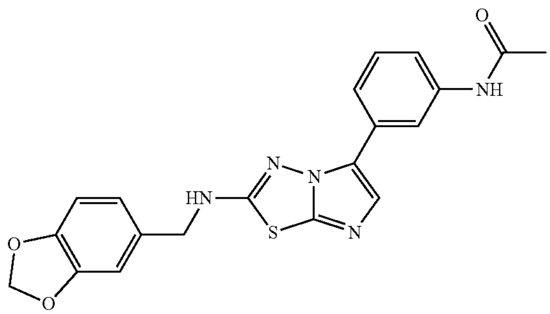 [SMILES: CC(=O)Nc1cccc(-c2cnc3sc(NCc4ccc5c(c4)OCO5)nn23)c1] | N-(3-{2-[(Benzo[1,3]dioxol-5-ylmethyl)-amino]-imidazo[2,1-b][1,3,4]thiadiazol-5-yl}-phenyl)-acetamide | 408 | |
| 400 | 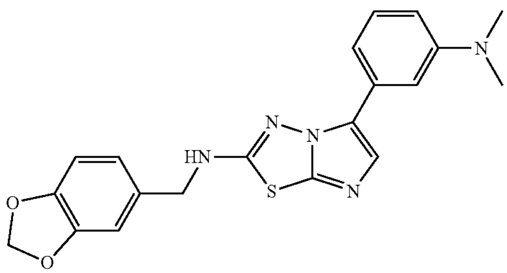 [SMILES: CN(C)c1cccc(-c2cnc3sc(NCc4ccc5c(c4)OCO5)nn23)c1] | Benzo[1,3]dioxol-5-ylmethyl-[5-(3-dimethylamino-phenyl)-imidazo[2,1-b][1,3,4]thiadiazol-2-yl]-amine | 394 | |
| 401 | 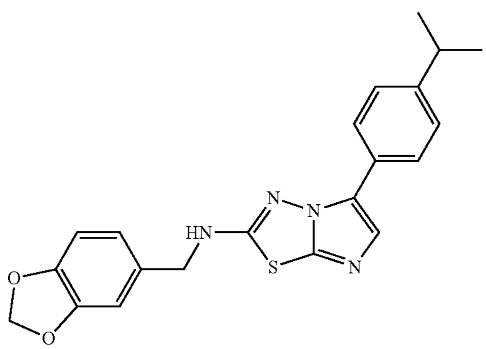 [SMILES: CC(C)c1ccc(-c2cnc3sc(NCc4ccc5c(c4)OCO5)nn23)cc1] | Benzo[1,3]dioxol-5-ylmethyl-[5-(4-isopropyl-phenyl)-imidazo[2,1-b][1,3,4]thiadiazol-2-yl]-amine | 393 | |
| 402 | 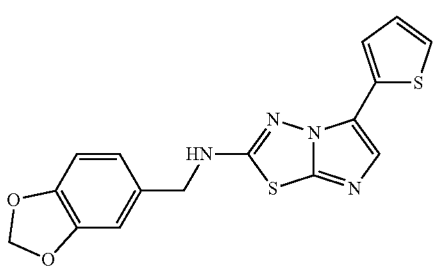 [SMILES: c1csc(-c2cnc3sc(NCc4ccc5c(c4)OCO5)nn23)c1] | Benzo[1,3]dioxol-5-ylmethyl-(5-thiophen-2-yl-imidazo[2,1-b][1,3,4]thiadiazol-2-yl)-amine | 357 | |
| 403 | 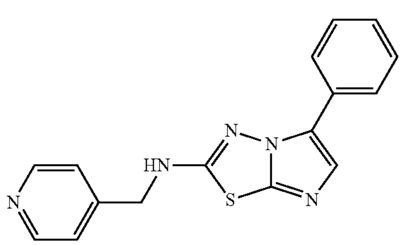 [SMILES: c1ccc(-c2cnc3sc(NCc4ccncc4)nn23)cc1] | (5-Phenyl-imidazo[2,1-b][1,3,4]thiadiazol-2-yl)-pyridin-4-ylmethyl-amine | 308 | |

-continued

| No | Structure | Name | HPLC/MS [M + H]+ | NMR DMSO |
|---|---|---|---|---|
| 404 | 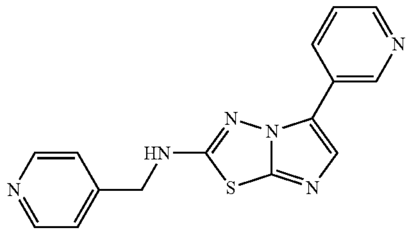 [SMILES: c1cncc(-c2cnc3sc(NCc4ccncc4)nn23)c1] | (5-Pyridin-3-yl-imidazo[2,1-b][1,3,4]thiadiazol-2-yl)-pyridin-4-ylmethyl-amine | 309 | |
| 405 | 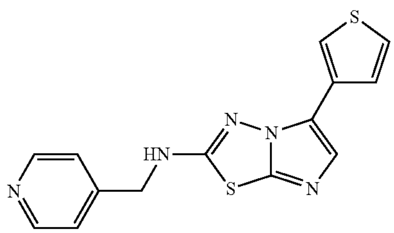 [SMILES: c1cc(CNc2nn3c(-c4ccsc4)cnc3s2)ccn1] | Pyridin-4-ylmethyl-(5-thiophen-3-yl-imidazo[2,1-b][1,3,4]thiadiazol-2-yl)-amine | 314 | |
| 406 | 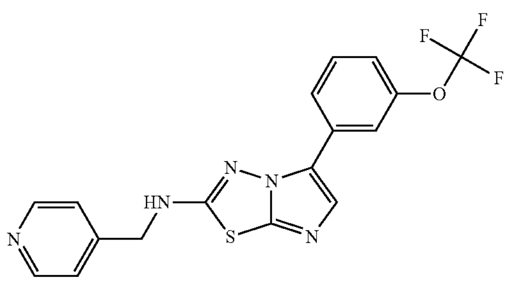 [SMILES: FC(F)(F)Oc1cccc(-c2cnc3sc(NCc4ccncc4)nn23)c1] | Pyridin-4-ylmethyl-[5-(3-trifluoromethoxy-phenyl)-imidazo[2,1-b][1,3,4]thiadiazol-2-yl]-amine | 392 | |
| 407 | 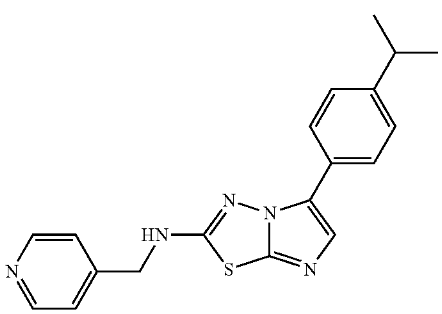 [SMILES: CC(C)c1ccc(-c2cnc3sc(NCc4ccncc4)nn23)cc1] | [5-(4-Isopropyl-phenyl)-imidazo[2,1-b][1,3,4]thiadiazol-2-yl]-pyridin-4-ylmethyl-amine | 350 | |
| 408 | 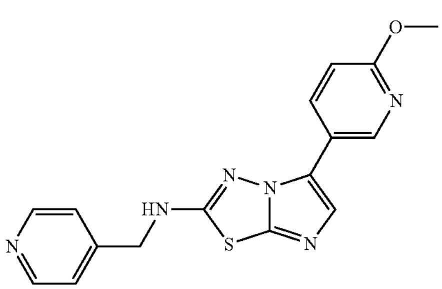 [SMILES: COc1ccc(-c2cnc3sc(NCc4ccncc4)nn23)cn1] | [5-(6-Methoxy-pyridin-3-yl)-imidazo[2,1-b][1,3,4]thiadiazol-2-yl]-pyridin-4-ylmethyl-amine | 339 | |

-continued

| No | Structure | Name | HPLC/MS [M + H]+ | NMR DMSO |
|---|---|---|---|---|
| 409 | 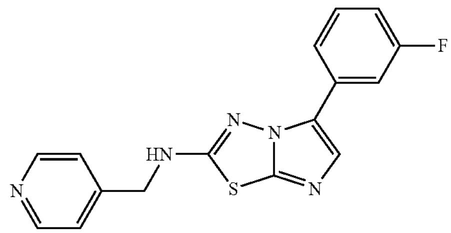 [SMILES: Fc1cccc(-c2cnc3sc(NCc4ccncc4)nn23)c1] | [5-(3-Fluoro-phenyl)-imidazo[2,1-b][1,3,4]thiadiazol-2-yl]-pyridin-4-ylmethyl-amine | 326 | |
| 410 | 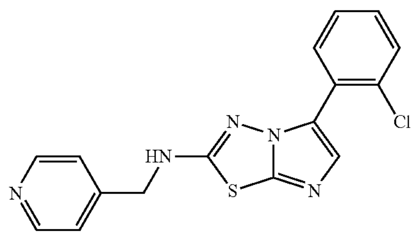 [SMILES: Clc1ccccc1-c1cnc2sc(NCc3ccncc3)nn12] | [5-(2-Chloro-phenyl)-imidazo[2,1-b][1,3,4]thiadiazol-2-yl]-pyridin-4-ylmethyl-amine | 342 | |
| 411 | 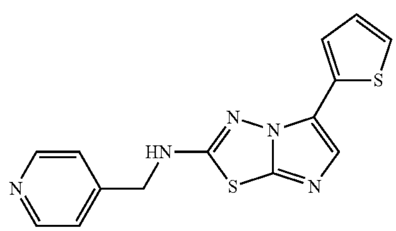 [SMILES: c1csc(-c2cnc3sc(NCc4ccncc4)nn23)c1] | Pyridin-4-ylmethyl-(5-thiophen-2-yl-imidazo[2,1-b][1,3,4]thiadiazol-2-yl)-amine | 314 | |
| 412 | 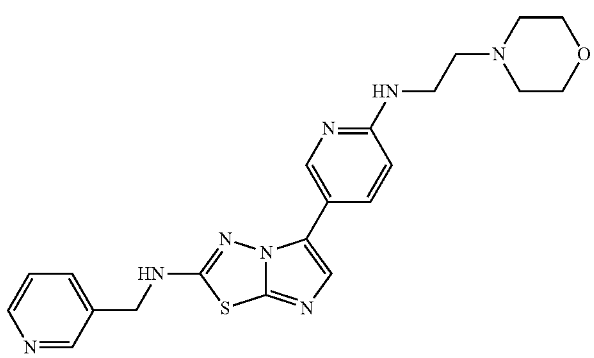 [SMILES: c1cncc(CNc2nn3c(-c4ccc(NCCN5CCOCC5)nc4)cnc3s2)c1] | {5-[6-(2-Morpholin-4-yl-ethylamino)-pyridin-3-yl]-imidazo[2,1-b][1,3,4]thiadiazol-2-yl}-pyridin-3-ylmethyl-amine | 438 | |
| 413 | 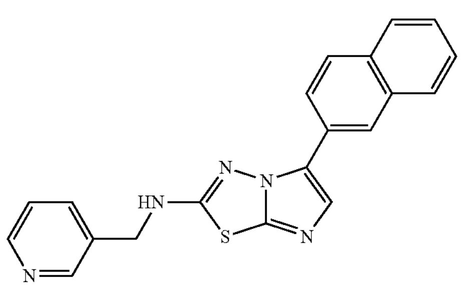 [SMILES: c1cncc(CNc2nn3c(-c4ccc5ccccc5c4)cnc3s2)c1] | (5-Naphthalen-2-yl-imidazo[2,1-b][1,3,4]thiadiazol-2-yl)-pyridin-3-ylmethyl-amine | 358 | |

-continued

| No | Structure | Name | HPLC/MS [M + H]+ | NMR DMSO |
|---|---|---|---|---|
| 414 | 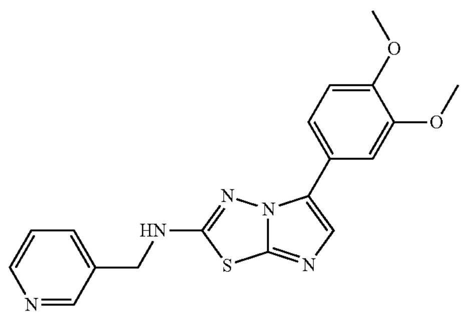 [SMILES: COc1ccc(-c2cnc3sc(NCc4cccnc4)nn23)cc1OC] | [5-(3,4-Dimethoxy-phenyl)-imidazo[2,1-b][1,3,4]thiadiazol-2-yl]-pyridin-3-ylmethyl-amine | 368 | δ 8.6 (s, 1H), 8.58 (t, 1H), 8.5 (d, 1H), 7.8 (d, 1H), 7.4 (m, 4H), 7.0 (d, 1H), 4.6 (d, 2H), 3.8 (s, 3H), 3.7 (s, 3H) |
| 415 | 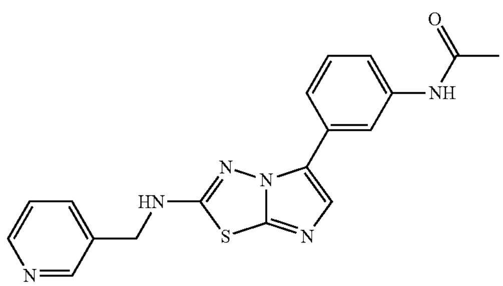 [SMILES: CC(=O)Nc1cccc(-c2cnc3sc(NCc4cccnc4)nn23)c1] | N-(3-{2-[(Pyridin-3-ylmethyl)-amino]-imidazo[2,1-b][1,3,4]thiadiazol-5-yl}-phenyl)-acetamide | 365 | |
| 416 | 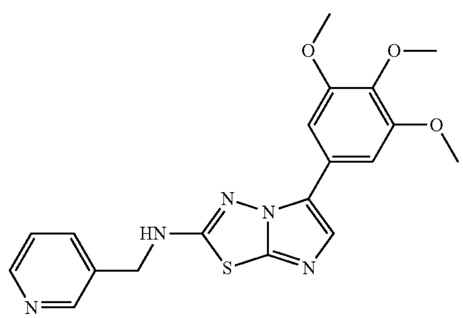 [SMILES: COc1cc(-c2cnc3sc(NCc4cccnc4)nn23)cc(OC)c1OC] | Pyridin-3-ylmethyl-[5-(3,4,5-trimethoxy-phenyl)-imidazo[2,1-b][1,3,4]thiadiazol-2-yl]-amine | 398 | |
| 417 | 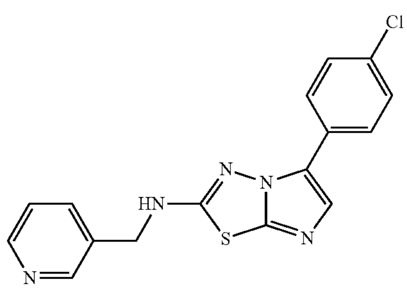 [SMILES: Clc1ccc(-c2cnc3sc(NCc4cccnc4)nn23)cc1] | [5-(4-Chloro-phenyl)-imidazo[2,1-b][1,3,4]thiadiazol-2-yl]-pyridin-3-ylmethyl-amine | 342 | |
| 418 | 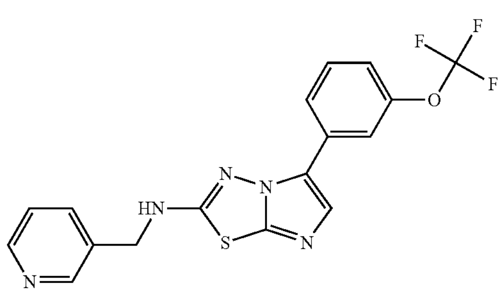 [SMILES: FC(F)(F)Oc1cccc(-c2cnc3sc(NCc4cccnc4)nn23)c1] | Pyridin-3-ylmethyl-[5-(3-trifluoromethoxy-phenyl)-imidazo[2,1-b][1,3,4]thiadiazol-2-yl]-amine | 392 | |

-continued

| No | Structure | Name | HPLC/MS [M + H]+ | NMR DMSO |
|---|---|---|---|---|
| 419 | 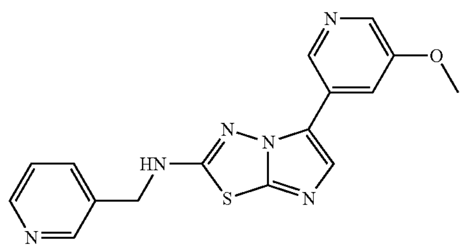 [SMILES: COc1cncc(-c2cnc3sc(NCc4cccnc4)nn23)c1] | [5-(5-Methoxy-pyridin-3-yl)-imidazo[2,1-b][1,3,4]thiadiazol-2-yl]-pyridin-3-ylmethyl-amine | 339 | |
| 420 | 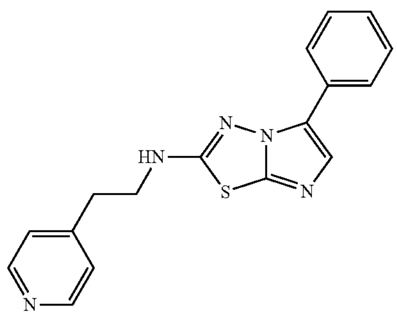 [SMILES: c1ccc(-c2cnc3sc(NCCc4ccncc4)nn23)cc1] | (5-Phenyl-imidazo[2,1-b][1,3,4]thiadiazol-2-yl)-(2-pyridin-4-yl-ethyl)-amine | 322 | |
| 421 | 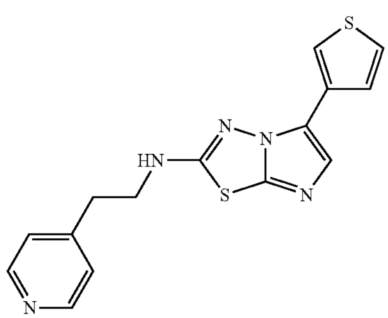 [SMILES: c1cc(CCNc2nn3c(-c4ccsc4)cnc3s2)ccn1] | (2-Pyridin-4-yl-ethyl)-(5-thiophen-3-yl-imidazo[2,1-b][1,3,4]thiadiazol-2-yl)-amine | 328 | |
| 422 | 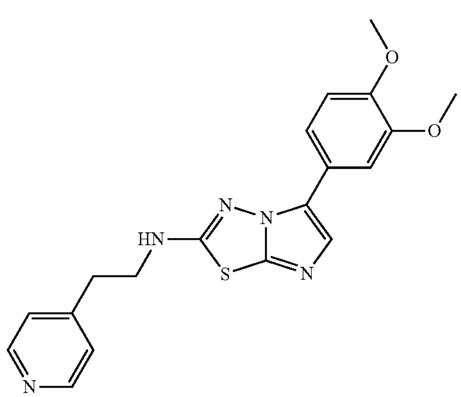 [SMILES: COc1ccc(-c2cnc3sc(NCCc4ccncc4)nn23)cc1OC] | [5-(3,4-Dimethoxy-phenyl)-imidazo[2,1-b][1,3,4]thiadiazol-2-yl]-(2-pyridin-4-yl-ethyl)-amine | 382 | δ 8.5 (d, 2H), 8.1 (t, 1H), 7.6 (s, 1H), 7.5 (d, 1H), 7.4 (s, 1H), 7.3 (d, 2H), 7.0 (d, 1H), 3.8 (d, 6H), 3.6 (m, 2H), 3.0 (m, 2H) |

-continued

| No | Structure | Name | HPLC/MS [M + H]+ | NMR DMSO |
|---|---|---|---|---|
| 423 | 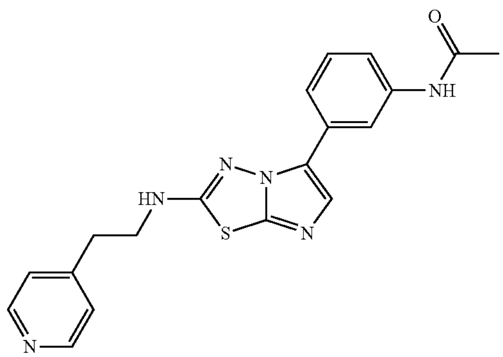 [SMILES: CC(=O)Nc1cccc(-c2cnc3sc(NCCc4ccncc4)nn23)c1] | N-{3-[2-(2-Pyridin-4-yl-ethylamino)-imidazo[2,1-b][1,3,4]thiadiazol-5-yl]-phenyl}-acetamide | 379 | |
| 424 | 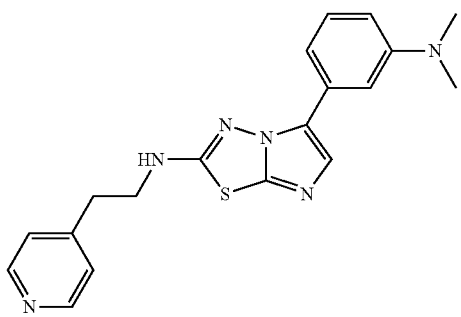 [SMILES: CN(C)c1cccc(-c2cnc3sc(NCCc4ccncc4)nn23)c1] | [5-(3-Dimethylamino-phenyl)-imidazo[2,1-b][1,3,4]thiadiazol-2-yl]-(2-pyridin-4-yl-ethyl)-amine | 365 | |
| 425 | 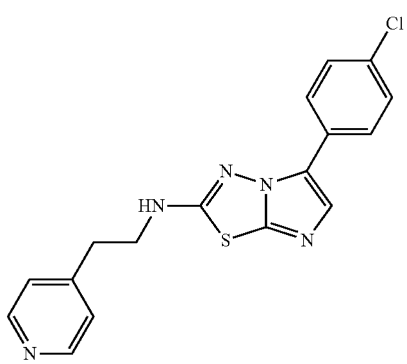 [SMILES: Clc1ccc(-c2cnc3sc(NCCc4ccncc4)nn23)cc1] | [5-(4-Chloro-phenyl)-imidazo[2,1-b][1,3,4]thiadiazol-2-yl]-(2-pyridin-4-yl-ethyl)-amine | 356 | |
| 426 | 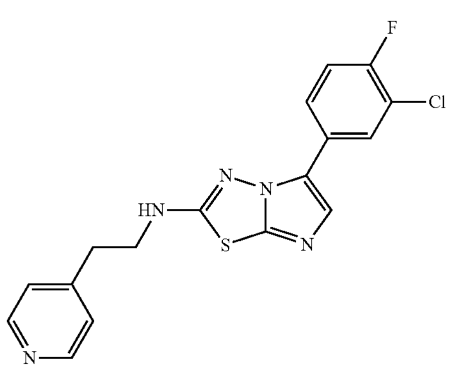 [SMILES: Fc1ccc(-c2cnc3sc(NCCc4ccncc4)nn23)cc1Cl] | [5-(3-Chloro-4-fluoro-phenyl)-imidazo[2,1-b][1,3,4]thiadiazol-2-yl]-(2-pyridin-4-yl-ethyl)-amine | 374 | |

| No | Structure | Name | HPLC/MS [M + H]+ | NMR DMSO |
|---|---|---|---|---|
| 427 | 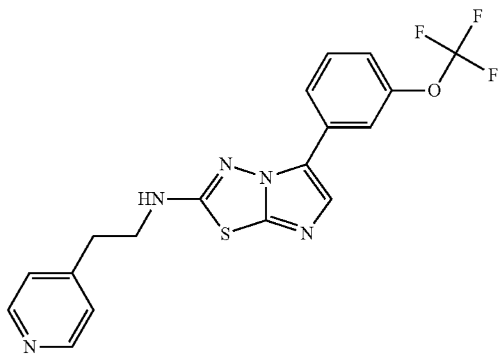 [SMILES: FC(F)(F)Oc1cccc(-c2cnc3sc(NCCc4ccncc4)nn23)c1] | (2-Pyridin-4-yl-ethyl)-[5-(3-trifluoromethoxy-phenyl)-imidazo[2,1-b][1,3,4]thiadiazol-2-yl]-amine | 406 | |
| 428 | 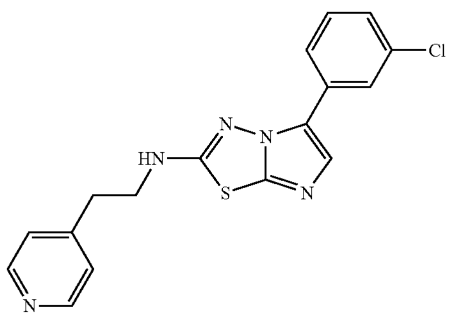 [SMILES: Clc1cccc(-c2cnc3sc(NCCc4ccncc4)nn23)c1] | [5-(3-Chloro-phenyl)-imidazo[2,1-b][1,3,4]thiadiazol-2-yl]-(2-pyridin-4-yl-ethyl)-amine | 356 | |
| 429 | 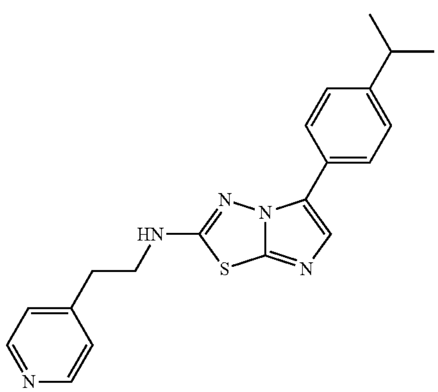 [SMILES: CC(C)c1ccc(-c2cnc3sc(NCCc4ccncc4)nn23)cc1] | [5-(4-Isopropyl-phenyl)-imidazo[2,1-b][1,3,4]thiadiazol-2-yl]-(2-pyridin-4-yl-ethyl)-amine | 364 | |
| 430 | 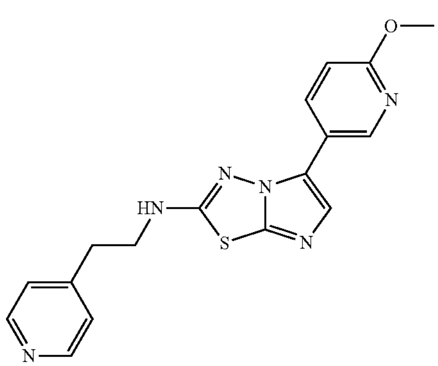 [SMILES: COc1ccc(-c2cnc3sc(NCCc4ccncc4)nn23)cn1] | [5-(6-Methoxy-pyridin-3-yl)-imidazo[2,1-b][1,3,4]thiadiazol-2-yl]-(2-pyridin-4-yl-ethyl)-amine | 353 | |

-continued

| No | Structure | Name | HPLC/MS [M + H]+ | NMR DMSO |
|---|---|---|---|---|
| 431 | 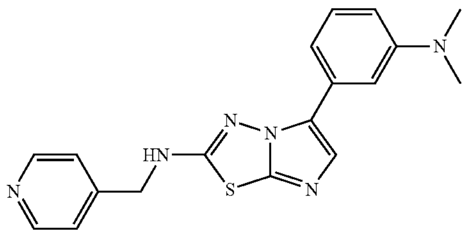 [SMILES: CN(C)c1cccc(-c2cnc3sc(NCc4ccncc4)nn23)c1] | [5-(3-Dimethylamino-phenyl)-imidazo[2,1-b][1,3,4]thiadiazol-2-yl]-pyridin-4-ylmethyl)-amine | 351 | |
| 432 | 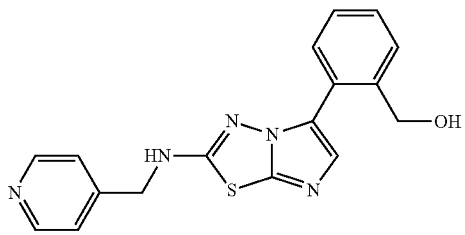 [SMILES: OCc1ccccc1-c1cnc2sc(NCc3ccncc3)nn12] | (2-{2-[(Pyridin-4-ylmethyl)-amino]-imidazo[2,1-b][1,3,4]thiadiazol-5-yl}-phenyl)-methanol | 338 | |
| 433 | 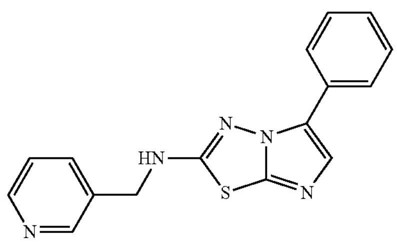 [SMILES: c1ccc(-c2cnc3sc(NCc4cccnc4)nn23)cc1] | (5-Phenyl-imidazo[2,1-b][1,3,4]thiadiazol-2-yl)-pyridin-3-ylmethyl-amine | 308 | |
| 434 | 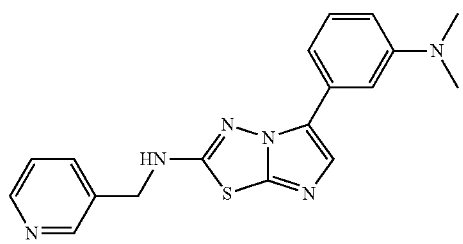 [SMILES: CN(C)c1cccc(-c2cnc3sc(NCc4cccnc4)nn23)c1] | [5-(3-Dimethylamino-phenyl)-imidazo[2,1-b][1,3,4]thiadiazol-2-yl]-pyridin-3-ylmethyl-amine | 351 | |
| 435 | 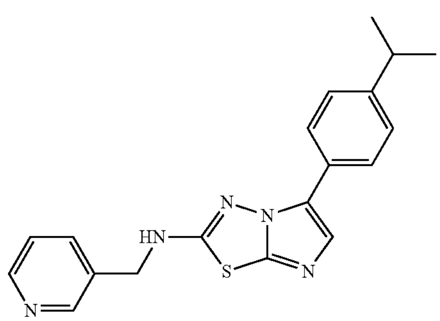 [SMILES: CC(C)c1ccc(-c2cnc3sc(NCc4cccnc4)nn23)cc1] | [5-(4-Isopropyl-phenyl)-imidazo[2,1-b][1,3,4]thiadiazol-2-yl]-pyridin-3-ylmethyl-amine | 350 | |
| 436 | 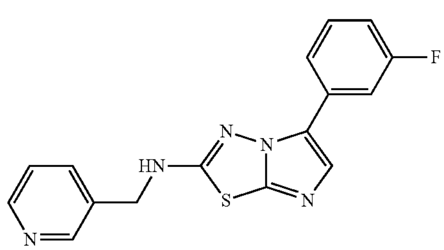 [SMILES: Fc1cccc(-c2cnc3sc(NCc4cccnc4)nn23)c1] | [5-(3-Fluoro-phenyl)-imidazo[2,1-b][1,3,4]thiadiazol-2-yl]-pyridin-3-ylmethyl-amine | 326 | |

| No | Structure | Name | HPLC/MS [M + H]+ | NMR DMSO |
|---|---|---|---|---|
| 437 | 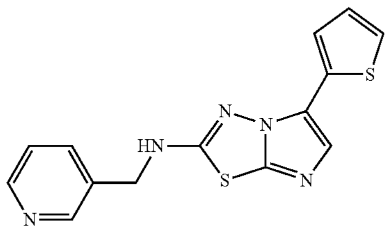 [SMILES: c1cncc(CNc2nn3c(-c4cccs4)cnc3s2)c1] | Pyridin-3-ylmethyl-(5-thiophen-2-yl-imidazo[2,1-b][1,3,4]thiadiazol-2-yl)-amine | 314 | |
| 438 | 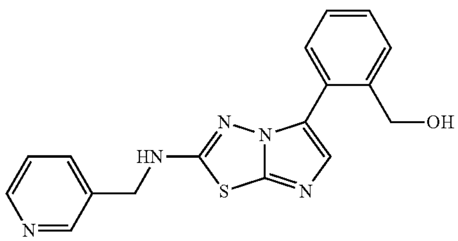 [SMILES: OCc1ccccc1-c1cnc2sc(NCc3cccnc3)nn12] | (2-{2-[(Pyridin-3-ylmethyl)-amino]-imidazo[2,1-b][1,3,4]thiadiazol-5-yl}-phenyl)-methanol | 338 | |
| 439 | 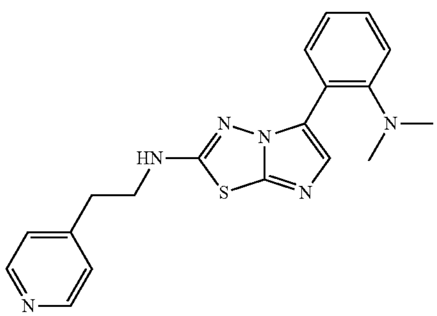 [SMILES: CN(C)c1ccccc1-c1cnc2sc(NCCc3ccncc3)nn12] | [5-(2-Dimethylamino-phenyl)-imidazo[2,1-b][1,3,4]thiadiazol-2-yl]-(2-pyridin-4-yl-ethyl)-amine | 365 | |
| 440 | 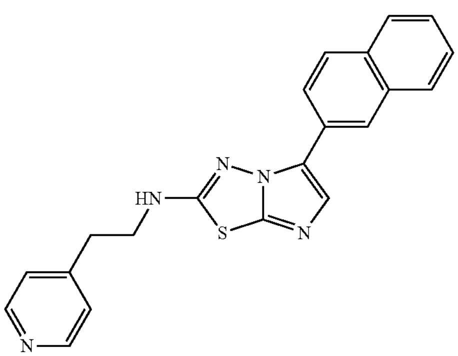 [SMILES: c1ccc2cc(-c3cnc4sc(NCCc5ccncc5)nn34)ccc2c1] | (5-Naphthalen-2-yl-imidazo[2,1-b][1,3,4]thiadiazol-2-yl)-(2-pyridin-4-yl-ethyl)-amine | 372 | |
| 441 | 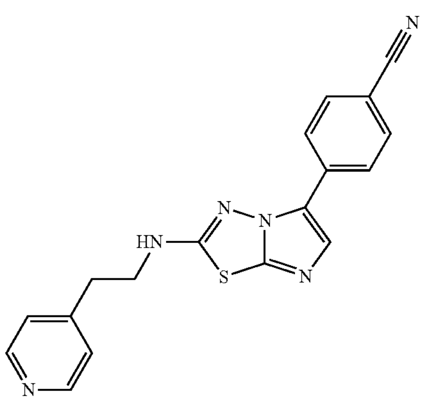 [SMILES: N#Cc1ccc(-c2cnc3sc(NCCc4ccncc4)nn23)cc1] | 4-[2-(2-Pyridin-4-yl-ethylamino)-imidazo[2,1-b][1,3,4]thiadiazol-5-yl]-benzonitrile | 347 | |

| No | Structure | Name | HPLC/MS [M + H]+ | NMR DMSO |
|---|---|---|---|---|
| 442 | 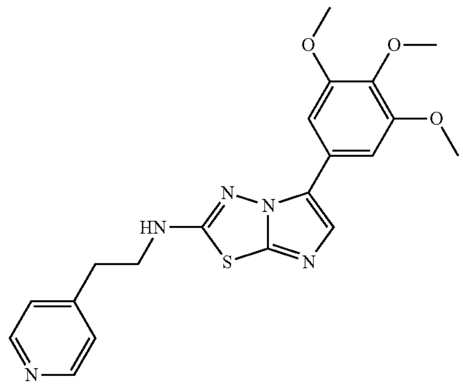 [SMILES: COc1cc(-c2cnc3sc(NCCc4ccncc4)nn23)cc(OC)c1OC] | (2-Pyridin-4-yl-ethyl)-[5-(3,4,5-trimethoxy-phenyl)-imidazo[2,1-b][1,3,4]thiadiazol-2-yl]-amine | 412 | |
| 443 | 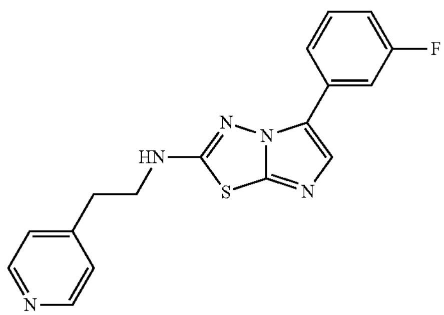 [SMILES: Fc1cccc(-c2cnc3sc(NCCc4ccncc4)nn23)c1] | [5-(3-Fluoro-phenyl)-imidazo[2,1-b][1,3,4]thiadiazol-2-yl]-(2-pyridin-4-yl-ethyl)-amine | 340 | |
| 444 | 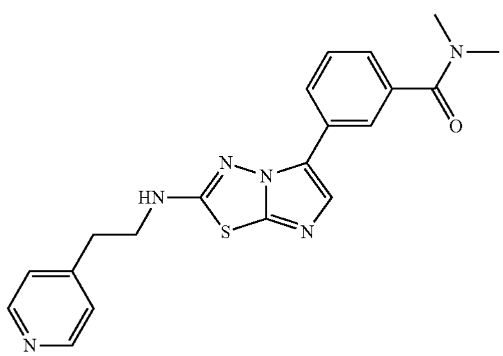 [SMILES: CN(C)C(=O)c1cccc(-c2cnc3sc(NCCc4ccncc4)nn23)c1] | N,N-Dimethyl-3-[2-(2-pyridin-4-yl-ethylamino)-imidazo[2,1-b][1,3,4]thiadiazol-5-yl]-benzamide | 393 | |
| 445 | 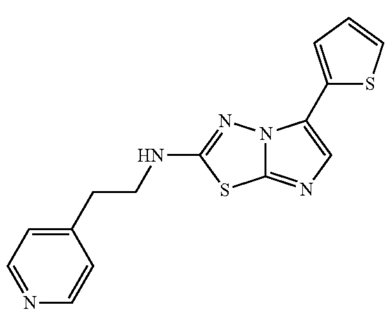 [SMILES: c1csc(-c2cnc3sc(NCCc4ccncc4)nn23)c1] | (2-Pyridin-4-yl-ethyl)-(5-thiophen-2-yl-imidazo[2,1-b][1,3,4]thiadiazol-2-yl)-amine | 328 | |

| No | Structure | Name | HPLC/MS [M + H]+ | NMR DMSO |
|---|---|---|---|---|
| 446 | 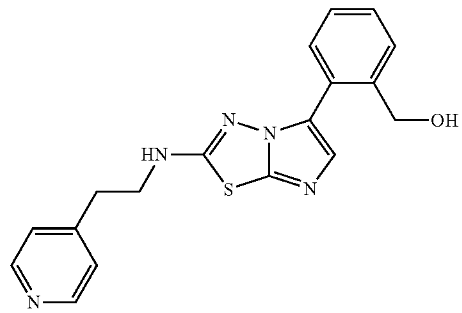 [SMILES: OCc1ccccc1-c1cnc2sc(NCCc3ccncc3)nn12] | {2-[2-(2-Pyridin-4-yl-ethylamino)-imidazo[2,1-b][1,3,4]thiadiazol-5-yl]-phenyl}-methanol | 352 | |
| 447 | 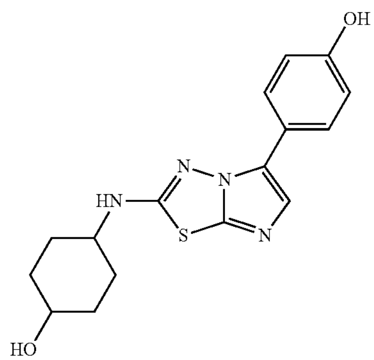 [SMILES: Oc1ccc(-c2cnc3sc(NC4CCC(O)CC4)nn23)cc1] | 4-[2-(4-Hydroxy-cyclohexylamino)-imidazo[2,1-b][1,3,4]thiadiazol-5-yl]-phenol | 331 | |
| 448 | 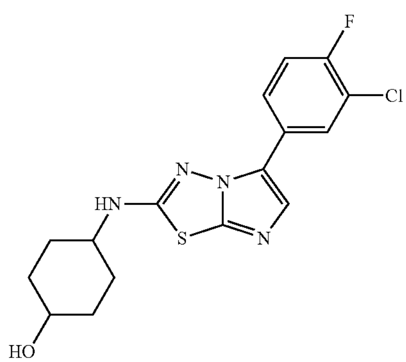 [SMILES: OC1CCC(Nc2nn3c(-c4ccc(F)c(Cl)c4)cnc3s2)CC1] | 4-[5-(3-Chloro-4-fluoro-phenyl)-imidazo[2,1-b][1,3,4]thiadiazol-2-ylamino]-cyclohexanol | 367 | |
| 449 | 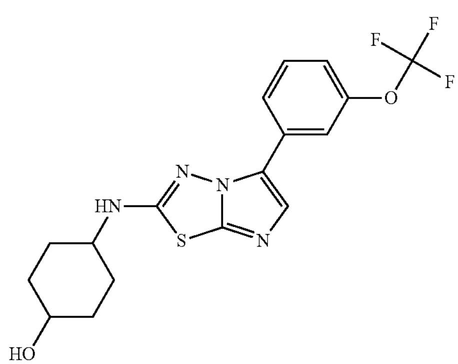 [SMILES: OC1CCC(Nc2nn3c(-c4cccc(OC(F)(F)F)c4)cnc3s2)CC1] | 4-[5-(3-Trifluoromethoxy-phenyl)-imidazo[2,1-b][1,3,4]thiadiazol-2-ylamino]-cyclohexanol | 399 | |

| No | Structure | Name | HPLC/MS [M + H]+ | NMR DMSO |
|---|---|---|---|---|
| 450 | 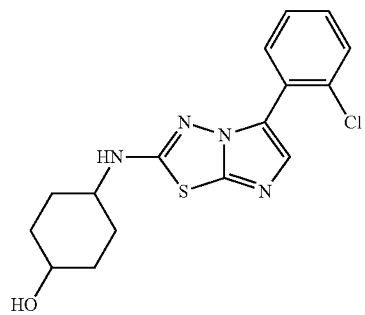 [SMILES: OC1CCC(Nc2nn3c(-c4ccccc4Cl)cnc3s2)CC1] | 4-[5-(2-Chloro-phenyl)-imidazo[2,1-b][1,3,4]thiadiazol-2-ylamino]-cyclohexanol | 349 | |
| 451 | 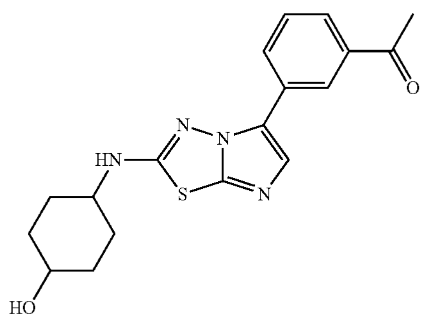 [SMILES: CC(=O)c1cccc(-c2cnc3sc(NC4CCC(O)CC4)nn23)c1] | 1-{3-[2-(4-Hydroxy-cyclohexylamino)-imidazo[2,1-b][1,3,4]thiadiazol-5-yl]-phenyl}-ethanone | 357 | |
| 452 | 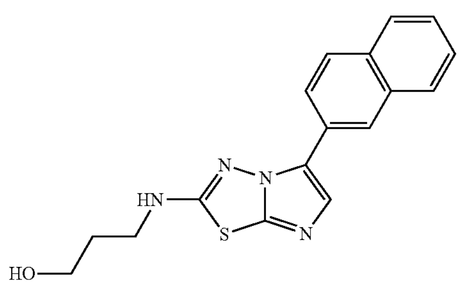 [SMILES: OCCCNc1nn2c(-c3ccc4ccccc4c3)cnc2s1] | 3-(5-Naphthalen-2-yl-imidazo[2,1-b][1,3,4]thiadiazol-2-ylamino)-propan-1-ol | 325 | |
| 453 | 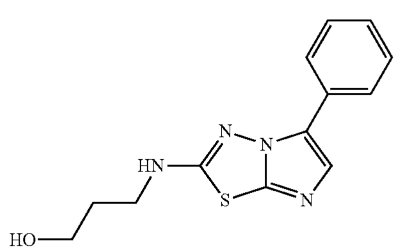 [SMILES: OCCCNc1nn2c(-c3ccccc3)cnc2s1] | 3-(5-Phenyl-imidazo[2,1-b][1,3,4]thiadiazol-2-ylamino)-propan-1-ol | 275 | |
| 454 | 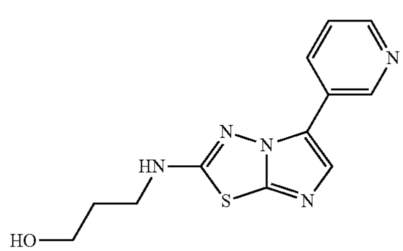 [SMILES: OCCCNc1nn2c(-c3cccnc3)cnc2s1] | 3-(5-Pyridin-3-yl-imidazo[2,1-b][1,3,4]thiadiazol-2-ylamino)-propan-1-ol | 276 | |

| No | Structure | Name | HPLC/MS [M + H]+ | NMR DMSO |
|---|---|---|---|---|
| 455 | 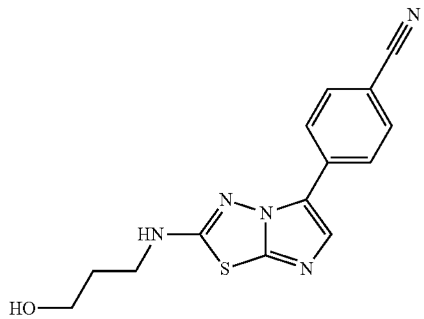 [SMILES: N#Cc1ccc(-c2cnc3sc(NCCCO)nn23)cc1] | 4-[2-(3-Hydroxy-propylamino)-imidazo[2,1-b][1,3,4]thiadiazol-5-yl]-benzonitrile | 300 | |
| 456 | 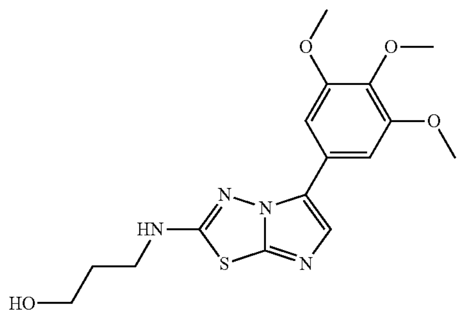 [SMILES: COc1cc(-c2cnc3sc(NCCCO)nn23)cc(OC)c1OC] | 3-[5-(3,4,5-Trimethoxy-phenyl)-imidazo[2,1-b][1,3,4]thiadiazol-2-ylamino]-propan-1-ol | 365 | |
| 457 | 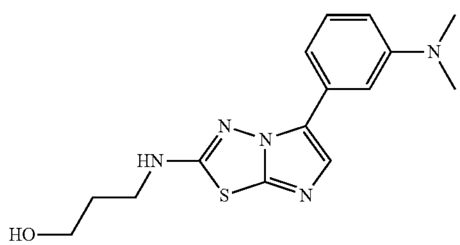 [SMILES: CN(C)c1cccc(-c2cnc3sc(NCCCO)nn23)c1] | 3-[5-(3-Dimethylamino-phenyl)-imidazo[2,1-b][1,3,4]thiadiazol-2-ylamino]-propan-1-ol | 318 | |
| 458 | 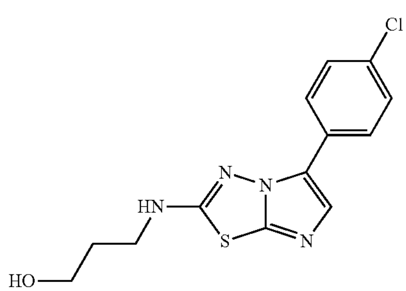 [SMILES: OCCCNc1nn2c(-c3ccc(Cl)cc3)cnc2s1] | 3-[5-(4-Chloro-phenyl)-imidazo[2,1-b][1,3,4]thiadiazol-2-ylamino]-propan-1-ol | 309 | |
| 459 | 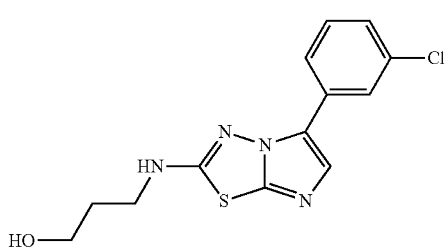 [SMILES: OCCCNc1nn2c(-c3cccc(Cl)c3)cnc2s1] | 3-[5-(3-Chloro-phenyl)-imidazo[2,1-b][1,3,4]thiadiazol-2-ylamino]-propan-1-ol | 309 | |

-continued

| No | Structure | Name | HPLC/MS [M + H]+ | NMR DMSO |
|---|---|---|---|---|
| 460 | 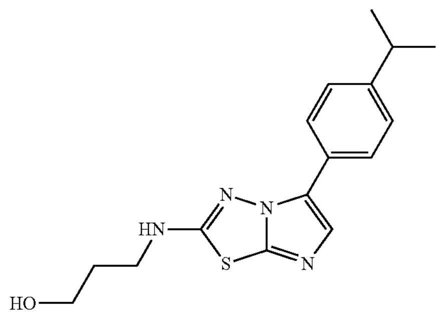 [SMILES: CC(C)c1ccc(-c2cnc3sc(NCCCO)nn23)cc1] | 3-[5-(4-Isopropyl-phenyl)-imidazo[2,1-b][1,3,4]thiadiazol-2-ylamino]-propan-1-ol | 317 | |
| 461 | 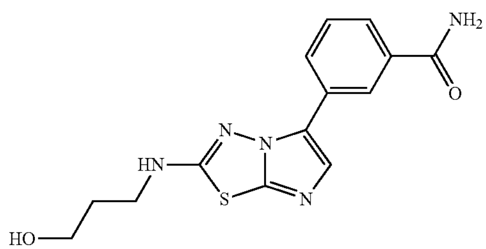 [SMILES: NC(=O)c1cccc(-c2cnc3sc(NCCCO)nn23)c1] | 3-[2-(3-Hydroxy-propylamino)-imidazo[2,1-b][1,3,4]thiadiazol-5-yl]-benzamide | 318 | |
| 462 | 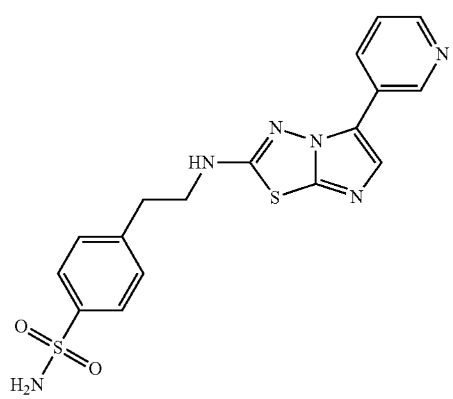 [SMILES: NS(=O)(=O)c1ccc(CCNc2nn3c(-c4cccnc4)cnc3s2)cc1] | 4-[2-(5-Pyridin-3-yl-imidazo[2,1-b][1,3,4]thiadiazol-2-ylamino)-ethyl]-benzenesulfonamide | 401 | |
| 463 | 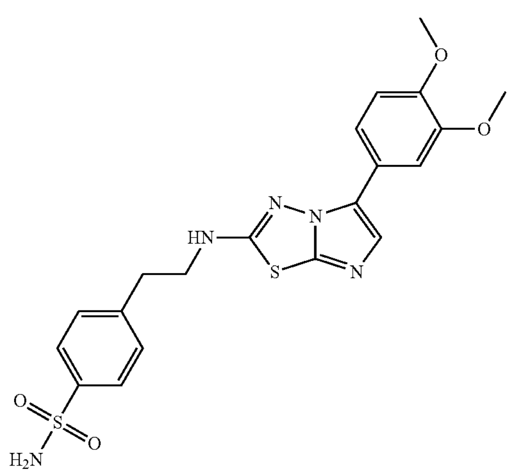 [SMILES: COc1ccc(-c2cnc3sc(NCCc4ccc(S(N)(=O)=O)cc4)nn23)cc1OC] | 4-{2-[5-(3,4-Dimethoxy-phenyl)-imidazo[2,1-b][1,3,4]thiadiazol-2-ylamino]-ethyl}-benzenesulfonamide | 461 | δ 8.1 (t, 1H), 7.7 (d, 2H), 7.6 (s, 1H), 7.5 (m, 3H), 7.4 (s, 1H), 7.3 (s, 2H), 7.0 (d, 1H), 3.8 (d, 6H), 3.6 (m, 2H), 3.0 (m, 2H) |

| No | Structure | Name | HPLC/MS [M + H]+ | NMR DMSO |
|---|---|---|---|---|
| 464 | 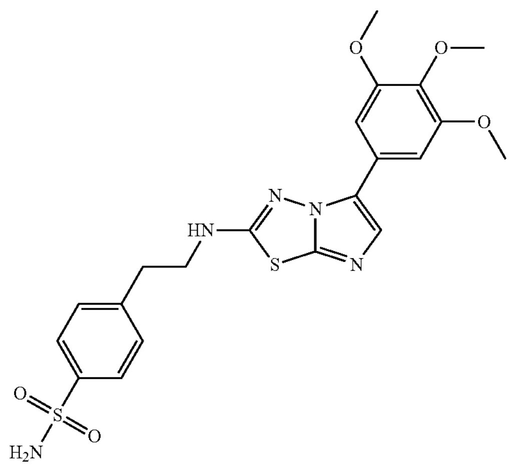 [SMILES: COc1cc(-c2cnc3sc(NCCc4ccc(S(N)(=O)=O)cc4)nn23)cc(OC)c1OC] | 4-{2-[5-(3,4,5-Trimethoxy-phenyl)-imidazo[2,1-b][1,3,4]thiadiazol-2-ylamino]-ethyl}-benzenesulfonamide | 491 | |
| 465 | 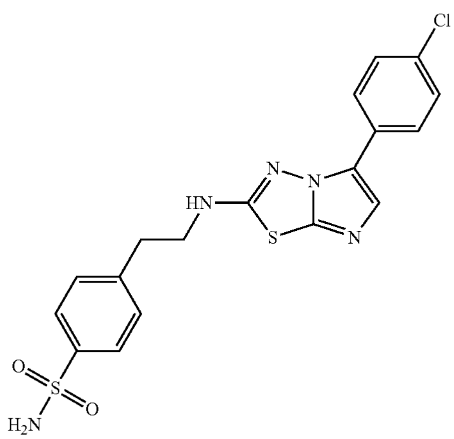 [SMILES: NS(=O)(=O)c1ccc(CCNc2nn3c(-c4ccc(Cl)cc4)cnc3s2)cc1] | 4-{2-[5-(4-Chloro-phenyl)-imidazo[2,1-b][1,3,4]thiadiazol-2-ylamino]-ethyl}-benzenesulfonamide | 434 | |
| 466 | 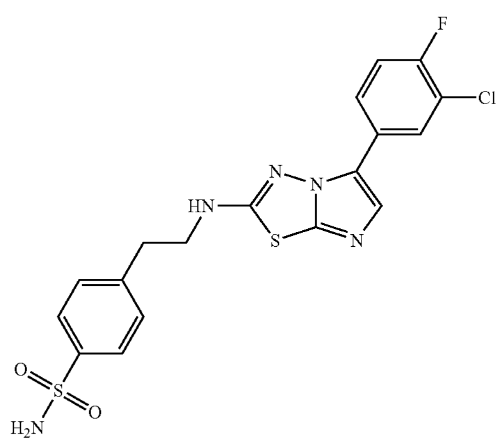 [SMILES: NS(=O)(=O)c1ccc(CCNc2nn3c(-c4ccc(F)c(Cl)c4)cnc3s2)cc1] | 4-{2-[5-(3-Chloro-4-fluoro-phenyl)-imidazo[2,1-b][1,3,4]thiadiazol-2-ylamino]-ethyl}-benzenesulfonamide | 452 | |

| No | Structure | Name | HPLC/MS [M + H]+ | NMR DMSO |
|---|---|---|---|---|
| 467 | 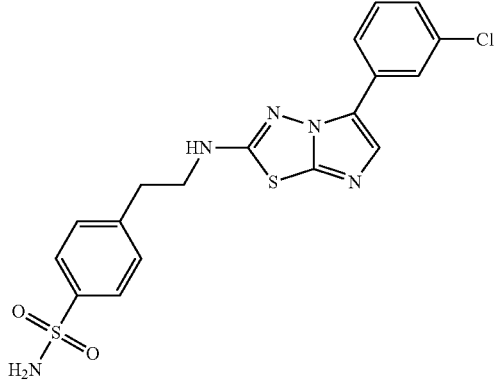 [SMILES: NS(=O)(=O)c1ccc(CCNc2nn3c(-c4cccc(Cl)c4)cnc3s2)cc1] | 4-{2-[5-(3-Chloro-phenyl)-imidazo[2,1-b][1,3,4]thiadiazol-2-ylamino]-ethyl}-benzenesulfonamide | 434 | |
| 468 | 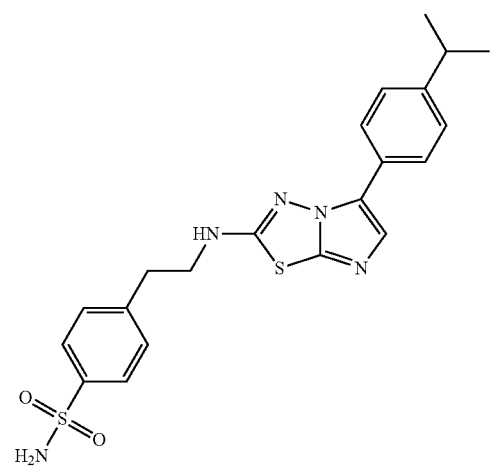 [SMILES: CC(C)c1ccc(-c2cnc3sc(NCCc4ccc(S(N)(=O)=O)cc4)nn23)cc1] | 4-{2-[5-(4-Isopropyl-phenyl)-imidazo[2,1-b][1,3,4]thiadiazol-2-ylamino]-ethyl]-benzenesulfonamide | 443 | |
| 469 | 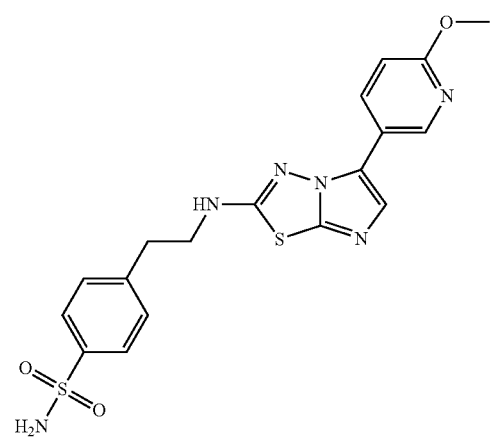 [SMILES: COc1ccc(-c2cnc3sc(NCCc4ccc(S(N)(=O)=O)cc4)nn23)cn1] | 4-{2-[5-(6-Methoxy-pyridin-3-yl)-imidazo[2,1-b][1,3,4]thiadiazol-2-ylamino]-ethyl}-benzenesulfonamide | 432 | |

| No | Structure | Name | HPLC/MS [M + H]+ | NMR DMSO |
|---|---|---|---|---|
| 470 | 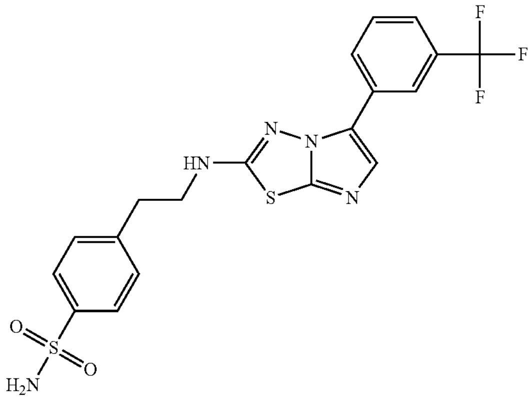 [SMILES: NS(=O)(=O)c1ccc(CCNc2nn3c(-c4cccc(C(F)(F)F)c4)cnc3s2)cc1] | 4-{2-[5-(3-Trifluoromethyl-phenyl)-imidazo[2,1-b][1,3,4]thiadiazol-2-ylamino]-ethyl}-benzenesulfonamide | 468 | |
| 471 | 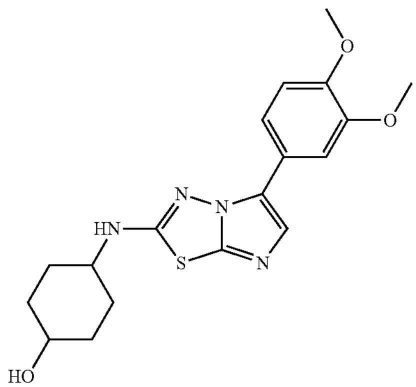 [SMILES: COc1ccc(-c2cnc3sc(NC4CCC(O)CC4)nn23)cc1OC] | 4-[5-(3,4-Dimethoxy-phenyl)-imidazo[2,1-b][1,3,4]thiadiazol-2-ylamino]-cyclohexanol | 375 | |
| 472 | 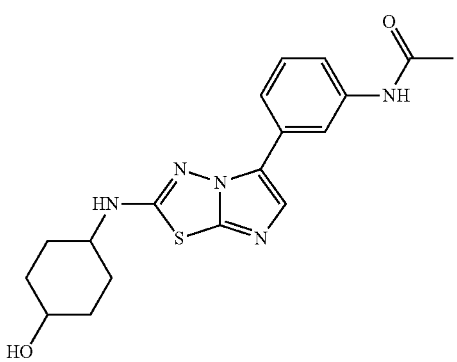 [SMILES: CC(=O)Nc1cccc(-c2cnc3sc(NC4CCC(O)CC4)nn23)c1] | N-{3-[2-(4-Hydroxy-cyclohexylamino)-imidazo[2,1-b][1,3,4]thiadiazol-5-yl]-phenyl}-acetamide | 372 | |
| 473 | 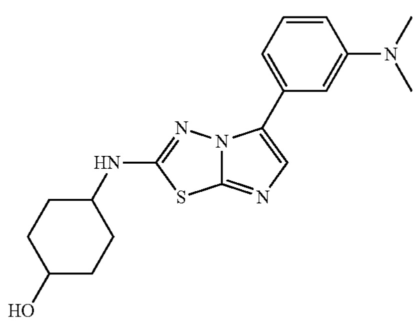 [SMILES: CN(C)c1cccc(-c2cnc3sc(NC4CCC(O)CC4)nn23)c1] | 4-[5-(3-Dimethylamino-phenyl)-imidazo[2,1-b][1,3,4]thiadiazol-2-ylamino]-cyclohexanol | 358 | |

-continued

| No | Structure | Name | HPLC/MS [M + H]+ | NMR DMSO |
|---|---|---|---|---|
| 474 | 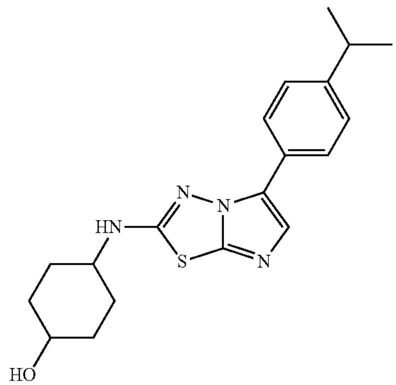 [SMILES: CC(C)c1ccc(-c2cnc3sc(NC4CCC(O)CC4)nn23)cc1] | 4-[5-(4-Isopropyl-phenyl)-imidazo[2,1-b][1,3,4]thiadiazol-2-ylamino]-cyclohexanol | 357 | |
| 475 | 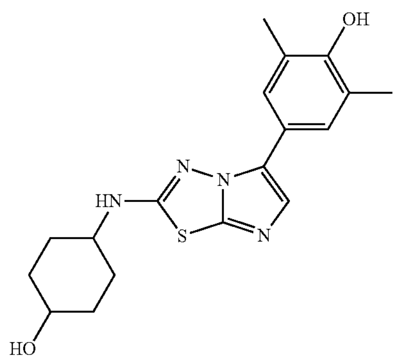 [SMILES: Cc1cc(-c2cnc3sc(NC4CCC(O)CC4)nn23)cc(C)c1O] | 4-[2-(4-Hydroxy-cyclohexylamino)-imidazo[2,1-b][1,3,4]thiadiazol-5-yl]-2,6-dimethyl-phenol | 359 | |
| 476 | 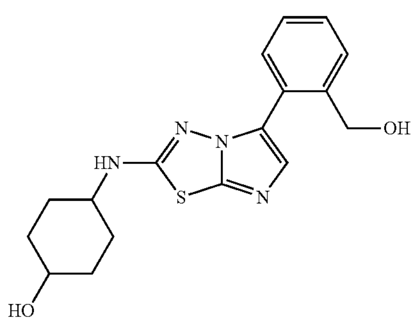 [SMILES: OCc1ccccc1-c1cnc2sc(NC3CCC(O)CC3)nn12] | 4-[5-(2-Hydroxymethyl-phenyl)-imidazo[2,1-b][1,3,4]thiadiazol-2-ylamino]-cyclohexanol | 345 | |
| 477 | 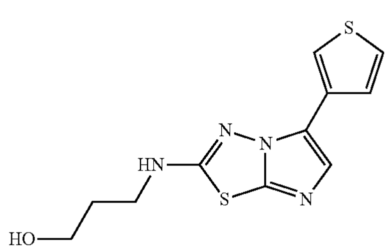 [SMILES: OCCCNc1nn2c(-c3ccsc3)cnc2s1] | 3-(5-Thiophen-3-yl-imidazo[2,1-b][1,3,4]thiadiazol-2-ylamino)-propan-1-ol | 281 | |

-continued

| No | Structure | Name | HPLC/MS [M + H]+ | NMR DMSO |
|---|---|---|---|---|
| 478 | 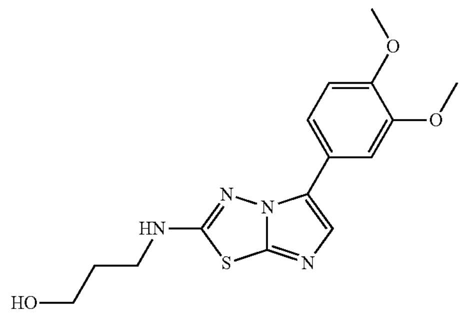 [SMILES: COc1ccc(-c2cnc3sc(NCCCO)nn23)cc1OC] | 3-[5-(3,4-Dimethoxy-phenyl)-imidazo[2,1-b][1,3,4]thiadiazol-2-ylamino]-propan-1-ol | 335 | |
| 479 | 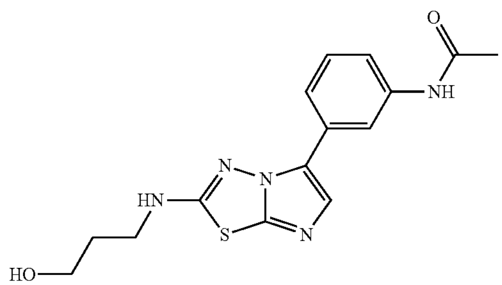 [SMILES: CC(=O)Nc1cccc(-c2cnc3sc(NCCCO)nn23)c1] | N-{3-[2-(3-Hydroxy-propylamino)-imidazo[2,1-b][1,3,4]thiadiazol-5-yl]-phenyl}-acetamide | 332 | |
| 480 | 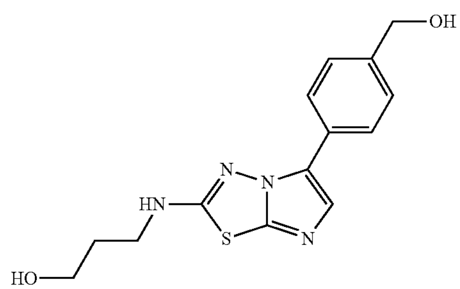 [SMILES: OCCCNc1nn2c(-c3ccc(CO)cc3)cnc2s1] | 3-[5-(4-Hydroxymethyl-phenyl)-imidazo[2,1-b][1,3,4]thiadiazol-2-ylamino]-propan-1-ol | 305 | |
| 481 | 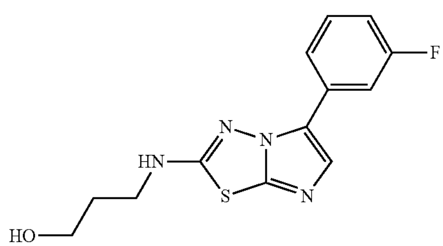 [SMILES: OCCCNc1nn2c(-c3cccc(F)c3)cnc2s1] | 3-[5-(3-Fluoro-phenyl)-imidazo[2,1-b][1,3,4]thiadiazol-2-ylamino]-propan-1-ol | 293 | |
| 482 | 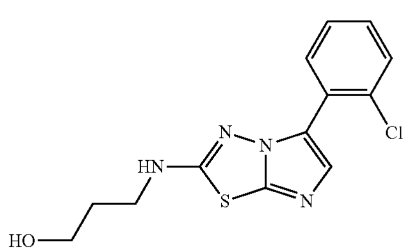 [SMILES: OCCCNc1nn2c(-c3ccccc3Cl)cnc2s1] | 3-[5-(2-Chloro-phenyl)-imidazo[2,1-b][1,3,4]thiadiazol-2-ylamino]-propan-1-ol | 309 | |

| No | Structure | Name | HPLC/MS [M + H]+ | NMR DMSO |
|---|---|---|---|---|
| 483 | 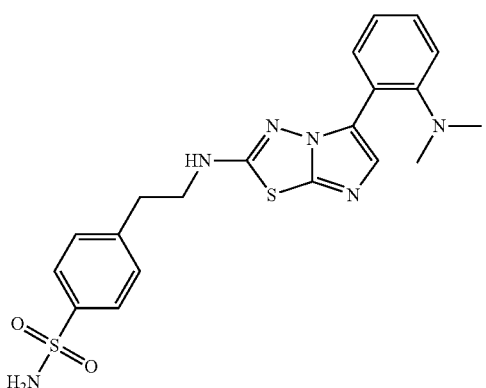 | 4-{2-[5-(2-Dimethylamino-phenyl)-imidazo[2,1-b][1,3,4]thiadiazol-2-ylamino]-ethyl}-benzenesulfonamide | 444 | |
| 484 | 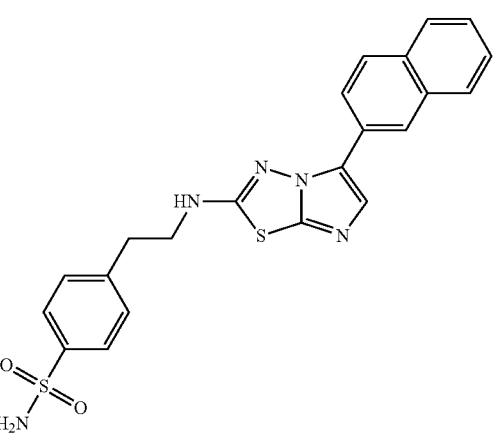 [SMILES: NS(=O)(=O)c1ccc(CCNc2nn3c(-c4ccc5ccccc5c4)cnc3s2)cc1] | 4-[2-(5-Naphthalen-2-yl-imidazo[2,1-b][1,3,4]thiadiazol-2-ylamino)-ethyl]-benzenesulfonamide | 451 | |
| 485 | 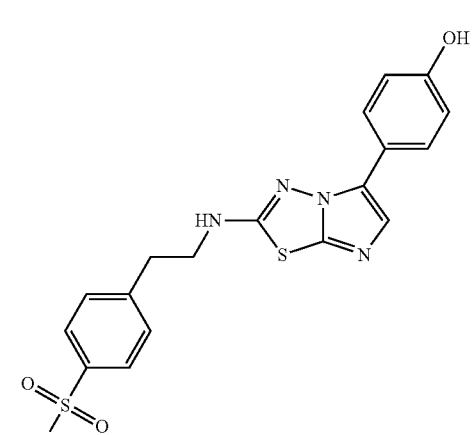 | 4-{2-[5-(4-Hydroxy-phenyl)-imidazo[2,1-b][1,3,4]thiadiazol-2-ylamino]-ethyl}-benzenesulfonamide | 416 | |

-continued

| No | Structure | Name | HPLC/MS [M + H]+ | NMR DMSO |
|---|---|---|---|---|
| 486 | 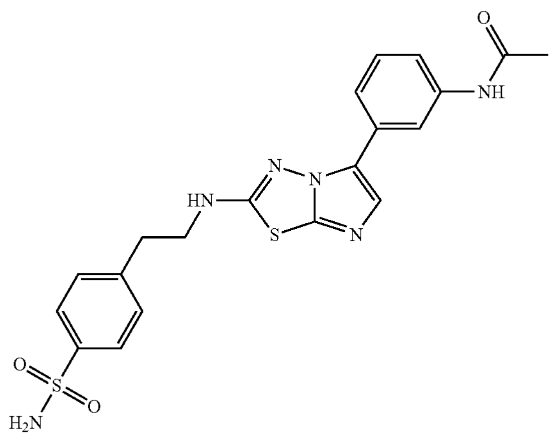 [SMILES: CC(=O)Nc1cccc(-c2cnc3sc(NCCc4ccc(S(N)(=O)=O)cc4)nn23)c1] | N-(3-{2-[2-(4-Sulfamoyl-phenyl)-ethylamino]-imidazo[2,1-b][1,3,4]thiadiazol-5-yl}-phenyl)-acetamide | 458 | |
| 487 | 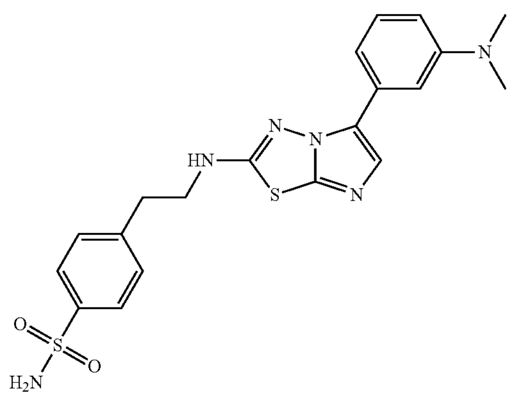 [SMILES: CN(C)c1cccc(-c2cnc3sc(NCCc4ccc(S(N)(=O)=O)cc4)nn23)c1] | 4-{2-[5-(3-Dimethylamino-phenyl)-imidazo[2,1-b][1,3,4]thiadiazol-2-ylamino]-ethyl}-benzenesulfonamide | 444 | |
| 488 | 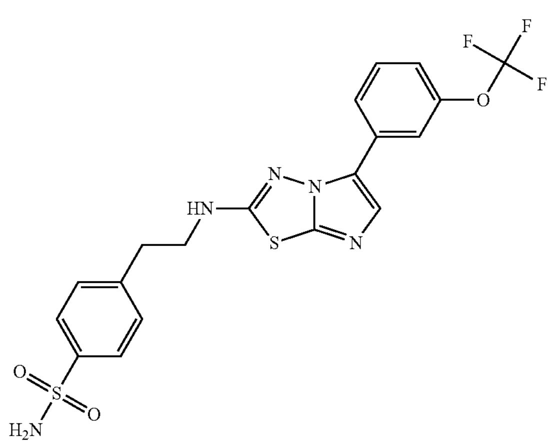 [SMILES: NS(=O)(=O)c1ccc(CCNc2nn3c(-c4cccc(OC(F)(F)F)c4)cnc3s2)cc1] | 4-{2-[5-(3-Trifluoromethoxy-phenyl)-imidazo[2,1-b][1,3,4]thiadiazol-2-ylamino]-ethyl}-benzenesulfonamide | 484 | |

-continued

| No | Structure | Name | HPLC/MS [M + H]+ | NMR DMSO |
|---|---|---|---|---|
| 489 | 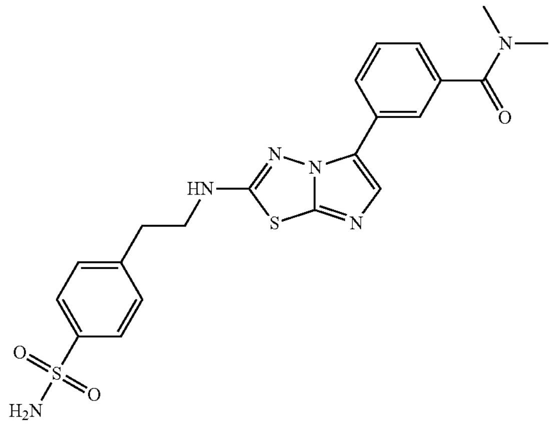 [SMILES: CN(C)C(=O)c1cccc(-c2cnc3sc(NCCc4ccc(S(N)(=O)=O)cc4)nn23)c1] | N,N-Dimethyl-3-{2-[2-(4-sulfamoyl-phenyl)-ethylamino]-imidazo[2,1-b][1,3,4]thiadiazol-5-yl}-benzamide | 472 | |
| 490 | 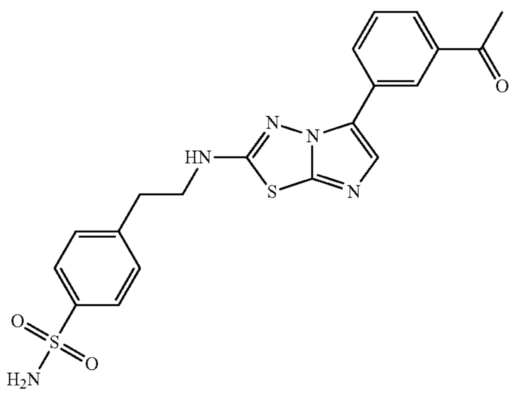 [SMILES: CC(=O)c1cccc(-c2cnc3sc(NCCc4ccc(S(N)(=O)=O)cc4)nn23)c1] | 4-{2-[5-(3-Acetyl-phenyl)-imidazo[2,1-b][1,3,4]thiadiazol-2-ylamino]-ethyl}-benzenesulfonamide | 443 | |
| 491 | 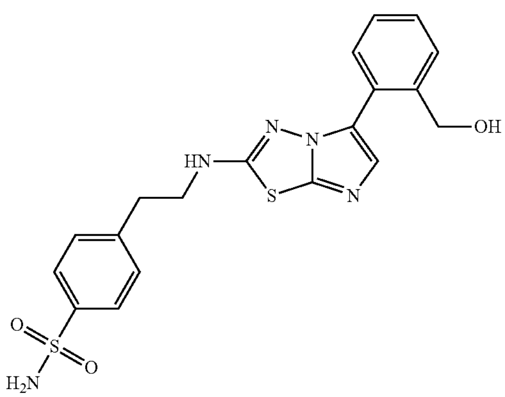 [SMILES: NS(=O)(=O)c1ccc(CCNc2nn3c(-c4ccccc4CO)cnc3s2)cc1] | 4-{2-[5-(2-Hydroxymethyl-phenyl)-imidazo[2,1-b][1,3,4]thiadiazol-2-ylamino]-ethyl}-benzenesulfonamide | 431 | |
| 492 | 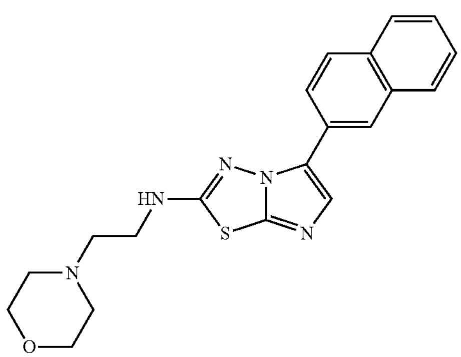 [SMILES: c1ccc2cc(-c3cnc4sc(NCCN5CCOCC5)nn34)ccc2c1] | (2-Morpholin-4-yl-ethyl)-(5-naphthalen-2-yl-imidazo[2,1-b][1,3,4]thiadiazol-2-yl)-amine | 380 | |

-continued

| No | Structure | Name | HPLC/MS [M + H]+ | NMR DMSO |
|---|---|---|---|---|
| 493 | 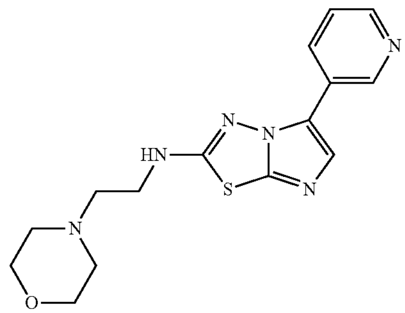 [SMILES: c1cncc(-c2cnc3sc(NCCN4CCOCC4)nn23)c1] | (2-Morpholin-4-yl-ethyl)-(5-pyridin-3-yl-imidazo[2,1-b][1,3,4]thiadiazol-2-yl)-amine | 331 | |
| 494 | 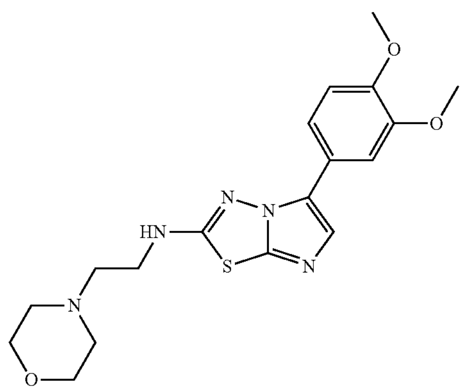 [SMILES: COc1ccc(-c2cnc3sc(NCCN4CCOCC4)nn23)cc1OC] | [5-(3,4-Dimethoxy-phenyl)-imidazo[2,1-b][1,3,4]thiadiazol-2-yl]-(2-morpholin-4-yl-ethyl)-amine | 390 | |
| 495 | 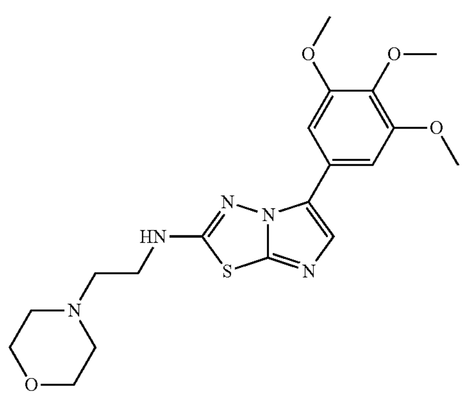 [SMILES: COc1cc(-c2cnc3sc(NCCN4CCOCC4)nn23)cc(OC)c1OC] | (2-Morpholin-4-yl-ethyl)-[5-(3,4,5-trimethoxy-phenyl)-imidazo[2,1-b][1,3,4]thiadiazol-2-yl]-amine | 421 | |
| 496 | 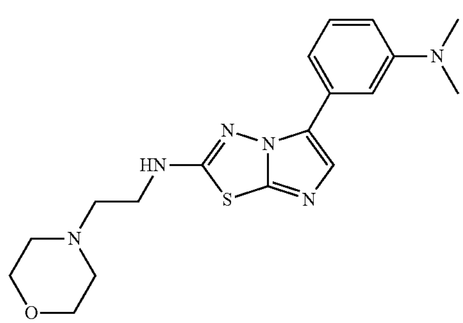 [SMILES: CN(C)c1cccc(-c2cnc3sc(NCCN4CCOCC4)nn23)c1] | [5-(3-Dimethylamino-phenyl)-imidazo[2,1-b][1,3,4]thiadiazol-2-yl]-(2-morpholin-4-yl-ethyl)-amine | 373 | |

-continued

| No | Structure | Name | HPLC/MS [M + H]+ | NMR DMSO |
|---|---|---|---|---|
| 497 | 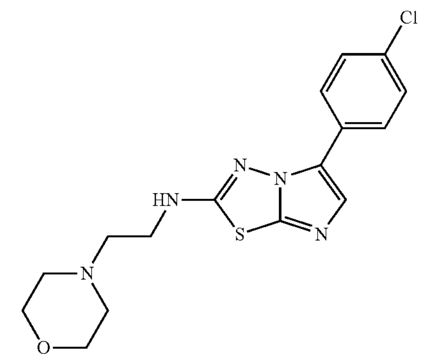 [SMILES: Clc1ccc(-c2cnc3sc(NCCN4CCOCC4)nn23)cc1] | [5-(4-Chloro-phenyl)-imidazo[2,1-b][1,3,4]thiadiazol-2-yl]-(2-morpholin-4-yl-ethyl)-amine | 364 | |
| 498 | 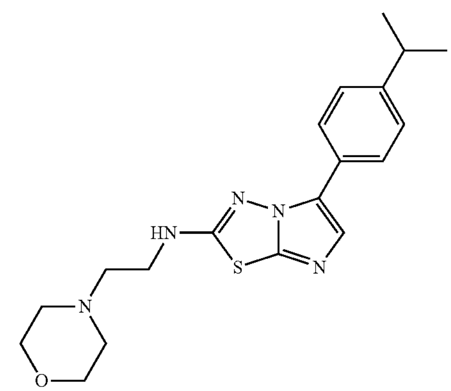 [SMILES: CC(C)c1ccc(-c2cnc3sc(NCCN4CCOCC4)nn23)cc1] | [5-(4-Isopropyl-phenyl)-imidazo[2,1-b][1,3,4]thiadiazol-2-yl]-(2-morpholin-4-yl-ethyl)-amine | 373 | |
| 499 | 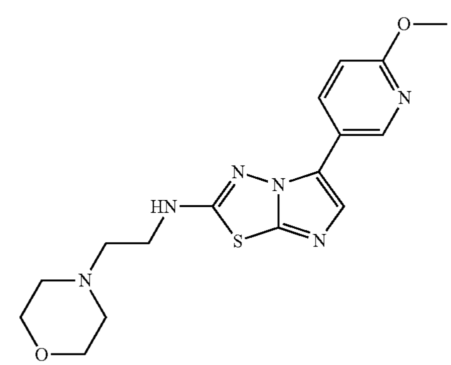 [SMILES: COc1ccc(-c2cnc3sc(NCCN4CCOCC4)nn23)cn1] | [5-(6-Methoxy-pyridin-3-yl)-imidazo[2,1-b][1,3,4]thiadiazol-2-yl]-(2-morpholin-4-yl-ethyl)-amine | 361 | |
| 500 | 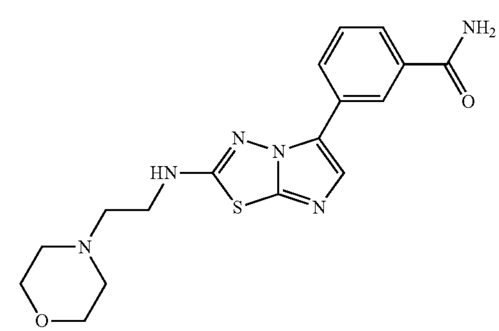 [SMILES: NC(=O)c1cccc(-c2cnc3sc(NCCN4CCOCC4)nn23)c1] | 3-[2-(2-Morpholin-4-yl-ethylamino)-imidazo[2,1-b][1,3,4]thiadiazol-5-yl]-benzamide | 373 | |

-continued

| No | Structure | Name | HPLC/MS [M + H]+ | NMR DMSO |
|---|---|---|---|---|
| 501 | 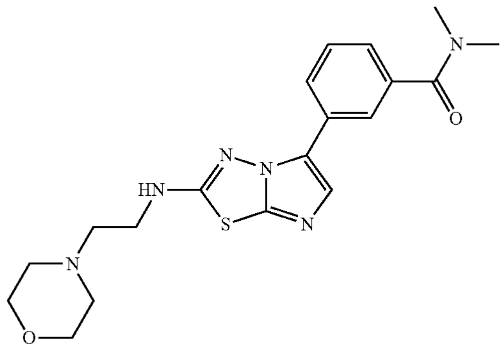 [SMILES: CN(C)C(=O)c1cccc(-c2cnc3sc(NCCN4CCOCC4)nn23)c1] | N,N-Dimethyl-3-[2-(2-morpholin-4-yl-ethylamino)-imidazo[2,1-b][1,3,4]thiadiazol-5-yl]-benzamide | 402 | |
| 502 | 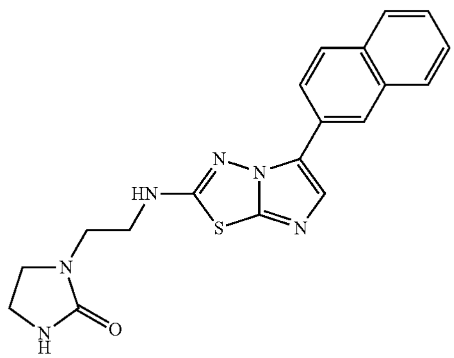 [SMILES: O=C1NCCN1CCNc1nn2c(-c3ccc4ccccc4c3)cnc2s1] | 1-[2-(5-Naphthalen-2-yl-imidazo[2,1-b][1,3,4]thiadiazol-2-ylamino)-ethyl]-imidazolidin-2-one | 379 | |
| 503 | 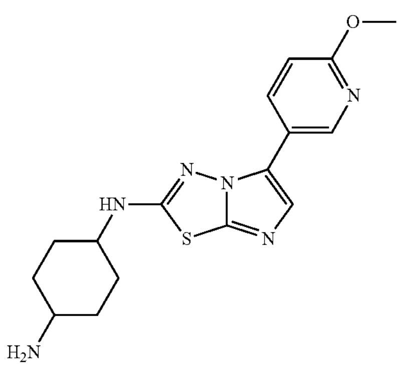 [SMILES: COc1ccc(-c2cnc3sc(NC4CCC(N)CC4)nn23)cn1] | N-[5-(6-Methoxy-pyridin-3-yl)-imidazo[2,1-b][1,3,4]thiadiazol-2-yl]-cyclohexane-1,4-diamine | 345 | |
| 504 | 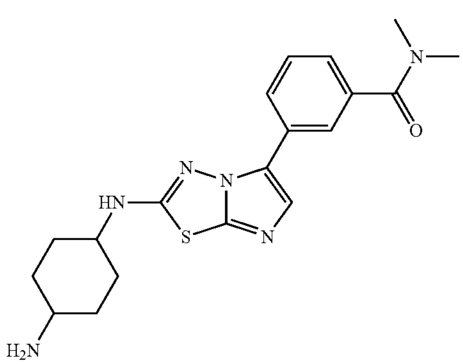 [SMILES: CN(C)C(=O)c1cccc(-c2cnc3sc(NC4CCC(N)CC4)nn23)c1] | 3-[2-(4-Amino-cyclohexylamino)-imidazo[2,1-b][1,3,4]thiadiazol-5-yl]-N,N-dimethyl-benzamide | 386 | |

| No | Structure | Name | HPLC/MS [M + H]+ | NMR DMSO |
|---|---|---|---|---|
| 505 | 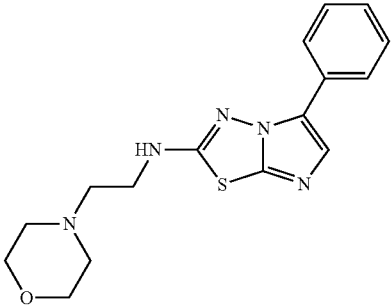 [SMILES: c1ccc(-c2cnc3sc(NCCN4CCOCC4)nn23)cc1] | (2-Morpholin-4-yl-ethyl)-(5-phenyl-imidazo[2,1-b][1,3,4]thiadiazol-2-yl)-amine | 330 | |
| 506 | 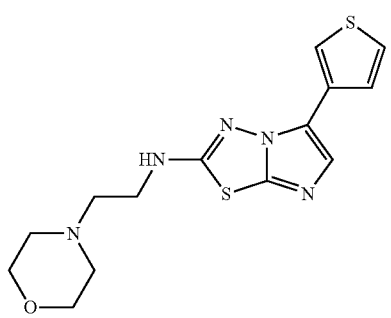 [SMILES: c1cc(-c2cnc3sc(NCCN4CCOCC4)nn23)cs1] | (2-Morpholin-4-yl-ethyl)-(5-thiophen-3-yl-imidazo[2,1-b][1,3,4]thiadiazol-2-yl)-amine | 336 | |
| 507 | 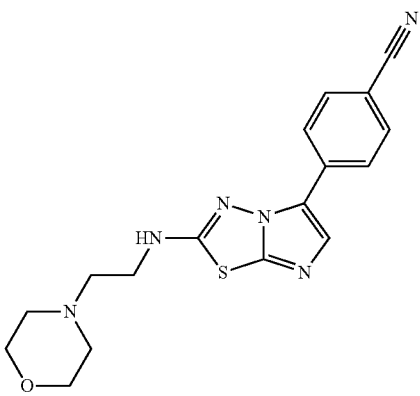 [SMILES: N#Cc1ccc(-c2cnc3sc(NCCN4CCOCC4)nn23)cc1] | 4-[2-(2-Morpholin-4-yl-ethylamino)-imidazo[2,1-b][1,3,4]thiadiazol-5-yl]-benzonitrile | 355 | |
| 508 | 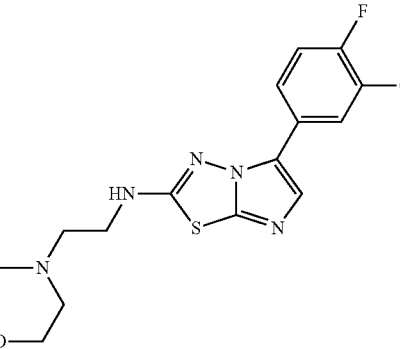 | [5-(3-Chloro-4-fluoro-phenyl)-imidazo[2,1-b][1,3,4]thiadiazol-2-yl]-(2-morpholin-4-yl-ethyl)-amine | 382 | |

-continued

| No | Structure | Name | HPLC/MS [M + H]+ | NMR DMSO |
|---|---|---|---|---|
| 509 | 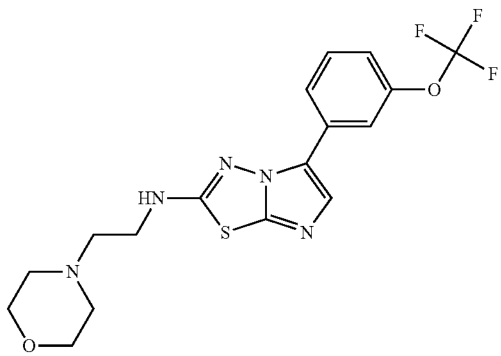 [SMILES: FC(F)(F)Oc1cccc(-c2cnc3sc(NCCN4CCOCC4)nn23)c1] | (2-Morpholin-4-yl-ethyl)-[5-(3-trifluoromethoxy-phenyl)-imidazo[2,1-b][1,3,4]thiadiazol-2-yl]-amine | 414 | |
| 510 | 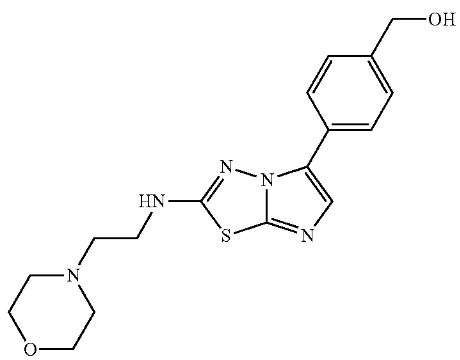 [SMILES: OCc1ccc(-c2cnc3sc(NCCN4CCOCC4)nn23)cc1] | {4-[2-(2-Morpholin-4-yl-ethylamino)-imidazo[2,1-b][1,3,4]thiadiazol-5-yl]-phenyl}-methanol | 360 | |
| 511 | 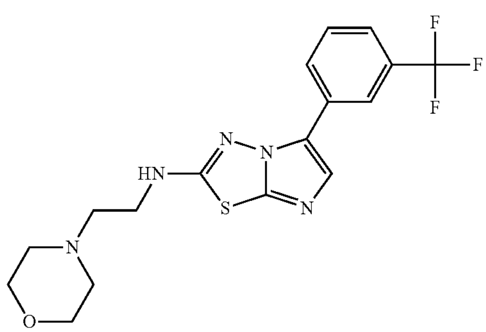 [SMILES: FC(F)(F)c1cccc(-c2cnc3sc(NCCN4CCOCC4)nn23)c1] | (2-Morpholin-4-yl-ethyl)-[5-(3-trifluoromethyl-phenyl)-imidazo[2,1-b][1,3,4]thiadiazol-2-yl]-amine | 398 | |
| 512 | 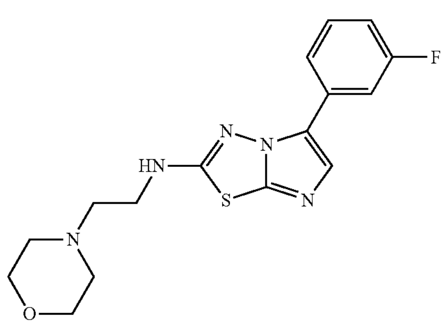 [SMILES: Fc1cccc(-c2cnc3sc(NCCN4CCOCC4)nn23)c1] | [5-(3-Fluoro-phenyl)-imidazo[2,1-b][1,3,4]thiadiazol-2-yl]-(2-morpholin-4-yl-ethyl)-amine | 348 | |

-continued

| No | Structure | Name | HPLC/MS [M + H]+ | NMR DMSO |
|---|---|---|---|---|
| 513 | 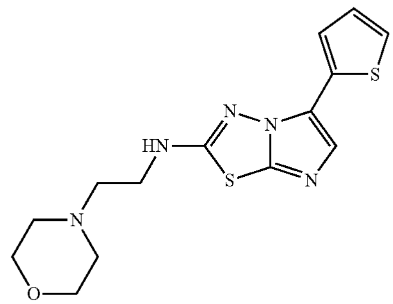 [SMILES: c1csc(-c2cnc3sc(NCCN4CCOCC4)nn23)c1] | (2-Morpholin-4-yl-ethyl)-(5-thiophen-2-yl-imidazo[2,1-b][1,3,4]thiadiazol-2-yl)-amine | 336 | |
| 514 | 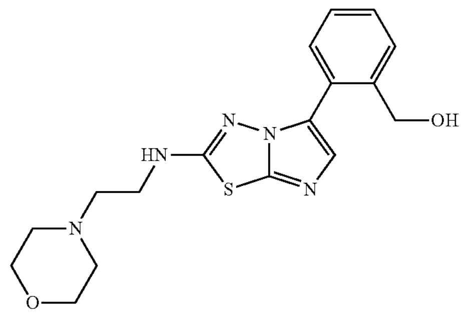 [SMILES: OCc1ccccc1-c1cnc2sc(NCCN3CCOCC3)nn12] | {2-[2-(2-Morpholin-4-yl-ethylamino)-imidazo[2,1-b][1,3,4]thiadiazol-5-yl]-phenyl}-methanol | 360 | |
| 515 | 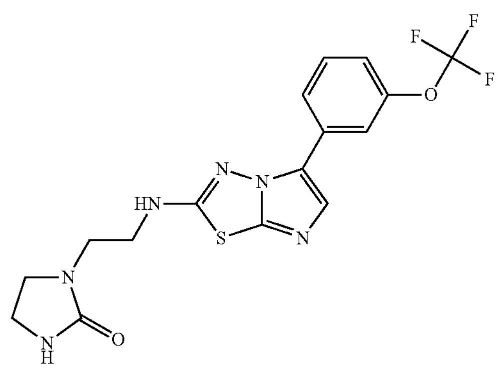 [SMILES: O=C1NCCN1CCNc1nn2c(-c3cccc(OC(F)(F)F)c3)cnc2s1] | 1-{2-[5-(3-Trifluoromethoxy-phenyl)-imidazo[2,1-b][1,3,4]thiadiazol-2-ylamino]-ethyl}-imidazolidin-2-one | 413 | |
| 516 | 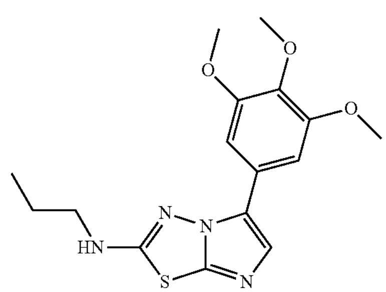 [SMILES: CCCNc1nn2c(-c3cc(OC)c(OC)c(OC)c3)cnc2s1] | Propyl-[5-(3,4,5-trimethoxy-phenyl)-imidazo[2,1-b]thiadiazol-2-yl]amine | 349 | δ 8.19 (s, 1H, NH), 7.68 (s, 1H, imidazole), 7.36 (s, 2H, benzene), 3.85 (s, 6H, methyl), 3.70 (s, 3H, methyl), 3.34 (dd, J = 6.9, 12.5, 2H, propyl), 1.69 (dd, J = 7.2, 14.3, 2H, propyl), 0.95 (t, J = 7.4, 3H, propyl). |
| 517 | 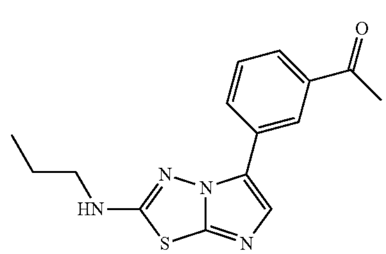 [SMILES: CCCNc1nn2c(-c3cccc(C(C)=O)c3)cnc2s1] | 1-[3-(2-Propylamino-imidazo[2,1-b][1,3,4]thiadiazol-5-yl)-phenyl]ethanone | 301 | |

| No | Structure | Name | HPLC/MS [M + H]+ | NMR DMSO |
|---|---|---|---|---|
| 518 | 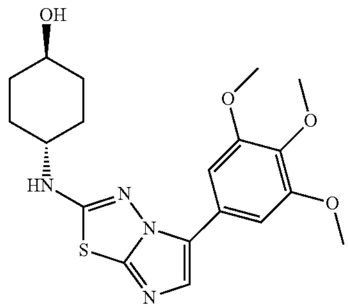 [SMILES: COc1cc(-c2cnc3sc(N[C@H]4CC[C@H](O)CC4)nn23)cc(OC)c1OC] | 4-[5-(3,4,5-Trimethoxy-phenyl)-imidazo[2,1-b][1,3,4]thiadiazol-2-ylamino]-cyclohexanol | 405 | δ 8.0 (d, 1H), 7.5 (s, 1H), 7.3 (s, 2H), 4.6 (d, 1H), 3.8 (s, 6H), 3.7 (s, 3H), 3.45 (m, 1H), 3.54 (m, 1H), 2.2 (m, 2H), 1.8 (m, 2H), 1.3 (m, 4H) |

EXAMPLE 7

Pharmaceutical Preparations

EXAMPLE A

Injection Vials

A solution of 100 g of an active ingredient according to the invention and 5 g of disodium hydrogen phosphate in 3 l of bidistilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

EXAMPLE B

Suppositories

A mixture of 20 g of an active ingredient according to the invention was melted with 100 g of soya lecithin and 1400 g of cocoa butter, poured into moulds and allowed to cool. Each suppository contained 20 mg of active ingredient.

EXAMPLE C

Solution

A solution was prepared from 1 g of an active ingredient according to the invention, 9.38 g of $NaH_2PO_4 \cdot 2 H_2O$, 28.48 g of $Na_2HPO_4 \cdot 12 H_2O$ and 0.1 g of benzalkonium chloride in 940 ml of bidistilled water. The pH was adjusted to 6.8, and the solution was made up to 1 l and sterilized by irradiation. This solution could be used in the form of eye drops.

EXAMPLE D

Ointment 500 mg of an active ingredient according to the invention were mixed with 99.5 g of Vaseline under aseptic conditions.

EXAMPLE E

Tablets

A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient.

EXAMPLE F

Coated Tablets

Tablets were pressed analogously to Example E and subsequently coated in a conventional manner with a coating of sucrose, potato starch, talc, tragacanth and dye.

EXAMPLE G

Capsules 2 kg of an active ingredient according to the invention were introduced into hard gelatin capsules in a conventional manner in such a way that each capsule contained 20 mg of the active ingredient.

EXAMPLE H

Ampoules

A solution of 1 kg of an active ingredient according to the invention in 60 l of bidistilled water was sterile filtered, transferred into ampoules, lyophilized under sterile conditions and sealed under sterile conditions. Each ampoule contained 10 mg of active ingredient.

EXAMPLE I

Inhalation Spray 14 g of an active ingredient according to the invention were dissolved in 10 l of isotonic NaCl solution, and the solution was transferred into commercially available spray containers with a pump mechanism. The solution could be sprayed into the mouth or nose.

One spray shot (about 0.1 ml) corresponded to a dose of about 0.14 mg.

The invention claimed is:
1. A compound of formula (I)

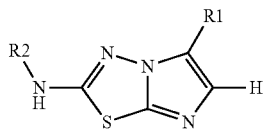

wherein:
R¹ is unsubstituted, mono- or bicyclic carboaryl or unsubstituted, mono- or bicyclic heteroaryl having 1 to 4 N, O and/or S atoms,
  each of which can be substituted by at least one substituent selected from: A, Hal, —CN, —(CH₂)ₙOR³, —CO—R³, —CO—N(R³)₂, —(CH₂)ₙN(R³)₂ and —SO₂N(R³)₂;
R² is A' or Cyc;
R³ is independently from each other in R¹, A' and Cyc: H, A, —OH, —OA, acyl or optionally substituted carboaryl;
A is independently from each other in R¹ and R³: unbranched or branched alkyl having 1-10 C atoms, in which one or two non-adjacent CH₂ groups may be replaced by N and/or NH, and/or in addition 1-7 H atoms may be replaced by Hal, —OH, morpholine and/or amino; and
A' is unbranched or branched alkyl having 1-10 C atoms, in which 1-7 H atoms may be replaced by: Cyc, —OR³, —N(R³)₂, Het¹ or optionally substituted carboaryl;
Het¹ is independently from each other in R¹ and A': saturated, unsaturated or aromatic, mono- or bicyclic heterocycle having 1 to 4 N, O and/or S atoms, optionally substituted by =O;
Cyc is independently from each other in R², R³ and A': cycloalkyl having 3-7 C atoms, which can be substituted by —OR³ or —N(R³)₂;
Hal is independently from each other in R¹ and A: F, Cl, Br or I; and
n is 0, 1, 2, 3 or 4;
or a physiologically acceptable salt thereof.
2. A compound of claim 1, wherein:
R¹ is unsubstituted phenyl, naphthyl, biphenyl, thienyl, thiophenyl, pyridyl or pyrazole, each of which can be substituted; and/or
R³ is H, A, —(CH₂)ₙC(H)ₘ(Hal)ₒ, —(CH₂)ₙOH, —(CH₂)ₚN(A)₂, —CO—A or —SO₂—A; and
m, o are independently from each other 0, 1, 2 or 3.
3. A compound of claim 1, wherein:
R¹ is Ar or Het;
R² is A, —(CH₂)ₙ—Cyc, —(CH₂)ₚOR³, —(CH₂)ₚAr¹ or —(CH₂)ₚHet¹;
R³ is H or A;
Ar is unsubstituted phenyl, naphthyl or biphenyl,
  which can be mono-, di-, tri-, tetra-or pentasubstituted by substituents selected from the group of A, Hal, —CN, —(CH₂)ₙOR³, —COA, —CHO, —CO—NR³(CH₂)ₙOR³, —CO—NR³(CH₂)ₚN(R³)₂, —CO—N(R³)₂, —(CH₂)ₙNR³—COA, —(CH₂)ₙNR³—SO₂A, —(CH₂)ₙN(R³)₂ and —SO₂N(R³)₂;
Het is unsubstituted, mono- or bicyclic heteroaryl having 1 to 4 N, O and/or S atoms,
  which can be mono- or disubstituted by substituents selected from: A, Hal, —OR³, —O(CH₂)ₚN(R³)₂ and —NR³(CH₂)ₚHet¹;
Ar¹ is unsubstituted phenyl,
  which can be mono-, di-, tri-, tetra-or pentasubstituted by substituents selected from: A, Hal, —OR³, —(CH₂)ₙN(R³)₂ and acyl;
Het¹ is independently from each other in Het and R²: saturated, unsaturated or aromatic, mono- or bicyclic heterocycle having 1 to 4 N, O and/or S atoms, optionally substituted by =O;
A is independently from each other in Ar, Het, Ar¹, R² and R³: unbranched or branched alkyl having 1-10 C atoms,
  in which one or two non-adjacent CH₂, groups may be replaced by N and/or NH, and/or in addition 1-7 H atoms may be replaced by Hal, —OH, morpholine and/or amino;
Cyc is cycloalkyl having 3-7 C atoms,
  which can be substituted by —OR³ or —N(R³)₂;
Hal is independently from each other in Ar, Het, Ar¹ and A: F, Cl, Br or I;
n is 0, 1, 2, 3 or 4; and
p is 1, 2, 3 or 4;
or a physiologically acceptable salt thereof.
4. A compound of claim 3, wherein:
Ar is phenyl,
  which is mono-, di-or trisubstituted by substituents selected from: A, —OA, —(CH₂)ₙOH, —COA and —NR³CH₃.
5. A compound of claim 3, wherein:
Ar is phenyl,
  which is mono-, di-or trisubstituted by substituents selected from trimethoxyphenyl, acetylphenyl and dimethylhydroxyphenyl.
6. A compound of claim 3, wherein:
R² is unbranched alkyl having 1-4 C atoms,
  which is optionally substituted by at least one substituent selected from: cyclopropyl, methoxy, phenoxy, hydroxyl, morpholine, tetrahydropyran, imidazolidin-2-on, furanyl, thienyl, pyridyl and optionally substituted phenyl.
7. A compound of claim 3, wherein:
R² is unbranched alkyl having 1-4 C atoms,
  which is optionally substituted by at least one substituent selected from: furanylmethyl, pyridylethyl or aminosulfonylphenyl.
8. A compound of claim 3, which is selected from:
4-{2-[5-(3,4,5-Trimethoxy-phenyl)-imidazo[2,1-b][1,3,4]thiadiazol-2-ylamino]-ethyl}-benzenesulfonamide;
4-{2-[(Furan-2-ylmethyl)-amino]-imidazo[2,1-b][1,3,4]thiadiazol-5-yl}-2,6-dimethyl-phenol;
(2-Pyridin-2-yl-ethyl)-[5-(3,4,5-trimethoxy-phenyl)-imidazo[2,1-b][1,3,4]thiadiazol-2-yl]-amine;
Thiophen-2-ylmethyl-[5-(3,4,5-trimethoxy-phenyl)-imidazo[2,1-b][1,3,4]thiadiazol-2-yl]-amine;
4-{2-[5-(3-Acetyl-phenyl)-imidazo[2,1-b][1,3,4]thiadiazol-2-ylamino]-ethyl}-benzenesulfonamide;
(2-Pyridin-4-yl-ethyl)-[5-(3,4,5-trimethoxy-phenyl)-imidazo[2,1-b][1,3,4]thiadiazol-2-yl]-amine;
(2-Morpholin-4-yl-ethyl)-[5-(3,4,5-trimethoxy-phenyl)-imidazo[2,1-b][1,3,4]thiadiazol-2-yl]-amine;
4-[5-(3,4,5-Trimethoxy-phenyl)-imidazo[2,1-b][1,3,4]thiadiazol-2-ylamino]-cyclohexanol;
Pyridin-3-ylmethyl-[5-(3,4,5-trimethoxy-phenyl)-imidazo[2,1b][1,3,4]thiadiazol-2-yl]-amine;
1-{3-[2-(2-Pyridin-4-yl-ethylamino)-imidazo[2,1-b][1,3,4]thiadiazol-5-yl]-phenyl}-ethanone;
2-Methoxy-4-{2-[(thiophen-2-ylmethyl)-amino]-imidazo[2,1-b][1,3,4]thiadiazol-5-yl}-phenol;

3-[5-(3,4,5-Trimethoxy-phenyl)-imidazo[2,1-b][1,3,4]
  thiadiazol-2-ylamino]-propan-1-ol;
1-{3-[2-(2-Morpholin-4-yl-ethylamino)-imidazo[2,1-b]
  [1,3,4]thiadiazol-5-yl]-phenyl}-ethanone;
(2-Phenoxy-ethyl)-[5-(3,4,5-trimethoxy-phenyl)-imidazo
  [2,1-b][1,3,4]thiadiazol-2-yl]-amine;
(Tetrahydro-pyran-4-ylmethyl)-[5-(3,4,5-trimethoxy-
  phenyl)-imidazo[2,1-b][1,3,4]thiadiazol-2-yl]-amine;
  and
Isobutyl-[5-(3,4,5-trimethoxy-phenyl)-imidazo[2,1-b][1,
  3,4]thiadiazol-2-yl]-amine.

9. A process for manufacturing a compound according to claim 1 comprising:
reacting the compound of formula (IV):

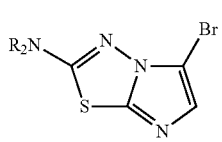

wherein R² has the meaning according to claim 1, with a compound of formula R¹-B(OH)₂ to yield a compound of formula (I)

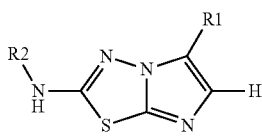

wherein R¹ and R² have the meaning according to claim 1.

10. A pharmaceutical composition comprising as active ingredient an effective amount of at least one compound according to claim 1 or a physiologically acceptable salt thereof together with at least one pharmaceutically tolerable adjuvant.

11. A pharmaceutical composition according to claim 10, wherein the active ingredient is combined with at least another active ingredient.

12. A pharmaceutical composition according to claim 11, wherein the at least another active ingredient is selected from the group consisting of: (1) oestrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors.

13. A compound selected from the following compounds:

(2-Pyridin-2-yl-ethyl)-(5-thiophen-3-yl-imidazo[2,1-b][1,3,4]
  thiadiazol-2-yl)-amine
[5-(3,4-Dimethoxy-phenyl)-imidazo[2,1-b][1,3,4]thiadiazol-
  2-yl]-furan-2-ylmethyl-amine
[5-(2-Chloro-phenyl)-imidazo[2,1-b][1,3,4]thiadiazol-2-yl]-
  furan-2-ylmethyl-amine
Cyclopropylmethyl-[5-(3,4-dimethoxy-phenyl)-imidazo[2,1-b]
  [1,3,4]thiadiazol-2-yl]-amine
Cyclopropylmethyl-[5-(4-isopropyl-phenyl)-imidazo[2,1-b]
  [1,3,4]thiadiazol-2-yl]-amine
4[2-(Cyclopropylmethyl-amino)-imidazo[2,1-b][1,3,4]
  thiadiazol-5-yl]-2,6-dimethyl-phenol
[5-(2-Chloro-phenyl)-imidazo[2,1-b][1,3,4]thiadiazol-2-yl]-
  cyclopropylmethyl-amine
[5-(2-Chloro-phenyl)-imidazo [2,1-b][1,3,4]thiadiazol-2-yl]-
  (2-pyridin-2-yl-ethyl)-amine
4-{2-[(Furan-2-ylmethyl)-amino]-imidazo[2,1-b][1,3,4]
  thiadiazol-5-yl}-N-(2-hydroxy-ethyl)-benzamide
Furan-2-ylmethyl-[5-(1-methyl-1H-pyrazol-4-yl)-imidazo
  [2,1-b][1,3,4]thiadiazol-2-yl]-amine
Cyclopropylmethyl-(5-naphthalen-2-yl-imidazo[2,1-b]
  [1,3,4]thiadiazol-2-yl)-amine
4[2-(Cyclopropylmethyl-amino)-imidazo[2,1-b][1,3,4]
  thiadiazol-5-yl]-N-(2-hydroxy-ethyl)-benzamide
{5-[6-(2-Morpholin-4-yl-ethylamino)-pyridin-3-yl]-imidazo
  [2,1-b][1,3,4]thiadiazol-2-yl)-(2-pyridin-2-yl-ethyl)-amine
[5-(2-Dimethylamino-phenyl)-imidazo[2,1-b][1,3,4]thiadiazol-
  2-yl]-(2-pyridin-2-yl-ethyl)-amine
(5-Naphthalen-2-yl-imidazo[2,1-b][1,3,4]thiadiazol-2-yl)-
  (2-pyridin-2-yl-ethyl)-amine
(5-Phenyl-imidazo[2,1-b][1,3,4]thiadiazol-2-yl)-(2-pyridin-
  2-yl-ethyl)-amine
(2-Pyridin-2-yl-ethyl)-(5-pyridin-4-yl-imidazo[2,1-b][1,3,4]
  thiadiazol-2-yl)-amine
(2-Pyridin-2-yl-ethyl)-(5-pyridin-3-yl-imidazo[2,1-b][1,3,4]
  thiadiazol-2-yl)-amine
N-{3-[2-(2-Pyridin-2-yl-ethylamino)-imidazo[2,1-b][1,3,4]
  thiadiazol-5-yl]-phenyl}-acetamide
(2-Pyridin-2-yl-ethyl)-[5-(3,4,5-trimethoxy-phenyl)-imidazo
  [2,1-b][1,3,4]thiadiazol-2-yl]-amine
[5-(4-Chloro-phenyl)-imidazo[2,1,b][1,3,4]thiadiazol-2-yl]-
  (2-pyridin-2-yl-ethyl)-amine
(2-Pyridin-2-yl-ethyl)-[5-(3-trifluoromethoxy-phenyl)-imidazo
  [2,1-b][1,3,4]thiadiazol-2-yl]-amine
[5-(3-Chloro-phenyl)-imidazo [2,1-b][1,3,4]thiadiazol-2-yl]-
  (2-pyridin-2-yl-ethyl)-amine
[5-(4-Isopropyl-phenyl)-imidazo[2,1-b][1,3,4]thiadiazol-2-yl]-
  (2-pyridin-2-yl-ethyl)-amine
{4[2-(2-Pyridin-2-yl-ethylamino)-imidazo[2,1-b][1,3,4]
  thiadiazol-5-yl]-phenyl}-methanol
(2-Pyridin-2-yl-ethyl)-[5-(3-trifluoromethyl-phenyl)-
  imidazo[2,1-b][1,3,4]thiadiazol-2-yl]-amine
N-(2-Hydroxy-ethyl)-4-(2-(2-pyridin-2-yl-ethylamino)-
  imidazo[2,1-b][1,3,4]thiadiazol-5-yl)-benzamide
[5-(1-Methyl-1H-pyrazol-4-yl)-imidazo[2,1-b][1,3,4]
  thiadiazol-2-yl]-(2-pyridin-2-yl-ethyl)-amine
{2-[2-(2-Pyridin-2-yl-ethylamino)-imidazo[2,1-b][1,3,4]
  thiadiazol-5-yl]-phenyl}-methanol
{5[6-(3-Diniethylamino-propoxy)-pyridin-3-yl]-imidazo
  [2,1-b][1,3,4]thiadiazol-2-yl}-furan-2-ylmethyl-amine
Furan-2-ylmethyl-(5-phenyl-imidazo[2,1-b][1,3,4]
  thiadiazol- 2-yl)-amine
Furan-2-ylmethyl-(5-pyridin-3-yl-imidazo[2,1-b][1,3,4]
  thiadiazol-2-yl)-amine
Furan-2-ylmethyl-(5-thiophen-3-yl-imidazo[2,1-b][1,3,4]
  thiadiazol-2-yl)-amine
4-{2-[(Furan-2-ylmethyl)-amino]-imidazo[2,1-b][1,3,4]
  thiadiazol-5-yl}-phenol
N-(3-{2-[(Furan-2-ylmethyl)-amino]-imidazo[2,1-b][1,3,4]
  thiadiazol-5-yl}-phenyl)-acetamide
(4-{2-[(Furan-2-ylmethyl)-amino]-imidazo[2,1-b][1,3,4]
  thiadiazol-5-yl}-phenyl)-methanol
4-(2-[(Furan-2-ylmethyl)-amino]-imidazo[2,1-b][1,3,4]
  thiadiazol-5-yl}-2-methoxy-phenol
4-{2-[(Furan-2-ylmethyl)-amino]-imidazo[2,1-b][1,3,4]
  thiadiazol-5-yl}-2,6-dimethyl-phenol
3-{2-[(Furan-2-ylmethyl)-amino]-imidazo[2,1-b][1,3,4]
  thiadiazol-5-yl}-N,N-dimethyl-benzamide
(2-{2-[(Furan-2-ylmethyl)-amino]-imidazo[2,1-b][1,3,4]
  thiadiazol-5-yl}-phenyl)-methanol
Cyclopropylmethyl-(5-phenyl-imidazo[2,1-b][1,3,4]
  thiadiazol-2-yl)-amine
Cyclopropylmethyl-(5-pyridin-3-yl-imidazo[2,1-b][1,3,4]
  thiadiazol-2-yl)-amine
Cyclopropylmethyl-(5-thiophen-3-yl-imidazo[2,1-b][1,3,4]
  thiadiazol-2-yl)-amine
4-[2-(Cyclopropylmethyl-amino)-imidazo[2,1-b][1,3,4]
  thiadiazol-5-yl]-phenol
N-{3-[2-(Cyclopropylmethyl-amino)-imidazo[2,1-b][1,3,4]
  thiadiazol-5-yl]-phenyl}-acetamide Cyclopropylmethyl-[5-(3-trifluoromethoxy-phenyl)-imidazo[2,1-b][1,3,4]thiadiazol-2-yl]-amine
[5-(3-Chloro-phenyl)-imidazo[2,1-b][1,3,4]thiadiazol-2-yl]-cyclopropylmethyl-amine
{4-[2-(Cyclopropylmethyl-amino)-imidazo[2,1-b][1,3,4]thiadiazol-5-yl]-phenyl}-methanol
3-[2-(Cyclopropylmethyl-amino)-imidazo[2,1-b][1,3,4]thiadiazol-5-yl]-N,N-dimethyl-benzamide
{2[2-(Cyclopropylmethyl-amino)-imidazo[2,1-b][1,3,4]thiadiazol-5-yl]-phenyl}-methanol
(4-Fluoro-benzyl)-(5-pyridin-3-yl-imidazo[2,1-b][1,3,4]thiadiazol-2-yl)-amine
N-{3-[2-(4-Fluoro-benzylamino)-imidazo[2,1-b][1,3,4]thiadiazol-5-yl]-phenyl}-acetamide
(4-Fluoro-benzyl)-[5-(5-methoxy-pyridin-3-yl)-imidazo[2,1-b][1,3,4]thiadiazol-2-yl]-amine
[5-(3-Aminomethyl-phenyl)-imidazo[2,1-b][1,3,4]thiadiazol-2-yl]-(4-fluoro-benzyl)-amine
[5-(2-Chloro-phenyl)-imidazo[2,1-b][1,3,4]thiadiazol-2-yl]-(4-fluoro-benzyl)-amine
{2-[2-(4-Fluoro-benzylamino)-imidazo[2,1-b][1,3,4]thiadiazol-5-yl]-phenyl}-methanol
(4-Methoxy-benzyl)-(5-naphthalen-2-yl-imidazo[2,1-b][1,3,4]thiadiazol-2-yl)-amine
3-[2-(4-Methoxy-benzylamino)-imidazo[2,1-b][1,3,4]thiadiazol-5-yl]-N,N-dimethyl-benzamide
[5-(2-Chloro-phenyl)-imidazo[2,1-b][1,3,4]thiadiazol-2-yl]-(4-methoxy-benzyl)-amine
Benzyl-(5-pyridin-4-yl-imidazo[2,1-b][1,3,4]thiadiazol-2-yl)-amine
Benzyl-(5-pyridin-3-yl-imidazo[2,1-b][1,3,4]thiadiazol-2-yl)-amine
3-(2-Benzylamino-imidazo[2,1-b][1,3,4]thiadiazol-5-yl)-N,N-dimethyl-benzamide
Benzyl-[5-(2-chloro-phenyl)-imidazo[2,1-b][1,3,4]thiadiazol-2-yl]-amine
[2-2-Benzylamino-imidazo[2,1-b][1,3,4]thiadiazol-5-yl)-phenyl]-methanol
(4-Fluoro-benzyl)-(5-naphthalen-2-yl-imidazo[2,1-b][1,3,4]thiadiazol-2-yl)-amine
[5-(4-Chloro-phenyl)-imidazo[2,1-b][1,3,4]thiadiazol-2-yl]-(4-fluoro-benzyl)-amine
(4-Fluoro-benzyl)-[5-(3-trifluoromethoxy-phenyl)-imidazo[2,1-b][1,3,4]thiadiazol-2-yl]-amine
(4-Fluoro-benzyl)-[5-(4-isopropyl-phenyl)-imidazo[2,1-b][1,3,4]thiadiazol-2-yl]-amine
(4-Fluoro-benzyl)-[5-(3-fluoro-phenyl)-imidazo[2,1-b][1,3,4]thiadiazol-2-yl]-amine
(4-Methoxy-benzyl)-(5-pyridin-4-yl-imidazo[2,1-b][1,3,4]thiadiazol-2-yl)-amine
[5-(3-Chloro-4-fluoro-phenyl)-imidazo[2,1-b][1,3,4]thiadiazol-2-yl]-(4-methoxy-benzyl)-amine
(4-Methoxy-benzyl)-[5-(3-trifluoromethoxy-phenyl)-imidazo[2,1-b][1,3,4]thiadiazol-2-yl]-amine
1-{3-(2-(4-Methoxy-benzylamino)-imidazo[2,1-b][1,3,4]thiadiazol-5-yl]phenyl}-ethanone
Benzyl-[5-(2-dimethylamino-phenyl)-imidazo[2,1-b][1,3,4]thiadiazol-2-yl]-amine
Benzyl-[5-(5-methoxy-pyridin-3-yl)-imidazo[2,1-b][1,3,4]thiadiazol-2-yl]amine
(2-Methoxy-ethyl)-(5-naphthalen-2-yl-imidazo[2,1-b][1,3,4]thiadiazol-2-yl)-amine
(2-Methoxy-ethyl)-(5-phenyl-imidazo[2,1-b][1,3,4]thiadiazol-2-yl)-amine
(2-Methoxy-ethyl)-(5-pyridin-3-yl-imidazo[2,1-b][1,3,4]thiadiazol-2-yl)-amine
(2-Methoxy-ethyl)-(5-thiophen-3-yl-imidazo[2,1-b][1,3,4]thiadiazol-2-yl)-amine
N-{3-[2-(2-Methoxy-ethylamino)-imidazo[2,1-b)][1,3,4]thiadiazol-5-yl]-phenyl}-acetamide
4-[2-(2-Methoxy-ethylamino)-imidazo[2,1-b][1,3,4]thiadiazol-5-yl]-benzonitrile
[5-(4-Chloro-phenyl)-imidazo[2,1-b][1,3,4]thiadiazol-2-yl]-(2-methoxy-ethyl)-amine
(2-Methoxy-ethyl)-[5-(3-trifluoromethoxy-phenyl)-imidazo[2,1-b][1,3,4]thiadiazo1-2-yl]-amine
[5-(4-Isopropyl-phenyl)-imidazo[2,1-b][1,3,4]thiadiazol-2-yl]-(2-methoxy-ethyl)-amine
(2-Methoxy-ethyl)-(5-thiophen-2-yl-imidazo[2,1-b][1,3,4]thiadiazol-2-yl)-amine
{2-[2-(2-Methoxy-ethylamino)-imidazo[2,1-b][1,3,4]thiadiazol-5-yl]-phenyl}-methanol
Cyclohexyl-[5-(3,4,5-trimethoxy-phenyl)-imidazo[2,1-b][1,3,4]thiadiazol-2-yl]-amine
[2-(2-Cyclohexylamino-imidazo[2,1-b][1,3,4]thiadiazol-5-yl)-phenyl]-methanol
[5-(2-Dimethylamino-phenyl)-imidazo[2,1-b][1,3,4]thiadiazol-2-yl]-isobutyl-amine
Isobutyl-(5-naphthalen-2-yl-imidazo[2,1-b][1,3,4]thiadiazol-2-yl)-amine
Isobutyl-(5-phenyl-imidazo[2,1-b] [1,3,4]thiadiazol-2-yl)-amine
Isobutyl-(5-thiophen-3-yl-imidazo[2,1-b][1,3,4]thiadiazol-2-yl)-amine
[5-(3,4-Dimethoxy-phenyl)-imidazo[2,1-b][1,3,4]thiadiazol-2-yl]-isobutyl-amine
[5-(3-Dimethylamino-phenyl)-imidazo[2,1-b][1,3,4]thiadiazol-2-yl]-isobutyl-amine
[5-(3-Chloro-4-fluoro-phenyl)-imidazo[2,1-b][1,3,4]thiadiazol-2-yl]-isobutyl-amine
Isobutyl-[5-(3-trifluoromethoxy-phenyl)-imidazo[2,1-b][1,3,4]thiadiazol-2-yl]-amine
Isobutyl-[5-(6-methoxy-pyridin-3-yl)-imidazo[2,1-b][1,3,4]thiadiazol-2-yl]-amine
1-[3-(2-Isobutylamino-imidazo[2,1-b][1,3,4]thiadiazol-5-yl)-phenyl]-ethanone
[5-(3-Chloro-4-fluoro-phenyl)-imidazo[2,1-b][1,3,4]thiadiazol-2-yl]-(2-methoxy-ethyl)-amine
[5-(3-Chloro-phenyl)-imidazo[2,1-b][1,3,4]thiadiazol-2-yl]-(2-methoxy-ethyl)-amine
(2-Methoxy-ethyl)-[5-(6-methoxy-pyridin-3-yl)-imidazo[2,1-b][1,3,4]thiadiazol-2-yl]-amine
[5-(3-Fluoro-phenyl)-imidazo[2,1-b][1,3,4]thiadiazol-2-yl]-(2-methoxy-ethyl)-amine
3-[2-(2-Methoxy-ethylamino)-imidazo[2,1-b][1,3,4]thiadiazol-5-yl]-N,N-dimethyl-benzamide
[5-(2-Chloro-phenyl)-imidazo[2,1-b][1,3,4]thiadiazol-2-yl]-(2-methoxy-ethyl)-amine
1-{3-[2-(2-Methoxy-ethylamino)-imidazo[2,1-b][1,3,4]thiadiazol-5-yl]-phenyl}-ethanone
[5-(2-Chloro-phenyl)-imidazo[2,1-b][1,3,4]thiadiazol-2-yl]-cyclohexyl-amine
1-[3-(2-Cyclohexylamino-imidazo[2,1-b][1,3,4]thiadiazol-5-yl)-phenyl]-ethanone
Isobutyl-(5-pyridin-3-yl-imidazo[2,1-b][1,3,4]thiadiazol-2-yl)-amine
[5-(4-Chloro-phenyl)-imidazo[2,1-b][1,3,4]thiadiazol-2-yl]-isobutyl-amine
3-(2-Isobutylamino-imidazo[2,1-b][1,3,4]thiadiazol-5-yl)-N,N-dimethyl-benzamide
[5-(2-Chloro-phenyl)-imidazo[2,1-b][1,3,4]thiadiazol-2-yl-isobutyl-amine
(5-Naphthalen-2-yl-imidazo[2,1-b][1,3,4]thiadiazol-2-yl)-(tetrahydro-pyran-4-ylmethyl)-amine
(5-Pytidin-3-yl-imidazo[2,1-b][1,3,4]thiadiazol-2-yl)-(tetrahydro-pyran-4-ylmethyl)-amine
(Tetrahydro-pyran-4-ylmethyl)-(5-thiophen-3-yl-imidazo[2,1-b][1,3,4]thiadiazol-2-yl)-amine
[5-(2-Dimethylam ino-phenyl)-imidazo[2,1-b][1,3,4]thiadiazol-2-yl]-(tetrahydro-pyran-4-ylmethyl)-amine
[5-(4-Chloro-phenyl)-imidazo[2,1-b][1,3,4]thiadiazol-2-yl]-(tetrahydro-pyran-4-ylmethyl)-amine
[5-(3-Chloro-phenyl)-imidazo[2,1-b][1,3,4]thiadiazol-2-yl]-(tetrahydro-pyran-4-ylmethyl)-amine
[5-(4-Isopropyl-phenyl)-imidazo[2,1-b][1,3,4]thiadiazol-2-yl]-(tetrahydro-pyran-4-ylmethyl)-amine
[5-(6-Methoxy-pyridin-3-yl)-imidazo[2,1-b][1,3,4]thiadiazol-2-yl]-(tetrahydro-pyran-4-ylmethyl)-amine
[5-(3-Fluoro-phenyl)-imidazo[2,1-b][1,3,4]thiadiazol-2-yl]-(tetrahydro-pyran-4-ylmethyl)-amine
[5-(2-Chloro-phenyl)-imidazo[2,1-b][1,3,4]thiadiazol-2-yl]-(tetrahydro-pyran-4-ylmethyl)-amine
1-(3-{2-[(Tetrahydro-pyran-4-ylmethyl)-amino]-imidazo[2,1-b][1,3,4]thiadiazol-5-yl}-phenyl)-ethanone
[5-(2-Dimethylamino-phenyl)-imidazo[2,1-b][1,3,4]thiadiazol-2-yl]-(2-phenoxy-ethyl)-amine
[5-(3-Chloro-4-fluoro-phenyl)-imidazo[2,1-b][1,3,4]thiadiazol-2-yl]-(2-phenoxy-ethyl)-amine
(2-Methyl-benzyl)-(5-pyridin-3-yl-imidazo[2,1-b][1,3,4]thiadiazol-2-yl)-amine (Tetrahydro-pyran-4-ylmethyl)-[5-(3-trifluoromethoxy-phenyl)-imidazo[2,1-b][1,3,4]thiadiazol-2-yl]-amine
[5-(5-Methoxy-pyridin-3-yl)-imidazo[2,1-b][1,3,4]thiadiazol-2-yl]-(tetrahydro-pyran-4-ylmethyl)-amine
N-(2-Hydroxy-ethyl)-4-{2-[(tetrahydro-pyran-4-ylmethyl)-amino]-imidazo[2,1-b][1,3,4]thiadiazol-5-yl}-benzamide
(2-Phenoxy-ethyl)-[5-(3-trifluoromethoxy-phenyl)-imidazo[2,1-b][1,3,4]thiadiazol-2-yl]-amine
[5-(3-Fluoro-phenyl)-imidazo[2,1-b][1,3,4]thiadiazol-2-yl]-(2-phenoxy-ethyl)-amine
N-(2-Hydroxy-ethyl)-4-1-2-(2-phenoxy-ethylamino)-imidazo[2,1-b][1,3,4]thiadiazol-5-yl}-benzamide
(2-{2-[(Tetrahydro-pyran-4-ylmethyl)-amino]-imidazo[2,1-b][1,3,4]thiadiazol-5-yl}-phenyl)-methanol
Benzyl-[5-(3-chloro-4-fluoro-phenyl)-imidazo[2,1-b][1,3,4]thiadiazol-2-yl]-amine
1-[3-(2-Benzylamino-imidazo[2,1-b][1,3,4]thiadiazol-5-yl)-phenyli-ethanone
Benzyl-[5-(3,4-dimethoxy-phenyl)-imidazo[2,1-b][1,3,4]thiadiazol-2-yl]-amine
Cyclohexyl-(5-naphthalen-2-yl-imidazo[2,1-b][1,3,4]thiadiazol-2-yl)-amine
Cyclohexyl-(5-pyridin-3-yl-imidazo[2,1-b][1,3,4]thiadiazol-2-yl)-amine
Cyclohexyl-(5-thiophen-3-yl-imidazo[2,1-b][1,3,4]thiadiazol-2-yl)-amine
Cyclohexyl-[5-(3,4-dimethoxy-phenyl)-imidazo[2,1-b][1,3,4]thiadiazol-2-yl]-amine
N-[3-(2-Cyclohexylamino-imidazo[2,1-b][1,3,4]thiadiazol-5-yl)-phenyl]-acetamide
4-(2-Cyclohexylamino-imidazo[2,1-b][1,3,4]thiadiazol-5-yl)-benzonitrile
[5-(4-Chloro-phenyl)-imidazo[2,1-b][1,3,4]thiadiazol-2-yl]-cyclohexyl-amine
[5-(3-Chloro-4-fluoro-phenyl)-imidazo[2,1-b][1,3,4]thiadiazol-2-yl]-cyclohexyl-amine
Cyclohexyl-[5-(3-trifluoromethoxy-phenyl)-imidazo[2,1-b][1,3,4]thiadiazol-2-yl]-amine
Cyclohexyl-[5-(5-methoxy-pyridin-3-yl)-imidazo[2,1-b][1,3,4]thiadiazol-2-yl]-amine
[5-(3-Chloro-phenyl)-imidazo[2,1-b][1,3,4]thiadiazol-2-yl]-cyclohexyl-amine
Cyclohexyl-[5-(3-fluoro-phenyl)-imidazo[2,1-b][1,3,4]thiadiazol-2-yl]-amine
(2-Methyl-benzyl)-(5-naplithalen-2-yl-imidazo[2,1-b][1,3,4]thiadiazol-2-yl)-amine
[5-(3,4-Dimethoxy-phenyl)-imidazo[2,1-b][1,3,4]thiadiazol-2-yl]-(2-methyl-benzyl)-amine
N-{3-[2-(2-Methyl-benzylamino)-imidazo[2,1-b)][1,3,4]thiadiazol-5-yl]-phenyl}-acetamide
[5-(3-Chloro-4-fluoro-phenyl)-imidazo[2,1-b][1,3,4]thiadiazol-2-yl]-(2-methyl-benzyl)-amine
(2-Methyl-benzyl)-[5-(3-trifluoromethoxy-phenyl)-imidazo[2,1-b][1,3,4]thiadiazol-2-yl]-amine
[5-(3-Chloro-phenyl)-imidazo[2,1-b][1,3,4]thiadiazol-2-yl]-(2-methyl-benzyl)-amine
1-{3-[2-(2-Methyl-benzylamino)-imidazo[2,1-b][1,3,4]thiadiazol-5-yl]-phenyl}-ethanone
Cyclopropylmethyl-[5-(6-methoxy-pyridin-3-yl)-imidazo[2,1-b][1,3,4]thiadiazol-2-yl]-amine
Cyclopropylmethyl-[5-(5-methoxy-pyridin-3-yl)-imidazo[2,1-b][1,3,4]thiadiazol-2-yl]-amine
4-[2-(Cyclopropylmethyl-amino)-imidazo[2,1-b][1,3,4]thiadiazol-5-yl]-2-methoxy-phenol
1-{3-[2-(2-Morpholin-4-yl-ethylamino)-imidazo[2,1-b][1,3,4]thiadiazol-5-yl]-phenyl}-ethanone
4-(2-Cyclohexylamino-imidazo[2,1-b][1,3,4]thiadiazol-5-yl)-phenol
2-Methoxy-4-[2-(2-methoxy-ethylamino)-imidazo[2,1-b][1,3,4]thiadiazol-5-yl]-phenol
(5-Naphthalen-2-yl-imidazo[2,1-b][1,3,4]thiadiazol-2-yl)-thiophen-2-ylmethyl-amine
[5-(3,4-Dimethoxy-phenyl)-imidazo[2,1-b][1,3,4]thiadiazol-2-yl]-thiophen-2-ylmethyl-amine
N-{3-[2-[(Thiophen-2-ylmethyl)-amino]-imidazo[2,1-b][1,3,4]thiadiazol-5-yl]-phenyl}-acetamide
4-{2-[(Thiophen-2-ylmethyl)-amino]-imidazo[2,1-b][1,3,4]thiadiazol-5-yl}-benzonitrile
Thiophen-2-ylmethyl-[5-(3,4,5-trimethoxy-phenyl)-imidazo[2,1-b][1,3,4]thiadiazol-2-yl]-amine
[5-(3-Chloro-4-fluoro-phenyl)-imidazo[2,1-b][1,3,4]thiadiazol-2-yl]-thiophen-2-ylmethyl-amine
Thiophen-2-ylmethyl-[5-(3-trifluoromethoxy-phenyl)-imidazo[2,1-b][1,3,4]thiadiazol-2-yl]-amine
[5-(5-Methoxy-pyridin-3-yl)-imidazo[2,1-b][1,3,4]thiadiazol-2-yl]-thiophen-2-ylmethyl-amine
[5-(6-Methoxy-pyridin-3-yl)-imidazo[2,1-b][1,3,4]thiadiazol-2-yl]-thiophen-2-ylmethyl-amine
[5-(3-Fluoro-phenyl)-imidazo[2,1-b][1,3,4]thiadiazol-2-yl]-thiophen-2-ylmethyl-amine
[5-(2-Chloro-phenyl)-imidazo[2,1-b][1,3,4]thiadiazol-2-yl]-thiophen-2-ylmethyl-amine
1-(3-{2[(Thiophen-2-ylmethyl)-amino]-imidazo[2,1-b][1,3,4]thiadiazol-5-yl)-phenyl}-ethanone
Benzo[1,3]dioxol-5-ylmethyl-(5-pyridin-3-yl-imidazo[2,1-b][1,3,4]thiadiazol-2-yl)-amine
Benzo[1,3]dioxol-5-ylmethyl-[5-(3,4-dimethoxy-phenyl)-imidazo[2,1-b][1,3,4]thiadiazo1-2-yl]-amine
4-{2-[(Benzo[1,3]dioxol-5-ylmethyl)-amino]-imidazo[2,1-b][1,3,4]thiadiazol-5-yl}-benzonitrile
Benzo[1,3]dioxol-5-ylmethyl-[5-(3,4,5-trimethoxy-plienyl)-imidazo[2,1-b][1,3,4]thiadiazol-2-yl]-amine
Benzo[1,3]dioxol-5-ylmethyl-[5-(4-chloro-phenyl)-imidazo[2,1-b][1,3,4]thiadiazol-2-yl]-amine
Benzo[1,3]dioxol-5-ylmethyl-[5-(3-chloro-4-fluoro-phenyl)-imidazo[2,1-b][1,3,4]thiadiazol-2-yl]-amine
Benzo[1,3]dioxol-5-ylmethyl-[5-(3-trifluoromethoxy-phenyl)-imidazo[2,1-b][1,3,4]thiadiazol-2-yl]-amine
Benzo[1,3]dioxol-5-ylmethyl-[5-(5-methoxy-pyridin-3-yl)-imidazo[2,1-b][1,3,4]thiadiazol-2-yl]-amine
Benzo[1,3]dioxol-5-ylmethyl-[5-(3-chloro-phenyl)-imidazo[2,1-b][1,3,4]thiadiazol-2-yl]-amine
Benzo[1,3]dioxol-5-ylmethyl-[5-(6-methoxy-pyridin-3-yl)-imidazo[2,1-b][1,3,4]thiadiazol-2-yl]-amine
Benzo[1,3]dioxol-5-ylmethyl-[5-(3-fluoro-phenyl)-imidazo[2,1-b][1,3,4]thiadiazol-2-yl]-amine
1-(3-{2-[(Benzo[1,3]dioxol-5-ylmethyl)-amino]-imidazo[2,1-b][1,3,4]thiadiazol-5-yl}-phenyl)-ethanone
(4-Dimethylamino-benzyl)-{5-[6-(3-dimethylamino-propoxy)-pyridin-3-yl]-imidazo[2,1-b][1,3,4]thiadiazol-2-yl)-amine
(4-Dimethylamino-benzyl)-(5-naphthalen-2-yl-imidazo[2,1-b][1,3,4]thiadiazol-2-yl)-amine
(4-Dimethylamino-benzyl)-(5-phenyl-imidazo[2,1-b][1,3,4]thiadiazol-2-yl)-amine
(4-Dimethylamino-benzyl)-(5-pyridin-3-yl-imidazo[2,1-b][1,3,4]thiadiazol-2-yl)-amine
(4-Dimethylamino-benzyl)-(5-thiophen-3-yl-imidazo[2,1-b][1,3,4]thiadiazol-2-yl)-amine
[5-(3,4-Dimethoxy-phenyl)-imidazo[2,1-b][1,3,4]thiadiazol-2-yl]-(4-dimethylamino-benzyl)-amine
N-{3-[2-(4-Dimethylamino-benzylamino)-imidazo[2,1-b][1,3,4]thiadiazol-5-yl]-phenyl}-acetamide
4-[2-(4-Dimethylamino-benzylamino)-imidazo[2,1-b][1,3,4]thiadiazol-5-yl]-benzonitrile
(4-Dimethylamino-benzyl)-[5-(3-dimethylamino-phenyl)-imidazo[2,1-b][1,3,4]thiadiazol-2-yl]-amine
[5-(4-Chloro-phenyl)-imidazo[2,1-b][1,3,4]thiadiazol-2-yl]-(4-dimethylamino-benzyl)-amine
[5-(3-Chloro-4-fluoro-phenyl)-imidazo[2,1-b][1,3,4]thiadiazol-2-yl]-(4-dimethylamino-benzyl)-amine
(4-Dimethylamino-benzyl)-[5-(3-trifluoromethoxy-phenyl)-imidazo[2,1-b][1,3,4]thiadiazol-2-yl]-amine
(4-Dimethylamino-benzyl)-[5-(5-methoxy-pyridin-3-yl)-imidazo[2,1-b][1,3,4]thiadiazol-2-yl]-amine
[5-(3-Chloro-phenyl)-imidazo[2,1-b][1,3,4]thiadiazol-2-yl]-(4-dimethylamino-benzyl)-amine
(4-Dimethylamino-benzyl)-[5-(4-isopropyl-phenyl)-imidazo[2,1-b][1,3,4]thiadiazol-2-yl]-amine
(4-Dimethylamino-benzyl)-[5-(6-methoxy-pyridin-3-yl)-imidazo[2,1-b][1,3,4]thiadiazol-2-yl]-amine
(4-Dimethylamino-benzyl)-[5-(3-fluoro-phenyl)-imidazo[2,1-b][1,3,4]thiadiazol-2-yl]-amine
4-[2-(4-Dimethylamino-benzylamino)-imidazo[2,1-b][1,3,4]thiadiazol-5-yl]-N-(2-hydroxy-ethyl)-benzamide
[5-(3-Chloro-phenyl)-imidazo[2,1-b][1,3,4]thiadiazol-2-yl]-(4-dimethylamino-benzyl)-amine
1-{3-[2-(4-Dimethylamino-benzylamino)-imidazo[2,1-b][1,3,4]thiadiazol-5-yl]-phenyl}-ethanone
[5-(2-Dimethylamino-phenyl)-imidazo[2,1-b][1,3,4]thiadiazol-2-yl]-(4-fluoro-benzyl)-amine

[5-(3-Dimethylamino-phenyl)-imidazo[2,1-b][1,3,4]thiadiazol-2-yl]-(4-fluoro-benzyl)-amine
3-[2-(4-Fluoro-benzylamino)-imidazo[2,1-b][1,3,4]thiadiazol-5-yl]-N,N-dimethyr-benzamide.
N-[3-(2-Benzylamino-imidazo[2,1-b][1,3,4]thiadiazol-5-yl]-phenyl]-acetamide
[5-(3-Dimethylamino-phenyl)-imidazo[2,1-b][1,3,4]thiadiazol-2-yl]-(2-methoxy-benzyl)-amine
(4-Fluoro-benzyl)-[5-(6-methoxy-pyridin-3-yl)-imidazo[2,1-b][1,3,4]thiadiazol-2-yl]-amine
Benzyl-[5-(6-methoxy-pyridin-3-yl)-imidazo[2,1-b][1,3,4]thiadiazol-2-yl]-amine
(2-Methyl-benzyl)-[5-(3,4,5-trimethoxy-phenyl)-imidazo[2,1-b][1,3,4]thiadiazol-2-yl]-amine
(4-Methoxy-benzyl)-(5-thiophen-3-yl-imidazo[2,1-b][1,3,4]thiadiazol-2-yl)-amine
(4-Methoxy-benzyl)-[5-(5-methoxy-pyridin-3-yl)-imidazo[2,1-b][1,3,4]thiadiazol-2-yl]-amine
(4-Methoxy-benzyl)-{5-[6-(2-morpholin-4-yl-ethylamino)-pyridin-3-yl]-imidazo[2,1-b][1,3,4]thiadiazol-2-yl}-amine
{2-[2-(4-Methoxy-benzylamino)-imidazo[2,1-b][1,3,4]thiadiazo1-5-yl]-phenyl}-methanol
4-(2-Benzylamino-imidazo[2,1-b][1,3,4]thiadiazol-5-yl)-benzonitrile
Benzyl-[5-(4-chloro-phenyl)-imidazo[2,1-b][1,3,4]thiadiazol-2-yl]-amine
Benzyl-[5-(3-trifluoromethoxy-phenyl)-imidazo[2,1-b][1,3,4]thiadiazol-2-yl]-amine
Benzyl-[5-(3-chloro-phenyl)-imidazo[2,1-b][1,3,4]thiadiazol-2-yl]-amine
(5-[6-(3-Dimethylamino-propoxy)-pyridin-3-yl]-imidazo[2,1-b][1,3,4]thiadiazol-2-yl)-(2-methoxy-ethyl)-amine
[5-(3,4-Dimethoxy-phenyl)-imidazo[2,1-b][1,3,4]thiadiazol-2-yl]-(2-methoxy-ethyl)-amine
Cyclohexyl-{5-[6-(2-morpholin-4-yl-ethylamino)-pyridin-3-yl]-imidazo[2,1-b][1,3,4]thiadiazol-2-yl}-amine
{5-[6-(3-Dimethylamino-propoxy)-pyridin-3-yl]-imidazo[2,1-b][1,3,4]thiadiazol-2-yl}-isobutyl-amine
Isobutyl-(5-pyridin-4-yl-imidazo[2,1-b][1,3,4]thiadiazol-2-yl)-amine
Isobutyl-[5-(5-methoxy-pyridin-3-yl)-imidazo[2,1-b][1,3,4]thiadiazol-2-yl]-amine
(2-Methoxy-ethyl)-{5-[6-(2-morpholin-4-yl-ethylamino)-pyridin-3-yl]-imidazo[2,1-b][1,3,4]thiadiazol-2-yl}-amine
[5-(2-Dimethylamino-phenyl)-imidazo[2,1-b][1,3,4]thiadiazol-2-yl]-(2-methoxy-ethyl)-amine
N-(2-Hydroxy-ethyl)-4-[2-(2-methoxy-ethylamino)-imidazo[2,1-b][1,3,4]thiadiazol-5-yl]-benzamide
Isobutyl-[5-(4-isopropyl-phenyl)-imidazo[2,1-b][1,3,4]thiadiazol-2-yl]-amine
[5-(3-Fluoro-phenyl)-imidazo[2,1-b][1,3,4]thiadiazol-2-yl]-isobutyl-amine
(5-Phenyl-imidazo[2,1-b][1,3,4]thiadiazol-2-yl)-(tetrahydro-pyran-4-ylmethyl)-amine
N,N-Dimethyl-3-{2-[(tetrahydro-pyran-4-ylmethyl)-amino]-imidazo[2,1-b][1,3,4]thiadiazol-5-yl}-benzamide
{5-[6-(3-Dimethylamino-propoxy)-pyridin-3-yl]-imidazo[2,1-b][1,3,4]thiadiazol-2-yl}-(2-phenoxy-ethyl)-amine
[5-(3-Dimethylamino-phenyl))-imidazo[2,1-b][1,3,4]thiadiazol-2-yl]-(2-phenoxy-ethyl)-amine
[5-(3-Fluoro-phenyl)-imidazo[2,1-b][1,3,4]thiadiazol-2-yl]-(2-methyl-benzyl)-amine
N-(2-Hydroxy-ethyl)-4-[2-(2-methyl-benzylamino)-imidazo[2,1-b][1,3,4]thiadiazol-5-yl]-benzamide
{2-[2-(2-Methyl-benzylamino)-imidazo[2,1-b][1,3,4]thiadiazol-5-yl]-phenyl}-methanol
(4-Methoxy-benzyl)-(5-pyridin-3-yl-imidazo[2,1-b][1,3,4]thiadiazol-2-yl)-amine
Benzyl-[5-(3-fluoro-phenyl)-imidazo[2,1-b][1,3,4]thiadiazol-2-yl]-amine
(2-Phenoxy-ethyl)-(5-thiophen-2-yl-imidazo[2,1-b][1,3,4]thiadiazo1-2-yl)-amine
[5-(3-Dimethylamino-phenyl)-imidazo[2,1-b][l,3,4]thiadiazol-2-yl]-(2-methyl-benzyl)-amine
(4-Fluoro-benzyl)-(5-[6-(2-morpholin-4-yl-ethylamino)-pyridin-3-yl]-imidazo[2,1-b][1,3,4]thiadiazol-2-yl)-amine
(4-Fluoro-benzyl)-(5-thiophen-3-yl-imidazo[2,1-b][1,3,4]thiadiazol-2-yl)-amine
[5-(3-Chloro-phenyl)-imidazo[2,1-b][1,3,4]thiadiazol-2-yl]-(4-fluoro-benzyl)-amine
N-{3-[2-(4-Methoxy-benzylamino)-imidazo[2,1-b][1,3,4]thiadiazol-5-yl]-phenyl}-acetamide
[5-(3-Chloro-phenyl)-imidazo[2,1-b][1,3,4]thiadiazol-2-yl]-(4-methoxy-benzyl)-amine
[5-(3-Fluoro-phenyl)-imidazo[2,1-b][1,3,4]thiadiazol-2-yl]-(4-methoxy-benzyl)-amine
Benzyl-{5-[6-(2-morpholin-4-yl-ethylamino)-pyridin-3-yl]-imidazo[2,1-b][1,3,4]thiadiazol-2-yl}-amine
1-{3-[2-(4-Fluoro-benzylamino)-imidazo[2,1-b] [1,3,4]thiadiazol-5-yl]-phenyl}-ethanone
(4-Fluoro-benzyl)-(5-thiophen-2-yl-imidazo[2,1-b][1,3,4]thiadiazol-2-yl)-amine
{5-[6-(3-Dimethylamino-propoxy)-pyridin-3-yl]-imidazo[2,1-b][1,3,4]thiadiazol-2-yl}-(4-methoxy-benzyl)-amine
(4-Methoxy-benzyl)-(5-phenyl-imidazo[2,1-b][1,3,4]thiadiazol-2-yl)-amine
[5-(3,4-Dimethoxy-phenyl)-imidazo[2,1-b][1,3,4]thiadiazol-2-yl]-(4-methoxy-benzyl)-amine
[5-(3-Dimethylamino-phenyl)-imidazo[2,1-b][1,3,4]thiadiazol-2-yl]-(4-methoxy-benzyl)-amine
[5-(4-Chloro-phenyl)-imidazo[2,1-b][1,3,4]thiadiazol-2-yl]-(4-methoxy-benzyl)-amine
N-(2-Hydroxy-ethyl)-4-[2-(4-methoxy-benzylamino)-imidazo[2,1-b][1,3,4]thiadiazol-5-yl]-benzamide
Benzyl-{516-(3-dimethylamino-propoxy)-pyridin-3-yl]-imidazo[2,1-b][1,3,4]thiadiazol-2-yl}-amine
[5-(3-Amino-phenyl)-imidazo[2,1-b][1,3,4]thiadiazol-2-yl]-benzyl-amine
Benzyl-(5-phenyl-imidazo[2,1-b][1,3,4]thiadiazol-2-yl)-amine
Benzyl-(5-thiophen-3-yl-imidazo[2,1-b][1,3,4]thiadiazol-2-yl)-amine
Benzyl-[5-(3-dimethylamino-phenyl)-imidazo[2,1-b][1,3,4]thiadiazol-2-yl]-amine
Benzyl-[5-(4-isopropyl-phenyl)-imidazo[2,1-b][1,3,4]thiadiazol-2-yl]-amine
3-(2-Cyclohexylamino-imidazo[2,1-b][1,3,4]thiadiazol-5-yl)-N,N-dimethyl-benzamide
4-(2-Isobutylamino-imidazo[2,1-b][1,3,4]thiadiazol-5-yl)-benzonitrile
Isobutyl-[5-(3,4,5-trimethoxy-phenyl)-imidazo[2,1-b][1,3,4]thiadiazol-2-yl]-amine
[2-(2-Isobutylamino-imidazo[2,1-b][1,3,4]thiadiazol-5-yl)-phenyn-methanol
(2-Methoxy-ethyl)-[5-(3,4,5-trimethoxy-phenyl)-imidazo[2,1-b][1,3,4]thiadiazol-2-yl]-amine
Cyclohcxyl-[5-(3-dimethylamino-phenyl)-imidazo[2,1-b][1,3,4]thiadiazol-2-yl]-amine
4-(2-Cyclohexylamino-imidazo[2,1-b][1,3,4]thiadiazol-5-yl)-N-(2-hydroxy-ethyl)-benzamide
N-(2-Hydroxy-ethyl)-4-(2-isobutylamino-imidazo[2,1-b][1,3,4]thiadiazol-5-yl)-benzamide
[5-[6-(3-Dimethylamino-propoxy)-pyridin-3-yl]-imidazo[2,1-b][1,3,4]thiadiazol-2-yl]-(tetrahydro-pyran-4-ylmethyl)-amine
N-(3-{2-[(Tetrahydro-pyran-4-ylmethyl)-amino]-imidazo[2,1-b][1,3,4]thiadiazol-5-yl}-phenyl)-acetamide
(Tetrahydro-pyran-4-ylmethyl)-[5-(3,4,5-trimethoxy-phenyl)-imidazo[2,1-b][1,3,4]thiadiazol-2-yl]-amine
(Tetrahydro-pyran-4-ylmethyl)-(5-thiophen-2-yl-imidazo[2,1-b][1,3,4]thiadiazol-2-yl)-amine
{5-[6-(2-Morpholin-4-yl-ethylamino)-pyridin-3-yl]-imidazo[2,1-b][1,3,4]thiadiazol-2-yl}-(2-phenoxy-ethyl)-amine
(2-Phenoxy-ethyl)-[5-(3,4,5-trimethoxy-phenyl)-imidazo[2,1-b][1,3,4]thiadiazol-2-yl]-amine
(2-Methyl-benzyl)-{5-[6-(2-morpholin-4-yl-ethylamino)-pyridin-3-yl]-imidazo[2,1-b][1,3,4]thiadiazol-2-yl}-amine
N-(2-Dimethylamino-ethyl)-3-[2-(2-methyl-benzylamino)-imidazo[2,1-b][1,3,4]thiadiazol-5-yl]-benzamide
N,N-Dimethyl-3-[2-(2-methyl-benzylamino)-imidazo[2,1-b][1,3,4]thiadiazol-5-yl]-benzamide
{5-[6-(2-Morpholin-4-yl-ethylamino)-pyridin-3-yl]-imidazo[2,1-b][1,3,4]thiadiazol-2-yl ktetrahydro-pyran-4-ylmethyl)-amine
(2-Phenoxy-ethyl)-(5-pyridin-3-yl-imidazo[2,1-b][1,3,4]thiadiazo1-2-yl)-amine
(2-Phenoxy-ethyl)-(5-thiophen-3-yl-imidazo[2,1-b][1,3,4]thiadiazol-2-yl)-amine
4-[2-(2-Phenoxy-ethylamino)-imidazo[2,1-b][1,3,4]thiadiazol-5-yl]-benzonitrile
[5-(5-Methoxy-pyridin-3-yl)-imidazo[2,1-b][1,3,4]thiadiazol-2-yl]-(2-phenoxy-ethyl)-amine N,N-Dimethyl-3-(2-(2-phenoxy-ethylamino)-imidazo[2,1-b][1,3,4]thiadiazol-5-yl]-benzamide
[5-(2-Chloro-phenyl)-imidazo[2,1-b][1,3,4]thiadiazol-2-yl]-(2-phenoxy-ethyl)-arnine
{2-[2-(2-Phenoxy-ethylamino)-imidazo[2,1-b][1,3,4]thiadiazol-5-yl]-phenyl}-methanol
(2-Methyl-benzyl)-(5-pyridin-4-yl-imidazo[2,1-b][1,3,4]thiadiazol-2-yl)-amine
4-[2-(4-Fluoro-benzylamino)-imidazo[2,1-b][1,3,4]thiadiazol-5-yl]-N-(2-hydroxy-ethyl)-benzamide
(4-Methoxy-benzyl)-[5-(6-methoxy-pyridin-3-yl)-imidazo[2,1-b][1,3,4]thiadiazol-2-yl]-arnine
4-{2-[(Tetrahydro-pyran-4-ylmethyl)-amino]-imidazo[2,1-b][1,3,4]thiadiazol-5-yl)-benzonitrile
(2-Phenoxy-ethyl)-(5-phenyl-imidazo[2,1-b][1,3,4]thiadiazol-2-yl)-amine
N-{3-[2-(2-Phenoxy-ethylamino)-imidazo[2,1-b][1,3,4]thiadiazol-5-yl]-phenyl}-acetamide
[5-(4-Isopropyl-phenyl)-imidazo[2,1-b][1,3,]thiadiazol-2-yl]-(2-phenoxy-ethyl)-amine
1-{3-[2-(2-Phenoxy-ethylamino)-imidazo[2,1-b][1,3,4]thiadiazol-5-yl]-phenyl}-ethanone
[5-(2-Chloro-phenyl)-imidazo[2,1-b][1,3,4]thiadiazol-2-yl]-(2-methyl-benzyl)-amine
(2-Phenoxy-ethyl)-(5-pyridin-4-yl-imidazo[2,1-b][1,3,4]thiadiazol-2-yl)-amine
1-{2-[5-(4-Isopropyl-phenyl)-imidazo[2,1-b][1,3,4]thiadiazol-2-ylamino]-ethyl}-imidazolidin-2-one
1-{2-[5-(3-Trifluoromethyl-phenyl)-imidazo[2,1-b][1,3,4]thiadiazol-2-ylaminol-ethyl]-imidazolidin-2-one
(3-Chloro-4-fluoro-benzyl)-(5-naphthalen-2-yl-imidazo[2,1-b][1,3,4]thiadiazol-2-yl)-amine
(3-Chloro-4-fluoro-benzyl)-(5-phenyl-imidazo[2,1-b][1,3,4]thiadiazol-2-yl)-amine
(3-Chloro-4-fluoro-benzyl)-(5-pyridin-3-yl-imidazo[2,1-b][1,3,4]thiadiazol-2-yl)-amine
(3-Chloro-4-fluoro-benzyl)-[5-(6-methoxy-pyridin-3-yl)-imidazo[2,1-b][1,3,4]thiadiazol-2-yl]-amine
(4-{2-[(Thiophen-2-ylmethyl)-amino]-imidazo[2,1-b][1,3,4]thiadiazol-5-yl]-phenyl)-methanol
Thiophen-2-ylmethyl-[5-(3-trifluoromethyl-phenyl)-imidazo[2,1-b][1,3,4]thiadiazol-2-yl]-amine
2-Methoxy-4-{2-[(thiophen-2-ylmethyl)-aminol-imidazo[2,1-b][1,3,4]thiadiazol-5-yl]-phenol
{4-[2-(4-Methoxy-benzylamino)-imidazo[2,1-b][1,3,4]thiadiazol-5-yl]-phenyl}-methanol
(4-Methoxy-benzyl)-[5-(3-trifluoromethyl-phenyl)-imidazo[2,1-b][1,3,4]thiadiazol-2-yl]-amine
2-Methoxy-4-[2-(4-methoxy-benzylamino)-imidazo[2,1-b][1,3,4]thiadiazol-5-yl]-phenol
4-[2-(4-Methoxy-benzylamino)-imidazo[2,1-b][1,3,4]thiadiazol-5-yl]-2,6-dimethyl-phenol
2,6-Dimethyl-4-[2-(2-phenoxy-ethylamino)-imidazo[2,1-b][1,3,4]thiadiazol-5-yl]-phenol
4-(2-(2-Methoxy-ethylamino)-imidazo[2,1-b][1,3,4]thiadiazol-5-yl]-phenol
(2-Methoxy-ethyl)-[5-(3-trifluoromethyl-phenyl)-imidazo[2,1-b][1,3,4]thiadiazol-2-yl]-amine
(3-Chloro-4-fluoro-benzyl)-(5-thiophen-3-yl-imidazo[2,1-b][1,3,4]thiadiazol-2-yl)-amine
N-(3-{2-[(Thiophen-2-ylmethyl)-amino]-imidazo[2,1-b][1,3,4]thiadiazol-5-yl]-phenyl)-methanesulfonamide
[4-(2-Benzylamino-imidazo[2,1-b][1,3,4]thiadiazol-5-yl)-phenyl]-methanol
4-{2-(Benzo[1,3]dioxol-5-ylmethyl)-amino]-imidazo[2,1-b][1,3,4]thiadiazol-5-yl}-phenol
Beno[1,3]dioxol-5-ylmethyl-[5-(3-trifluoromethyl-phenyl)-imidazo[2,1-b][1,3,4]thiadiazol-2-yl]-amine
N-{3-[2-(2-Phenoxy-ethylamino)-imidazo[2,1.-b][1,3,4]thiadiazol-5-yl]-phenyl}-methanesulfonamide
N-{3-[2-(2-Methoxy-ethylamino)-imidazo[2,1-b][1,3,4]thiadiazol-5-yl]-phenyl}-methanesulfonamide
N-[3-(2-Cyclohexylamino-imidazo[2,1-b][1,3,4]thiadiazol-5-yl)-phenyl]-methanesulfonamide
4-(2-Isobutylamino-imidazo[2,1-b][1,3,4]thiadiazol-5-yl)-phenol
[4-(2-Isobutylamino-imidazo[2,1-b][1,3,4]thiadiazol-5-yl)-phenyl]-methanol
3-(2-Isobutylamino-imidazo[2,1-b][1,3,4]thiadiazol-5-yl)-benzamide
(4-{2-[(Tettahydro-pyran-4-ylmethyl)-amino]-imidazo[2,1-b][1,3,4]thiadiazol-5-yl]-phenyl)-methanol
(Tetrahydro-pyran-4-ylmethyl)-[5-(3-trifluoromethyl-phenyl)-imidazo[2,1-b][1,3,4]thiadiazol-2-yl]-amine
2-Methoxy-4-{2-[(tetrahydro-pyran-4-ylmethyl)-aminol-imidazo[2,1-b][1,3,4]thiadiazol-5-yl]-phenol
2,6-Dimethyl-4-{2-[(tetrahydro-pyran-4-ylmethyl)-amino]midazo[2,1-b][1,3,4]thiadiazol-5-yl]-phenol
N-(3-{2-[(Tetrahydro-pyran-4-ylmethyl)-amino]-irnidazo[2,1-b][1,3,4]thiadiazol-5-yl]-phenyl)-methanesulfonamide
1-(3-{2-[(Furan-2-ylmethyl)-amino]-imidazo[2,1-b][1,3,4]thiadiazol-5-yl]-phenyl)-ethanone
N-(3-{2-[(Furan-2-ylmethyl)-amino]-imidazo[2,1-b][1,3,4]thiadiazol-5-yl]-phenyl)-methanesulfonamide
Isobutyl-[5-(3-trifluoromethyl-phenyl)-imidazo[2,1-b][1,3,4]thiadiazol-2-yl]-amine
N-[3-(2-Isobutylamino-imidazo[2,1-b][1,3,4]thiadiazol-5-yl)-phenyl]-methanesulfonamide
4-{2-[(Tetrahydro-pyran-4-ylmethyl)-amino]-imidazo[2,1-b][1,3,4]thiadiazol-5-yl}-phenol
[5-(3-Fluoro-phenyl)-imidazo[2,1-b][1,3,4]thiadiazol-2-yl]-furan-2-ylmethyl-amine
Cyclopropylmethyl-[5-(3-fluoro-phenyl)-imidazo[2,1-b][1,3,4]thiadiazol-2-yl]-amine
3-[2-(Cyclopropylmethyl-amino)-imidazo[2,1-b][1,3,4]thiadiazol-5-yl]-benzamide
N-{3-[2-(Cyclopropylmethyl-amino)-imidazo[2,1-b][1,3,4]thiadiazol-5-yl]-phenyl}-methanesulfonamide
(2-Pyridin-4-yl-ethyl)-(5-pyridin-3-yl-imidazo[2,1-b][1,3,4]thiadiazol-2-yl)-amine
[5-(3-Dimethylamino-phenyl)-imidazo[2,1-b][1,3,4]thiadiazol-2-yl]-(2-pyridin-2-yl-ethyl)-amine
[5-(6-Methoxy-pyridin-3-yl)-imidazo[2,1-b][1,3,4]thiadiazol-2-yl]-(2-pyridin-2-yl-ethyl)-amine
[5-(3-Fluoro-phenyl)-imidazo[2,1-b][1,3,4]thiadiazol-2-yl]-(2-pyridin2-yl-ethyl)-amine
1-{3-[2-(2-Pyridin-2-yl-ethylamino)-imidazo[2,1-b][1,3,4]thiadiazol-5-yl]-phenyl}-ethanone
3-{5[6-(2-Morpholin-4-yl-ethylamino)-pyridin-3-yl]-imidazo[2,1-b][1,3,4]thiadiazol-2-ylamino}-propan-1-ol
{5-[6-(2-Morpholin-4-yl-ethylamino)-pyridin-3-yl]-imidazo[2,1-b][1,3,4]thiadiazol-2-yl}-(2-pyridin-4-yl-ethyl)-amine
(2-Pyridin-4-yl-ethyl)-(5-pyridin-4-yl-imidazo[2,1-b][1,3,4]thiadiazol-2-yl)-amine
(2-Pyridin-4-yl-ethyl)-[5-(3-trifluoromethyl-phenyl)-imidazo[2,1-b][1,3,4]thiadiazol1-2-yl]-amine
[5-(3,4-Dimethoxy-phenyl)-imidazo[2,1-b][1,3,4]thiadiazol-2-yl]-pyridin-4-ylmethyl-amine
[5-(3-Chloro-4-fluoro-phenyl)-imidazo[2,1-b][1,3,4]thiadiazol-2-yl]-pyridin-4-ylmethyl-amine
[5-(5-Methoxy-pyridin-3-yl)-imidazo[2,1-b][1,3,4]thiadiazol-2-yl]-pyridin-4-ylmethyl-amine
[5-(3-Chloro-phenyl)-imidazo[2,1-b][1,3,4]thiadiazol-2-yl]-pyridin-4-ylmethyl-amine
1-(3-{2-[(Pyridin-4-ylmethyl)-amino]-imidazo[2,1-b][1,3,4]thiadiazol-5-yl]-phenyl)-ethanone
Pyridin-3-ylmethyl-(5-thiophen-3-yl-imidazo[2,1-b][1,3,4]thiadiazol-2-yl)-amine
[5-(3-Chloro-4-fluoro-phenyl)-imidazo[2,1-b][1,3,4]thiadiazol-2-yl]-pyridin-3-ylmethyl-amine
[5-(3-Chloro-phenyl)-imidazo[2,1-b][1,3,4]thiadiazol-2-yl]-pyridin-3-ylmethyl-amine
[5-(6-Methoxy-pyridin-3-yl)-imidazo[2,1-b][1,3,4]thiadiazol-2-yl]-pyridin-3-ylmethyl-amine
[5-(2-Chloro-phenyl)-imidazo[2,1-b][1,3,4]thiadiazol-2-yl}-pyridin-3-ylmethyl-amine
1-(3-{2-[(Pyridin-3-ylmethyl)-amino]-imidazo[2,1-b][1,3,4]thiadiazol-5-yl]-phenyl)-ethanone
1-{3-[2-(2-Pyridin-4-yl-ethylamino)-imidazo[2,1-b][1,3,4]thiadiazol-5-yl]-phenyl}-ethanone
4-(5-Naphthalen-2-yl-imidazo[2,1-b][l,3,4]thiadiazol-2-ylamino)-cyclohexanol
4-(5-Phenyl-imidazo[2,1-b][1,3,4]thiadiazol-2-ylamino)-cyclohexanol
4-[5-(3,4,5-Trimethoxy-phenyl)-imidazo[2,1-b][1,3,4]thiadiazol-2-ylaminol-cyclohexanol
4-[5-(4-Chloro-plienyl)-imidazo[2,1-b][1,3,4]thiadiazol-2-ylamino-cyclohexanol
4-[5-(6-Methoxy-pyridin-3-yl)-imidazo[2,1-b][1,3,4]thiadiazol-2-ylaminol-cyclohexanol 4-[5-(3-Fluoro-phenyl)-imidazo[2,1-b][1,3,4]thiadiazol-2-ylamino]-cyclohexanol
3-[5-(3-Trifluorometlioxy-phenyl)-imidazo[2,1-b][1,3,4]thiadiazol-2-ylamino]-propan-1-ol
3-[5-(6-Methoxy-pyridin-3-yl)-imidazo[2,1-b][1,3,4]thiadiazol-2-ylamino]-propan-1-ol
1-{3-[2-(3-Hydroxy-propylamino)-imidazo[2,1-b][1,3,4]thiadiazol-5-yl]-phenyl}-ethanone
Benzyl-[5-(3-trifluoromethyl-phenyl)-imidazo[2,1-b][1,3,4]thiadiazol-2-yl]-amine
Cyclohexyl-[5-(3-trifluoromethyl-phenyl)-imidazo[2,1-b][1,3,4]thiadiazol-2-yl]-amine
(2-Methyl-benzyl)-[5-(3-trifluoromethyl-phenyl)-imidazo[2,1-b][1,3,4]thiadiazol-2-yl]-amine
[5-(3-Chloro-4-fluoro-phenyl)-imidazo[2,1-b][1,3,4]thiadiazol-2-yl]-furan-2-ylmethyl-amine
Furan-2-ylmethyl-[5-(6-methoxy-pyridin-3-yl)-imidazo[2,1-b][1,3,4]thiadiazol-2-yl]-amine
[5-(3-Chloro-4-fluoro-phenyl)-imidazo[2,1-b][1,3,4]thiadiazol-2-yl]-(2-pyridin-2-yl-ethyl)-amine
[5-(5-Methoxy-pyridin-3-yl)-imidazo[2,1-b][1,3,4]thiadiazol-2-yl]-(2-pyridin-2-yl-ethyl)-amine
4-[2-(Cyclopropylmethyl-amino)-imidazo[2,1-b][1,3,4]thiadiazol-5-yl]benzonitrile
[5-(3-Chloro-4-fluoro-phenyl)-imidazo[2,1-b][1,3,4]thiadiazol-2-yl]-cyclopropylmethyl-amine
1-{3[2-(Cyclopropylmethyl-amino)-imidazo[2,1-b][1,3,4]thiadiazol-5-yl]-phenyl}-ethanone
{5-[6-(3-Dimethylamino-propoxy)-pyridin-3-yl]-imidazo[2,1-b][1,3,4]thiadiazol-2-yl]-thiophen-2-ylmethyl-amine
(5-Pyridin-3-yl-imidazo[2,1-b][1,3,4]thiadiazol-2-yl)-thiophen-2-ylmethyl-amine
(5-Thiophen-3-yl-imidazo[2,1-b][1,3,4]thiadiazol-2-yl)-thiophen-2-ylmethyl-amine
[5-(3-Dimethylamino-phenyl)-imidazo[2,1-b][1,3,4]thiadiazol-2-yl]-thiophen-2-ylmethyl-amine
(2-{2-[(Thiophen-2-ylmethyl)-amino]-imidazo[2,1-b][1,3,4]thiadiazol-5-yl]-phenyl)-methanol
Benzo[1,3]dioxol-5-ylmethyl-{5-[6-(2-morpholin-4-yl-ethylamino)-pyridin-3-yl]-imidazo[2,1-b][1,3,4]thiadiazol-2-yl}-amine
Benzo[1,3]dioxol-5-ylmethyl-(5-phenyl-imidazo[2,1-b][1,3,4]thiadiazol-2-yl)-amine
Benzo[1,3]dioxol-5-ylmethyl-[5-pyridin-4-yl-imidazo[2,1-b][1,3,4]thiadiazol-2-yl]-amine
3-[2-[(Benzo[1,3]dioxol-5-ylmethyl)-amino}-imidazo[2,1-b][1,3,4]thiadiazol-5-yl]-N,N-dimethyl-benzamide
Benzo[1,3]dioxol-5-ylmethyl-[5-(2-chloro-phenyl)-imidazo[2,1-b][1,3,4]thiadiazol-2-yl]-amine
3-[2-(4-Dimethylamino-benzylamino)-imidazo[2,1-b][1,3,4]thiadiazol-5-yl]-N,N-dimethyl-benzamide
{5-[6-(2-Morpholin-4-yl-ethylamino)-pyridin-3-yl]-imidazo[2,1-b][1,3,4]thiadiazol-2-yl}-thiophen-2-ylmethyl-amine
[5-(2-Dimethylamino-phenyl)-imidazo[2,1-b][1,3,4]thiadiazol-2-yl]-thiophen-2-ylmethyl-amine
(5-Phenyl-imidazo[2,1-b][1,3,4]thiadiazol-2-yl)-thiophen-2-ylmethyl-amine
(5-Pyridin-4-yl-imidazo[2,1-b][1,3,4]thiadiazol-2-yl)-thiophen-2-ylmethyl-amine
N-(2-Hydroxy-ethyl)-4-{2-[(thiophen-2-ylmethyl)-amino]-imidazo[2,1-b][1,3,4]thiadiazol-5-yl]-benzamide
N,N-Dimethyl-3-{2-[(thiophen-2-ylmethyl)-amino]-imidazo[2,1-b][1,3,4]thiadiazol-5-yl]-benzamide
Benzo[1,3]dioxol-5-ylmethyl-{5-[6-(3-dimethylamino-propoxy)-pyridin-3-yl]-imidazo[2,1-b][1,3,4]thiadiazol-2-yl}-amine
Benzo[1,3]dioxol-5-ylmethyl-(5-naphthalen-2-yl-imidazo[2,1-b][1,3,4]thiadiazol-2-yl)-amine
N-(3-{2-[(Benzo[1,3]dioxol-5-ylmethyl)-amino]-imidazo[2,1-b][1,3,4]thiadiazol-5-yl]-phenyl)-acetamide
Benzo[1,3]dioxol-5-ylmethyl-[5-(3-dimethylamino-phenyl)-imidazo[2,1-b][1,3,4]thiadiazol-2-yl]-amine
Benzo[1,3]dioxol-5-ylmethyl-[5-(4-isopropyl-phenyl)-imidazo[2,1-b][1,3,4]thiadiazol-2-yl]-amine
Benzo[1,3]dioxol-5-ylmethyl-(5-thiophen-2-yl-imidazo[2,1-b][1,3,4]thiadiazol-2-yl)-amine
(5-Phenyl-imidazo[2,1-b][1,3,4]thiadiazol-2-yl)-pyridin-4-ylmethyl-amine
(5-Pyridin-3-yl-imidazo[2,1-b][1,3,4]thiadiazol-2-yl)-pyridin-4-ylmethyl-amine
Pyridin-4-ylmethyl-(5-thiophen-3-yl-imidazo[2,1-b][1,3,4]thiadiazol-2-yl)-amine
Pyridin-4-ylmethyl-[5-(3-trifluoromethoxy-phenyl)-imidazo[2,1-b][1,3,4]thiadiazol-2-yl]-amine
[5-(4-Isopropyl-phenyl)-imidazo[2,1-b][1,3,4]thiadiazol-2-yl]-pyridin-4-ylmethyl-amine
[5-(6-Methoxy-pyridin-3-yl)-imidazo[2,1-b][1,3,4]thiadiazol-2-yl]-pyridin-4-ylmethyl-amine
[5-(3-Fluoro-phenyl)-imidazo[2,1-b][1,3,4]thiadiazol-2-yl]-pyridin-4-ylmethyl-amine
[5-(2-Chloro-phenyl)-imidazo[2,1-b][1,3,4]thiadiazol-2-yl]-pyridin-4-ylmethyl-amine
Pyridin-4-ylmethyl-(5-thiophen-2-yl-imidazo[2,1-b][1,3,4]thiadiazol-2-yl)-amine
(5-[6-(2-Morpholin-4-yl-ethylamino)-pyridin-3-yl]-imidazo[2,1-13][1,3,4]thiadiazol-2-yl}-pyridin-3-ylmethyl-amine
(5-Naphthalen-2-yl-imidazo[2,1-b][1,3,4]thiadiazol-2-yl)-pyridin-3-ylmethyl-amine
[5-(3,4-Dimethoxy-phenyl)-imidazo[2,1-b][1,3,4]thiadiazol-2-yl]-pyridin-3-ylmethyl-amine
N-(3-{2-[(Pyridin-3-ylmethyl)-amino]-imidazo[2,1-b][1,3,4]thiadiazol-5-yl]-phenyl)-acetamide
Pyridin-3-ylmethyl-[5-(3,4,5-trimethoxy-phenyl)-imidazo[2,1-b][1,3,4]thiadiazol-2-yl]-amine
[5-(4-Chloro-phenyl)-imidazo[2,1-b][1,3,4]thiadiazol-2-yl]-pyridin-3-ylmethyl-amine
Pyridin-3-ylmethyl-[5-(3-trifluoromethoxy-phenyl)-imidazo[2,1-b][1,3,4]thiadiazol-2-yl]-amine
[5-(5-Methoxy-pyridin-3-yl)-imidazo[2,1-b][1,3,4]thiadiazol-2-yl]-pyridin-3-ylmethyl-amine
(5-Phenyl-imidazo[2,1-b][1,3,4]thiadiazol-2-yl)-(2-pyridin-4-yl-ethyl)-amine
(2-Pyridin-4-yl-ethyl)-(5-thiophen-3-yl-imidazo[2,1-b][1,3,4]thiadiazol-2-yl)-amine
[5-(3,4-Dimethoxy-phenyl)-imidazo[2,1-b][1,3,4]thiadiazol-2-yl]-(2-pyridin-4-yl-ethyl)-amine
N-{3-[2-(2-Pyridin-4-yl-ethylamino)-imidazo[2,1-b][1,3,4]thiadiazol-5-yl]-phenyl}-acetamide
[5-(3-Dimethylamino-phenyl)-imidazo[2,1-b][1,3,4]thiadiazol-2-yl]-(2-pyridin-4-yl-ethyl)-amine
[5-(4-Chloro-phenyl)-imidazo[2,1-b][1,3,4]thiadiazol-2-yl]-(2-pyridin-4-yl-ethyl)-amine
[5-(3-Chloro-4-fluoro-phenyl)-imidazo[2,1-b][1,3,4]thiadiazol-2-yl]-(2-pyridin-4-yl-ethyl)-amine
(2-Pyridin-4-yl-ethyl)-[5-(3-trifluoromethoxy-phenyl)-imidazo[2,1-b][1,3,4]thiadiazol-2-yl]-amine
[5-(3-Chloro-phenyl)-imidazo[2,1-b][1,3,4]thiadiazol-2-yl]-(2-pyridin-4-yl-ethyl)-amine
[5-(4-Isopropyl-phenyl)-imidazo[2,1-b][1,3,4]thiadiazol-2-yl]-(2-pyridin-4-yl-ethyl)-amine
[5-(6-Methoxy-pyridin-3-yl)-imidazo[2,1-b][1,3,4]thiadiazol-2-yl]-(2-pyridin-4-yl-ethyl)-amine
[5-(3-Dimethylamino-phenyl)-imidazo[2,1-b][1,3,4]thiadiazol-2-yl]-pyridin-4-ylmethyl-amine
(2-{2-[(Pyridin-4-ylmethyl)-amino]-imidazo[2,1-b][1,3,4]thiadiazol-5-yl]-phenyl)-methanol
(5-Phenyl-imidazo[2,1-b][1,3,4]thiadiazol-2-yl)-pyridin-3-ylmethyl-amine
[5-(3-Dimethylamino-phenyl)-imidazo[2,1-b][1,3,4]thiadiazol-2-yl]-pyridin-3-ylmethyl-amine
[5-(4-Isopropyl-phenyl)-imidazo[2,1-b][1,3,4]thiadiazol-2-yl]-pyridin-3-ylmethyl-amine
[5-(3-Fluoro-phenyl)-imidazo[2,1-b][1,3,4]thiadiazol-2-yl]-pyridin-3-ylmethyl-amine
Pyridin-3-ylmethyl-(5-thiophen-2-yl-imidazo[2,1-b][1,3,4]thiadiazol-2-yl)-amine
(2-{2-[(Pyridin-3-ylmethyl)-amino]imidazo[2,1-b][1,3,4]thiadiazol-5-yl]-phenyl)-methanol
[5-(2-Dimethylamino-phenyl)-imidazo[2,1-b][l,3,4]thiadiazol-2-yl]-(2-pyridin-4-yl-ethyl)-amine
(5-Naphthalen-2-yl-imidazo[2,1-b][1,3,4]thiadiazol-2-yl)-(2-pyridin-4-yl-ethyl)-amine
4-(2-Pyridin-4-yl-ethylamino)-imidazo[2,1-b][1,3,4]thiadiazol-5-yl]-benzonitrile
(2-Pyridin-4-yl-ethyl)-[5-(3,4,5-trimethoxy-phenyl)-imidazo[2,1-b][1,3,4] thiadiazol-2-yl-amine
[5-(3-Fluoro-phenyl)-imidazo[2,1-b][1,3,4]thiadiazol-2-yl]-(2-pyridin-4-yl-ethyl)-amine N,N-Dimethyl-3-[2-(2-pyridin-4-yl-ethylamino)-imidazo[2,1-b][1,3,4]thiadiazol-5-yl]-benzamide
(2-Pyridin-4-yl-ethyl)-(5-thiophen-2-yl-imidazo[2,1-b][1,3,4]thiadiazol-2-yl)-amine
{2-[2-(2-Pyridin-4-yl-ethylamino)-imidazo[2,1-b]{1,3,4]thiadiazol-5-yl]-phenyl}-methanol
4-[2-(4-Hydroxy-cyclohexylamino)-imidazo[2,1-b][1,3,4]thiadiazol-5-yl]phenol
4-[5-(3-Chloro-4-fluoro-phenyl)-imidazo[2,1-b][1,3,4]thiadiazol-2-ylamino]-cyclohexanol
4-[5-(3-Trifluoromethoxy-phenyl)-imidazo[2,1-b][1,3,4]thiadiazol-2-ylamino]-cyclohexanol
4-[5-(2-Chloro-phenyl)-imidazo[2,1-b][1,3,4]thiadiazol-2-ylamino]-cyclohexanol
1-{3-[2-(4-Hydroxy-cyclohexylamino)-imidazo[2,1-b][1,3,4]thiadiazol-5-yl]-phenyl}-ethanone
3-(5-Naphthalen-2-yl-imidazo[2,1-b][1,3,4]thiadiazol-2-ylamino)-propan-1-ol
3-(5-Phenyl-imidazo[2,1-b][1,3,4]thiadiazol-2-ylamino)-propan-1-ol
3-(5-Pyridin-3-yl-imidazo[2,1-b][1,3,4]thiadiazol-2-ylamino)-propan-1-ol
4-[2-(3-Hydroxy-propylamino)-imidazo[2,1-b][1,3,4]thiadiazol-5-yl]-benzonitrile
3-[5-(3,4,5-Trimethoxy-phenyl)-imidazo[2,1-b][1,3,4]thiadiazol-2-ylamino]-propan-1-ol
3-[5-(3-Dimethylamino-phenyl)-imidazo[2,1-b][1,3,4]thiadiazol-2-ylamino]-propan-1-ol
3-[5-(4-Chloro-phenyl)-imidazo[2,1-b][1,3,4]thiadiazol-2-ylamino]-propan-1-ol
3-[5-(3-Chloro-phenyl)-imidazo[2,1-b][1,3,4]thiadiazol-2-ylamino]-propan-1-ol
3-[5-(4-Isopropyl-phenyl)-imidazo[2,1-b][1,3,4]thiadiazol-2-ylamino]-propan-1-ol
3-[2-(3-Hydroxy-propylamino)-imidazo[2,1-b][1,3,4]thiadiazol-5-yl]-benzamide
4-[2-(5-Pyridin-3-yl-imidazo[2,1-b][1,3,4]thiadiazol-2-ylamino)-ethyl]-benzenesulfonamide
4-{2-[5-(3,4-Dimethoxy-phenyl)-imidazo[2,1-b][1,3,4]thiadiazol-2-ylaminol-ethyl}-benzenesulfonamide
4-{2-[5-(3,4,5-Trimethoxy-phenyl)-imidazo[2,1-b][1,3,4]thiadiazol-2-ylamino1-ethyl}-benzenesulfonamide
4-{2-[5-(4-Chloro-phenyl)-imidazo[2,1-b][1,3,4]thiadiazol-2-ylamino]-ethyl}-benzenesulfonamide
4-{2-[5-(3-Chloro-4-fluoro-phenyl)-imidazo[2,1-b][1,3,4]thiadiazol-2-ylamino]-ethyl}-benzenesulfonamide
4-{2-[5-(3-Chloro-phenyl)-imidazo[2,1-b][1,3,4]thiadiazol-2-ylamino}ethyl]-benzenesulfonamide
4-{2-[5-(4-Isopropyl-phenyl)-imidazo[2,1-b][1,3,4]thiadiazol-2-ylamino]-ethyl}-benzenesulfonamide
4-{2-[5-(6-Methoxy-pyridin-3-yl)-imidazo[2,1-b][1,3,4]thiadiazol-2-ylamino]-ethyl}-benzenesulfonamide
4-{2-[5-(3-Trifluoromethyl-phenyl)-imidazo[2,1-b][1,3,4]thiadiazol-2-ylamino]-ethyl}-benzenesulfonamide
4-[5-(3,4-Dimethoxy-phenyl)-imidazo[2,1-b][1,3,4]thiadiazol-2-ylamino]-cyclohexanol
N-{3-[2-(4-Hydroxy-cyclohexylamino)-imidazo[2,1-b][1,3,4]thiadiazol-5-yl]-phenyl}-acetamide
4-[5-(3-Dimethylamino-phenyl)-imidazo[2,1-b][1,3,4]thiadiazol-2-ylaminol-cyclohexanol
4-[5-(4-Isopropyl-phenyl)-imidazo[2,1-b][1,3,4]thiadiazol-2-ylamino]-cyclohexanol
4-[2-(4-Hydroxy-cyclohexylamino)-imidazo[2,1-b][1,3,4]thiadiazol-5-yl]-2,6-dimethyl-phenol
4-[5-(2-Hydroxymethyl-phenyl)-imidazo[2,1-b][1,3,4]thiadiazol-2-ylaminol-cyclohexanol
3-(5-Thiophen-3-yl-imidazo[2,1-b][1,3,4]thiadiazol-2-ylamino)-propan-1-ol
3-[5-(3,4-Dimethoxy-phenyl)-imidazo[2,1-b][1,3,4]thiadiazol-2-ylaminopropan-1-ol
N-{3-[2-(3-Hydroxy-propylamino)-imidazo[2,1-b][1,3,4]thiadiazol-5-yl-phenyl}-acetamide
3-[5-(4-Hydroxymethyl-phenyl)-imidazo[2,1-b][1,3,4]thiadiazol-2-ylamino1-propan-1-ol
3-[5-(3-Fluoro-phenyl)-imidazo[2,1-b][1,3,4]thiadiazol-2-ylaminol-propan-1-ol
3-[5-(2-Chloro-phenyl)-imidazo[2,1-b][1,3,4]thiadiazol-2-ylamino}-propan-1-ol
4-{2-[5-(2-Dimethylamino-phenyl)-imidazo[2,1-b][1,3,4]thiadiazol-2-ylamino]-ethyl}-benzenesulfonamide
4-[2-(5-Naphthalen-2-yl-imidazo[2,1-b][1,3,4]thiadiazol-2-ylamino)-ethyl]-benzenesulfonamide
4-{2-[5-(4-Hydroxy-phenyl)-imidazo[2,1-b][1,3,4]thiadiazol-2-ylaminol-ethyl}-benzenesulfonamide
N-(3-{2-[2-(4-Sulfamoyl-phenyl)-ethylamino]-imidazo[2,1-b][1,3,4]thiadiazol-5-yl}-phenyl)-acetamide
4-{2-[5-(3-Dimethylamino-phenyl)-imidazo[2,1-b][1,3,4]thiadiazol-2-ylaminol-ethyl}-benzenesulfonamide
4-{2-[5-(3-Trifluoromethoxy-phenyl)-imidazo[2,1-b][1,3,4]thiadiazol-2-ylamino]-ethyl}-benzenesulfonamide
N,N-Dimethyl-3-{2-[2-(4-sulfamoyl-phenyl)-ethylamino]-imidazo[2,1-b][1,3,4]thiadiazol-5-yl}-benzamide
4-{2-[5-(3-Acetyl-phenyl)-imidazo[2,1-b][1,3,4]thiadiazol-2-ylamino]-ethyl}-benzenesulfonamide
4-{2-[5-(2-Hydroxymethyl-phenyl)-imidazo[2,1-b][1,3,4]thiadiazol-2-ylamino1-ethyl}-benzenesulfonamide
(2-Morpholin-4-yl-ethyl)-(5-naphthalen-2-yl-imidazo[2,1-b][1,3,4]thiadiazol-2-yl)-amine
(2-Morpholin-4-yl-ethyl)-(5-pyridin-3-yl-imidazo[2,1-b][1,3,4]thiadiazol-2-yl)-amine
[5-(3,4-Dimethoxy-phenyl)-imidazo[2,1-b][1,3,4]thiadiazol-2-yl]-(2-morpholin-4-yl-ethyl)-amine
(2-Morpholin-4-yl-ethyl)-[5-(3,4,5-trimethoxy-phenyl)-imidazo[2,1-b][1,3,4]thiadiazol-2-yl]-amine
[5-(3-Dimethylamino-phenyl)-imidazo[2,1-b][1,3,4]thiadiazol-2-yl]-(2-morpholin-4-yl-ethyl)-amine
[5-(4-Chloro-phenyl)-imidazo[2,1-b][1,3,4]thiadiazol-2-yl]-(2-morpholin-4-yl-ethyl)-amine
[5-(4-Isopropyl-phenyl)-imidazo[2,1-b][1,3,4]thiadiazol-2-yl]-(2-morpholin-4-yl-ethyl)-amine
[5-(6-Methoxy-pyridin-3-yl)-imidazo[2,1-b] [1,3,4]thiadiazol-2-yl]-(2-morpholin-4-yl-ethyl)-amine
3-[2-(2-Morpholin-4-yl-ethylamino)-imidazo[2,1-b][1,3,4]thiadiazol-5-yl]-benzamide
N,N-Dimethyl-3-[2-(2-morpholin-4-yl-ethylamino)-imidazo[2,1-b][1,3,4]thiadiazol-5-yl]-benzamide
1-[2-(5-Naphthalen-2-yl-imidazo[2,1-b][1,3,4]thiadiazol-2-ylamino)-ethyl]-imidazolidin-2-one
N-[5-(6-Methoxy-pyridin-3-yl)-imidazo[2,1-b][1,3,4]thiadiazol-2-yl]-cyclohexane-1,4-diamine
3-[2-(4-Amino-cyclohexylamino)-imidazo[2,1-b][1,3,4]thiadiazol-5-yl]-N,N-dimethyl-benzamide
(2-Morpholin-4-yl-ethyl)-(5-phenyl-imidazo[2,1-b][1,3,4]thiadiazol-2-yl)-amine
(2-Morpholin-4-yl-ethyl)-(5-thiophen-3-yl-imidazo[2,1-b][1,3,4]thiadiazol-2-yl)-amine
4-[2-(2-Morpholin-4-yl-ethylamino)-imidazo[2,1-b][1,3,4]thiadiazol-5-yl]-benzonitrile
[5-(3-Chloro-4-fluoro-phenyl)-imidazo[2,1-b][1,3,4]thiadiazol-2-yl]-(2-morpholin-4-yl-ethyl)-amine
(2-Morpholin-4-yl-ethyl)-[5-(3-trifluoromethoxy-phenyl)-imidazo[2,1-b][1,3,4]thiadiazol-2-yl]-amine
{4-[2-(2-Morpholin-4-yl-ethylamino)-imidazo[2,1-b][1,3,4]thiadiazol-5-yl]-phenyl}-methanol
(2-Morpholin-4-yl-ethyl)-(5-(3-trifluoromethyl-phenyl)-imidazo[2,1-b][1,3,4]thiadiazol-2-yl)-amine
[5-(3-Fluoro-phenyl)-imidazo[2,1-b][1,3,4]thiadiazol-2-yl]-(2-morpholin-4-yl-ethyl)-amine
(2-Morpholin-4-yl-ethyl)-(5-thiophen-2-yl-imidazo[2,1-b][1,3,4]thiadiazol-2-yl)-amine
{2-[2-(2-Morpholin-4-yl-ethylamino)-imidazo[2,1-b][1,3,4]thiadiazol-5-yl]-phenyl}-methanol
1-{2-[5-(3-Trifluoromethoxy-phenyl)-imidazo[2,1-b][1,3,4]thiadiazol-2-ylamino)-ethyl}-imidazolidin-2-one
Propyl-[5-(3,4,5-trimethoxy-phenyl)-imidazo[2,1-b]thiadiazol-2-yl]amine
1-[3-(2-Propylamino-imidazo[2,1-b][1,3,4]thiadiazol-5-yl)-phenyl]ethanone and
4-[5-(3,4,5-Trimethoxy-phenyl)-imidazo[2,1-b][1,3,4]thiadiazol-2-ylamino)-cyclohexanol.

14. A pharmaceutical composition comprising at least one compound according to claim 1 or a physiologically acceptable salt thereof.

\* \* \* \* \*

UNITED STATES PATENT AND TRADEMARK OFFICE
CERTIFICATE OF CORRECTION

PATENT NO. : 8,389,554 B2
APPLICATION NO. : 13/056331
DATED : March 5, 2013
INVENTOR(S) : Guenter Hoelzemann et al.

It is certified that error appears in the above-identified patent and that said Letters Patent is hereby corrected as shown below:

In The Claims:

Column 260, line 63 (Claim 8), reads: "dazo[2,1b][1,3,4]thiadiazol-2-yl]-amine;"
Should read: --dazo[2,1-b][1,3,4]thiadiazol-2-yl]-amine;--.

Column 262, line 1 (Claim 13), reads: "4[2-(Cyclopropylmethyl-amino)-imidazo[2,1-b][1,3,4]"
Should read: --4-[2-(Cyclopropylmethyl-amino)-imidazo[2,1-b][1,3,4]--.

Column 264, line 45 (Claim 13), reads: "(5-Pytidin-3-yl-imidazo[2,1-b][1,3,4]thiadiazol-2-yl)-(tetrahydro-"
Should read: --(5-Pyridin-3-yl-imidazo[2,1-b][1,3,4]thiadiazol-2-yl)-(tetrahydro- --.

Column 268, line 22 (Claim 13), reads: "Benzyl-[516-(3-dimethylamino-propoxy)-pyridin-3-yl]-"
Should read: --Benzyl-[5-[6-(3-dimethylamino-propoxy)-pyridin-3-yl]- --.

Column 270, line 9 (Claim 13), reads: "N-(3-{2-[(Tetrahydro-pyran-4-ylmethyl)-amino]-irnidazo"
Should read: --N-(3-{2-[(Tetrahydro-pyran-4-ylmethyl)-amino]-imidazo--.

Page 1 of 1

Signed and Sealed this
Second Day of July, 2013

Teresa Stanek Rea
*Acting Director of the United States Patent and Trademark Office*